(12) United States Patent
Wu et al.

(10) Patent No.: US 9,359,371 B2
(45) Date of Patent: Jun. 7, 2016

(54) BICYCLIC SUBSTITUTED PYRIMIDINE COMPOUNDS

(71) Applicant: Xuanzhu Pharma Co., Ltd., Shandong (CN)

(72) Inventors: Frank Wu, Shandong (CN); Aichen Wang, Shandong (CN)

(73) Assignee: XUANZHU PHARMA CO., LTD., Shandong (CN)

( * ) Notice: Subject to any disclaimer, the term of this patent is extended or adjusted under 35 U.S.C. 154(b) by 0 days.

(21) Appl. No.: 14/421,703

(22) PCT Filed: Aug. 14, 2013

(86) PCT No.: PCT/CN2013/000953
§ 371 (c)(1),
(2) Date: Feb. 13, 2015

(87) PCT Pub. No.: WO2014/026467
PCT Pub. Date: Feb. 20, 2014

(65) Prior Publication Data
US 2015/0232474 A1    Aug. 20, 2015

(30) Foreign Application Priority Data

Aug. 14, 2012    (CN) .......................... 2012 1 0289185

(51) Int. Cl.
| | |
|---|---|
| *C07D 403/04* | (2006.01) |
| *A61K 31/506* | (2006.01) |
| *C07D 491/08* | (2006.01) |
| *C07D 403/14* | (2006.01) |
| *C07D 401/14* | (2006.01) |
| *A61K 31/5377* | (2006.01) |
| *A61K 31/55* | (2006.01) |
| *C07D 239/47* | (2006.01) |
| *A61K 31/505* | (2006.01) |
| *C07D 487/10* | (2006.01) |
| *A61K 45/00* | (2006.01) |

(52) U.S. Cl.
CPC ............ *C07D 491/08* (2013.01); *A61K 31/505* (2013.01); *A61K 31/506* (2013.01); *A61K 31/5377* (2013.01); *A61K 31/55* (2013.01); *A61K 45/00* (2013.01); *C07D 239/47* (2013.01); *C07D 401/14* (2013.01); *C07D 403/04* (2013.01); *C07D 403/14* (2013.01); *C07D 487/10* (2013.01)

(58) Field of Classification Search
CPC .. C07D 401/04; C07D 401/14; C07D 403/04; C07D 403/14; C07D 453/06; C07D 471/10; C07D 487/08; C07D 487/10; C07D 498/08; A61K 31/505; A61K 31/506
USPC .......... 540/524; 544/122, 295, 296, 330, 331; 514/212.08, 235.8, 252.14, 255.05, 514/275
See application file for complete search history.

(56) References Cited

U.S. PATENT DOCUMENTS

| | | |
|---|---|---|
| 6,656,935 B2 | 12/2003 | Yamada et al. |
| 7,501,409 B2 | 3/2009 | Murakami et al. |
| 9,139,581 B2 | 9/2015 | Song et al. |
| 2014/0288063 A1 | 9/2014 | Wu et al. |

FOREIGN PATENT DOCUMENTS

| | | |
|---|---|---|
| CN | 102372697 A | 3/2012 |
| CN | 102887889 A | 1/2013 |
| EP | 1 219 609 A1 | 7/2002 |
| EP | 1223170 A1 | 7/2002 |
| EP | 1 277 741 A1 | 1/2003 |
| JP | 2002-338466 A | 11/2002 |
| JP | 2011-518219 A | 6/2011 |
| WO | WO 01/19802 A1 | 3/2001 |
| WO | WO 02/20058 A1 | 3/2002 |
| WO | WO 2008/024974 A1 | 2/2008 |
| WO | WO 2012/071519 A1 | 5/2012 |

OTHER PUBLICATIONS

Haddad et al., Phosphodiesterase type 5 inhibitos for treating erectile dysfunction and lower urinary tract symptoms secondary to benign prostatic hyperplasia: A comprehensive review, Arab Journal of Urology, 13, pp. 155-161 (2015).*
Das et al., PDE5 inhibitors as therapeutics for heart disease, diabetes and cancer, Pharmacology & Therapeutics, 147, pp. 12-21 (2015).*
English language abstract and machine-assisted English translation for CN 102372697 extracted from espacenet.com database on Jan. 9, 2015, 58 pages.
English language abstract for CN 102887889 extracted from espacenet.com database on Jan. 9, 2015, 1 page.
English language abstract for WO 01/19802 extracted from espacenet.com database on Jan. 9, 2015, 1 page.
International Search Report for Application No. PCT/CN2013/000953 dated Oct. 31, 2013, 7 pages.
Cantrell, Matthew A. et al.,Tadalafil: a phosphodiesterase-5 inhibitor for benign prostatic hyperplasia. Pharmacotherapy (2013), 33(6): 639-649.
Gandhi, Hemang et al., Effect of preoperative oral sildenafil on severe pulmonary artery hypertension in patients undergoing mitral valve replacement. Indian Journal of Pharmacology (2014), 46(3): 281-285.

(Continued)

*Primary Examiner* — Deepak Rao
(74) *Attorney, Agent, or Firm* — Howard & Howard Attorneys PLLC

(57) ABSTRACT

Disclosed are bicyclic group substituted pyrimidine compounds, pharmaceutical acceptable salts thereof or stereoisomers thereof. Also disclosed are preparation methods, pharmaceutical formulations, and pharmaceutical compositions of the compounds, and use of the compounds, pharmaceutical formulations, and pharmaceutical compositions for preparing a medicament for treating and/or preventing sexual dysfunction diseases and diseases with lower urinary tract symptoms.

16 Claims, No Drawings

(56) References Cited

OTHER PUBLICATIONS

Sastry, B. K. S. et al., Clinical efficacy of sildenafil in primary pulmonary hypertension. Journal of the American College of Cardiology (2004), 43(7): 1149-53.
Tinel, Hanna et al., Pre-clinical evidence for the use of phosphodiesterase-5 inhibitors for treating benign prostatic hyperplasia and lower urinary tract symptoms. BJU Int (2006), 98: 1259-1263.
Ueckert, Stefan et al., Phosphodiesterase inhibitors in clinical urology. Expert Review of Clinical Pharmacology (2013), 6(3): 323-332.
Wu, Xiaojing et al., Additional use of a phosphodiesterase 5 inhibitor in patients with pulmonary hypertension secondary to chronic systolic heart failure: a meta-analysis. European Journal of Heart Failure (2014), 16(4): 444-453.
English language abstract and machine-assisted English translation for JP 2002-338466 extracted from espacenet.com database on Mar. 30, 2016, 62 pages.
English language abstract for JP 2011-518219 extracted from espacenet.com database on Mar. 30, 2016, 2 pages.
English language abstract for WO 02/20058 extracted from espacenet.com database on Mar. 30, 2016, 1 page.

\* cited by examiner

BICYCLIC SUBSTITUTED PYRIMIDINE COMPOUNDS

CROSS-REFERENCE TO RELATED APPLICATIONS

This application is the National Stage of International Patent Application No. PCT/CN2013/000953, filed on Aug. 14, 2013, which claims priority to and all the advantages of Chinese Patent Application No. CN 201210289185.3, filed on Aug. 14, 2012, the content of which is incorporated herein by reference.

FIELD OF THE INVENTION

The present invention relates to the technical field of medicine and pharmacy, and particularly relates to bicyclic group substituted pyrimidine compounds, the pharmaceutically acceptable salts thereof or stereoisomers thereof, the preparation methods, pharmaceutical formulations and pharmaceutical compositions of the compounds, and use of the compounds for preparing a medicament for enhancing the signal transduction of cGMP. In particular, the invention relates to the use of the compounds for preparing a medicament for treating and/or preventing sexual dysfunction and diseases with lower urinary tract symptoms.

BACKGROUND cGMP (guanosine-3',5'-cyclic monophosphate, cyclic guanosine monophosphate) is a cyclic nucleotide found in animal and plant cells. It is an intracellular second messenger and is involved in various cell responses. It can be hydrolyzed by PDE-5 (phosphodiesterase-5). When PDE-5 is inhibited, the cGMP will increase, which will result in various physiological effects, e.g., relaxation of the vascular smooth muscle. Therefore, PDE-5 inhibitors can be used for the treatment of diseases, including hypertension, heart failure, pulmonary hypertension, erectile dysfunction, prostatic hyperplasia and female sexual dysfunction, etc.

Erectile dysfunction (ED) is the most common sexual dysfunction of men, characterized by continuous inability to achieve or maintain a penile erection for satisfactory sexual performance. ED is classified into organic ED, psychological ED and mixed ED. Although ED is non-fatal, it has a significant negative impact on the life quality as well as relationship of the couples.

There have been many treatments for ED, mainly including three types: peripheral drug treatment, central drug treatment and gene therapy. Peripheral drug treatment mainly employs phosphodiesterase-5 inhibitors (e.g. Sildenafil), also includes the employment of narceine, soluble Guanylate cyclase activator, Rho kinase agonist or local alprostadil. Central drug treatment employs dopamine receptor agonist, α-adrenergic receptor antagonist, 5-hydroxy tryptamine (5-HT) receptor agonist, oxytocin, oxytocin receptor agonist, etc. Gene therapy is based on the fact that ion channel is the essential substance for regulating the tension of smooth muscle of corpus cavernosum, and relaxes corpus cavernosum by injecting into corpus cavernosum the plasmid hMaxi-K (pVAX-hSLO) expressing hSlo gene, which expresses in the smooth muscle of corpus cavernosum and generates more potassium ion channels.

Currently, there are many treatments for ED. Phosphodiesterase-5 (PDE-5) inhibitors represented by Sildenafil (Viagra) are the first-line drugs for treating ED, also the most favourite treatment of the patients. At present, PDE-5 inhibitors on the market include Sildenafil, Vardenafil, Tadalafil, Udenafil and Avanafil. These drugs are taken orally and conveniently, and have fast and definite effect. Among them, Sildenafil and Tadalafil are important profitable products of Pfizer and Eli Lilly, respectively. Thus, these drugs have a huge potential market.

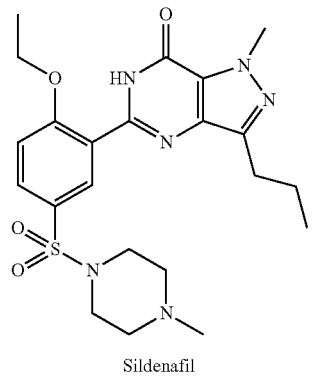

Sildenafil

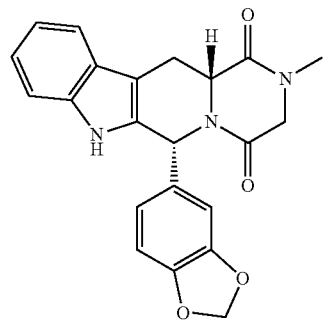

Tadalafil

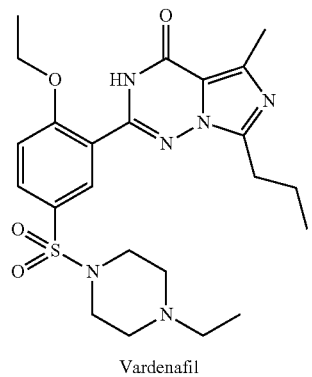

Vardenafil

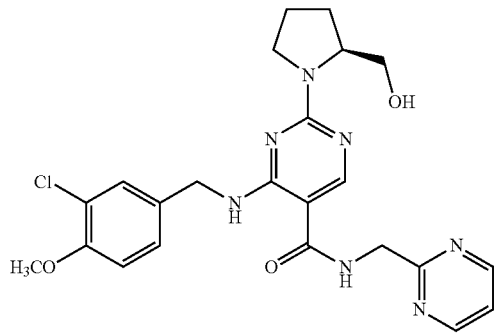

Avanafil

The structures of the compounds as disclosed in the patent application WO200119802 (Publication date: 2001 Mar. 22) of Tanabe Seiyaku Co., LTD are as following:

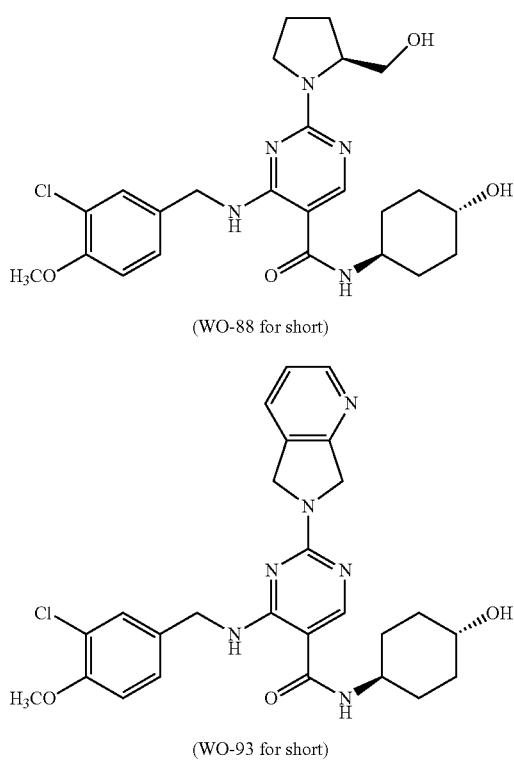

(WO-88 for short)

(WO-93 for short)

From the view of epidemiology, many elderly male patients who suffer from ED may also suffer from other diseases of genitourinary system, e.g. lower urinary tract symptoms (LUTS) such as benign prostatic hyperplasia (BPH), overactive bladder (OAB) and the like. These diseases bring about great distress to the elderly patients, and seriously affect their life. By pathological analysis, it has been found that the pathogenesis of ED and LUTS are the same, which are both in relevance to contraction of smooth muscle or proliferation of smooth muscle cell. Therefore, it is possible that LUTS, which has the same pathogenesis, can be treated by using PDE-5 inhibitor. Tadalafil has been approved by FDA for use in the treatment of benign prostatic hyperplasia.

With the clinical application of PDE-5 inhibitors, some potential safety problems of the drugs are emerging. Among the drugs, Sildenafil and Vardenafil not only have inhibition on PDE-5, but also have a certain inhibitory effect on PDE-6, which affects the function of retina. As a result, the two drugs affect the eyesight of the users. In this aspect, reports about Sildenafil are more than Vardenafil. Therefore, the two drugs have a poor selectivity for PDE-5. Tadalafil has a good selectivity for PDE-6, however, it has a certain inhibitory effect on PDE-11. Although the clinical pharmacological effects of PDE-11 are unknown, there is still potential risk. It was reported in some references that Tadalafil could cause an osphyalgia. Whether the symptom of osphyalgia is related to PDE-11 remains to be proven. In addition, the increased dosage of Vardenafil due to its low bioavailability is a disadvantage for long-term use of patient. The half-life of Tadalafil, as long as about 16 h in human, can easily result in drug interactions if a patient takes other drugs simultaneously. For example, the combined use of nitrate drugs and Tadalafil can excessively decrease the blood pressure, which can be life-threatening.

Avanafil, one of the second-generation PDE-5 inhibitors, has a good selectivity to PDE-6, with the ration PDE-6/5 of about 120. Moreover, it has no inhibitory effect on PDE-11, which guarantees the safety of clinical medication. However, its enzymatic activity in vitro is low, and the clinical dosage is high (50 mg, 100 mg and 200 mg), higher than Sildenafil, Vardenafil and Tadalafil. This can be a hazard for the safety of clinical medication. In addition, the increase of dosage will result in an increase of treatment costs. There is large potential improvement for Avanafil from the view of pharmacoeconomics. The most common adverse reactions reported in the clinical studies included headache, flushing, nasal congestion, nasopharyngitis and backache. A rare side effect of Avanafil is sudden decrease or loss of eyesight of the men taking this drug. Due to its low bioavailability, high clinical dosage and short half-life (about 1.2 h in human), Avanafil can only be used in single therapy of ED, but is not suitable for treating BPH, OAB and other diseases. Consequently, it is significant to develop a PDE-5 inhibitor with a high selectivity for PDE-5, a stronger pharmacological activity, a high bioavailability, more safety as well as an appropriate half-life (long but not overlong) so as to improve the life quality of elderly patients (treating ED, BPH and LUTS).

SUMMARY OF THE INVENTION

One of the technical problems to be solved by the present invention is to provide bicyclic group substituted pyrimidine compounds that act as PDE-5 inhibitors with high safety and strong activity, and their use in manufacture of a medicament for treating and/or preventing sexual dysfunction and diseases with lower urinary tract symptoms.

The technical solution of this invention is (1) A compound of Formula (I), or a pharmaceutically acceptable salt or a stereoisomer thereof,

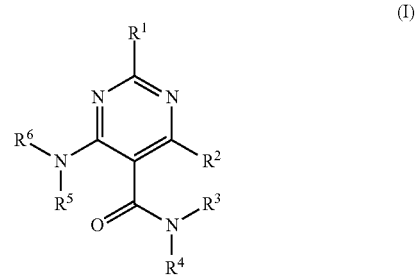

wherein $R^1$ is selected from the group consisting of 6 to 7 membered N-containing fused heterocyclyl, 7 to 12 membered N-containing spiro heterocyclyl and 7 to 12 membered N-containing bridged heterocyclyl; each attached to pyrimidyl via nitrogen and optionally substituted with a substituent selected from the group consisting of halogen, cyano, amino, hydroxyl, $C_{1-6}$ alkyl, halo $C_{1-6}$ alkyl, hydroxyl $C_{1-6}$ alkyl, $C_{1-6}$ alkoxyl, $C_{1-6}$ alkylcarbonyl and $C_{1-6}$ alkoxylcarbonyl, wherein the number of the substituent is 1 to 4;

$R^2$ is selected from the group consisting of hydrogen, hydroxyl, amino, cyano, $C_{1-6}$ alkylamino, di($C_{1-6}$ alkyl) amino, $C_{1-6}$ alkyl, halo $C_{1-6}$ alkyl, hydroxyl $C_{1-6}$ alkyl and $C_{1-6}$ alkoxyl;

$R^3$ and $R^4$ are each independently selected from hydrogen and -M-$R^7$,

M is selected from a single bond and $C_{1-6}$ alkylene optionally substituted with substituent $L_1$, $R^7$ is selected from 3 to 14 membered cyclic group optionally substituted with substituent $L_2$, or $R^3$ and $R^4$ together with nitrogen attached to $R^3$ and $R^4$ form a 5 to 6 membered N-containing heterocyclyl optionally substituted with substituent $L_3$, said substituents $L_1$, $L_2$ and $L_3$ are selected from the group consisting of halogen, hydroxyl, cyano, amino, $C_{1-6}$ alkylamino, di($C_{1-6}$ alkyl)amino, oxo, $C_{1-6}$ alkyl, hydroxyl $C_{1-6}$ alkyl, halo $C_{1-6}$ alkyl, $C_{1-6}$ alkoxyl, $C_{1-6}$ alkylcarbonyl, $C_{1-6}$ alkylsulfonyl and di($C_{1-6}$ alkyl)phosphino, wherein the number of the substituent is 1 to 4;

$R^5$ and $R^6$ are each independently selected from hydrogen and -Q-$R^8$,

Q is selected from a single bond and $C_{1-6}$ alkylene optionally substituted with substituent $L_4$, $R^8$ is selected from the group consisting of 6 to 14 membered aryls, 5 to 7 membered monocyclic heterocyclyl, 8 to 9 membered fused cyclyl and 8 to 9 membered fused heterocyclyl; each optionally substituted with substituent $L_5$, said substituents $L_4$ and $L_5$ are selected from the group consisting of halogen, hydroxyl, $C_{1-6}$ alkyl, halo $C_{1-6}$ alkyl, carboxyl $C_{1-6}$ alkyl, $C_{2-6}$ alkenyl, $C_{2-6}$ alkynyl, $C_{1-6}$ alkoxyl, halo $C_{1-6}$ alkoxyl, amino, $C_{1-6}$ alkylamino, di($C_{1-6}$ alkyl)amino, cyano, nitro, $C_{1-6}$ alkylcarbonyl, sulfonyl amino and $C_{1-6}$ alkyl sulfonyl amino, wherein the number of the substituent is 1 to 4.

(2) The compound of Formula (I) in item (1), or a pharmaceutically acceptable salt or a stereoisomer thereof, wherein $R^2$ is preferably selected from the group consisting of hydrogen, hydroxyl and methyl; $R^4$ is preferably hydrogen; $R^6$ is preferably hydrogen.

(3) The compound of Formula (I) of item (1) and item (2), or a pharmaceutically acceptable salt or a stereoisomer thereof, wherein $R^5$ is -Q-$R^8$, Q is selected from $C_{1-6}$ alkylene, $R^8$ is preferably selected from the group consisting of 6 to 10 membered aryls, 5 to 7 membered monocyclic heterocyclyl, 8 to 9 membered fused cyclyl and 8 to 9 membered fused heterocyclyl; each optionally substituted with substituent $L_5$, said substituent $L_5$ is selected from the group consisting of halogen, hydroxyl, $C_{1-6}$ alkyl, halo $C_{1-6}$ alkyl, carboxyl $C_{1-6}$ alkyl, $C_{1-6}$ alkoxyl, halo $C_{1-6}$ alkoxyl, amino, $C_{1-6}$ alkylamino, di($C_{1-6}$ alkyl)amino, cyano, nitro, $C_{1-6}$ alkylcarbonyl, sulfonyl amino and $C_{1-6}$ alkyl sulfonyl amino, wherein the number of the substituent is 1 to 4.

(4) The compound of Formula (I) of item (1) to (3), or a pharmaceutically acceptable salt or a stereoisomer thereof, wherein $R^1$ is selected from the group consisting of 6 to 7 membered N-containing fused heterocyclyl, 7 to 12 membered N-containing spiro heterocyclyl and 7 to 12 membered N-containing bridged heterocyclyl; each attached to pyrimidyl via nitrogen and optionally substituted with a substituent selected from the group consisting of halogen, cyano, amino, hydroxyl, $C_{1-6}$ alkyl, halo $C_{1-6}$ alkyl, hydroxyl $C_{1-6}$ alkyl, $C_{1-6}$ alkoxyl, $C_{1-6}$ alkylcarbonyl and $C_{1-6}$ alkoxylcarbonyl, wherein the number of the substituent is 1 to 4.

(5) The compound of Formula (I) of item (1) to item (4), or a pharmaceutically acceptable salt or a stereoisomer thereof, wherein $R^1$ is preferably selected from the group consisting of 6 to 7 membered N-containing fused heterocyclyl, 7 to 10 membered N-containing spiro heterocyclyl and 7 to 8 membered N-containing bridged heterocyclyl; each attached to pyrimidyl via nitrogen and optionally substituted with a substituent selected from the group consisting of halogen, cyano, amino, hydroxyl, $C_{1-6}$ alkyl, halo $C_{1-6}$ alkyl, hydroxyl $C_{1-6}$ alkyl and $C_{1-6}$ alkoxyl, wherein the number of the substituent is 1 to 4;

$R^3$ is -M-$R^7$,

M is preferably selected from a single bond and $C_{1-6}$ alkylene, $R^7$ is preferably selected from the group consisting of phenyl, 5 to 7 membered monocyclic heterocyclyl, 4 to 7 membered cycloalkyl, 8 to 9 fused cyclyl, 7 to 10 membered spiro cyclyl, 7 to 10 membered bridged cyclyl, 7 to 10 membered spiro heterocyclyl and 7 to 10 membered bridged heterocyclyl; each optionally substituted with substituent $L_2$, or $R^3$ and $R^4$ together with nitrogen attached to $R^3$ and $R^4$ form a 5 to 6 membered N-containing heterocyclyl optionally substituted with substituent $L_3$, said substituents $L_2$ and $L_3$ are selected from the group consisting of halogen, hydroxyl, cyano, amino, $C_{1-6}$ alkylamino, di($C_{1-6}$ alkyl)amino, oxo, $C_{1-6}$ alkyl, hydroxyl $C_{1-6}$ alkyl, halo $C_{1-6}$ alkyl and $C_{1-6}$ alkoxyl, wherein the number of the substituent is 1 to 4;

$R^5$ is -Q-$R^8$,

Q is preferably selected from methylene and ethylene, $R^8$ is preferably selected from the group consisting of phenyl, 5 to 7 membered monocyclic heterocyclyl, 8 to 9 membered fused cyclyl and 8 to 9 fused heterocyclyl; each optionally substituted with substituent $L_5$, said substituent $L_5$ is preferably selected from the group consisting of fluoro, chloro, methyl, trifluoromethyl, methoxyl, ethoxyl, trifluoromethoxyl, dimethylamino and carboxylmethyl, wherein the number of the substituent is 1 to 4;

$R^2$ is further preferably hydrogen; $R^4$ is further preferably hydrogen; $R^6$ is further preferably hydrogen.

(6) The compound of Formula (I) in item (5), or a pharmaceutically acceptable salt or a stereoisomer thereof, wherein $R^7$ is further preferably selected from the group consisting of phenyl, tetrahydrofuranyl, tetrahydrothienyl, tetrahydropyrrolyl, imidazolidinyl, pyrazolidinyl, piperidinyl, morpholinyl, piperazinyl, 2-oxo-azacycloheptanyl, 2-oxo-piperazinylfuranyl, dihydrothienyl, dihydropyrrolyl, dihydrooxazolyl, dihydropyrazolyl, thienyl, pyrrolyl, imidazolyl, thiazolyl, pyrazolyl, pyrimidyl, pyridyl, pyrazinyl, oxazolyl, cyclobutyl, cyclopentyl, cyclohexyl, cycloheptyl, naphthyl, indolyl, benzimidazolyl, 2,3-dihydrobenzfuranyl, quinolinyl, benzo[d][1,3]-meta-dioxa-cyclopentenyl, 7 to 10 membered spiro cyclyl, 7 to 10 membered bridged cyclyl, 7 to 10 membered spiro heterocyclyl and 7 to 10 membered bridged heterocyclyl; each optionally substituted with substituent $L_2$, or $R^3$ and $R^4$ together with nitrogen attached to $R^3$ and $R^4$ form a 5 to 6 membered N-containing heterocyclyl optionally substituted with substituent $L_3$, said substituents $L_2$ and $L_3$ are further preferably selected from the group consisting of halogen, hydroxyl, cyano, amino, $C_{1-6}$ alkylamino, di($C_{1-6}$ alkyl)amino, oxo, $C_{1-6}$ alkyl, hydroxyl $C_{1-6}$ alkyl, halo $C_{1-6}$ alkyl and $C_{1-6}$ alkoxyl, wherein the number of the substituent is 1 to 4;

$R^8$ is further preferably selected from the group consisting of phenyl, 8 to 9 membered fused cyclyl and 8 to 9 fused heterocyclyl; each optionally substituted with substituent $L_5$, said substituent $L_5$ is further preferably selected from the group consisting of fluoro, chloro, methyl, trifluoromethyl, methoxyl, ethoxyl, trifluoromethoxyl, dimethylamino and carboxylmethyl, wherein the number of the substituent is 1 to 4.

(7) The compound of Formula (I) of item (5) and item (6), or a pharmaceutically acceptable salt or a stereoisomer thereof, wherein $R^1$ is further preferably selected from the group consisting of 6 to 7 membered N-containing fused heterocyclyl, 7 to 10 membered N-containing spiro heterocyclyl and 7 to 8 membered N-containing bridged heterocyclyl; each attached to pyrimidyl via nitrogen and optionally substituted with a substituent more preferably selected from the group consisting of fluoro, chloro, amino, hydroxyl, $C_{1-6}$ alkyl and hydroxyl $C_{1-6}$ alkyl, wherein the number of the substituent is 1 to 2;

M is further preferably selected from the group consisting of a single bond, methylene and ethylene, $R^7$ is more preferably selected from the group consisting of cyclopentyl, cyclohexyl and cycloheptyl; each optionally substituted with substituent $L_2$, said substituent $L_2$ is more preferably selected from the group consisting of fluoro, chloro, hydroxyl, amino, methylamino, dimethylamino, methyl, ethyl and methoxyl, wherein the number of the substituent is 1 to 2;

$R^8$ is more preferably phenyl optionally substituted with substituent $L_5$, said substituent $L_5$ is more preferably selected from the group consisting of fluoro, chloro, methyl, trifluoromethyl, methoxyl, ethoxyl and trifluoromethoxyl, wherein the number of the substituent is 1 to 4.

(8) The compound of Formula (I) of item (5) and item (6), or a pharmaceutically acceptable salt or a stereoisomer thereof, wherein $R^1$ is preferably selected from the group consisting of 6 to 7 membered N-containing fused heterocyclyl and 7 to 10 membered N-containing spiro heterocyclyl; each attached to pyrimidyl via nitrogen and optionally substituted with a substituent selected from the group consisting of fluoro, chloro, amino, hydroxyl, $C_{1-6}$ alkyl and hydroxyl $C_{1-6}$ alkyl, wherein the number of the substituent is 1 to 2;

M is preferably selected from the group consisting of a single bond, methylene and ethylene, $R^7$ is preferably selected from the group consisting of piperidinyl, morpholinyl, piperazinyl, 2-oxo-azacycloheptanyl, 2-oxo-piperazinylfuranyl and 7 to 10 membered spiro cyclyl; each optionally substituted with substituent $L_2$, or $R^3$ and $R^4$ together with nitrogen attached to $R^3$ and $R^4$ form piperidinyl, piperazinyl or morpholinyl; each optionally substituted with substituent $L_3$, said substituents $L_2$ and $L_3$ are preferably selected from the group consisting of fluoro, chloro, hydroxyl, amino, methylamino, dimethylamino, oxo, trifluoromethyl, methyl, ethyl and methoxyl, wherein the number of the substituent is 1 to 2;

$R^8$ is preferably phenyl optionally substituted with substituent $L_5$, said substituent $L_5$ is preferably selected from the group consisting of fluoro, chloro, methyl, trifluoromethyl, methoxyl, ethoxyl and trifluoromethoxyl, wherein the number of the substituent is 1 to 4.

(9) The compound of Formula (I) of item (5) and (6), or a pharmaceutically acceptable salt or a stereoisomer thereof, wherein $R^1$ is preferably selected from the group consisting of 6 to 7 membered N-containing fused heterocyclyl, 7 to 10 membered N-containing spiro heterocyclyl and 7 to 8 membered N-containing bridged heterocyclyl; each attached to pyrimidyl via nitrogen and optionally substituted with a substituent preferably selected from the group consisting of fluoro, chloro, amino, hydroxyl, $C_{1-6}$ alkyl and hydroxyl $C_{1-6}$ alkyl, wherein the number of the substituent is 1 to 2;

M is preferably selected from the group consisting of a single bond, methylene and ethylene, $R^7$ is preferably selected from the group consisting of phenyl, thienyl, pyrrolyl, imidazolyl, thiazolyl, pyrazolyl, pyrimidyl, pyridyl, pyrazinyl, oxazolyl, naphthyl, indolyl, quinolinyl and 7 to 10 membered bridged cyclyl; each optionally substituted with substituent $L_2$, or $R^3$ and $R^4$ together with nitrogen attached to $R^3$ and $R^4$ form piperidinyl, piperazinyl or morpholinyl; each optionally substituted with substituent $L_3$, said substituents $L_2$ and $L_3$ are preferably selected from the group consisting of fluoro, chloro, hydroxyl, amino, methylamino, dimethylamino, oxo, trifluoromethyl, methyl, ethyl and methoxyl, wherein the number of the substituent is 1 to 2;

$R^8$ is preferably selected from the group consisting of phenyl and 8 to 9 membered fused cyclyl; each optionally substituted with $L_5$, said substituent $L_5$ is preferably selected from the group consisting of fluoro, chloro, methyl, trifluoromethyl, methoxyl, ethoxyl and trifluoromethoxyl, wherein the number of the substituent is 1 to 4.

(10) The compound of Formula (I) of item (5) and item (6), or a pharmaceutically acceptable salt or a stereoisomer thereof, wherein $R^1$ is preferably selected from the group consisting of

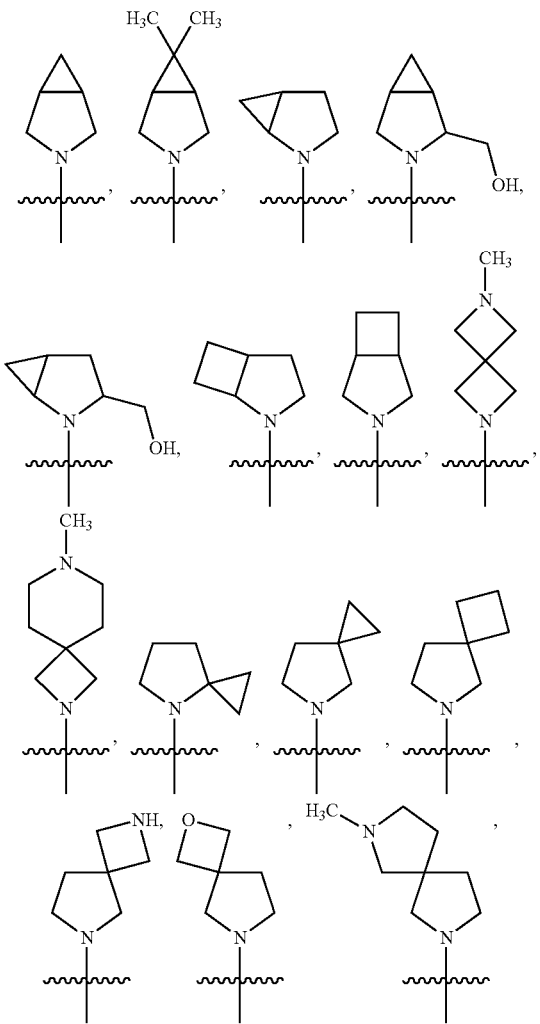

-continued
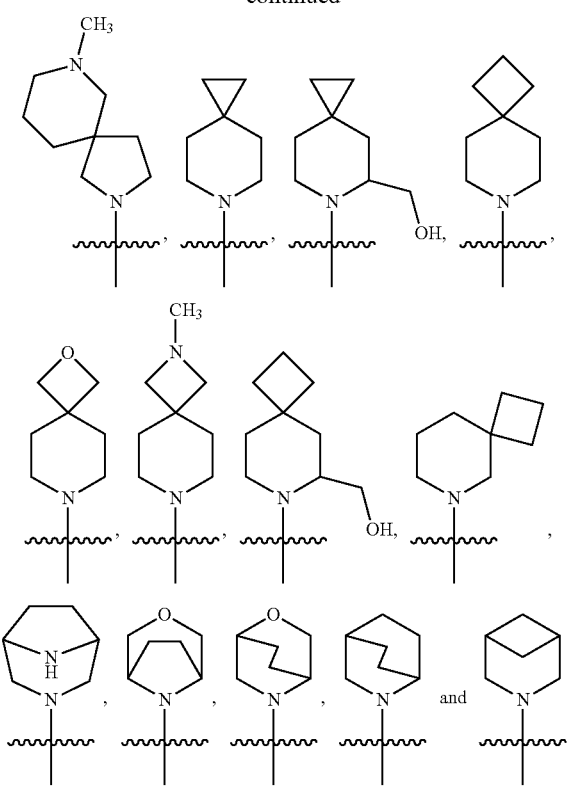
$R^3$ is preferably selected from the group consisting of
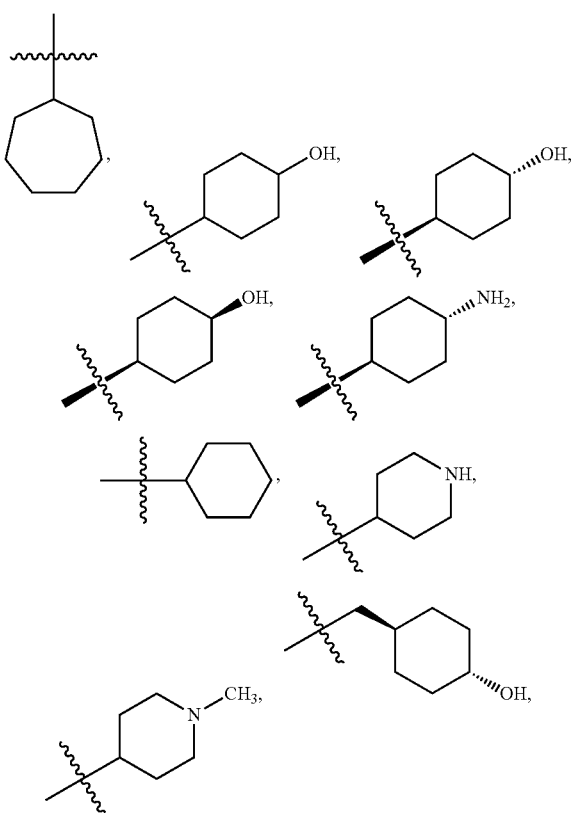
-continued
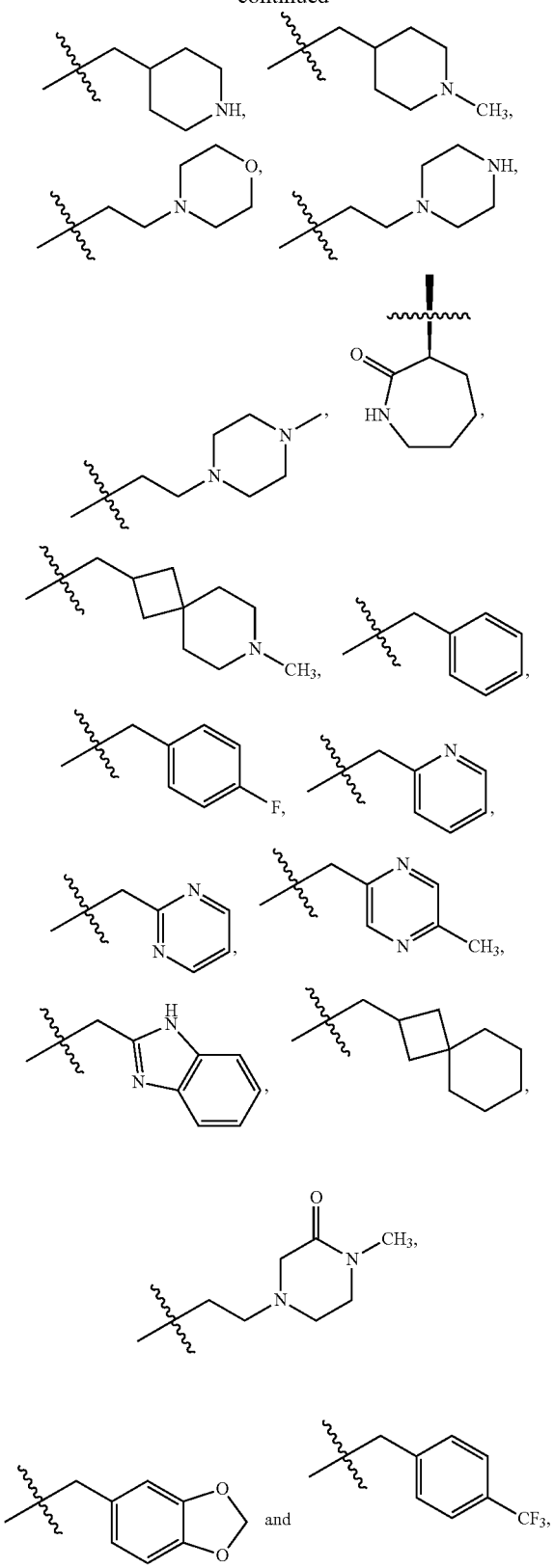
or $R^3$ and $R^4$ together with nitrogen attached to $R^3$ and $R^4$ form

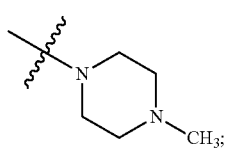
$R^5$ is preferably selected from the group consisting of
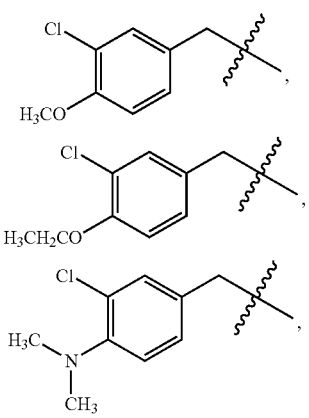
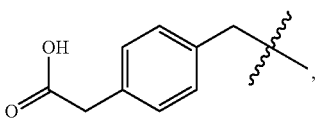
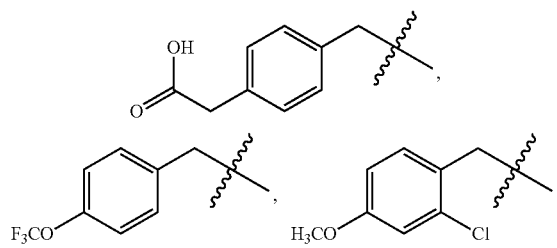
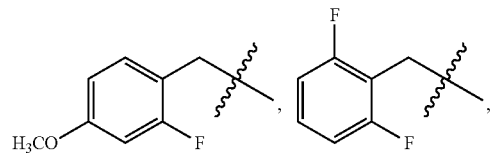
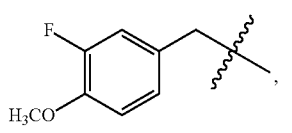
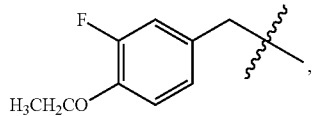
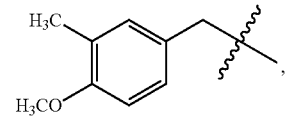
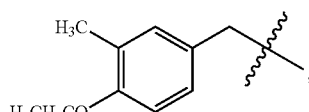
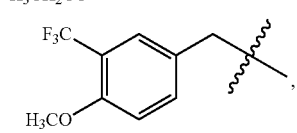
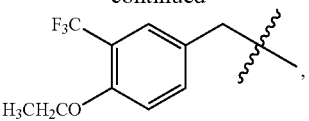
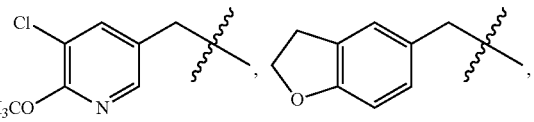
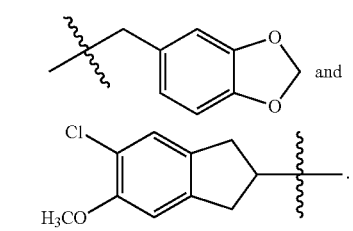
(11) The compound of Formula (I) of item (5) and item (6), or a pharmaceutically acceptable salt or a stereoisomer thereof, wherein $R^1$ is more preferably selected from the group consisting of
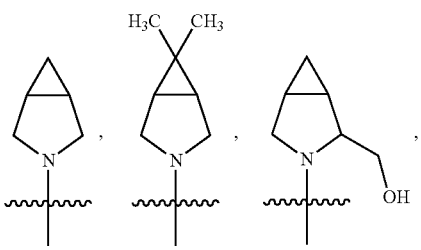
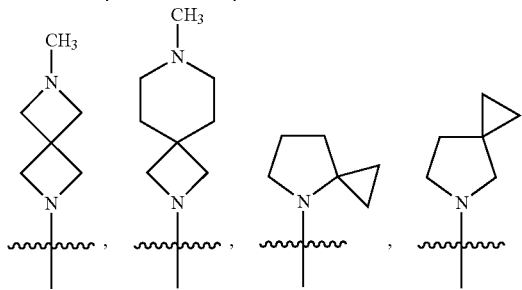
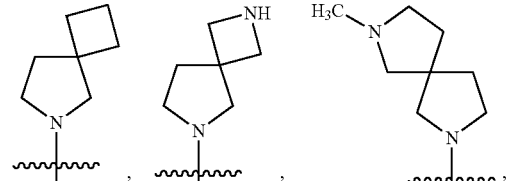
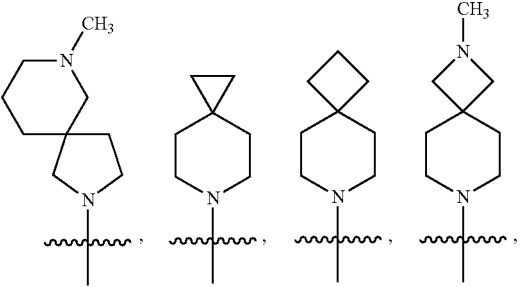

-continued
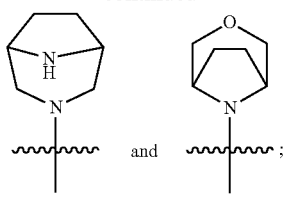
and
$R^3$ is more preferably selected from the group consisting of
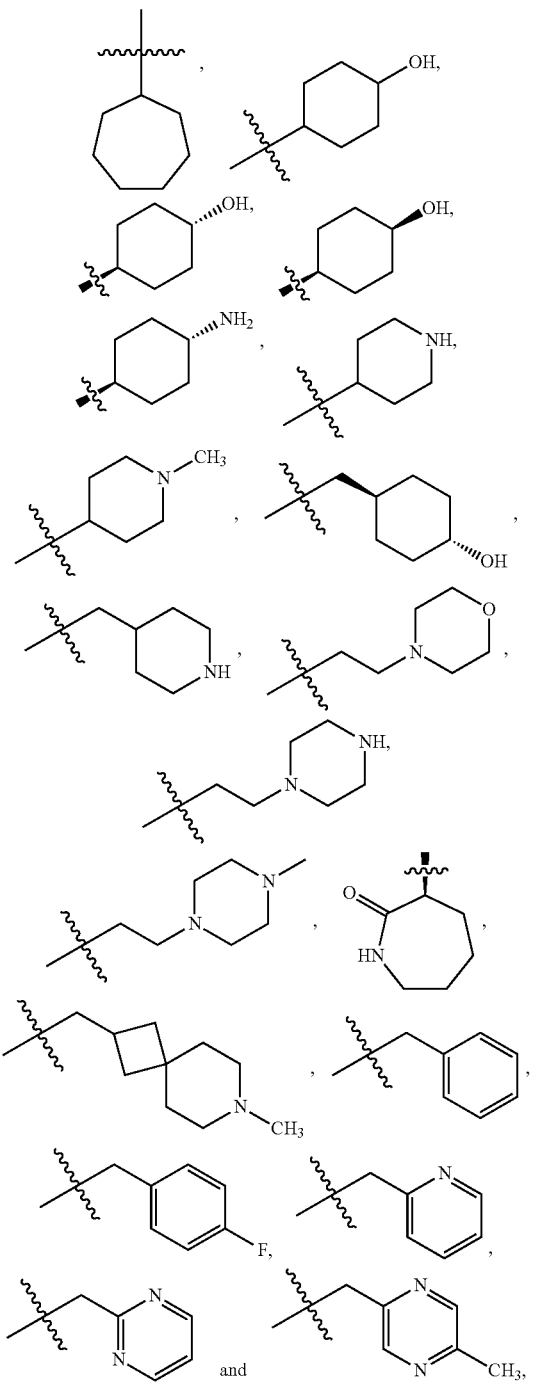
and
or $R^3$ and $R^4$ together with nitrogen attached to $R^3$ and $R^4$ form
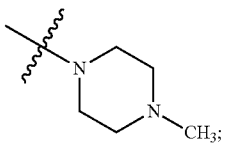
$R^5$ is more preferably selected from
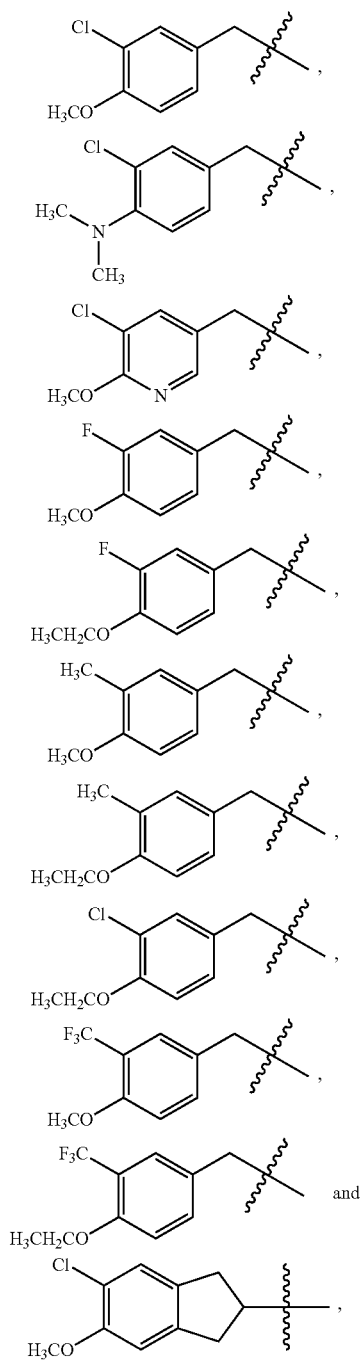

The particularly preferred compounds include the following:
| Compound | Structure |
|---|---|
| 1 | 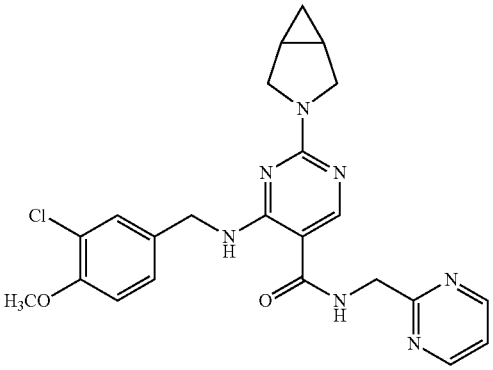 [SMILES: COc1ccc(CNc2nc(N3CC4CC4C3)ncc2C(=O)NCc2ncccn2)cc1Cl] |
| 2 | 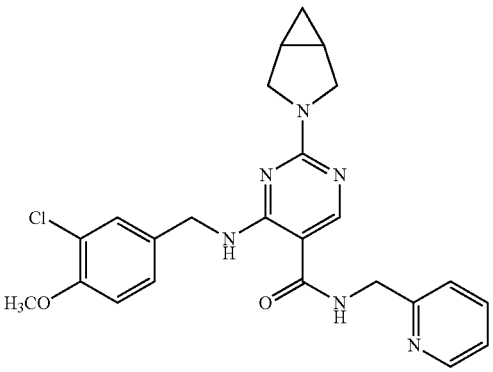 [SMILES: COc1ccc(CNc2nc(N3CC4CC4C3)ncc2C(=O)NCc2ccccn2)cc1Cl] |
| 3 | 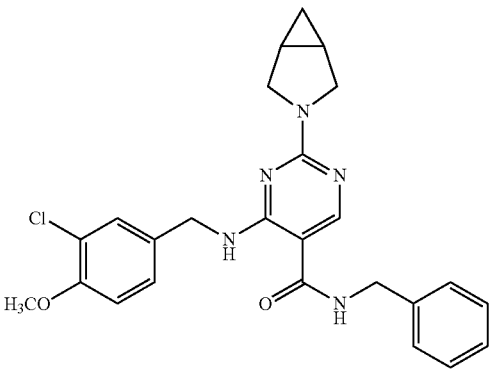 |
| 4 | 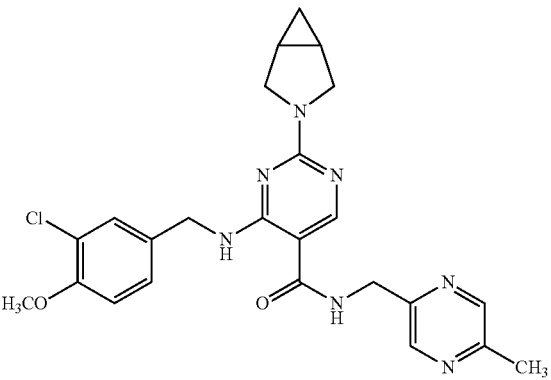 [SMILES: COc1ccc(CNc2nc(N3CC4CC4C3)ncc2C(=O)NCc2cnc(C)cn2)cc1Cl] |

-continued
| Compound | Structure |
|---|---|
| 5 | 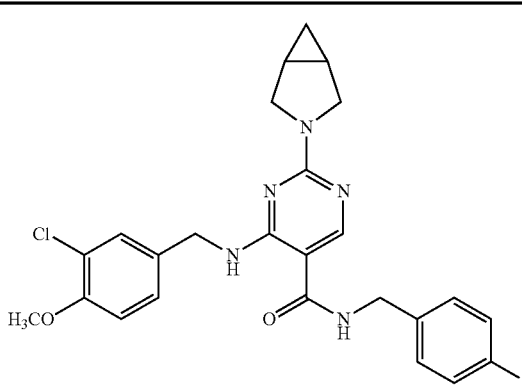 |
| 6 | 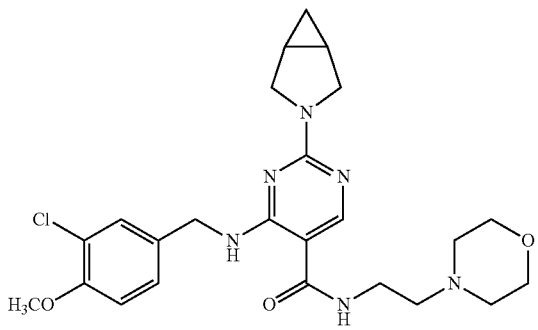 [SMILES: COc1ccc(CNc2nc(N3CC4CC4C3)ncc2C(=O)NCCN2CCOCC2)cc1Cl] |
| 7 | 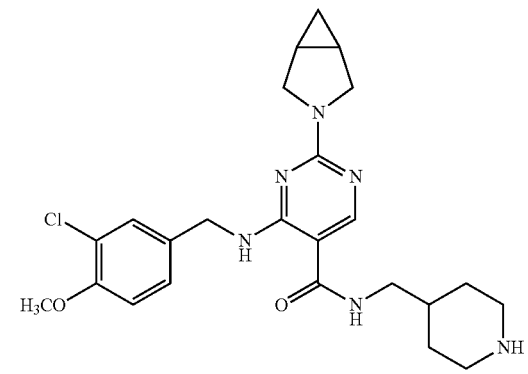 [SMILES: COc1ccc(CNc2nc(N3CC4CC4C3)ncc2C(=O)NCC2CCNCC2)cc1Cl] |
| 8 | 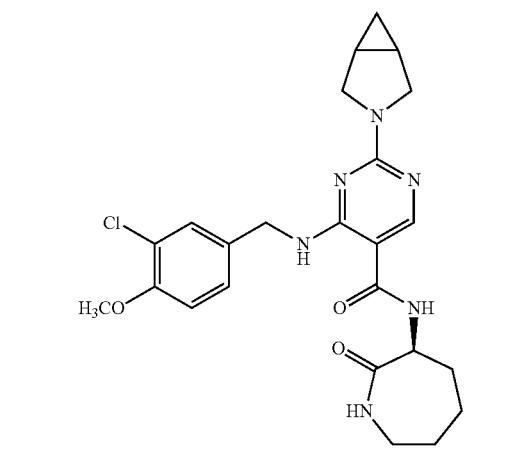 [SMILES: COc1ccc(CNc2nc(N3CC4CC4C3)ncc2C(=O)N[C@H]2CCCCNC2=O)cc1Cl] |

-continued
| Compound | Structure |
|---|---|
| 9 | 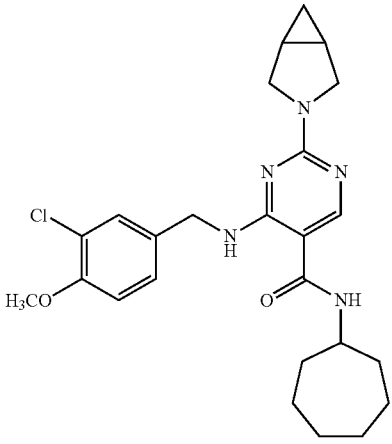 [SMILES: COc1ccc(CNc2nc(N3CC4CC4C3)ncc2C(=O)NC2CCCCCC2)cc1Cl] |
| 10 | 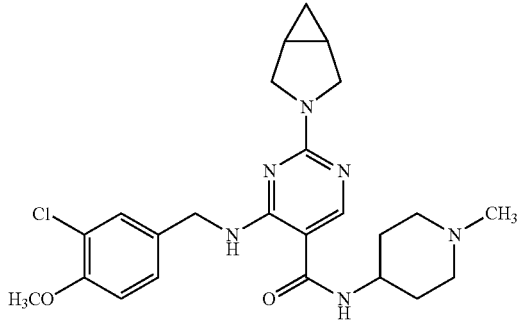 [SMILES: COc1ccc(CNc2nc(N3CC4CC4C3)ncc2C(=O)NC2CCN(C)CC2)cc1Cl] |
| 11 | 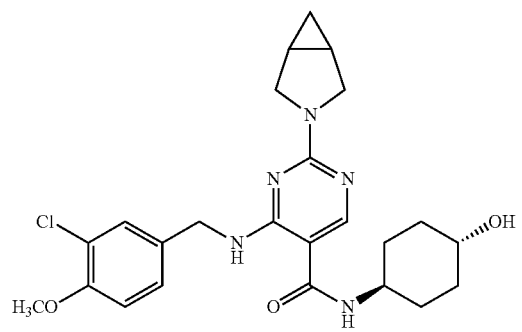 |
| 12 | 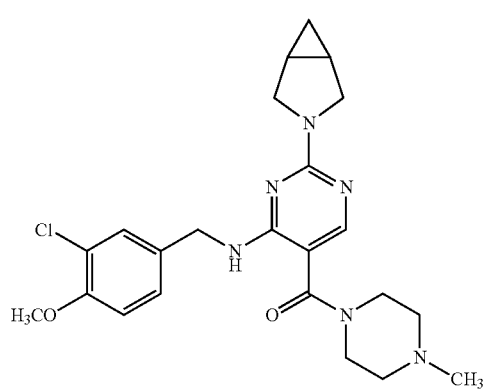 [SMILES: COc1ccc(CNc2nc(N3CC4CC4C3)ncc2C(=O)N2CCN(C)CC2)cc1Cl] |

-continued
| Compound | Structure |
|---|---|
| 13 | 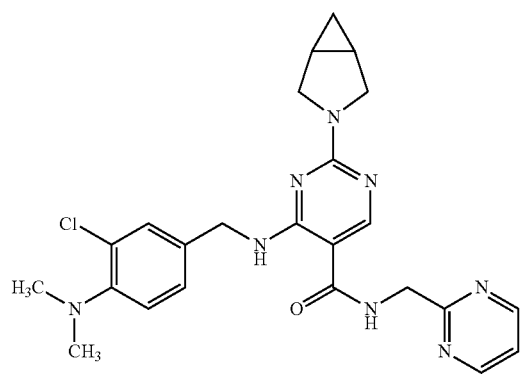 [SMILES: CN(C)c1ccc(CNc2nc(N3CC4CC4C3)ncc2C(=O)NCc2ncccn2)cc1Cl] |
| 14 | 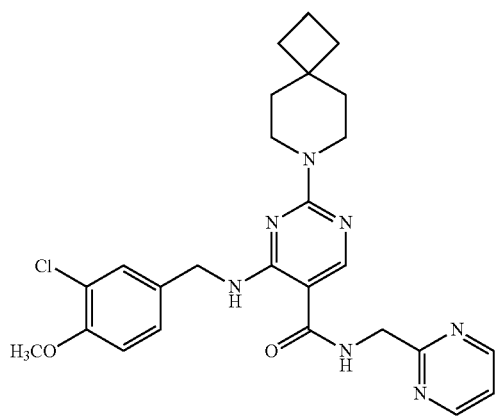 [SMILES: COc1ccc(CNc2nc(N3CCC4(CCC4)CC3)ncc2C(=O)NCc2ncccn2)cc1Cl] |
| 15 | 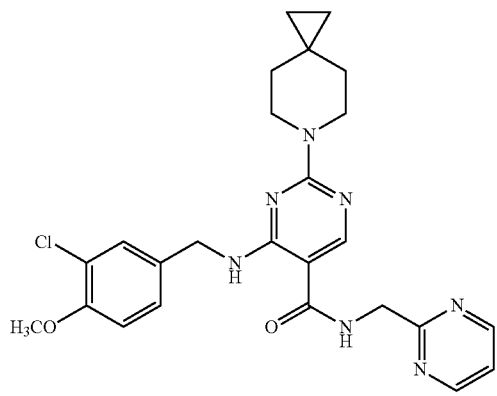 [SMILES: COc1ccc(CNc2nc(N3CCC4(CC3)CC4)ncc2C(=O)NCc2ncccn2)cc1Cl] |
| 16 | 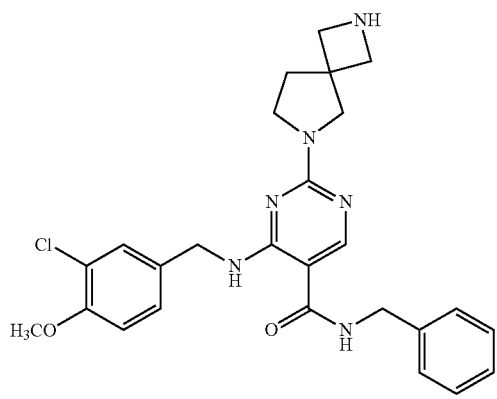 [SMILES: COc1ccc(CNc2nc(N3CCC4(CNC4)C3)ncc2C(=O)NCc2ccccc2)cc1Cl] |

-continued
| Compound | Structure |
|---|---|
| 17 | 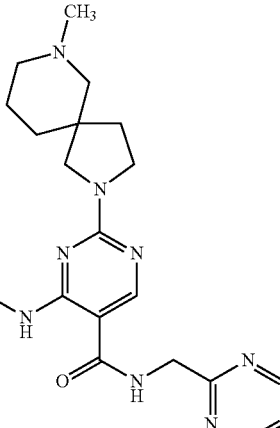 |
| 18 | 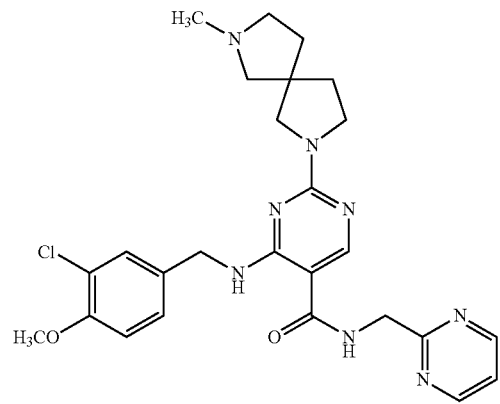 [SMILES: COc1ccc(CNc2nc(N3CCC4(CCN(C)C4)C3)ncc2C(=O)NCc2ncccn2)cc1Cl] |
| 19 | 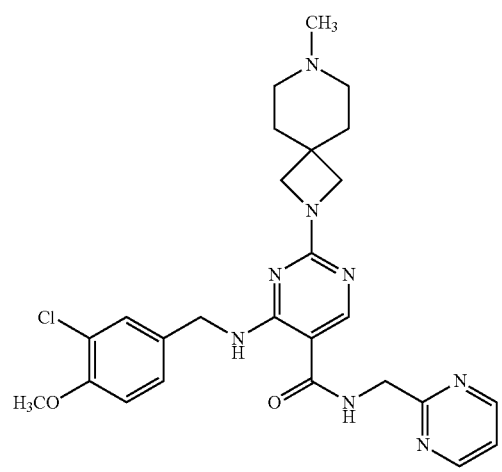 [SMILES: COc1ccc(CNc2nc(N3CC4(CCN(C)CC4)C3)ncc2C(=O)NCc2ncccn2)cc1Cl] |

-continued
| Compound | Structure |
|---|---|
| 20 | 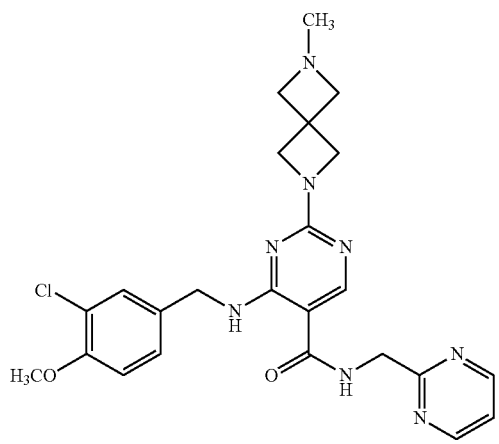 [SMILES: COc1ccc(CNc2nc(N3CC4(CN(C)C4)C3)ncc2C(=O)NCc2ncccn2)cc1Cl] |
| 21 | 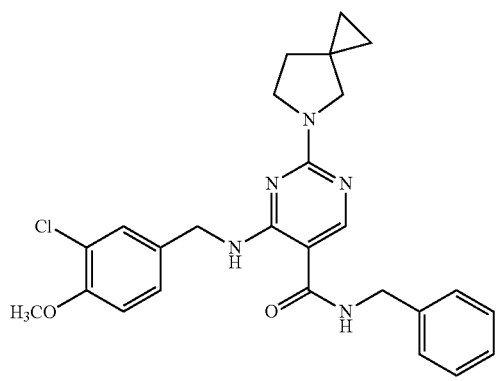 |
| 22 | 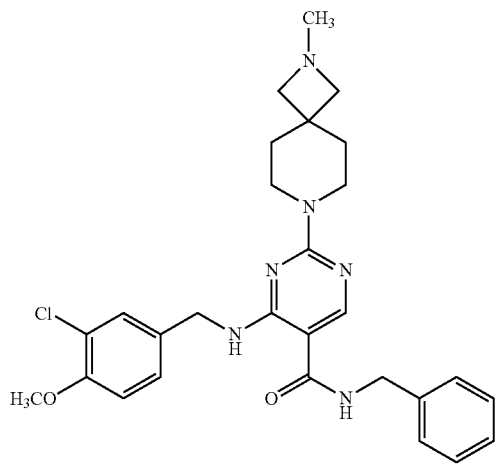 [SMILES: COc1ccc(CNc2nc(N3CCC4(CC3)CN(C)C4)ncc2C(=O)NCc2ccccc2)cc1Cl] |

-continued
| Compound | Structure |
|---|---|
| 23 | 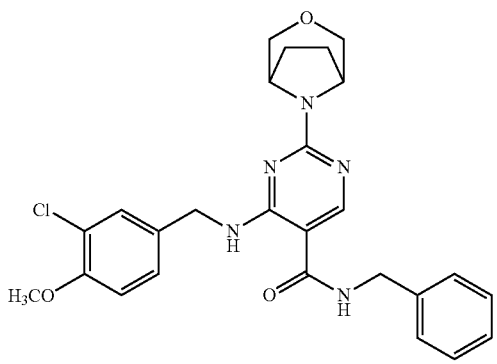 [SMILES: COc1ccc(CNc2nc(N3C4CCC3COC4)ncc2C(=O)NCc2ccccc2)cc1Cl] |
| 24 | 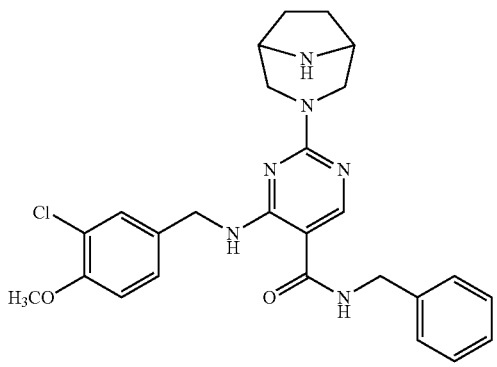 [SMILES: COc1ccc(CNc2nc(N3CC4CCC(C3)N4)ncc2C(=O)NCc2ccccc2)cc1Cl] |
| 25 | 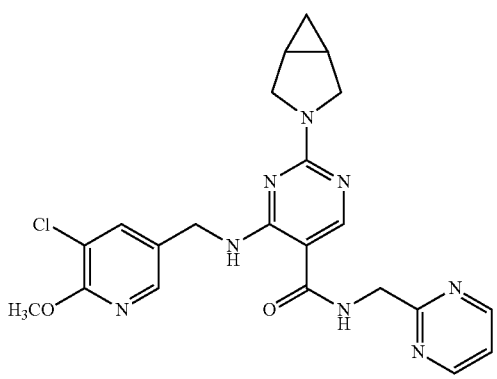 [SMILES: COc1ncc(CNc2nc(N3CC4CC4C3)ncc2C(=O)NCc2ncccn2)cc1Cl] |
| 26 | 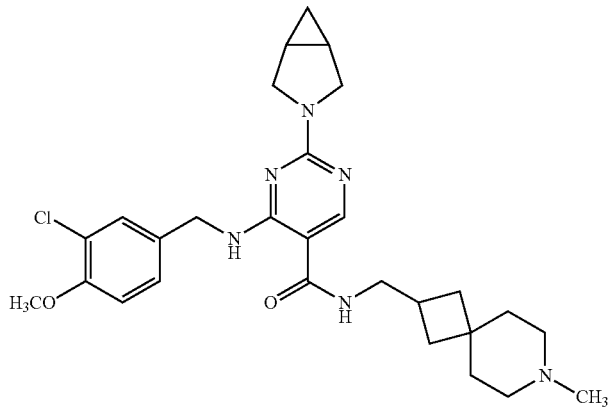 [SMILES: COc1ccc(CNc2nc(N3CC4CC4C3)ncc2C(=O)NCC2CC3(CCN(C)CC3)C2)cc1Cl] |

-continued
| Compound | Structure |
|---|---|
| 27 | 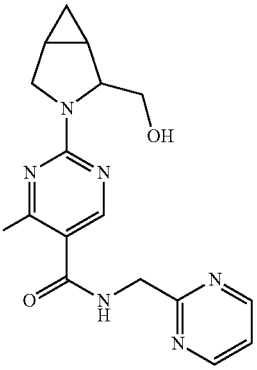 |
| 28 | 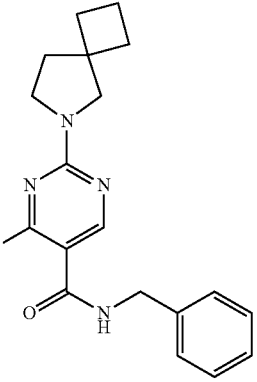 |
| 29 | 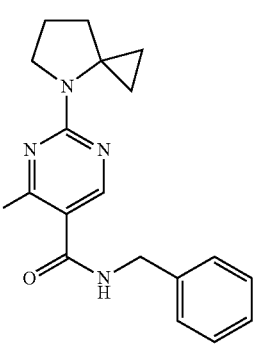 |
| 30 | 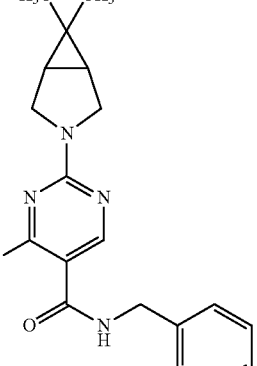 |

| Compound | Structure |
|---|---|
| 31 | 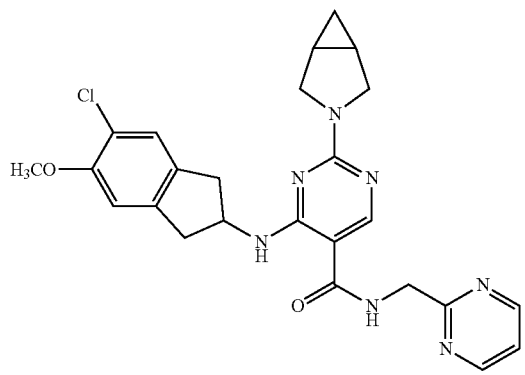 [SMILES: COc1cc2c(cc1Cl)CC(Nc1nc(N3CC4CC4C3)ncc1C(=O)NCc1ncccn1)C2] |
| 32 | 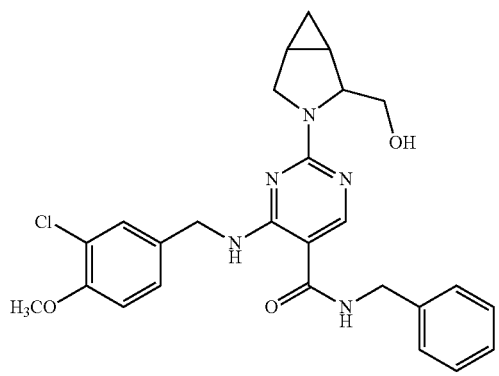 |
| 33 | 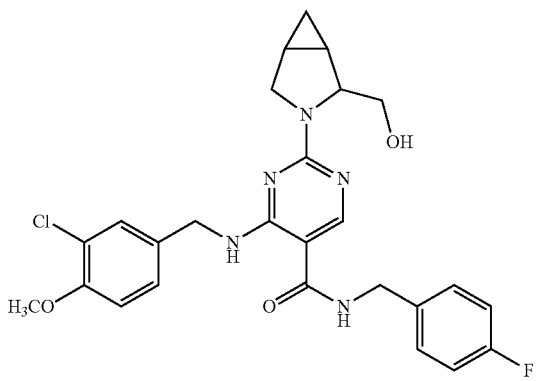 [SMILES: COc1ccc(CNc2nc(N3CC4CC4C3CO)ncc2C(=O)NCc2ccc(F)cc2)cc1Cl] |
| 34 | 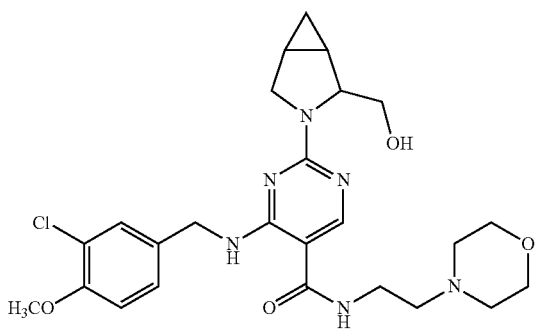 [SMILES: COc1ccc(CNc2nc(N3CC4CC4C3CO)ncc2C(=O)NCCN2CCOCC2)cc1Cl] |

| Compound | Structure |
|---|---|
| 35 | 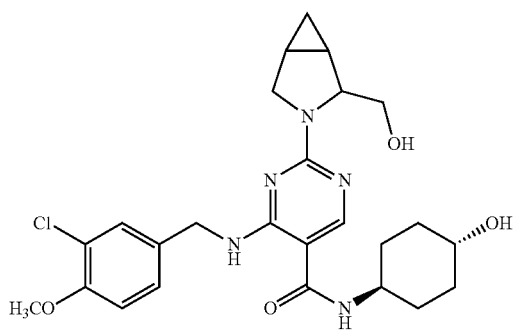 [SMILES: COc1ccc(CNc2nc(N3CC4CC4C3CO)ncc2C(=O)N[C@H]2CC[C@H](O)CC2)cc1Cl] |
| 36 | 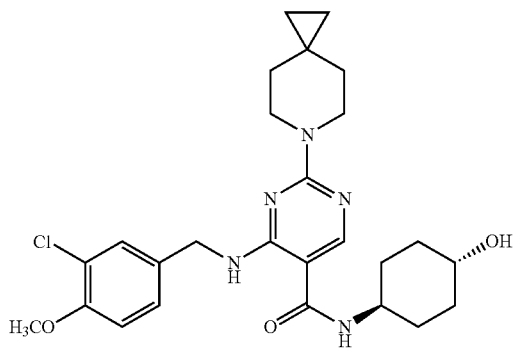 [SMILES: COc1ccc(CNc2nc(N3CCC4(CC3)CC4)ncc2C(=O)N[C@H]2CC[C@H](O)CC2)cc1Cl] |
| 37 | 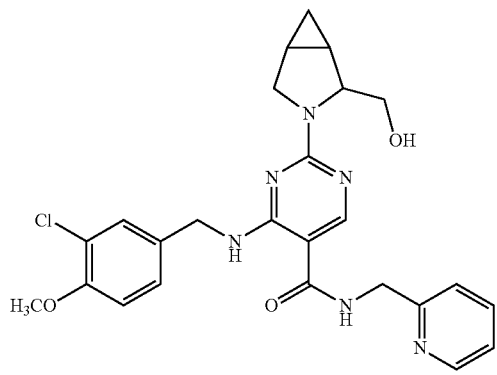 [SMILES: COc1ccc(CNc2nc(N3CC4CC4C3CO)ncc2C(=O)NCc2ccccn2)cc1Cl] |
| 38 | 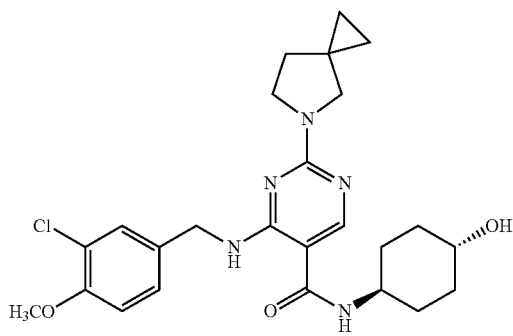 [SMILES: COc1ccc(CNc2nc(N3CCC4(CC4)C3)ncc2C(=O)N[C@H]2CC[C@H](O)CC2)cc1Cl] |

| Compound | Structure |
|---|---|
| 39 | 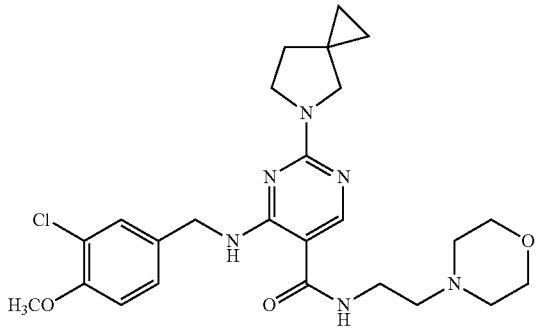 [SMILES: COc1ccc(CNc2nc(N3CCC4(CC4)C3)ncc2C(=O)NCCN2CCOCC2)cc1Cl] |
| 40 | 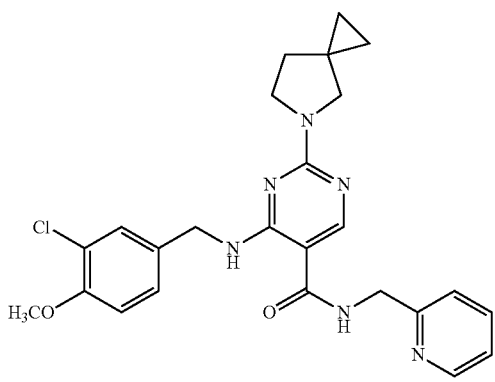 [SMILES: COc1ccc(CNc2nc(N3CCC4(CC4)C3)ncc2C(=O)NCc2ccccn2)cc1Cl] |
| 41 | 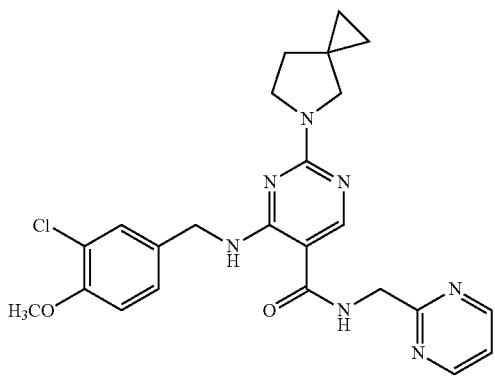 [SMILES: COc1ccc(CNc2nc(N3CCC4(CC4)C3)ncc2C(=O)NCc2ncccn2)cc1Cl] |
| 42 | 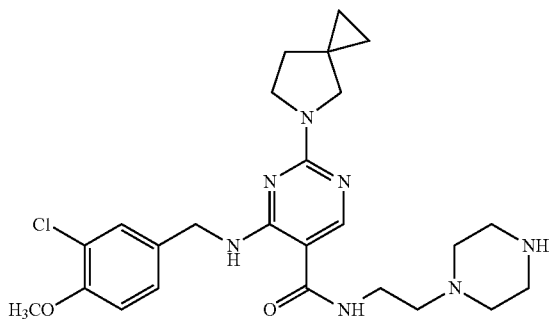 [SMILES: COc1ccc(CNc2nc(N3CCC4(CC4)C3)ncc2C(=O)NCCN2CCNCC2)cc1Cl] |

| Compound | Structure |
|---|---|
| 43 | 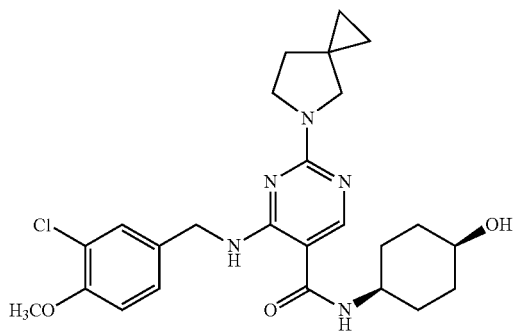 [SMILES: COc1ccc(CNc2nc(N3CCC4(CC4)C3)ncc2C(=O)N[C@H]2CC[C@@H](O)CC2)cc1Cl] |
| 44 | 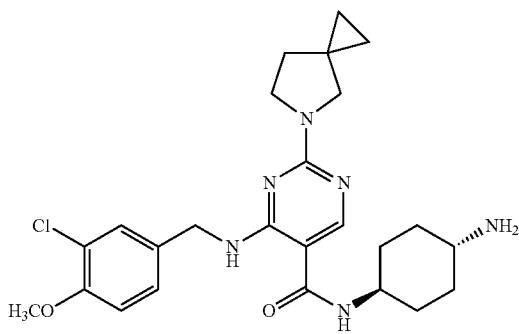 [SMILES: COc1ccc(CNc2nc(N3CCC4(CC4)C3)ncc2C(=O)N[C@H]2CC[C@H](N)CC2)cc1Cl] |
| 45 | 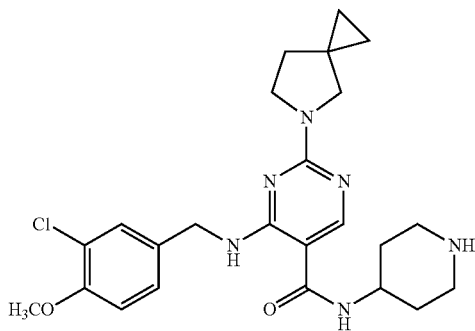 [SMILES: COc1ccc(CNc2nc(N3CCC4(CC4)C3)ncc2C(=O)NC2CCNCC2)cc1Cl] |
| 46 | 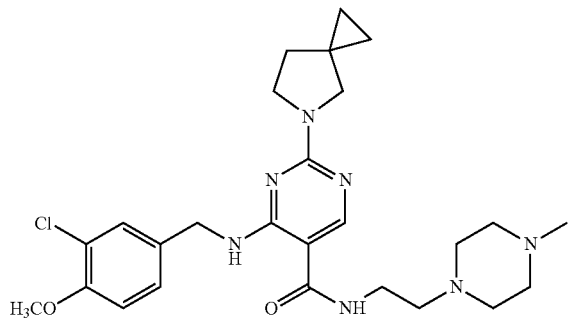 [SMILES: COc1ccc(CNc2nc(N3CCC4(CC4)C3)ncc2C(=O)NCCN2CCN(C)CC2)cc1Cl] |

| Compound | Structure |
|---|---|
| 47 | 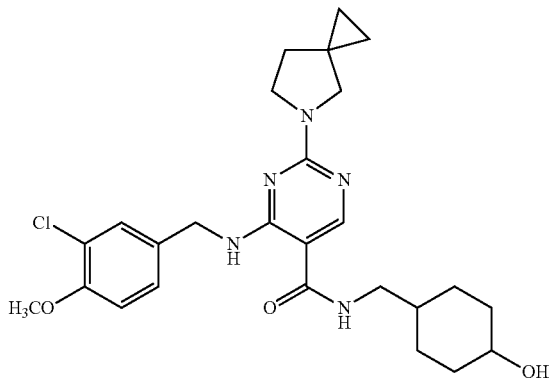 [SMILES: COc1ccc(CNc2nc(N3CCC4(CC4)C3)ncc2C(=O)NCC2CCC(O)CC2)cc1Cl] |
| 48 | 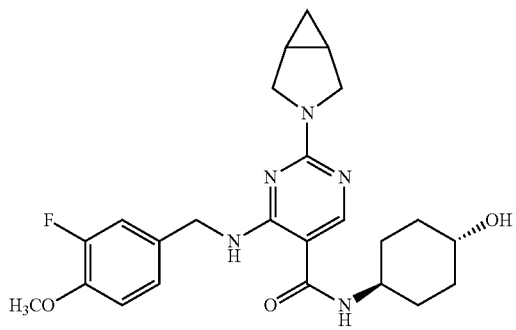 |
| 49 | 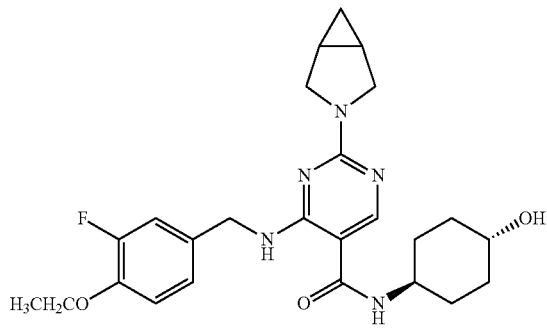 |
| 50 | 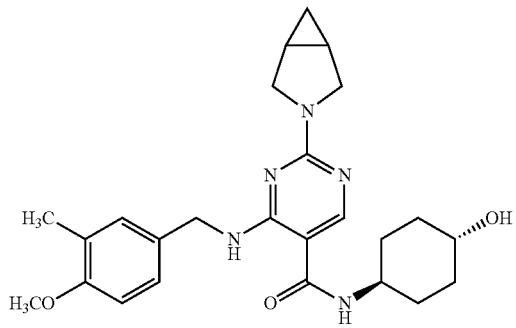 [SMILES: COc1ccc(CNc2nc(N3CC4CC4C3)ncc2C(=O)N[C@H]2CC[C@H](O)CC2)cc1C] |

-continued

| Compound | Structure |
|---|---|
| 51 | 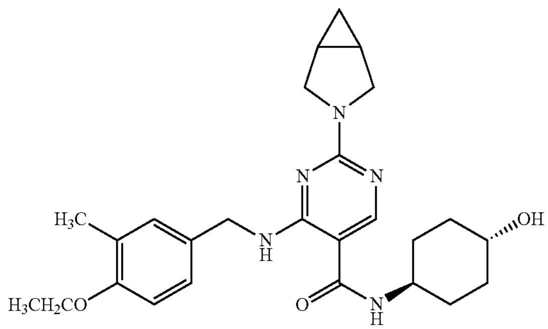 |
| 52 | 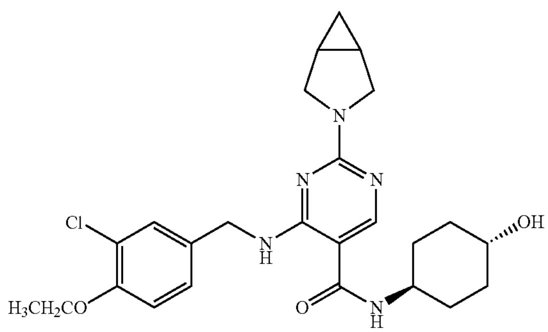 |
| 53 | 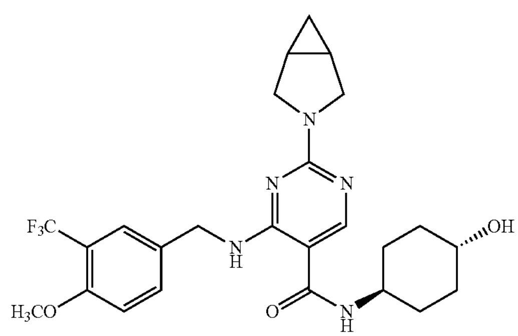 [SMILES: COc1ccc(CNc2nc(N3CC4CC4C3)ncc2C(=O)N[C@H]2CC[C@H](O)CC2)cc1C(F)(F)F] |
| 54 | 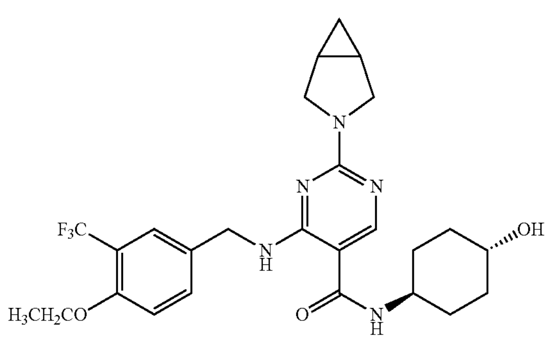 |

| Compound | Structure |
|---|---|
| 55 | 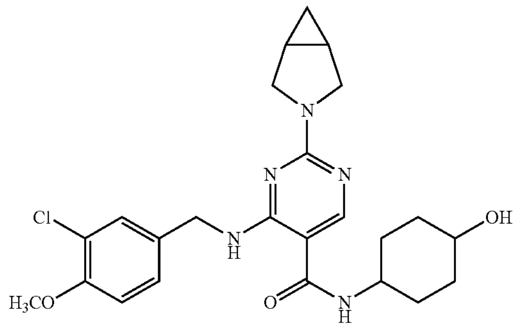 [SMILES: COc1ccc(CNc2nc(N3CC4CC4C3)ncc2C(=O)NC2CCC(O)CC2)cc1Cl] |

The term "halo" of the present invention refers to being substituted by halogen. "Halogen" refers to a fluorine, chlorine, bromine or iodine atom, etc.

The term "$C_{1-6}$ alkyl" of the present invention refers to a straight or branched chain alkyl containing from 1 to 6 carbon atoms, e.g. methyl, ethyl, n-propyl, isopropyl, n-butyl, isobutyl, sec-butyl, tert-butyl, n-pentyl, isopentyl, 2-methyl-butyl, neopentyl, 1-ethyl-propyl, n-hexhyl, isohexyl, 3-methyl-pentyl, 2-methyl-pentyl, 1-methyl-pentyl, 3,3-dimethyl-butyl, 2,2-dimethyl-butyl, 1,1-dimethyl-butyl, 1,2-dimethyl-butyl, 1,3-dimethyl-butyl, 2,3-dimethyl-butyl, 2-ethyl-butyl, 1,2-dimethyl-propyl, etc; preferably, $C_{1-4}$ alkyls. The term "$C_{1-4}$ alkyl" of the present invention refers to specific examples containing from 1 to 4 carbon atoms within the above examples.

The term "$C_{1-6}$ alkylene" of the present invention refers to a straight or branched chain alkane derived from the above alkyl by eliminating a hydrogen atom, including —$(CH_2)_t$— (t is integer from 1 to 6), e.g. methylene, ethylene, propylene, etc; preferably, $C_{1-4}$ alkylenes. The term "$C_{1-4}$ alkylene" of the present invention refers to specific examples containing from 1 to 4 carbon atoms within the above examples.

The term "$C_{1-6}$ alkoxy" of the present invention refers to a group in which the term "$C_{1-6}$ alkyl" connect to other structures via an oxygen atom, such as methoxy, ethoxy, propoxy, isopropoxy, butoxy, isobutoxy, tert-butoxy, sec-butoxy, pentoxy, neopentoxy, hexoxy, etc.

The term "halo $C_{1-6}$ alkyl" of the present invention refers to the group derived from "$C_{1-6}$ alkyl" in which one or more hydrogen atoms are substituted by one or more "halogen atoms". Said "halogen atoms" and "$C_{1-6}$ alkyl" are as defined above.

The term "hydroxyl $C_{1-6}$ alkyl" of the present invention refers to the group derived from "$C_{1-6}$ alkyl" in which one or more hydrogen atoms are substituted by one or more hydroxyls. Said "$C_{1-6}$ alkyl" has the meaning as defined above.

The term "$C_{2-6}$ alkenyl" of the present invention refers to a straight, branched chain or cyclic alkenyl containing from 2 to 6 carbon atoms and at least one double bond, e.g. vinyl, 1-propenyl, 2-propenyl, 1-butenyl, 2-butenyl, 1,3-butadienyl, 1-pentenyl, 2-pentenyl, 3-pentenyl, 1,3-pentadienyl, 1,4-pentadienyl, 1-hexenyl, 2-hexenyl, 3-hexenyl, 1,4-hexadienyl. $C_{4-6}$ cyclic alkenyls include cyclopentenyl, 1,3-cyclopentadienyl, cyclohexenyl, 1,4-cyclohexadienyl, etc.

The term "$C_{2-6}$ alkynyl" of the present invention refers to a straight or branched chain alkynyl containing from 2 to 6 carbon atoms and at least one triple bond, e.g. ethynyl, propynyl, 2-butynyl, 2-pentynyl, 3-pentynyl, 4-methyl-2-pentynyl, 2-hexynyl, 3-hexynyl, 5-methyl-2-hexynyl, etc.

The terms "carboxyl $C_{1-6}$ alkyl, $C_{1-6}$ alkyl carbonyl, $C_{1-6}$ alkoxy carbonyl, $C_{1-6}$ alkyl amino, di($C_{1-6}$ alkyl)amino, $C_{1-6}$ alkyl sulfonyl amino, di($C_{1-6}$ alkyl)phosphino" of the present invention refer to groups which connect to another structure in the manner of HOOC—$C_{1-6}$ alkyl-, $C_{1-6}$ alkyl-C(O)—, $C_{1-6}$ alkyl-O—C(O)—, $C_{1-6}$ alkyl-NH—, ($C_{1-6}$ alkyl)$_2$N—, $C_{1-6}$ alkyl-SO$_2$—NH— or ($C_{1-6}$ alkyl)$_2$P—; wherein "$C_{1-6}$ alkyl" and "$C_{1-6}$ alkylene" have the meanings as defined above; preferably, refer to carboxyl $C_{1-4}$ alkyl, $C_{1-4}$ alkyl carbonyl, $C_{1-4}$ alkoxy carbonyl, $C_{1-4}$ alkyl amino, di($C_{1-4}$ alkyl)amino, $C_{1-4}$ alkyl sulfonyl amino. Said "carboxyl $C_{1-4}$ alkyl, $C_{1-4}$ alkyl carbonyl, $C_{1-4}$ alkoxy carbonyl, $C_{1-4}$ alkyl amino, di($C_{1-4}$ alkyl)amino, $C_{1-4}$ alkyl sulfonyl amino" refer to those containing from 1 to 4 carbon atoms within the above examples; wherein said "$C_{1-4}$ alkyl" and "$C_{1-4}$ alkylene" have the meanings as defined above.

The term "6 to 7 membered N-containing fused heterocyclyl" refers to a kind of cyclic structure which contains 6 to 7 carbon atoms or/and heteroatoms (wherein at least one heteroatom is nitrogen atom) and which is formed by at least two rings sharing two adjacent atoms. Examples of said heteroatoms include but are not limited to N, S, O, SO or SO$_2$. 6 to 7 membered saturated or partially saturated N-containing fused heterocyclyls are included within the term. Examples include but are not limited to

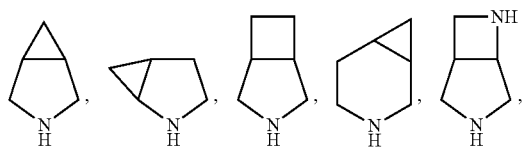

etc.

The term "7 to 12 membered N-containing spiro heterocyclyl" refers to a kind of cyclic structure which contains 7 to 12 carbon atoms or/and heteroatoms (wherein at least one heteroatom is nitrogen atom) and which is formed by at least two rings sharing one atoms. Examples of said heteroatoms include but are not limited to N, S, O, SO or SO$_2$. Examples of the term include but are not limited to

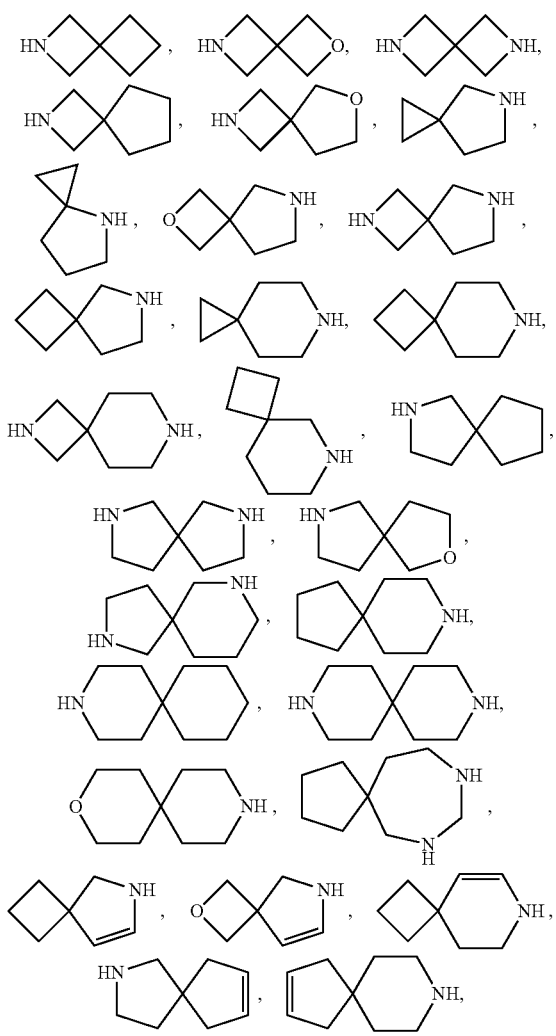

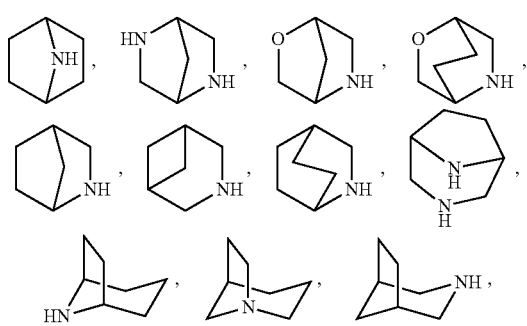

etc. Preferred embodiments are 7 to 10 membered N-containing spiro heterocyclyl, which refer to cyclic structures containing 7 to 10 ring atoms within the above examples.

The term "7 to 12 membered N-containing bridged heterocyclyl" refers to a kind of cyclic structure which contains 7 to 12 carbon atoms or/and heteroatoms (wherein at least one heteroatom is nitrogen atom) and which is formed by two rings sharing two atoms which are not adjacent to each other. Examples of said heteroatoms include but are not limited to N, S, O, SO or $SO_2$. Examples of the term include but are not limited to

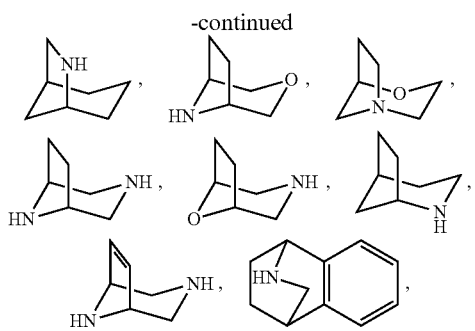

-continued etc. Preferred embodiments are 7 to 8 membered N-containing bridged heterocyclyl, which refer to cyclic structures containing 7 to 8 ring atoms within the above examples.

The term "3 to 14 membered cyclic group" of the present invention refer to a cyclic structure containing 3 to 14 ring atoms, including 3 to 8 membered cyclic alkyl, 4 to 10 membered fused cyclyl, 6 to 14 membered aryl, 7 to 10 membered spiro cyclyl, 7 to 10 membered bridged cyclyl, 3 to 8 membered heterocyclyl, 5 to 8 membered heteroaryl, 6 to 14 membered fused heterocyclyl, 6 to 14 membered fused heteroaryl, 7 to 10 membered spiro heterocyclyl and 7 to 10 membered bridged heterocyclyl. Said heteroatoms include nitrogen, oxygen, sulfur, etc, as well as oxo carbon atom, oxo nitrogen atom, and oxo sulfur atom.

"3 to 8 membered cycloalkyl" refer to cyclic alkyl containing 3 to 8 carbon atoms. Examples include but are not limited to cyclopropyl, cyclobutyl, cyclopentyl, cyclohexyl, cycloheptyl, cyclooctyl, 1-methylcyclopropyl, 1-pentylcyclopropyl, 1,2-diethylcyclobutyl, 1-methylcyclobutyl, 1-butylcyclobutyl, 1,3-dimethylcyclobutyl, 1-methylcyclopentyl, 1-butylcyclopentyl, 1-methylcyclohexyl, 1-ethylcyclopentyl, cyclopentenyl, cyclohexenyl, cycloheptenyl, cyclooctenyl, etc. Said "4 to 7 membered cycloalkyl" refer to cyclic structures containing 4 to 7 ring atoms within the above examples.

The term "4 to 10 membered fused cyclyl" refers to a fused ring which contains 4 to 10 ring carbon atoms and is formed by two or more rings sharing two adjacent atoms. Examples include but are not limited to bicyclo[1.1.0]butyl, bicyclo[2.1.0]pentyl, bicyclo[3.1.0]hexyl, bicyclo[4.1.0]heptyl, bicyclo[3.3.0]octyl, bicyclo[4.2.0]octyl, decalin, as well as benzo 3 to 8 membered cycloalkyl, benzo $C_{4-6}$ cycloalkenyl, 2,3-dihydro-1H-indenyl, 1H-indenyl, 1,2,3,4-tetrahydronaphthyl, 1,4-dihydronaphthyl, etc. Preferred embodiments are 8 to 9 membered fused cyclyl, which refer to cyclic structures containing 8 to 9 ring atoms within the above examples.

The term "7 to 10 membered spiro cyclyl" refers to a kind of cyclic structure which contains 7 to 10 carbon atoms and is formed by at least two rings sharing one atom. Examples include but are not limited to

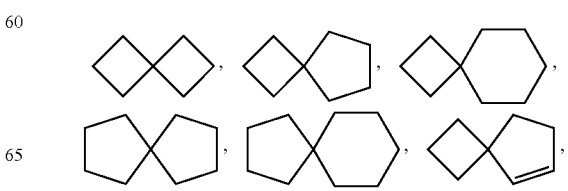

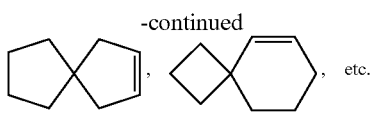, etc.

The term "7 to 10 membered bridged cyclyl" refers to cyclic structure which contains 7 to 10 carbon atoms and is formed by two rings sharing two atoms which are not adjacent to each other. Examples include but are not limited to

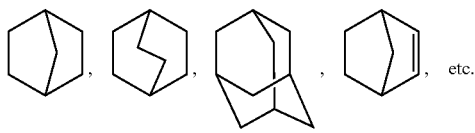, etc.

The term "6 to 14 membered aryl" refer to an aromatic group containing 6 to 14 carbon atoms, including 6 to 8 membered aryl and 8 to 14 membered fused aryl. "6 to 8 membered aryl" refer to monocyclic aryl containing 6 to 8 carbon atoms, e.g. phenyl, cyclooctatetraenyl, etc. "8 to 14 membered fused aryl" refer to a unsaturated aromatic fused ring which contains 8 to 14 ring carbon atoms and is formed by two or more rings sharing two adjacent carbon atoms. Examples include but are not limited to naphthalene, anthracene, phenanthrene, etc. Said "6 to 10 membered aryl" refer to cyclic structures containing 6 to 10 ring atoms within the above examples.

The term "3 to 8 membered heterocyclyl" refers to a cyclic group which contains 3 to 8 ring atoms (including at least one heteroatom). Examples include but are not limited to aziridinyl, diazacyclopropyl, azetidine, 1,2-diazacyclobutyl, pyrrolidyl, oxiranyl, dioxacyclopropyl, thiiranyl, oxacyclobutyl, 1,2-dioxacyclobutyl, thiacyclobutyl, tetrahydrofuryl, tetrahydropyranyl, tetrahydrothienyl, tetrahydropyrrolyl, imidazolidinyl, pyrazolidyl, piperidinyl, morpholinyl, piperazinyl, 2-oxoazacycloheptyl, 2-oxapiperazinyl, dihydrothienyl, dihydropyrrolyl, dihydrooxazolyl, dihydropyrazolyl, tetrahydrooxazolyl, tetrahydroisoxazolyl, tetrahydrothiazolyl, 1,1-dioxoisothiazolinyl, azacyclobutadienyl, 4,5-dihydroimidazolyl, 1,2,3-triazolyl, 1,2,4-triazolyl, pyridin-2-one, pyridin-4-one, 1,2-diazacycloheptatrienyl, 1,3-diazacycloheptatrienyl, 1,4-diazacycloheptatrienyl, etc. Said "5 to 7 membered monocyclic heterocyclyl" of the present invention refer to cyclic structures containing 5 to 7 ring atoms within the above examples.

The term "5 to 8 membered heteroaryl" refers to an aromatic cyclic group which contains 5 to 8 ring atoms (including at least one heteroatom). Examples include but are not limited to furanyl, thienyl, pyrrolyl, imidazolyl, pyrazolyl, thiazolyl, isothiazolyl, thiadiazolyl, oxazolyl, isoxazolyl, oxadiazolyl, imidazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, pyridyl, pyrimidyl, 1,4-dioxacyclohexadienyl, 2H-1,2-oxazinyl, 4H-1,2-oxazinyl, 6H-1,2-oxazinyl, 4H-1,3-oxazinyl, 6H-1,3-oxazinyl, 4H-1,4-oxazinyl, pyridazinyl, pyrazinyl, 1,2,3-triazinyl, 1,2,4-triazinyl, 1,3,5-triazinyl, 1,3,4-triazinyl, 1,2,4,5-tetrazinyl, oxacycloheptatrienyl, thiacycloheptatrienyl, azacycloheptatrienyl, 1,3-diazacycloheptatrienyl, azacyclooctatetraenyl, etc.

The term "6 to 14 membered fused heteroaryl" refer to an unsaturated aromatic fused cyclic structure, which contains 6 to 14 ring atoms (including at least one heteroatom) and is formed by two or more rings sharing two adjacent atoms. Examples include but are not limited to benzofuranyl, benzoisofuranyl, benzothienyl, indolyl, benzooxazolyl, benzoimidazolyl, indazolyl, benzotriazole, quinolyl, isoquinolyl, acridinyl, phenanthridinyl, benzopyridazinyl, phthalazinyl, quinazolinyl, quinoxalinyl, phenazinyl, pteridinyl, purinyl, naphthyridinyl, etc.

The term "6 to 14 membered fused heterocyclyl" refers to a fused cyclic structure which contains 6 to 14 ring atoms (including at least one heteroatom) and is formed by two or more rings sharing two adjacent atoms. Examples include but are not limited to

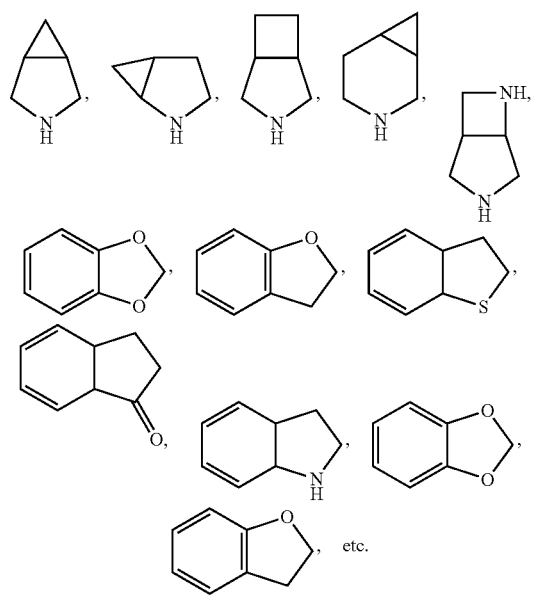

Preferred embodiments are 8 to 9 membered fused heterocyclyl, which refer to cyclic structures containing 8 to 9 ring atoms within the above examples.

The term "7 to 10 membered spiro heterocyclyl" refers to a spiro cyclic structure which contains 7 to 10 ring atoms (including at least one heteroatom) and is formed by two or more rings sharing one atom. Examples include but are not limited to

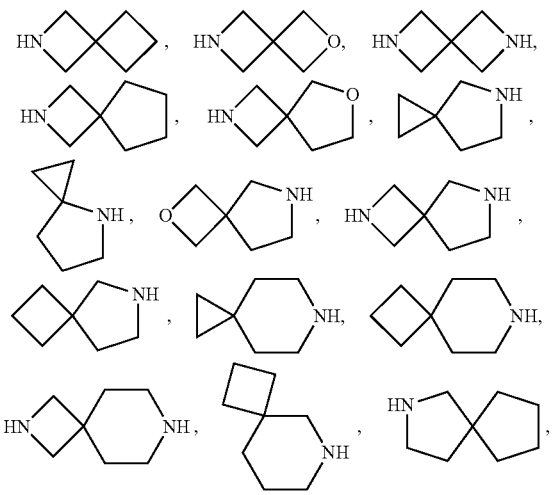

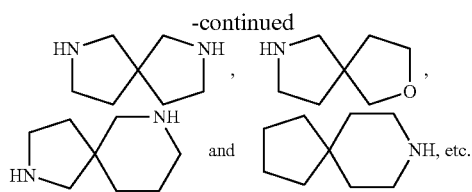

The term "7 to 10 membered bridged heterocyclyl" refers to a bridged cyclic structure which contains 7 to 10 ring atoms (including at least one heteroatom) and is formed by two or more rings sharing two atoms which are not adjacent to each other. Examples include but are not limited to

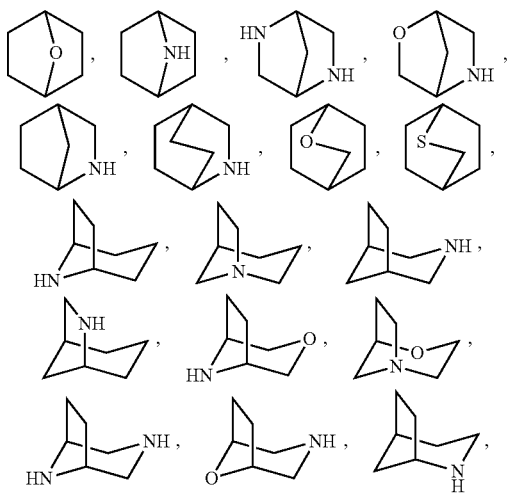

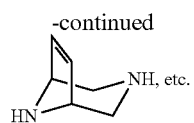

The term "5 to 6 membered N-containing heterocyclyl" refer to a cyclic structure containing 5 to 6 ring atoms (including at least one heteroatom, wherein at least one of said heteroatoms is nitrogen atom). Examples include but are not limited to pyrrolidyl, imidazolidinyl, pyrazolidyl, piperidinyl, piperazidinyl, morpholinyl, dihydropyrrolyl, dihydropyrazolyl, dihydroxazinyl, etc.

The term "oxo" of the present invention refers to C=O, N—O, S=O or

The compounds of the present invention can be synthesized by the method depicted in the schemes below and/or other technology known by those skilled in the art, without being limited to the method as described below.

The meanings of the abbreviations in the present invention are provided as follows.

THF refers to tetrahydrofuran,
DCM refers to dichloromethane,
THF refers to tetrahydrofuran,
DMF refers to N,N-dimethylformamide,
DIEA refers to N,N-diisopropyl ethylamine, and
HATU refers to 2-(7-azabenzotriazole)-N,N,N',N'-tetramethyluronium hexafluorophosphate.

Reaction schemes
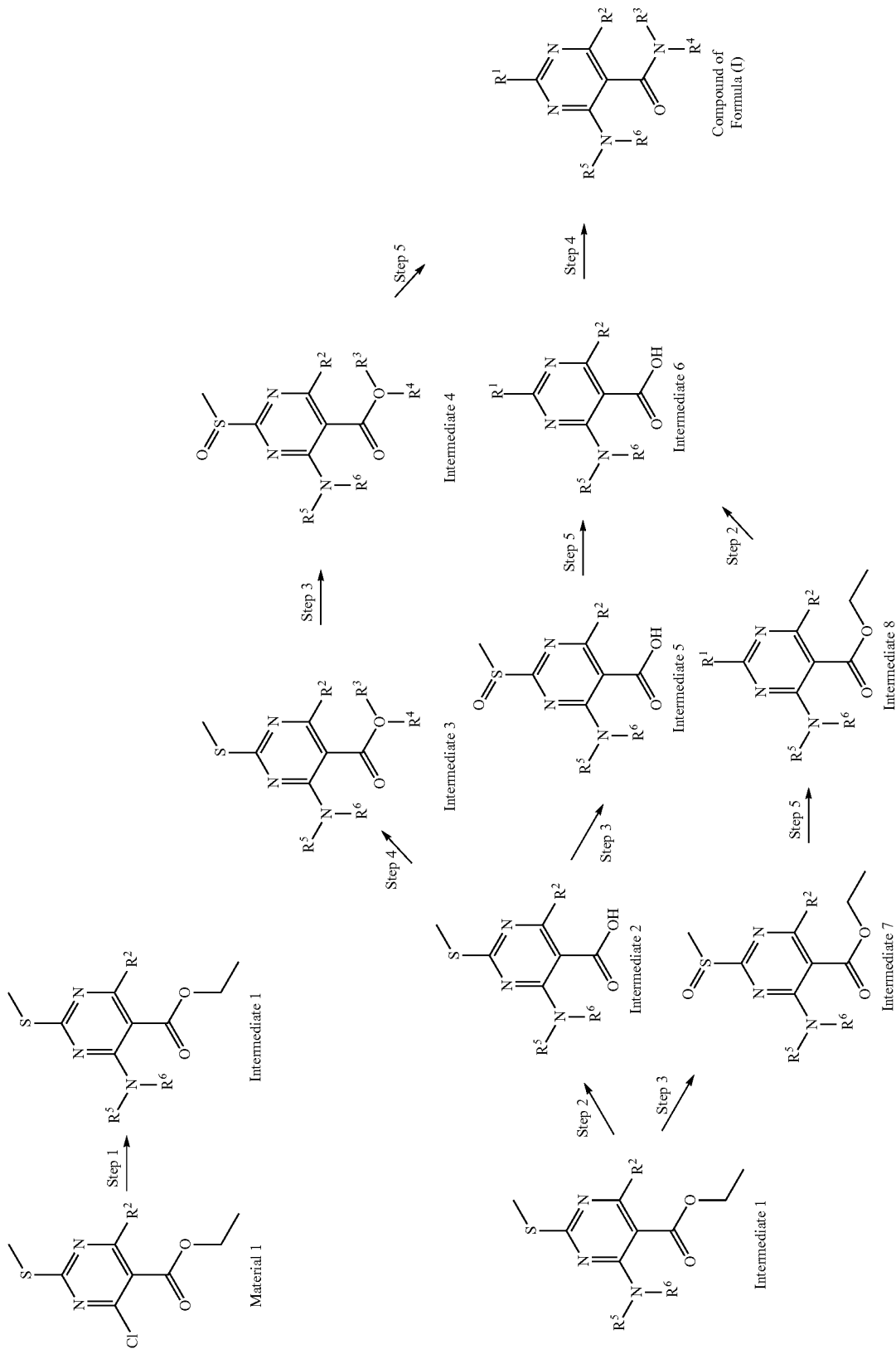

Reaction Steps
Step 1
Material 1 and material 2 were dissolved in an organic solvent. The solution was placed in an ice bath, and an organic alkali was added. The reaction was carried out with stirring. After the reaction was complete, the reaction mixture was extracted. The organic phase was dried and concentrated to give Intermediate 1. The organic solvent is preferably selected from DCM or THF. The organic alkali is preferably triethylamine.

Step 2
The corresponding intermediate was dissolved in a mixture of organic alcohol solvent and water, followed by addition of alkali. The reaction was carried out with stirring. After the reaction, the solvent was removed. The residue was adjusted to acidic and filtrated to give a solid, which was dried in vacuo to give the corresponding product. Preferably, the mixture was ethanol-water mixture. The organic alkali is preferably NaOH.

Step 3
The corresponding intermediate was dissolved in an organic solvent, followed by addition of m-CPBA. The reaction was conducted at ambient temperature and then quenched with water. The reaction mixture was extracted, dried and concentrated to give the corresponding product. The organic solvent is preferably DCM.

Step 4
The corresponding intermediate, Material 3 and HATU were dissolved in an organic solvent, and added with DIEA dropwisely. The reaction mixture was stirred at ambient temperature to complete the reaction, and then added with water, extracted, dried, concentrated and purified by column chromatography to give the corresponding product. The organic solvent is preferably selected from DCM or THF.

Step 5
The corresponding intermediate was dissolved in an organic solvent, and Material 4 was added. DIEA was added dropwisely. The reaction was conducted at ambient temperature or with heating. After the reaction, the reaction mixture was added with water, extracted, dried, concentrated and purified by column chromatography to give the corresponding product. The organic solvent is preferably THF.

Material 2 was $R^5R^6NH$ and was used in Step 1; Material 3 was $R^3R^4NH$ and was used in Step 4; Material 4 was $R^1H$ and was used in Step 5; $R^1, R^2, R^3, R^4, R^5$ and $R^6$ were defined as the above.

Preparation Method 1 of the Compound of Formula (I)
(1) Intermediate 1 was dissolved in a mixture of organic alcohol solvent and water, and an alkali was added. The reaction was carried out with stirring. After the reaction, the solvent was removed. The residue was adjusted to acidic and filtrated to give a solid, which was dried in vacuo to give Intermediate 2. Preferably, the mixture was ethanol-water mixture. The organic alkali is preferably NaOH.

(2) Intermediate 2, Material 3 and HATU were dissolved in an organic solvent. DIEA was added dropwisely. The reaction mixture was stirred at ambient temperature to complete the reaction, and then added with water, extracted, dried, concentrated and purified by column chromatography to give Intermediate 3. The organic solvent is preferably selected from DCM or THF (3) Intermediate 3 was dissolved in an organic solvent, followed by addition of m-CPBA. The reaction was conducted at ambient temperature and then quenched with water. The reaction mixture was extracted, dried and concentrated to give Intermediate 4. The organic solvent is preferably DCM.

(4) Intermediate 4 was dissolved in an organic solvent, and Material 4 was added. DIEA was added dropwisely. The reaction was conducted at ambient temperature or with heating. After the reaction, the reaction mixture was added with water, extracted, dried, concentrated and purified by column chromatography to give the compound of Formula (I) as the product. The organic solvent is preferably THF.

Preparation Method 2 of Compound of Formula (I)
(1) Intermediate 1 was dissolved in a mixture of organic alcohol solvent and water, and an alkali was added. The reaction was carried out with stirring. After the reaction, the solvent was removed. The residue was adjusted to acidic and filtrated to give a solid, which was dried in vacuo to give Intermediate 2. Preferably, the mixture was ethanol-water mixture. The alkali is preferably NaOH.

(2) Intermediate 2 was dissolved in an organic solvent, and m-CPBA was added. The reaction was conducted at ambient temperature and then quenched with water. The reaction mixture was extracted, dried and concentrated to give Intermediate 5. The organic solvent is preferably DCM.

(3) Intermediate 5 was dissolved in an organic solvent, and Material 4 was added. DIEA was added dropwisely. The reaction was conducted at ambient temperature or with heating. After the reaction, the reaction mixture was added with water, extracted, dried, concentrated and purified by column chromatography to give Intermediate 6. The organic solvent is preferably THF (4) Intermediate 6, Material 3 and HATU were dissolved in an organic solvent. DIEA was added dropwisely. The reaction mixture was stirred at ambient temperature to complete the reaction, and then added with water, extracted, dried, concentrated and purified by column chromatography to give the compound of Formula (I) as the product. The organic solvent is preferably selected from DCM or THF.

Preparation Method 3 of Compound of Formula (I)
(1) Intermediate 1 was dissolved in an organic solvent, and m-CPBA was added. The reaction was conducted at ambient temperature and then quenched with water. The reaction mixture was extracted, dried and concentrated to give Intermediate 7. The organic solvent is preferably DCM.

(2) Intermediate 7 was dissolved in an organic solvent, and Material 4 was added. DIEA was added dropwisely. The reaction was conducted at ambient temperature or with heating. After the reaction, the reaction mixture was added with water, extracted, dried, concentrated and purified by column chromatography to to give Intermediate 8. The organic solvent is preferably THF (3) Intermediate 8 was dissolved in a mixture of organic alcohol solvent and water, and an alkali was added. The reaction was carried out with stirring. After the reaction, the solvent was removed. The residue was adjusted to acidic and filtrated to give a solid, which was dried in vacuo to give Intermediate 6. Preferably, the mixture was a mixture of ethanol and water. The alkali is preferably NaOH.

(4) Intermediate 6, Material 3 and HATU were dissolved in an organic solvent. DIEA was added dropwisely. The reaction mixture was stirred at ambient temperature to complete the reaction, and then added with water, extracted, dried, concentrated and purified by column chromatography to give the compound of Formula (I) as the product. The organic solvent is preferably selected from DCM or THF.

Clinically, the compound of Formula (I) of the present invention can be used in a free form or in the form of its pharmaceutically acceptable salt. The compound of Formula (I) of the present invention is alkaline. It can form an acid salt by reaction with inorganic or organic acid. The "pharmaceutically acceptable salt" of the compound of Formula (I) as claimed in the present application includes alkali metal salt, e.g. sodium salt, potassium salt, lithium salt, etc; alkaline earth metal salt, e.g. calcium salt, magnesium salt, etc; other metal salt, e.g. aluminium salt, ferrum salt, zinc salt, copper salt, nickel salt, cobalt salt, etc; inorganic alkali salt, e.g. ammonium salt; organic alkali salt, e.g. tert-octylamine salt, dibenzylamine salt, morpholine salt, glucosamine salt, phenylglycine alkyl ester salt, ethanediamine salt, N-methylglucosamine salt, guanidine salt, diethylamine salt, triethylamine salt, dicyclohexylamine salt, N,N'-dibenzylethanediamine salt, chloroprocaine salt, procaine salt, diethanolamine salt, N-benzyl-phenethylamine salt, piperazidine salt, tetramethylamine salt, tri(hydroxymethyl) aminomethane salt; haloid acid salt, e.g. hydrofluoride salt, hydrochloride salt, hydrobromide salt, hydroiodide salt, etc; inorganic acid salt, e.g. nitrate, perchlorate, sulfate, phosphate, etc; low alkyl sulfonate, e.g. methanesulfonate, trifluoromethanesulfonate, ethanesulfonate, etc; aryl sulfonate, e.g. benzenesulfonate, p-toluene sulfate, etc; organic acid salt, e.g. acetate, malate, Fumarate, succinate, citrate, tartrate, oxalate, maleate, etc; amino acid salt, e.g. glycinate, trimethylglycinate, argininate, ornithinate, glutamate, aspartate, etc.

The "stereoisomers" of the compounds in present invention include conformational isomers and configurational isomers. Configurational isomers further include cis-trans isomers and optical isomers. "Stereoisomers" can be racemates and mixtures thereof, single enantiomers, mixture of diastereomer and single diastereomers, when the compound of the present invention possesses one or more chiral centers. The compounds of the present invention may possess asymmetric centers, each of which independently generates two optical isomers. All the possible mixtures, pure compounds and partially pure compounds of the optical isomers and diastereomers are in the scope of the present invention. Unless specified otherwise, the compounds of the present invention include cis-isomers and trans-isomers if the compounds have double bonds.

The compounds of the present invention may exist as tautomers, which have different attachment of hydrogen by swift of one or more double bonds. For example, ketone and its enol form are ketone-enol tautomers. The tautomers and mixture thereof are in the scope of the present invention.

The compounds of Formula (I), pharmaceutically acceptable salts or stereoisomers thereof of the present invention can be administrated orally, parenterally (intravenously, intramuscularly, subcutaneously or via rectum, etc), via lung or topically to mammals, e.g. human. The daily dosage of the compound of the present invention is about 0.01 mg to 1000 mg, preferably 2.5 mg to 200 mg.

The compounds of Formula (I), pharmaceutically acceptable salts or stereoisomers thereof of the present invention may constitute pharmaceutical compositions with one or more pharmaceutical carriers. Said pharmaceutical compositions can be made into clinically conventional pharmaceutical formulations, and can be administered orally or parenterally to the patients in need of the treatment, e.g. tablet, granule, capsule, powder, injection, inhalation, sublingual preparation, syrup, gel, ointment, suppository, lotion, nasal drop, spray, transdermal preparation, etc. The preparations can be conventionally prepared by addition of pharmaceutical carriers, e.g. excipient, binder, humidizer, disintegrating agent, thickening agent, etc.

The compounds of Formula (I), pharmaceutically acceptable salts or stereoisomers thereof of the present invention may constitute pharmaceutical compositions with one or more second therapeutically active agents; wherein therapeutically active agents are selected from the group consisting of vasodilator, prostaglandin E1, prostacyclin, α-adrenoreceptor blocker, mixed α,β-blocker, α-blocker, 5α-reductase inhibitor, α2-adrenoreceptor blocker, ACE inhibitor, NEP inhibitor, central dopaminergic agent, vasoactive intestinal peptide, calcium channel blocker, thiazines and the mixture thereof.

The compounds of Formula (I), pharmaceutically acceptable salts or stereoisomers thereof of the present invention have good activity of inhibiting PDE-5 (phosphodiesterase-5), and may be used in manufacture of a medicament for treating and/or preventing sexual dysfunction and diseases with lower urinary tract symptoms.

The beneficial effects of the compounds of the present invention are further illustrated by the in vitro and in vivo studies below. However, it should not be interpreted as admission that the compounds of the present invention only possess the following beneficial effects.

Experiment 1: Measurement of Enzymatic Activity In Vitro

Test compound: Some compounds of the present invention, of which the structures were shown above, and which were prepared according to the methods in Example 1 to Example 54; Avanafil was purchased commercially, of which the structure was shown above.

PDE-5A enzyme: humanized PDE-5 enzyme, SignalChem, Cat#93-31G-20.

Method: enzyme assay, Caliper Mobility-Shift PDE-5A Assay:

The test compound was accurately weighed, dissolved in DMSO, mixed thoroughly and formulated into 10 mM. The above stock solution was diluted to a concentration of 0.5 mM with DMSO, and then was gradiently diluted by a dilution factor of 3.162, resulting in 11 concentrations in total.

To a 96-well plate, 20 µL, of 10 µM FL-cGMP as the substrate was added; then 1 µL, of solution of the compound in DMSO or DMSO solution without compound was added, and then 29 µL of 1.38 ng/µL PDE-5A enzyme buffer (100 mM Hepes pH 7.5, 5 mM $MgCl_2$, 0.002% Brij-35) was added. The maximum final concentration of the compound was 10 µM. The plate was incubated at 30° C. for 1 h, and 20 µL of 70 µM EDTA was then added to stop the reaction. 26 µL of solution of each well was transferred to a 384-well plate. The conversion was read on a EZ reader II. The inhibition rate was calculated by the formula below, and used to calculate $IC_{50}$ by Prism 5.0 Inhibition rate=[Conversion (ZPE)−Conversion (sample)]×100/[Conversion (ZPE)−Conversion (HPE)]

Note: HPE: control without enzyme; ZPE: control without a test compound

Results and Conclusions:

It was demonstrated that all the example compounds of the present invention show an $IC_{50}$ less than 1 µM on PDE-5A enzyme, and have an inhibitory effect on PDE-5A enzyme. The activity of the preferable compounds is as follows.

TABLE 1

| $IC_{50}$ of the compounds of the present invention on PDE-5A | | | |
|---|---|---|---|
| Compound | PDE-5A (nM) | Compound | PDE-5A (nM) |
| Compound 1 | 6.04 | Avanafil | 12.25 |
| Compound 2 | 2.12 | Avanafil | 17.32 |
| Compound 3 | 12.88 | Avanafil | 9.29 |
| Compound 4 | 4.63 | Avanafil | 17.32 |
| Compound 5 | 17.4 | Avanafil | 17.32 |
| Compound 6 | 4.25 | Avanafil | 17.32 |
| Compound 8 | 13.2 | Avanafil | 17.32 |
| Compound 9 | 23.2 | Avanafil | 17.32 |

TABLE 1-continued

IC$_{50}$ of the compounds of the present invention on PDE-5A

| Compound | PDE-5A (nM) | Compound | PDE-5A (nM) |
|---|---|---|---|
| Compound 11 | 4.02 | Avanafil | 17.32 |
| Compound 15 | 26.76 | Avanafil | 12.53 |
| Compound 21 | 17.31 | Avanafil | 10.77 |
| Compound 25 | 47.01 | Avanafil | 10.77 |
| Compound 27 | 10.39 | Avanafil | 10.77 |
| Compound 28 | 22.65 | Avanafil | 10.77 |
| Compound 32 | 4.63 | Avanafil | 10.77 |
| Compound 34 | 34.88 | Avanafil | 20.86 |
| Compound 35 | 47.22 | Avanafil | 20.86 |
| Compound 36 | 52.42 | Avanafil | 20.86 |
| Compound 37 | 33.33 | Avanafil | 20.86 |
| Compound 39 | 21.37 | Avanafil | 26.04 |
| Compound 40 | 11.88 | Avanafil | 26.04 |
| Compound 41 | 22.91 | Avanafil | 26.04 |
| Compound 43 | 15.4 | Avanafil | 8.557 |
| Compound 46 | 14.9 | Avanafil | 6.993 |

Conclusions: It was demonstrated by Table 1 that the compounds of the present invention have a good inhibitory activity on PDE-5A enzyme.

Experiment 2: Measurement of Enzyme Activity In Vitro

Test compound: Some compounds of the present invention, of which the structures were shown above, and which were prepared according to the methods in Example 1 to Example 54; Avanafil was purchased commercially, of which the structure was shown above. Compound 88 (WO-88) was disclosed in WO200119802A, the structure and preparation method of which were described in Example 55.

Source of PDE-5 enzyme: human blood platelets

Method: enzyme assay

The test compound or solvent was incubated at 25° C. for 15 min with enzyme solution (35 μg/mL) in Tris-HCl buffer of pH 7.5. 1 μM cGMP and 0.01 μM [$^3$H] cGMP were then added to activate the reaction. The mixture was incubated for 20 min. The reaction was stopped at 100° C. By addition of snake venom nucleotidase, the product [$^3$H] GMP was converted into [$^3$H] Guanosine, which was separated with AG1-X2 resin. Then the amount of [$^3$H] Guanosine was measured. The initial concentration of the test compound was 1 μM, and was serially diluted by a half-log gradient to result in 8 concentrations.

IC$_{50}$ was analysed and calculated by MathIQ™ software (ID Business Solutions Ltd., UK).

All the example compounds of the present invention show an IC$_{50}$ less than 1 μM on PDE-5 enzyme, and have an inhibitory effect on PDE-5 enzyme. The activity of the preferable compounds is as follows.

TABLE 2

IC$_{50}$ of the compound of the present invention ON PDE-5

| Compound | PDE-5 (nM) |
|---|---|
| Compound 1 | 6.04 |
| Compound 3 | 0.91 |
| Compound 11 | 1.31 |
| Compound 38 | 0.8 |
| Compound 46 | 0.31 |
| Compound 48 | 7.99 |
| Compound 50 | 7.72 |

Conclusions: It was demonstrated by Table 2 that the compounds of the present invention have a good inhibition activity on PDE-5.

TABLE 2-1

IC$_{50}$ of the compound of the present invention on PDE-5 (repetition of Example 2)

| Compound | PDE-5 (nM) |
|---|---|
| Compound 11 | 0.41 |
| WO-88 | 0.59 |

It was demonstrated by the repetition of Example 2 that the inhibitory effect of Compound 11 of the present invention was similar to that of Compound WO-88.

Experiment 3: Measurement of Enzyme Activity on PDE-6 Enzyme In Vitro

Test compound: Some compounds of the present invention, of which the structures were shown above, and which were prepared according to the methods in Example 1 to Example 54; Avanafil was purchased commercially, of which the structure was shown above.

Source of enzyme: PDE-6, bovine retinal PDE-6

Method: The test compound or solvent was incubated at 25° C. for 15 min with enzyme solution (0.2 μg/mL) in Tris-HCl buffer of pH 7.5. 100 μM cGMP and 0.03 μM [$^3$H] cGMP were then added to activate the reaction. The mixture was incubated for 20 min. The reaction was stopped at 100° C. By addition of snake venom nucleotidase, the product [$^3$H] GMP was converted into [$^3$H] Guanosine, which was separated with AG1-X2 resin. The amount of [$^3$H] Guanosine was measured. The initial concentration of the test compound was 10 μM, and was serially diluted by a half-log gradient to result in 8 concentrations.

TABLE 3

IC$_{50}$ of the compound of the present invention on PDE-6

| Compound | PDE-6 (nM) |
|---|---|
| Compound 3 | 8.89 |
| Compound 11 | 61 |
| Compound 38 | 58 |
| Compound 46 | 310 |
| Compound 48 | 1110 |
| Compound 50 | 660 |

Experiment 4: Measurement of Pharmacological Activity on PDE-11 Enzyme In Vitro

Test compound: Some compounds of the present invention, of which the structures were shown above, and which were prepared according to the methods in Example 1 to Example 54; Avanafil was purchased commercially, of which the structure was shown above.

Method: enzyme assay, Caliper Mobility-Shift PDE-11 Assay

The test compound was accurately weighed, dissolved in DMSO, mixed thoroughly and formulated into 10 mM. The above stock solution was diluted to a concentration of 0.5 mM with DMSO, and then was gradiently diluted by a dilution factor of 3.162, resulting in 11 concentrations in total.

To a 96-well plate, 20 μL of 10 μM FL-cGMP as the substrate was added; then 1 μL solution of the compound in DMSO or DMSO solution without compound was added; and then 29 μL of 0.28 ng/μL PDE-11 enzyme buffer (100 mM Hepes pH 7.5, 5 mM MgCl$_2$, 0.002% Brij-35) was added. The maximum final concentration of the compound was 10 μM. The plate was incubated at 30° C. for 1 h, and 20 μL of 70 μM EDTA was then added to stop the reaction. 26 μL of solution of each well was transferred to a 384-well plate. The conversion was read on a EZ reader II. The Inhibition rate was calculated by the formula below, and used to calculate $IC_{50}$ by Prism 5.0 Inhibition rate=[Conversion (ZPE)−Conversion (sample)]×100/[Conversion (ZPE)−Conversion (HPE)]

Note: HPE: control without enzyme; ZPE: control without compound

TABLE 4

$IC_{50}$ of the compound of the present invention on PDE-11

| Compound | PDE-11 (μM) |
|---|---|
| Compound 1 | >10 |
| Compound 2 | >10 |
| Compound 4 | >10 |
| Compound 5 | >10 |
| Compound 6 | >10 |
| Compound 7 | >10 |
| Compound 8 | >10 |
| Compound 9 | >10 |
| Compound 11 | >10 |
| Compound 14 | >10 |
| Compound 18 | >10 |
| Compound 42 | >10 |
| Compound 44 | >10 |
| Compound 46 | >10 |
| Compound 47 | >10 |

Conclusion of Enzyme Activity Experiment In Vitro:

By comparing the enzyme activity data of the compounds on PDE-5 enzyme and PDE-6 enzyme in Experiment 2 to Experiment 4, the selectivity of the compounds of the present invention on PDE-5 enzyme and PDE-6 enzyme was obtained as follows.

TABLE 4-1

Enzyme selectivity of the compounds on PDE-5 and PDE-6

| Compound | PDE-5 ($IC_{50}$ nM) | PDE-6 ($IC_{50}$ nM) | Selectivity (PDE-6/PDE-5) |
|---|---|---|---|
| Compound 3 | 0.91 | 8.89 | 98 |
| Compound 11 | 0.41 | 61 | 148 |
| Compound 38 | 0.8 | 58 | 73 |
| Compound 46 | 0.31 | 310 | 1000 |
| Compound 48 | 7.99 | 1110 | 140 |
| Compound 50 | 7.72 | 660 | 85 |

Selectivity (%) = $IC_{50}$ for PDE-6/$IC_{50}$ for PDE-5 *100%

According to Table 4-1, the larger the ratio between $IC_{50}$ of PDE-6 and $IC_{50}$ of PDE-5, the better the selectivity on PDE-5 enzyme was. When the selectivity was >70, the selectivity of the compound on PDE-5 enzyme was high. By comparing the selective inhibition on PDE-5 and PDE-6, it was found that Compound 3, 11, 38, 48 and 50 of the present invention had a higher selectivity on PDE-5 enzyme than to PDE-6.

Moreover, it was shown in Table 4 that $IC_{50}$ of the compounds of the present invention on PDE-11 enzyme were all >10 μM, whereas $IC_{50}$ of the compounds of the present invention on PDE-5 were all less than 10 nM. The selectivity obtained by $IC_{50}$ on PDE-11 enzyme/$IC_{50}$ on PDE-5 was over 1000, which indicated that the selectivity of the compounds of the present invention on PDE-5 enzyme was higher than the selectivity on PDE-11.

Experiment 5: Assay of Pharmacological Activity In Vivo (Intravenous Injection)

Test compound: Some compounds of the present invention, of which the structures were shown above, and which were prepared according to the methods in Example 1 to Example 54; Avanafil was purchased commercially, of which the structure was shown above.

Method:

After accommodating with the environment, the New Zealand rabbits were grabbed everyday. When the rabbits were accustomed to the repeated grabbing, drug administration was began. The animals were randomly divided into groups by weight. The test compounds were separately dissolved in menstruum. (Table 5: Avanafil and Compound 11 were separately dissolved in 60% PEG-400+23% 0.1 M hydrochloric acid+17% water for injection; Table 6: Avanafil was dissolved in 2.5% 1 M hydrochloric acid solution+NaCl solution for injection, Compound 38 was dissolved in 1.25% 1 M hydrochloric acid solution+NaCl solution for injection). The corresponding test compounds were injected into the auricular veins of animals of each group. The dosage of the compounds in Table 5 was 10 mg/kg, and the administration volume was 1 mL/kg. The dosage of the compounds in Table 6 was 10 mg/kg, and the administration volume was 2 mL/kg. 0.2 mg/kg sodium nitroprussiate was intravenously injected into the rabbits 5 min after the administration of the test compounds, with the administration volume of 0.5 mL/kg.

The length of the rabbit's penis was measured with a digital caliper before and 10, 15, 30, 50, 60, 90 and 120 min after the administration. Touch of the rabbit's penis by the caliper was avoided during the measurements.

TABLE 5

Effect of intravenous administration on the length of New Zealand rabbit's penis (AUC)

| Compound | AUC (mm × min) |
|---|---|
| Avanafil | 317.9 |
| Compound 11 | 323.3 |

TABLE 6

Effect of intravenous administration on the length of New Zealand rabbit's penis (AUC)

| Compound | AUC (mm × min) |
|---|---|
| Avanafil | 421.2 |
| Compound 38 | 772.8 |

Conclusions: It was shown in Table 5 and Table 6 that the compounds of the present invention can promote the erection of New Zealand rabbit's penis.

Experiment 6: Assay of Pharmacological Activity In Vivo (Oral Administration)

Test compound: Some compounds of the present invention, of which the structures were shown above, and which were prepared according to the methods in Example 1 to Example 54; Avanafil was purchased commercially, of which the structure was shown above.

Method:

After accommodating with the environment, the New Zealand rabbits were grabbed everyday. When the rabbits were accustomed to the repeated grabbing, drug administration was began. The animals were randomly divided into groups by weight, with 6 rabbits of each group. The test compounds were separately dissolved in menstruum. (Avanafil and Compound 38 were separately suspended in 0.5% methyl cellulose). The corresponding test compounds were orally administrated to animals of each group. The dosage was 100 mg/kg, and the administration volume was 1 mL/kg. The length of the rabbit's penis was measured with a digital caliper before and 5, 10, 15, 30, 50, 60, 90, 120, 180 and 240 min after the administration. Touch of the rabbit's penis by the caliper was avoided during the measurements.

TABLE 7

Effect of oral administration on the length of
New Zealand rabbit's penis (AUC)

| Compound | AUC (mm × min) |
|---|---|
| Avanafil | 199.4 |
| Compound 38 | 802.7 |

Conclusions: It was shown in Table 7 that the compounds of the present invention can promote the erection of New Zealand rabbit's penis.

Experiment 7: Assay of Pharmacological Activity In Vivo (Oral Administration)

Test compound: Some compounds of the present invention, of which the structures were shown above, and which were prepared according to the methods in Example 1 to Example 54; Avanafil was purchased commercially, of which the structure was shown above.

Method:

After accommodating with the environment, the New Zealand rabbits were grabbed everyday. When the rabbits were accustomed to the repeated grabbing, drug administration was began. The animals were randomly divided into groups by weight, with 6 rabbits of each group. The test compounds were separately dissolved in menstruum (Avanafil and Compound 11 were separately suspended in 0.5% methyl cellulose). The corresponding test compounds were orally administered to animals of each group. The dosage was 70 mg/kg, and the administration volume was 1 mL/kg. SNP (0.2 mg/kg, 0.5 mL/kg) was injected into the auricular veins of rabbits 60 min after the administration of the test compounds. The length of the rabbit's penis was measured with a digital caliper before and 10, 15, 30, 50, 60, 65, 70, 75, 90, 110, 120 and 180 min after the administration. Touch of the rabbit's penis by the caliper was avoided during the measurements.

TABLE 8

Effect of oral administration on the length of
New Zealand rabbit's penis (AUC)

| Compound | AUC (mm × min) |
|---|---|
| Compound 3 | 46.26 |
| Compound 11 | 540.7 |
| Compound 38 | 654.0 |

Conclusions: It was shown in Table 8 that the compounds of the present invention can promote the erection of New Zealand rabbit's penis.

Experiment 8: Detection of Inhibitory Effect of the Compounds of the Present Invention on hERG Potassium Channel by the Patch Clamp Method Rapidly activated human delayed rectifying outward potassium current (IKr) is mainly mediated by hERG ion channel and is involved in repolarization of human cardiac muscle cell. Clinically, blocking of the current by a drug is the main cause of QT interval prolongation syndrome, acute arrhythmia and even sudden death. The main purpose of the experiment is to test the blocking effect of the compounds of the present invention on hERG channel, and to determine the half maximal inhibitory concentration ($IC_{50}$) of the compounds.

The experiment mainly included: (1) recording hERG current by patch clamp technique on CHO-K1 cell line which stably expressed hERG channel; (2) calculating the Inhibition rate of each concentration according to hERG tail current; (3) testing each compound at 5 concentrations to calculate $IC_{50}$; (4) testing 2 cells at each concentration; (5) a positive control.

1. Information of Test Compounds

Test compound: Some compounds of the present invention, of which the structures were shown above, were prepared according to Example 1 to Example 54; Vardenafil and Avanafil were purchased commercially, of which the structures were shown above. The structures and synthesis of Compound 88 (WO-88) and Compound 93 (WO-93) as disclosed in WO200119802A were described in Example 55 and Example 56.

Drug for positive control: Amitriptyline hydrochloride (Sigma-Aldrich, an international standard blocker for hERG channel)

Source: Sigma-Aldrich, Inc., 3050 Spruce Street, St. Louis, Mo. 63103, USA

Lot number: 039K1600

Amount: 9.62 mg

Minimum content: 98%

2. Preparation of Solution and Compounds

Extracellular solution (mM): N-2-hydroxyethylpiperazine-N'-2-ethanesulfonic acid (HEPES) 10, NaCl 145, KCl 4, $CaCl_2$ 2, $MgCl_2$ 1, Glucose 10, adjusted to a pH of 7.4 with 1N sodium hydroxide; adjusted to an osmotic pressure of 290-300 mOsm; preserved at 4° C. after filtration.

Pippette Solution (in mM): KCl 120, KOH 31.25, $CaCl_2$ 5.374, $MgCl_2$ 1.75, Ethylene glycol-bis($\beta$-aminoethyl ether)-N,N,N',N'-tetraacetic acid (EGTA) 10, HEPES 10, Na2-ATP 4, adjusted to a pH of 7.2 with 1N potassium hydroxide; adjusted to an osmotic pressure of 280-290 mOsm; preserved at −20° C. after filtration.

Preparation of compounds: Some of the compounds of the present invention and Amitriptyline hydrochloride as the positive control drug were separately dissolved in 100% DMSO (Merck, 61850125001730), then prepared into stock solutions of 30 mM. Before the experiment, the above stock solutions were diluted with DMSO to a concentration of 1000-fold of the experimental concentration. Then the diluted solutions were further diluted with extracellular solution by 1:1000 to the required experimental concentration. The final concentration of DMSO in the extracellular solution was kept as 0.1%.

3. Cell Line

Stable cell line CHO-hERG was purchased from AVIVA Company. The hERG current on the cell line was recorded. For the purpose of quality control, the smallest seal resistance was no less than 500 MΩ, and the hERG current was no less than 0.4 nA.

4. Electrophysiological Test

The hERG current was recorded by a whole-cell patch clamp technique. Cell suspension was added into a 35-mm culture dish. The culture dish was placed on the objective table of an inverted microscope. Upon cell attachment, perfusion was conducted with the extracellular solution at a flow rate of 1-2 mL/min.

Glass microelectrode with the pipette tip resistance of 2-5 MΩ was controlled by a microelectrode puller via a two-step process. After the whole-cell record was set up, the clamp potential was kept at −80 mV. The cell was depolarized to +60 mV by applying a voltage stimulus, and then repolarized to −50 mV to obtain the hERG tail current. Recordation was conducted after the current was stable. The extracellular perfusion was started from the lowest concentration, with 5-10 min for each concentration until the current was stable, and then conducted with the next concentration.

5. Data Collection and Analysis

Stimulus payment and signal collection were performed by A/D-D/A conversion using Digidata 1440 (Molecular Devices) and pCLAMP software (Version 10.2, Molecular Devices). Signal amplification was performed on a patch clamp amplifier (Multiclamp 700B, Molecular Devices), with a filter of 1 KHz. Further data analysis and curve fitting were conducted by Clampfit (version 10.2, Molecular Devices) and Prism. The data were presented as mean value±standard deviation.

In the process of data analysis, the peak value and the baseline of the tail current were corrected when determining the blocking effect on hERG. The effect of the compound at different concentrations was represented by the Inhibition rate of the tail current. $IC_{50}$ was obtained by fitting with Logistic equation.

$$y = \left[\frac{max - min}{1 + \left(\frac{[drug]}{IC_{50}}\right)^{nH}}\right] + min$$

y: Inhibition rate; max: 100%; min: 0%; [drug]: concentration of the test compound; nH: slope; $IC_{50}$: half maximal inhibitory concentration of the test compound 6. Result In this experiment, the blocking effect of the compounds on hERG current was detected by the whole-cell patch clamp techniques on CHO-K1 cell line that stably expressed hERG channel.

The half maximal inhibitory concentration ($IC_{50}$) of the test compound was obtained by best-fitting with Logistic equation. The blocking effect on hERG was shown in Table 1. Amitriptyline is one of the most widely-used drugs for blocking the hERG current. Therefore, it was used as a positive control drug in the study. The result was shown in Table 9.

TABLE 9

$IC_{50}$ of the compounds of the present invention on hERG current as recorded on stable CHO-K1 cell line

| Compound | $IC_{50}$ (µM) |
| --- | --- |
| Avanafil | 14.57 |
| Vardenafil | 21.96 |
| Compound 3 | >27.80 |
| Compound 11 | >30 |
| Compound 48 | 8.76 |
| Compound 50 | >30 |
| WO-88 | >30 |
| WO-93 | >30 |

It was shown in Table 9 that none of Compound 3, 11 and 50 of the present invention had a significant inhibitory effect on hERG channel, and Compound 48 had slight inhibitory effect on hERG channel, suggesting that the compounds of the present invention could effectively avoid QT interval prolongation syndrome in clinical application.

Experiment 9: Assay of Pharmacokinetics (PK) of the Compounds of the Present Invention in SD Rats 1. Experimental Design

| | Animal number | Gender | Administration route | time for Blood collection | Sample type |
| --- | --- | --- | --- | --- | --- |
| Compound 2, 14, 21, 32, 38, 39, 40, 41 | 3* | male | intragastric administration (po) | 0 min, 5 min, 15 min, 30 min, 1 h, 2 h, 4 h, 6 h, 8 h, 24 h | plasma |
| | 3* | male | intravenous injection (iv) | 0 min, 5 min, 15 min, 30 min, 1 h, 2 h, 4 h, 6 h, 8 h, 24 h | |
| Compound 11, 48, 49, 50, 51, 52, 53, 54, WO-88, WO-93 | 3* | male | intragastric administration (po) | 0.17 h, 0.5 h, 1 h, 2 h, 4 h, 6 h, 8 h, 24 h | |
| | 3* | male | intravenous injection (iv) | 0.083 h, 0.25 h, 0.5 h, 1 h, 2 h, 4 h, 6 h, 8 h, 24 h | |
| Compound 43, 46 | 3* | male | intragastric administration (po) | 0.17 h, 0.5 h, 1 h, 2 h, 4 h, 6 h, 8 h, 24 h | |
| | 3* | male | intravenous injection (iv) | 0.083 h, 0.25 h, 0.5 h, 1 h, 2 h, 4 h, 6 h, 8 h, 24 h | |

Note:
*refers to 3 animals/compound/dosage group

2. Test Compound

Compound 1-54 of the present invention were prepared by the methods described in Example 1 to Example 54 of the present invention.

The control drug Avanafil, of which the structure was stated above, was purchased commercially.

Compound 88 (WO-88) and Compound 93 (WO-93) as disclosed in WO200119802A, were synthesised as described in Example 55 and Example 56.

Dissolution:

The control drug Avanafil was dissolved in 10% 0.1M dilute hydrochloric acid (diluted by 1:100)+90% normal saline;

Compound 2 and 11 were dissolved in 5% DMSO+60% PEG 400+35% sterile water for injection;

Compound 14 was dissolved in 1% DMSO+99% (50% PEG 400 aqueous solution);

Compound 21 was dissolved in 5% DMSO+60% PEG 400+35% sterile water for injection;

Compound 32 was dissolved in 5% DMSO+60% PEG 400+35% sterile water for injection (iv), or was dissolved in 1% NMP+2% solutol+97% sterile water for injection (po);

Compound 38 was dissolved in 5% DMSO+95% (6% HP-β-CD solution);

Compound 39 was dissolved in 5% DMSO+94% (6% HP-β-CD solution)+1% 0.1M HCl solution;

Compound 40 was dissolved in 5% DMSO+93.5% (6% HP-β-CD solution)+1.5% 0.1M HCl solution;

Compound 41 was dissolved in 5% DMSO+93% (6% HP-β-CD solution)+2% 0.1M HCl solution;

Compound 43 was dissolved in 1.2% 0.2 mol/L aqueous solution of hydrochloric acid+5% glucose injection;

Compound 46 was dissolved in 5% glucose injection;

Compound 48, 50 and 51 were dissolved in 0.9% sodium chloride injection;

Compound 49 and 54 were dissolved in 5% solutol+95% (0.9% sodium chloride injection);

Compound 52 was dissolved in 4.3% solutol+95.7% (0.9% sodium chloride injection);

Compound 53 was dissolved in 5% solutol+95% (5% sodium chloride injection, adjusted to a pH of about 4);

Compound WO-88 was dissolved in 10% DMF+90% sterile water for injection;

Compound WO-93 was dissolved in 30% DMF+20% PEG 400+50% sterile water for injection;

The internal standard for Compound 14, 43 and 46 was Vardenafil, which was purchased commercially and had a structure as stated above;

The internal standard for Compound 11, 48, 49, 50, 51, 52, 53, 54, WO-88 and WO-93 was Avanafil, which was purchased commercially and had a structure as stated above;

The internal standard for Compound 2, 21, 32, 38, 39, 40 and 41 was Compound Q, of which the structure is

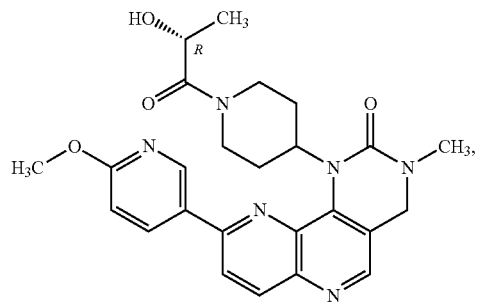

and was prepared according to the method as described in Example Q.

3. Equipment

Instrument: API 4000 LC-MS/MS or API 3000 LC-MS/MS

Chromatographic column: Agilent XDB $C_{18}$ (2.1×50 mm, 5 μm) or Waters C18 (2.10×50 mm, 5 μm)

| 4. Drug delivery to animals and blood collection | | | | |
|---|---|---|---|---|
| | Intravenous injection (IV) | | Intragastric administration (PO) | |
| Compound | Dosage (mg/kg) | Dose volume (mL/kg) | Dosage (mg/kg) | Dose volume (mL/kg) |
| Avanafil | 2 | 2 | 2 | 2 |
| Compound 2 | 1 | 2 | 2 | 4 |
| Compound 11 | 1 | 2 | 1 | 2 |
| Compound 14 | 1 | 2 | 1 | 2 |
| Compound 32 | 1 | 2 | 2 | 4 |
| Compound 38 | 1 | 2 | 2 | 4 |
| Compound 40 | 1 | 2 | 2 | 4 |
| Compound 41 | 1 | 2 | 2 | 4 |
| Compound 43 | 1 | 2 | 2 | 4 |
| Compound 46 | 1 | 1 | 2 | 2 |
| Compound 48 | 2 | 2 | 5 | 5 |
| Compound 49 | 2 | 2 | 5 | 5 |
| Compound 50 | 2 | 2 | 5 | 5 |
| Compound 51 | 2 | 2 | 5 | 5 |
| Compound 52 | 2 | 2 | 5 | 5 |
| Compound 53 | 2 | 2 | 5 | 5 |
| Compound 54 | 2 | 2 | 5 | 5 |
| WO-88 | 1 | 2 | 1 | 2 |
| WO-93 | 1 | 2 | 1 | 2 |

Collection of the rat's blood: The animal was fixed. The tail was warmed with a water bath 10 min before the collection time. About 200 μL of whole blood was collected from the tail vein. The collected blood was collected into anticoagulant tubes containing heparin sodium. The blood samples were centrifuged at 4° C. by 8000 rpm for 6 min to give the plasma samples, which should be prepared within 30 min after the collection of blood. The plasma samples were stored in a freezer of −80° C. until test.

5. Method 5.1 Compound 2, 14, 21

(1) The test compound was removed from the freezer (−80° C.), thawed at ambient temperature, and then vortexed for 5 min;

(2) 20 μL of test compound was precisely measured into a 1.5 mL centrifuge tube;

(3) 800 μL of internal standard solution was added;

(4) the mixture was vortexed for 10 min and centrifuged for 5 min (12000 rpm);

(5) 600 μL of supernate was precisely measured into a 96-well plate and dried under $N_2$;

(6) 200 μL of mixed solution (methanol: water=7:3) was added, mixed by vortex, and analyzed by LC-MS/MS.

5.2 Compound 32, 38, 39, 40, 41, 43, 46

(1) The test compound was removed from the freezer (−80° C.), thawed at ambient temperature, and then vortexed for 5 min;

(2) 20 μL of test compound was precisely measured into a 1.5 mL centrifuge tube;

(3) 200 μL of internal standard solution was added;

(4) the mixture was vortexed for 3 min and centrifuged for 5 min (12000 rpm);

(5) 100 μL of supernate was precisely measured, and 100 μL of water was added, and the resultant mixture was mixed by vortex, and analyzed by LC-MS/MS.

5.3 Control Drug Avanafil, Compound 48, 49, 50, 51, 52, 53, 54

(1) The test compound was removed from the freezer (−80° C.), thawed at ambient temperature, and then vortexed for 5 min;

(2) 20 μL of test compound was precisely measured into a 1.5 mL centrifuge tube;

(3) 200 μL of internal standard solution was added;

(4) the mixture was vortexed for 3 min and centrifuged for 5 min (12000 rpm);

(5) 50 μL of supernate was precisely measured, and 150 μL of water was added, and the resultant mixture was mixed by vortex, and analyzed by LC-MS/MS.

5.4 Compound 11

(1) The test compound was removed from the freezer (−80° C.), thawed at ambient temperature, and then vortexed for 3 min;

(2) 30 μL of test compound was precisely measured into a 1.5 mL centrifuge tube;

(3) 30 μL of internal standard solution (100 ng/mL) and 200 μL of water were added, then 1 mL of MTBE solution was added;

(4) the mixture was vortexed for 10 min and centrifuged for 5 min (10000 rpm); (5) 400 μL of supernate was precisely measured and dried under $N_2$; 200 μL of mixed solution (methanol:water=1:1) was added, mixed by vortex, and analyzed by LC-MS/MS.

5.5 Compound WO-88

(1) The test compound was removed from the freezer (−80° C.), thawed at ambient temperature, and then vortexed for 3 min;

(2) 20 μL of test compound was precisely measured into a 1.5 mL centrifuge tube;

(3) 200 μL of internal standard solution in methanol (containing Avanafil as internal standard of 50 ng/mL) was added;

(4) the mixture was vortexed for 3 min and centrifuged for 5 min (12000 rpm);
(5) 100 µL of supernate was precisely measured, and 100 µL of water was added, and the resultant mixture was mixed by vortex, and analyzed by LC-MS/MS.

5.6 Compound WO-93
(1) The test compound was removed from the freezer (−80° C.), thawed at ambient temperature, and then vortexed for 3 min;
(2) 20 µL of test compound was precisely measured into a 1.5 mL centrifuge tube;
(3) 600 µL of internal standard MTBE solution (containing Avanafil as internal standard of 10 ng/mL);
(4) the mixture was vortexed for 10 min and centrifuged for 5 min (12000 rpm);
(5) 400 µL of supernate was precisely measured and dried under $N_2$; 200 µL of mixed solution (methanol:water=1:1) was added, mixed by vortex, and analyzed by LC-MS/MS.

6. Data Analysis

The result output by Analyst 1.5.1 of AB Company was used as the concentration of the tested sample (plasma sample). The mean value, standard deviation, variable coefficient and the like were calculated by Microsoft Excel (except for the result directly output by Analyst 1.5.1). Parameters of PK were calculated by Pharsight Phoenix 6.2 software. Formula for calculating oral bioavailability: $F\% = AUCinf_{-po} * Dose_{iv} / AUCinf_{-iv} * Dose_{po}$.

TABLE 10

Assessment of PK of the compounds in rats after intravenous injection

| Test compound | Dose (mg/kg) | $T_{1/2}$ (h) | $AUC_{inf}$ (h * ng/mL) | $Cl_{obs}$ (L/h/kg) | $Vss_{obs}$ (L/kg) |
|---|---|---|---|---|---|
| Avanafil | 2 | 0.53 | 382 | 5.31 | 3.56 |
| Compound 2 | 1 | 1.78 | 219 | 4.63 | 10.57 |
| Compound 11 | 1 | 2.40 | 858 | 1.18 | 3.44 |
| Compound 14 | 1 | 1.47 | 237 | 4.26 | 8.73 |
| Compound 32 | 1 | 1.68 | 212 | 4.81 | 12.05 |
| Compound 38 | 1 | 3.50 | 1033 | 1.01 | 4.47 |
| Compound 40 | 1 | 2.73 | 205 | 4.88 | 16.40 |
| Compound 41 | 1 | 0.83 | 188 | 5.35 | 6.62 |
| Compound 43 | 1 | 1.3 | 318 | 3.23 | 5.18 |
| Compound 46 | 1 | 13.9 | 214 | 4.74 | 86.40 |
| Compound 48 | 2 | 4.4 | 2062 | 1.02 | 4.59 |
| Compound 49 | 2 | 3.9 | 3862 | 0.52 | 2.46 |
| Compound 50 | 2 | 4.1 | 2582 | 0.78 | 4.48 |
| Compound 51 | 2 | 8.8 | 4402 | 0.47 | 5.58 |
| Compound 52 | 2 | 4.6 | 3713 | 0.54 | 3.02 |
| Compound 53 | 2 | 1.8 | 1498 | 1.34 | 2.33 |
| Compound 54 | 2 | 2.3 | 1429 | 1.43 | 3.87 |
| WO-88 | 1 | 1.0 | 347 | 2.9 | 3.6 |
| WO-93 | 1 | 2.6 | 709 | 1.5 | 5.0 |

TABLE 11

Assessment of PK of the compounds in rats after intragastric administration

| Test compound | Dose (mg/kg) | $T_{1/2}$ (h) | $AUC_{inf}$ (h * ng/mL) | $C_{max}$ (ng/mL) | $T_{max}$ (h) | F % |
|---|---|---|---|---|---|---|
| Avanafil | 2 | 0.51 | 50 | 18 | 0.33 | 4.5 |
| Compound 2 | 2 | 2.95 | 69 | 12 | 1.0 | 12 |
| Compound 11 | 1 | 2.03 | 604 | 133 | 1 | 70.4 |
| Compound 14 | 1 | 2.85 | 36 | 5.2 | 36 | 15 |
| Compound 32 | 2 | 2.26 | 24 | 6.5 | 0.5 | 3.5 |
| Compound 38 | 2 | 2.11 | 704 | 124 | 6.0 | 35 |
| Compound 40 | 2 | 3.58 | 57 | 13.9 | 0.5 | 9.5 |
| Compound 41 | 2 | 0.91 | 67 | 43.8 | 0.5 | 17.7 |
| Compound 43 | 2 | 3.31 | 139 | 19.5 | 2.0 | 18 |
| Compound 48 | 5 | 2.0 | 2333 | 415 | 2 | 63 |
| Compound 49 | 5 | 4.1 | 5835 | 505 | 4 | 60 |
| Compound 50 | 5 | 5.4 | 4718 | 377 | 6 | 65 |
| Compound 51 | 5 | 7.3 | 5802 | 402 | 6 | 52 |
| Compound 52 | 5 | 8.4 | 6004 | 392 | 6 | 65 |
| Compound 53 | 5 | NA | 917* | 156 | 4 | 25 |
| Compound 54 | 5 | 2.7 | 1415 | 200 | 4 | 40 |
| WO-88 | 1 | 2.8 | 63 | 29 | 0.5 | 23 |
| WO-93 | 1 | 2.8 | 89 | 15 | 4 | 16 |

$T_{1/2}$ was half-life;
$AUC_{inf}$ was area under concentration-time curve $_{0 \to \infty}$;
CL was clearance rate;
Vss was apparent volume of distribution;
$C_{max}$ was peak concentration of the compound in plasma;
$T_{max}$ was the time at which the compound reached the peak concentration in plasma;
F % was absolute bioavailability;
NA was not available;
917* represented that $AUC_{inf}$ of the compound which was intragastricly administrated to the rat could not be calculated due to incomplete clearance.

7. Conclusions

It was shown in Table 10 and Table 11 that the compounds of the present invention had longer half-lives and better AUC/dose than Avanafil, as measured in rats with iv and po administration, and were suitable for treating diseases caused by PDE-5 and BPH. Moreover, the compounds of the present invention had better oral bioavailability and wider clinical application than Avanafil. As compared with Compound WO-88, Compound 11 of the present invention had longer half-life and higher exposure quality (AUC) when administrated by intravenous injection. Compound 11 of the present invention had higher exposure quality (AUC) and bioavailability than Compound WO-88 when administrated by intragastric route.

EMBODIMENTS

The present invention is further illustrated by the following examples. It should be understood, however, that the present invention is not limited to the specific examples. All the embodiments which are achieved based on the above teachings of the invention fall within the scope of the present invention.

3-Chloro-4-methoxybenzylamine hydrochloride salt was obtained from Chemfun (Shanghai) Pharmaceutical Technology Co., Ltd.

Ethyl 4-chloro-2-(methylthio)pyrimidine-5-carboxylate was obtained from Nanjing Far Top Biotechnology Co., Ltd.

Preparation of 3-azabicyclo[3.1.0]hexane hydrochloride salt

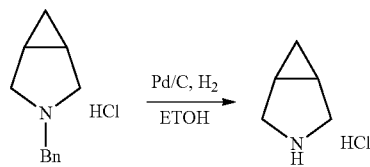 [SMILES: c1ccc(CN2CC3CC3C2)cc1 ; Cl ; C1NCC2CC12 ; Cl]

(wherein 3-benzyl-3-azabicyclo[3.1.0]hexane hydrochloride salt was obtained from PharmaBlock (Nanjing) R&D Co., Ltd).

Trans-4-hydroxycyclohexylamine was obtained from Shanghai Darui Finechemical Co., Ltd.

Example Q

Preparation (R)-1-(1-(2-hydroxypropionyl)piperidine-4-yl)-9-(6-methoxypyridin-3-yl)-3-methyl-3,4-dihydropyrimido[5,4-c][1,5]naphthyridin-2(1H)-one (internal standard compound Q)

(1) Preparation: 6-bromopyridin-3-amine

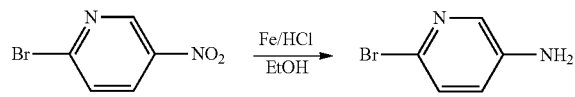

To a solution of 2-bromo-5-nitropyridine (2.03 g, 10 mmol) in ethanol (48 mL), iron powder (2.8 g, 50 mmol), concentrated hydrochloric acid (1.9 mL) and water (9.1 mL) were sequentially added. The mixture was reacted under reflux for 5 h, cooled and filtrated. The filtrate was concentrated, adjusted to a pH of about 7 to 8 and extracted with DCM. The organic phase was dried over sodium sulfate and concentrated under reduced pressure to give a reddish brown solid (1.58 g, 91.3% yield).

(2) Preparation: diethyl 2-(((6-bromopyridin-3-yl)amino)methylene)malonate

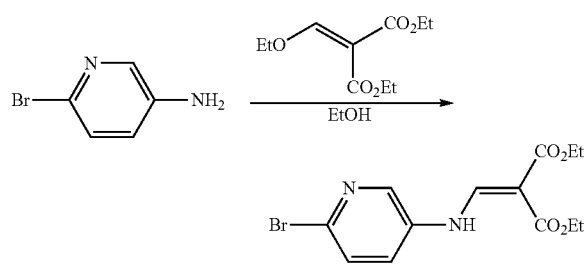

To ethanol (400 mL) 6-bromopyridine-3-amine (40.3 g, 0.233 mol) and diethyl 2-(ethoxymethylene)malonate (56.5 g, 0.261 mol) were added. The mixture was reacted under reflux for 5 h and cooled. A solid was formed and filtrated under reduced pressure. The filter residue was washed with petroleum ether to give a faint yellow solid (71 g, 89.0% yield).

(3) Preparation: ethyl 6-bromo-4-hydroxy-1,5-naphthyridine-3-carboxylate

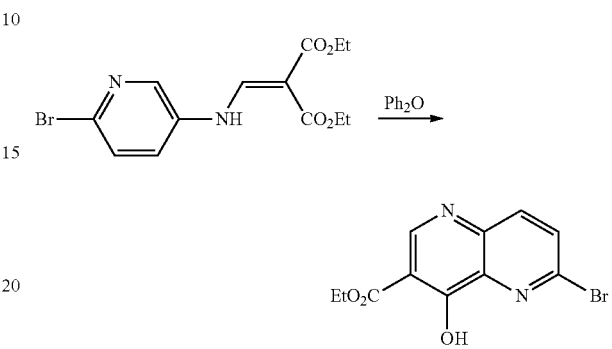

Diethyl 2-(((6-bromopyridin-3-yl)amino)methylene) malonate (36 g, 0.105 mol) was added to boiling diphenyl ether (185 mL) in batch in 5 min. The mixture was reacted under reflux for 45 min. The exhaustion of materials was indicated by TLC (ethyl acetate/petroleum ether=1/3). The mixture was cooled, poured into petroleum ether to form a solid and filtrated under reduced pressure. A khaki solid was obtained (17.1 g, 54.8% yield).

(4) Preparation: ethyl 4,6-dichloro-1,5-naphthyridine-3-carboxylate

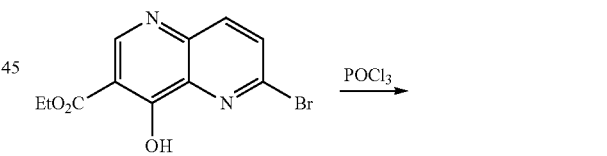

To phosphorus oxychloride (50 mL) were added ethyl 6-bromo-4-hydroxy-1,5-naphthyridine-3-carboxylate (15 g, 50.5 mmol) and N,N-dimethylaniline (5 mL). The mixture was reacted under reflux for 3 h, then cooled. Phosphorus oxychloride was removed under reduced pressure. The residue was poured into ice water, adjusted to a pH of about 8 and extracted with DCM. The organic phase was dried over sodium sulfate, concentrated and purified by silica gel col- (5) Preparation: ethyl 4-((1-(tert-butoxy carbonyl)piperidin-4-yl)amino)-6-chloro-1,5-naphthyridine-3-carboxylate

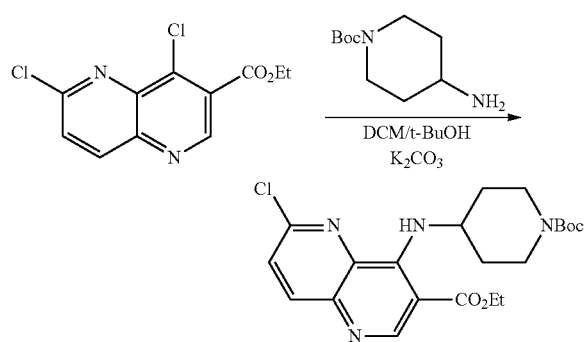

Ethyl 4,6-dichloro-1,5-naphthyridine-3-carboxylate (0.5 g, 1.85 mmol) and tert-butyl 4-aminopiperidine-1-carboxylate (0.45 g, 2.22 mmol) were dissolved in the mixture of DCM (5 mL) and tert-butyl alcohol (5 mL). Potassium carbonate (0.612 g, 4.43 mmol) was added to the solution. The reaction mixture was stirred at ambient temperature for 24 h and filtrated under reduced pressure. The solid was washed by DCM. The filtrate was concentrated under reduced pressure. The residue was recrystallized in diethyl ether to give a faint yellow solid (0.73 g, 90.9% yield).

(6) Preparation: tert-butyl 4-((6-chloro-3-(hydroxymethyl)-1,5-naphthyridin-4-yl)amino) piperidine-1-carboxylate

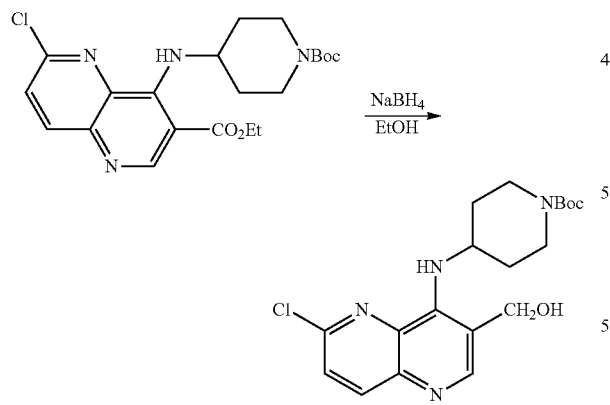

To ethanol (10 mL) was added ethyl 4((1-(tert-butoxycarbonyl)piperidin-4-ylamino)-6-chloro-1,5-naphthyridine-3-carboxylate (0.43 g, 1.0 mmol). Sodium borohydride (0.228 g, 6 mmol) was added to the mixture in batch. After stirring at ambient temperature for 18 h, ethanol was removed under reduced pressure. 10 mL of water was added followed by extraction with DCM. The organic phase was dried over sodium sulfate and concentrated under reduced pressure to give a solid (0.39 g) which was used in the subsequent procedure without further purification.

(7) Preparation: tert-butyl 4-((6-chloro-3-formyl-1,5-naphthyridin-4-ylamino) piperidine-1-carboxylate

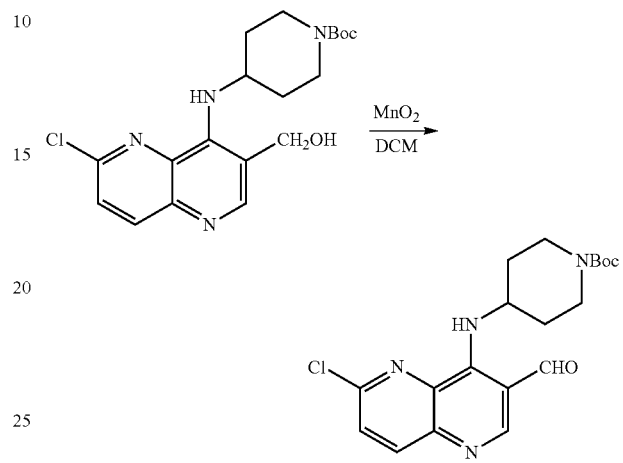

In DCM (10 mL) was dissolved tert-butyl 4-((6-chloro-3-(hydroxymethyl)-1,5-naphthyridin-4-yl)amino)piperidine-1-carboxylate (0.39 g, 1 mmol). Manganese dioxide (2.14 g, 32 mmol) was added to the solution. The reaction mixture was stirred at ambient temperature for 3 h and filtrated. The solid was washed with DCM. The filtrate was concentrated to give a solid which was recrystallized in methanol. A white solid was obtained (0.311 g, 79.6% yield).

(8) Preparation: tert-butyl 4-((6-chloro-3-((methylamino)methyl)-1,5-naphthyridin-4-yl)amino) piperidine-1-carboxylate

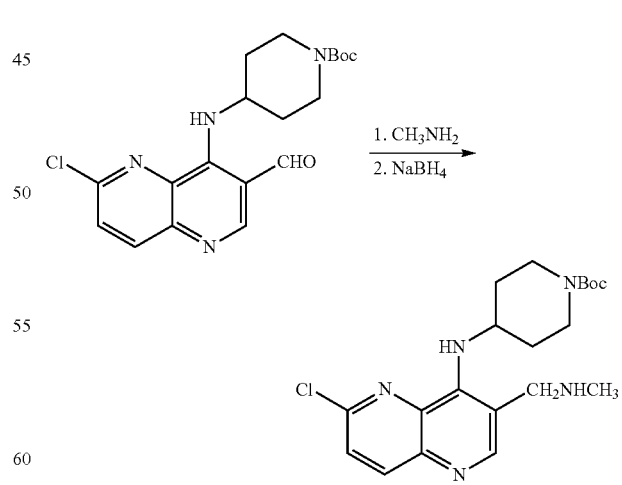

In ethanol was dissolved tert-butyl 4-((6-chloro-3-formyl-1,5-naphthyridin-4-yl)amino) piperidine-1-carboxylate (0.31 g, 0.79 mmol), and was added an ethanol solution of aminomethane (27%, 0.59 mL). After stirring at ambient temperature for 24 h, the exhaustion of material was indicated by LC-MS. Then, sodium borohydride (0.181 g, 4.60 mmol) was added to the mixture, followed by stirring at ambient temperature for 18 h. The reaction was quenched with saturated aqueous sodium carbonate. Then ethanol was removed under reduced pressure, followed by extraction with DCM. The organic phase was dried over sodium sulfate and concentrated under reduced pressure to give a solid (0.27 g, 84.2% yield).

(9) Preparation: tert-butyl 4-(9-chloro-3-methyl-2-oxo-3,4-dihydropyrimido[5,4-c][1,5]naphthyridin-1(2H)-yl)piperidine-1-carboxylate

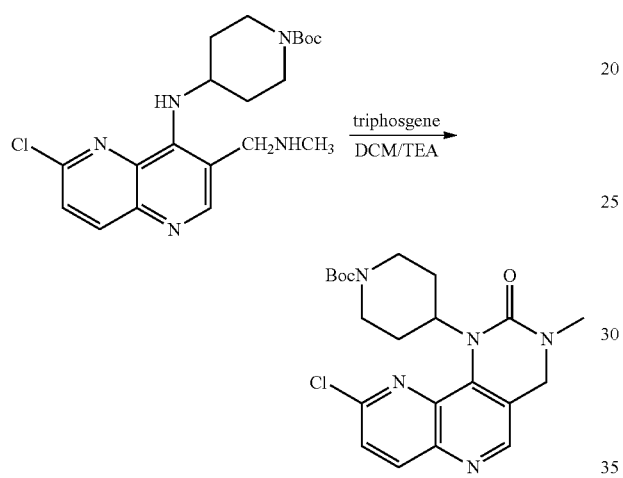

In DCM (10 mL) was dissolved tert-butyl 4-((6-chloro-3-((methylamino)methyl)-1,5-naphthyridin-4-yl)amino)piperidine-1-carboxylate (0.312 g, 0.77 mmol). The solution was cooled in an ice bath, and triphosgene (0.274 g, 0.923 mmol) and triethylamine (0.324 mL) were added. Then the reaction mixture was stirred at ambient temperature for 2 h. The reaction was quenched with saturated aqueous sodium carbonate and extracted with DCM. The organic phase was dried over sodium sulfate. The solvent was removed under reduced pressure to give a solid (0.332 g), which was used in the subsequent procedure without further purification.

(10) Preparation: tert-butyl 4-(9-(6-methoxypyridin-3-yl)-3-methyl-2-oxo-3,4-dihydropyrimido[5,4-c][1,5]naphthyridin-1(2H)-yl)piperidine-1-carboxylate

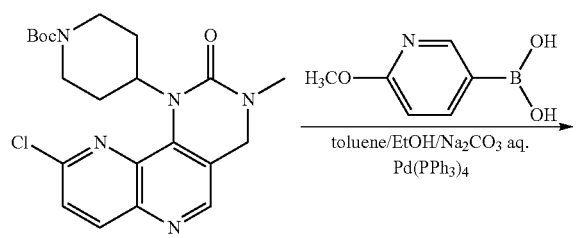

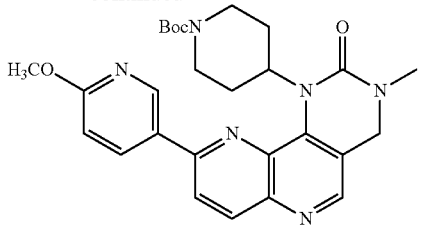

In the mixture of toluene (6 mL) and ethanol (2 mL) were dissolved tert-butyl 4-(9-chloro-3-methyl-2-oxo-3,4-dihydropyrimido[5,4-c][1,5]naphthyridin-1 (2H)-yl)piperidine-1-carboxylate (0.104 g, 0.241 mmol) and 6-methoxypyridine-3-boronic acid (40.7 mg, 0.266 mmol). To the solution were added tetrakis triphenylphosphine palladium (0) (5 mg) and aqueous sodium carbonate (2 N, 0.36 mL). The mixture was reacted under reflux under the protection of nitrogen for 16 h, then cooled to ambient temperature and filtrated. The organic phase was concentrated under reduced pressure, dissolved in DCM, washed sequentially with water and brine, dried over sodium sulfate, concentrated and purified by silica gel column chromatography (ethyl acetate/petroleum ether=2/1) to give the product (75 mg, 61.7% yield).

(11) Preparation: 9-(6-methoxypyridin-3-yl)-3-methyl-1-(piperidin-4-yl)-3,4-dihydropyrimido[5,4-c][1,5]naphthyridin-2(1H)-one hydrochloride salt

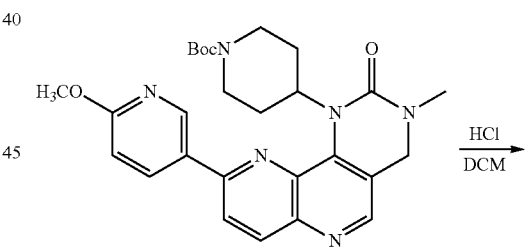

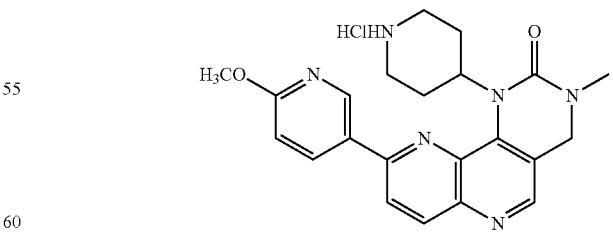

In DCM (10 mL) was dissolved tert-butyl 4-(9-(6-methoxypyridin-3-yl)-3-methyl-2-oxo-3,4-dihydropyrimido[5,4-c][1,5]naphthyridin-1(2H)-yl)piperidine-1-carboxylate (75 mg, 0.149 mmol). The solution was purged with hydrogen chloride gas for 0.5 h and a precipitate was formed. The precipitate was filtrated under reduced pressure, washed sequentially with DCM and diethyl ether and dried to give a solid (50 mg, 76.1% yield).

(12) Preparation: (R)-1-[1-(2-hydroxypropionyl)piperidine-4-yl]-9-(6-methoxypyridin-3-yl)-3-methy-3,4-dihydropyrimido[5,4-c][1,5]naphthyridin-2 (1H)-one (Compound 2)

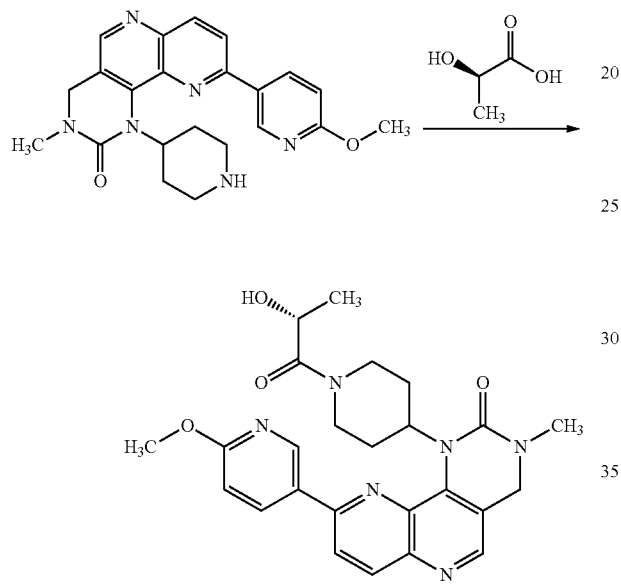

To DCM (20 mL) were added 9-(6-methoxypyridin-3-yl)-3-methyl-1-(piperidin-4-yl)-3,4-dihydropyrimido[5,4-c][1,5]naphthyridin-2(1H)-one hydrochloride salt (Compound 1) (100 mg, 0.227 mmol) and triethylamine (0.177 mL). The mixture was stirred at ambient temperature for 0.5 h. Then to the mixture were sequentially added (R)-lactic acid (26.7 mg, 0.296 mmol), 1-hydroxybenzotriazole (37.8 mg, 0.280 mmol) and 1-ethyl-(3-dimethyllaminopropyl)carbodiimide hydrochloride (70.8 mg, 0.37 mmol). The reaction mixture was stirred at ambient temperature for 2 h, and the completion of the reaction was indicated by TLC (DCM/methanol=10/1). The reaction mixture was washed sequentially with saturated aqueous sodium carbonate, water and brine. The organic phase was dried over sodium sulfate, concentrated and purified by silica gel column chromatography (DCM/methanol=10/1) to give a white solid (88 mg, 81.4% yield).

Molecular formula: $C_{25}H_{28}N_6O_4$ Molecular weight: 476.53 MS (M+H): 477.2

$^1$H-NMR (400 MHz, CDCl$_3$): δ 8.76 (1H, d), 8.59 (1H, s), 8.42 (1H, d), 8.17-8.13 (1H, m), 7.97 (1H, d), 6.91 (1H, d), 5.11-5.01 (1H, m), 4.72 (1H, t), 4.54-4.37 (3H, m), 4.03 (3H, d), 4.00-3.86 (1H, br s), 3.82 (1H, d), 3.06 (3H, s), 2.99-2.68 (3H, m), 2.59-2.30 (2H, m), 2.28-2.10 (1H, m), 1.40 (1.5 H, d), 1.27 (1.5 H, d).

Example 1

Preparation: 2-(3-azabicyclo[3.1.0]hexan-3-yl)-4-((3-chloro-4-methoxybenzyl)amino)-N-(pyrimidin-2-ylmethyl)pyrimidine-5-formamide (Compound 1)

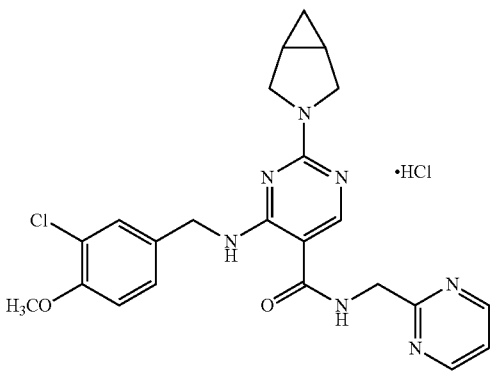 [SMILES: COc1ccc(CNc2nc(N3CC4CC4C3)ncc2C(=O)NCc2ncccn2)cc1Cl ; Cl]

(1) Preparation: ethyl 4-((3-chloro-4-methoxybenzyl)amino)-2-(methylthio)pyrimidine-5-carboxylate

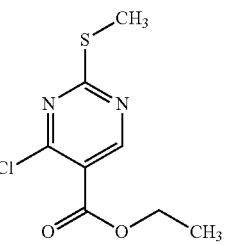 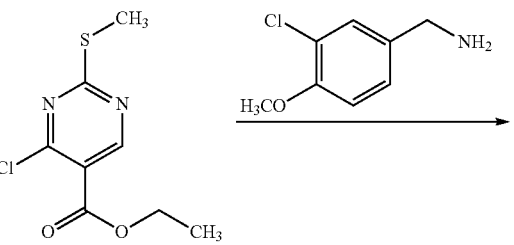

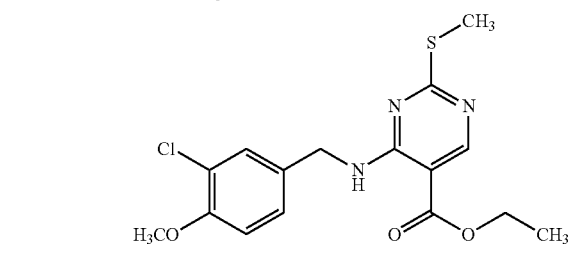

In DCM (100 mL) were dissolved ethyl 4-chloro-2-(methylthio) pyrimidine-5-carboxylate (5.0 g, 21.55 mmol), 3-chloro-4-methoxybenzylamine (4.0 g, 23.4 mmol) and triethylamine (4.35 g, 43.1 mmol). The reaction mixture was stirred at ambient temperature for 10 h and washed with water. The organic phase was dried over magnesium sulfate and concentrated to give ethyl 4-((3-chloro-4-methoxybenzyl)amino)-2-(methylthio)pyrimidine-5-carboxylate as a solid (6.0 g, 76% yield).

(2) Preparation: 4-((3-chloro-4-methoxybenzyl)amino)-2-(methylthio)pyrimidine-5-carboxylic acid

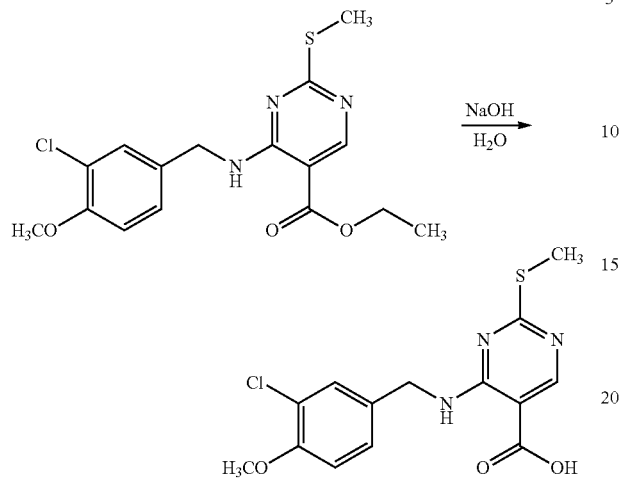

In a mixture of water (10 mL), methanol (30 mL) and THF (30 mL) were dissolved ethyl 4-((3-chloro-4-methoxybenzyl)amino)-2-(methylthio) pyrimidine-5-carboxylate (6.0 g, 16.3 mmol) and sodium hydroxide (1.14 g, 28.57 mmol). The reaction was conducted for 10 h at 60° C. The reaction mixture was cooled to ambient temperature and adjusted to a pH of 4 by addition of dilute hydrochloric acid dropwise. A solid was precipitated, filtrated, washed with methanol and dried to give 4-((3-chloro-4-methoxybenzyl)amino)-2-(methylthio)pyrimidine-5-carboxylic acid (4.2 g, 76% yield).

(3) Preparation: 4-((3-chloro-4-methoxybenzyl)amino)-2-(methylthio)-N-(pyrimidin-2-ylmethyl)pyrimidine-5-formamide

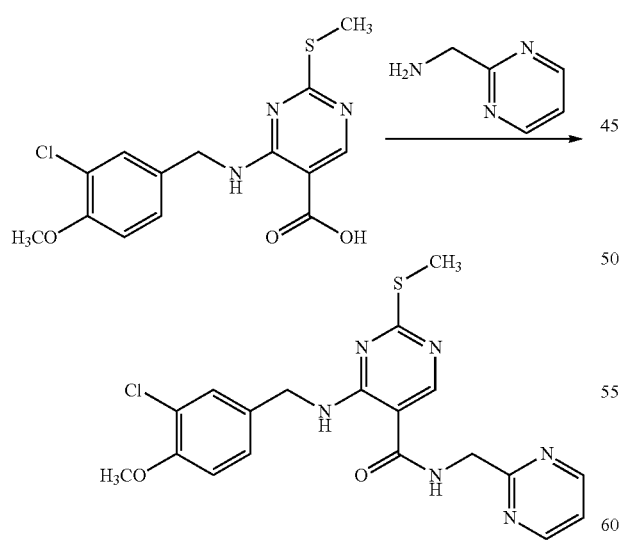

In DMF (60 mL) were dissolved 4-((3-chloro-4-methoxybenzyl)amino)-2-(methylthio) pyrimidine-5-carboxylic acid (1.0 g, 2.95 mmol), pyrimidine 2-ylmethylamine (570 mg, 5.22 mmol) and HATU (2-(7-azabenzotriazole)-N,N,N',N'-tetramethyluronium hexafluorophosphate, 2.64 g, 6.96 mmol), then DIEA (152 mg, 1.2 mmol) was added dropwisely. The reaction mixture was stirred at 60° C. overnight, extracted with DCM after water was added and washed with brine. The organic phase was dried over sodium sulfate. The solvent was removed by rotary evaporation, then the solid obtained was purified by silica gel column chromatography (DCM/methanol=50/1) to give 4-((3-chloro-4-methoxybenzyl)amino)-2-(methylthio)-N-(pyrimidin-2-ylmethyl)pyrimidine-5-formamide (350 mg, 13% yield).

(4) Preparation: 4-((3-chloro-4-methoxybenzyl)amino)-2-(methylsulfinyl)-N-(pyrimidin-2-ylmethyl)pyrimidine-5-formamide

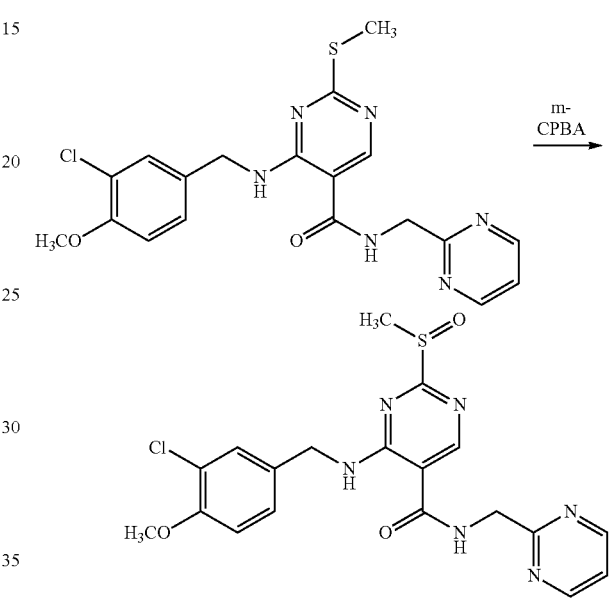

In DCM (5 mL) was dissolved 4-((3-chloro-4-methoxybenzyl)amino)-2-(methylthio)-N-(pyrimidin-2-ylmethyl) pyrimidine-5-formamide (150 mg, 0.35 mmol). m-CPBA (3-chloroperbenzoic acid, 110 mg, 0.64 mmol) was added at 0° C. The reaction was conducted for 30 min at ambient temperature. Then the reaction mixture was washed with water and extracted with DCM. The organic phase was dried, and the solvent was removed by rotary evaporation. Purification was performed by silica gel column chromatography (DCM/methanol=50/1) to give solid 4-((3-chloro-4-methoxybenzyl)amino)-2-(methylsulphinyl)-N-(pyrimidin-2-ylmethyl)pyrimidine-5-formamide (100 mg, 64% yield).

(5) Preparation: 2-(3-azabicyclo[3.1.0]hexan-3-yl)-4-(3-chloro-4-methoxybenzylamino)-N-(pyrimidine-2-ylmethyl) pyrimidine-5-formamide

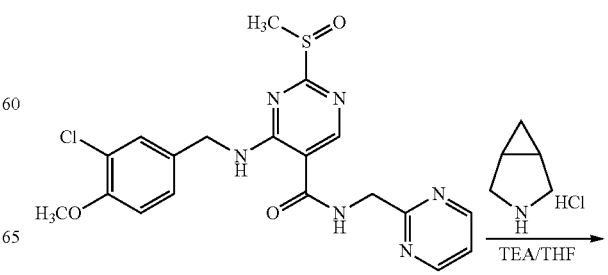

79
-continued

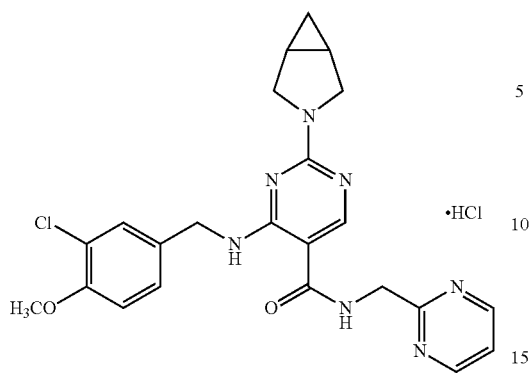

In absolute anhydrous THF (10 mL) was dissolved 4-((3-chloro-4-methoxybenzyl)amino)-2-(methylsulphinyl)-N-(pyrimidin-2-ylmethyl) pyrimidine-5-formamide (100 mg, 0.22 mmol). Several drops of triethylamine were added, then 3-azabicyclo[3.1.0]hexan hydrochloride salt (42 mg, 0.35 mmol) was added. The reaction mixture was heated to reflux overnight. The solvent was removed by rotary evaporation, and water was added, followed by extraction with DCM. The organic phase was dried over sodium sulfate and purified by silica gel column chromatography (DCM/methanol=20/1 to 10/1). 2-(3-azabicyclo[3.1.0]hexan-3-yl)-4-((3-chloro-4-methoxybenzyl)amino)-N-(pyrimidin-2-ylmethyl)pyrimidine-5-formamide as a white solid was obtained (40 mg, 39% yield).

Molecular formula: $C_{23}H_{24}ClN_7O_2$ Molecular weight: 465.9 MS (m/e): 466.0 (M+1)

$^1$H-NMR (400 MHz, DMSO-d$_6$, hydrochloride salt): δ 13.20 (br s, 1H), 10.06 (t, 1H), 9.66 (t, 1H), 8.78 (d, 2H), 8.56 (s, 1H), 7.46 (d, 1H), 7.42 (t, 1H), 7.33 (d, 1H), 7.10 (d, 1H), 4.58 (m, 4H), 3.92 (m, 2H), 3.89 (s, 3H), 3.63 (m, 2H), 1.81 (d, 2H), 0.80 (m, 1H), 0.25 (s, 1H).

Example 1-1

Preparation: 2-(3-azabicyclo[3.1.0]hexan-3-yl)-4-((3-chloro-4-methoxy benzyl)amino)-N-(pyrimidine-2-ylmethyl)pyrimidine-5-formamide (Compound 1)

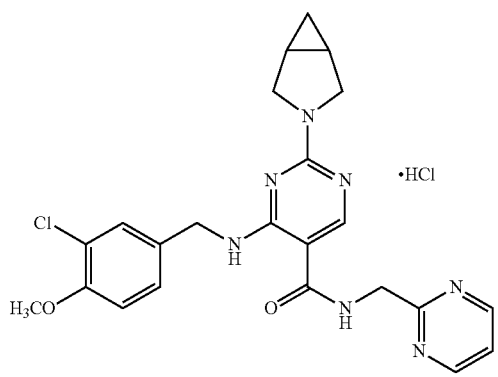 [SMILES: COc1ccc(CNc2nc(N3CC4CC4C3)ncc2C(=O)NCc2ncccn2)cc1Cl ; Cl]

80

The procedures (1) to (4) were analogous to procedures (1) to (4) of Example 1.

(5) Preparation: 2-(3-azabicyclo[3.1.0]hexan-3-yl)-4-((3-chloro-4-methoxybenzyl)amino)-N-(pyrimidin-2-ylmethyl)pyrimidine-5-formamide

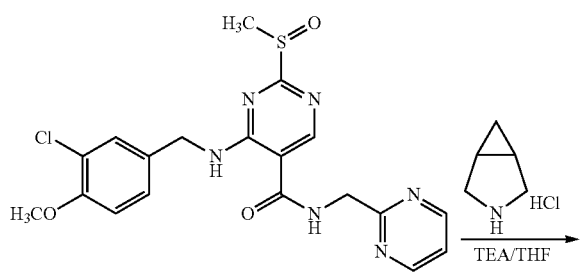

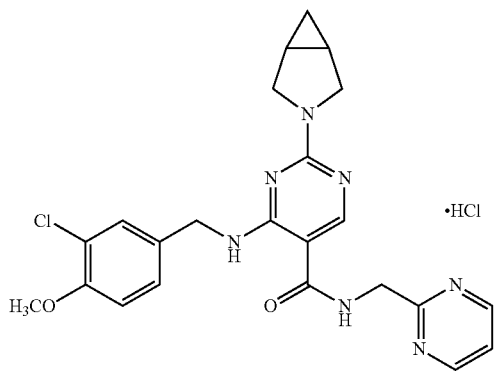

In absolute anhydrous THF (10 mL) was dissolved 4-((3-chloro-4-methoxybenzyl)amino)-2-(methylsulfinyl)-N-(pyrimidin-2-ylmethyl)pyrimidine-5-formamide (100 mg, 0.22 mmol). Triethylamine (0.22 g, 2.2 mmol) was added dropwisely, and 3-azabicyclo[3.1.0]hexan hydrochloride salt (42 mg, 0.35 mmol) was added. The reaction mixture was heated to reflux overnight. The solvent was removed by rotary evaporation, and water was added, followed by extraction with DCM. The organic phase was dried over sodium sulfate and purified by silica gel column chromatography (DCM/methanol=20/1 to 10/1) to give a solid. The solid was dissolved in methanol (0.05 mL), and hydrochloric acid (1 mol/L) was added. The solvent was removed to give 2-(3-azabicyclo[3.1.0]hexan-3-yl)-4-((3-chloro-4-methoxybenzyl)amino)-N-(pyrimidin-2-ylmethyl)pyrimidine-5-formamide hydrochloride (40 mg, 39% yield).

Molecular formula: $C_{23}H_{24}ClN_7O_2$ Molecular weight: 465.9 MS (m/e): 466.0 (M+H$^+$)

$^1$H-NMR (400 MHz, DMSO-d$_6$, hydrochloride salt): δ 13.20 (br s, 1H), 10.06 (t, 1H), 9.66 (t, 1H), 8.78 (d, 2H), 8.56 (s, 1H), 7.46 (d, 1H), 7.42 (t, 1H), 7.33 (d, 1H), 7.10 (d, 1H), 4.60-4.58 (m, 4H), 3.92-3.87 (m, 2H), 3.84 (s, 3H), 3.63 (m, 2H), 1.81 (d, 2H), 0.80 (m, 1H), 0.25 (s, 1H).

Example 2

Preparation: 2-(3-azabicyclo[3.1.0]hexan-3-yl)-4-((3-chloro-4-methoxy benzyl)amino)-N-(pyridin-2-ylmethyl)pyrimidine-5-formamide (Compound 2)

(1) Preparation: 4-((3-chloro-4-methoxybenzyl)amino)-2-(methylsulfinyl)pyrimidine-5-carboxylic acid

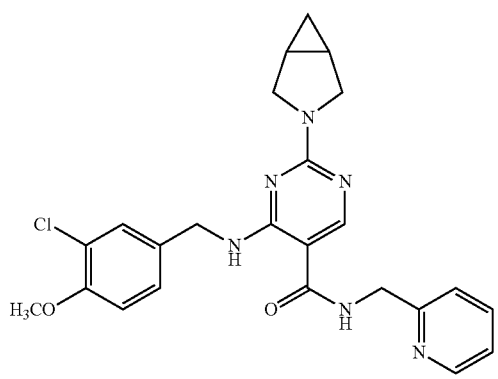 [SMILES: COc1ccc(CNc2nc(N3CC4CC4C3)ncc2C(=O)NCc2ccccn2)cc1Cl]

In DCM (20 mL) was dissolved 4-((3-chloro-4-methoxybenzyl)amino)-2-(methylthio) pyrimidine-5-carboxylic acid (200 mg, 0.59 mmol). The solution was cooled in an ice bath and m-CPBA (101 mg, 0.59 mmol) was then added. The reaction was warmed to ambient temperature for 5 h. Then water was added and the reaction mixture was extracted with DCM. The organic phase was dried and concentrated to give a solid. The product was used in the subsequent procedure without further purification.

(2) Preparation: 2-(3-azabicyclo[3.1.0]hexan-3-yl)-4-((3-chloro-4-methoxybenzyl)amino) pyrimidine-5-carboxylic acid

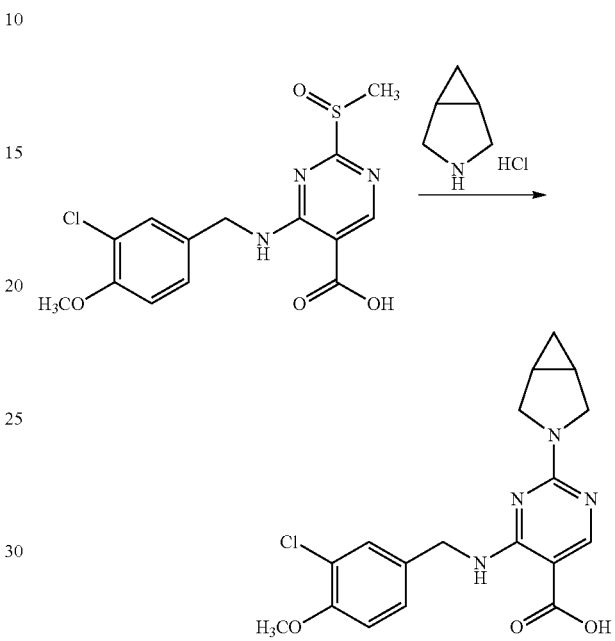

In THF (15 mL) were dissolved 4-((3-chloro-4-methoxybenzyl)amino)-2-(methylsulfinyl)pyrimidine-5-carboxylic acid (196 mg, 0.55 mmol) and 3-azabicyclo[3.1.0]hexan hydrochloride salt (79 mg, 0.66 mmol). The solution was cooled in an ice bath and triethylamine (167 mg, 1.65 mmol) was then added dropwisely. The reaction was warmed to ambient temperature for 5 h. Then water was added and the reaction mixture was extracted with DCM. The organic phase was dried and concentrated to give a solid. The product was used in the subsequent procedure without further purification.

(3) Preparation: 2-(3-azabicyclo[3.1.0]hexan-3-yl)-4-((3-chloro-4-methoxybenzyl)amino)-N-(pyridin-2-ylmethyl)pyrimidine-5-formamide

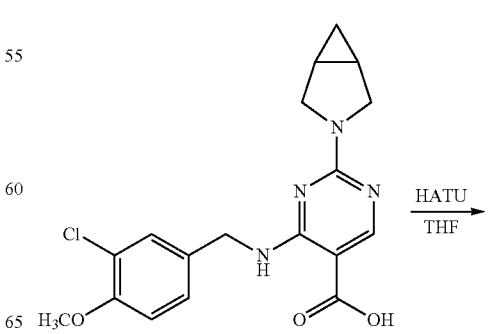

-continued

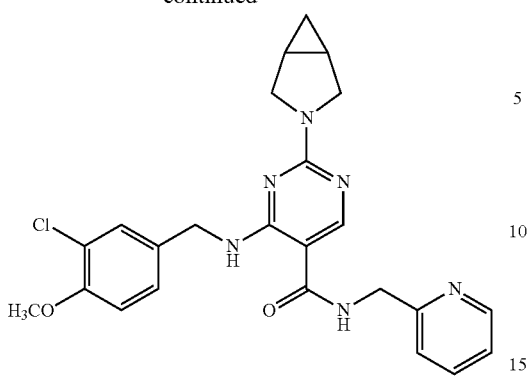

In THF (50 mL) were dissolved 2-(3-azabicyclo[3.1.0]hexan-3-yl)-4-((3-chloro-4-methoxybenzyl)amino)pyrimidine-5-carboxylic acid, pyridine-2-ylmethylamine (69 mg, 0.64 mmol) and triethylamine (0.2 mL). The solution was cooled in an ice bath and HATU (266 mg, 0.70 mmol) was then added. The reaction was conducted at ambient temperature for 18 h. The reaction mixture was concentrated, followed by addition of water and extraction with ethyl acetate. The organic phase was dried, concentrated and purified by silica gel column chromatography (DCM/methanol=50/1) to give 2-(3-azabicyclo[3.1.0]hexan-3-yl)-4-((3-chloro-4-methoxybenzyl)amino)-N-(pyridin-2-ylmethyl)pyrimidine-5-formamide (60 mg, 24% yield).

Molecular formula: $C_{24}H_{25}ClN_6O_2$ Molecular weight: 464.9 MS (m/e): 464.9 (M+1)

$^1$H-NMR (400 MHz, CDCl$_3$): δ 9.00 (t, 1H), 8.53 (t, 1H), 8.36 (s, 1H), 7.66 (m, 1H), 7.39 (s, 1H), 7.36 (m, 1H), 7.28 (d, 1H), 7.20 (d, 2H), 6.86 (d, 1H), 4.64 (d, 2H), 4.56 (m, 2H), 3.89 (d, 2H), 3.88 (s, 3H), 3.53 (m, 2H), 1.63 (m, 2H), 0.74 (m, 1H), 0.22 (m, 1H).

Example 2-1

Preparation: 2-(3-azabicyclo[3.1.0]hexan-3-yl)-4-((3-chloro-4-methoxy benzyl)amino)-N-(pyridin-2-ylmethyl)pyrimidine-5-formamide

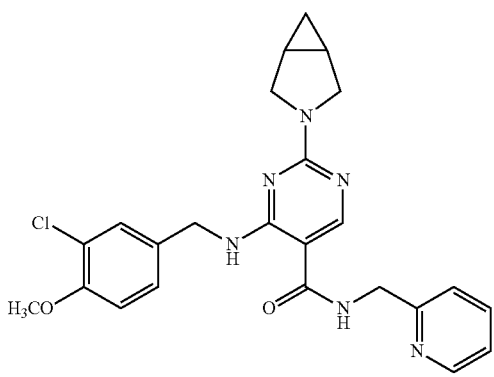 [SMILES: COc1ccc(CNc2nc(N3CC4CC4C3)ncc2C(=O)NCc2ccccn2)cc1Cl]

The procedures (1) to (2) were analogous to procedures (1) to (2) of Example 2.

(3) Preparation: 2-(3-azabicyclo[3.1.0]hexan-3-yl)-4-((3-chloro-4-methoxybenzyl)amino)-N-(pyridin-2-ylmethyl)pyrimidine-5-formamide

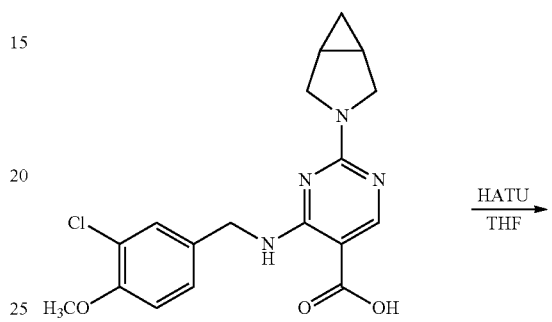

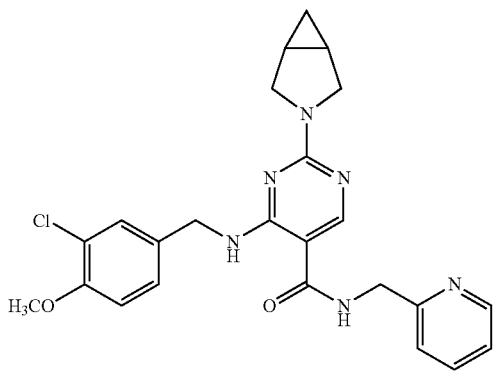 [SMILES: COc1ccc(CNc2nc(N3CC4CC4C3)ncc2C(=O)NCc2ccccc2)cc1Cl]

In THF (50 mL) were dissolved 2-(3-azabicyclo[3.1.0]hexan-3-yl)-4-((3-chloro-4-methoxybenzyl)amino)pyrimidine-5-carboxylic acid (202 mg, 0.54 mmol), pyridine-2-ylmethylamine (69 mg, 0.64 mmol) and triethylamine (0.2 mL). The solution was cooled in an ice bath and HATU (266 mg, 0.70 mmol) was then added. The reaction was conducted at ambient temperature for 18 h. The reaction mixture was concentrated and the obtained solid was purified by silica gel column chromatography (DCM/methanol=50/1) to give 2-(3-azabicyclo[3.1.0]hexan-3-yl)-4-((3-chloro-4-methoxybenzyl)amino)-N-(pyridin-2-ylmethyl)pyrimidine-5-formamide (60 mg, 24% yield).

Molecular formula: $C_{24}H_{25}ClN_6O_2$ Molecular weight: 464.9 MS (m/e): 464.9 (M+H$^+$)

$^1$H-NMR (400 MHz, CDCl$_3$): δ 9.00 (t, 1H), 8.53 (t, 1H), 8.36 (s, 1H), 7.69-7.66 (m, 1H), 7.39 (s, 1H), 7.36 (m, 1H), 7.28 (d, 1H), 7.20 (d, 2H), 6.86 (d, 1H), 4.64 (d, 2H), 4.56 (m, 2H), 3.89 (d, 2H), 3.88 (s, 3H), 3.53 (m, 2H), 1.63 (m, 2H), 0.74 (m, 1H), 0.22 (m, 1H).

Example 3

Preparation: N-benzyl-2-(3-azabicyclo[3.1.0]hexan-3-yl)-4-((3-chloro-4-methoxybenzyl)amino)pyrimidine-5-formamide (Compound 3)

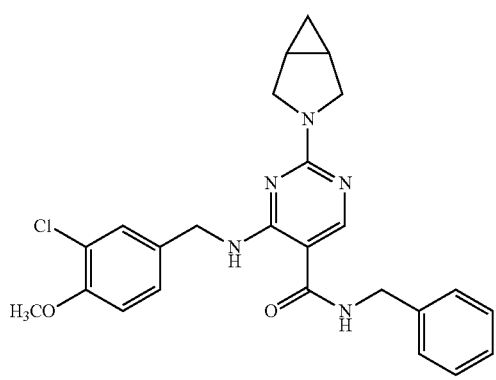

(1) Preparation: N-benzyl-4-((3-chloro-4-methoxybenzyl)amino)-2-(methylthio) pyrimidine-5-formamide

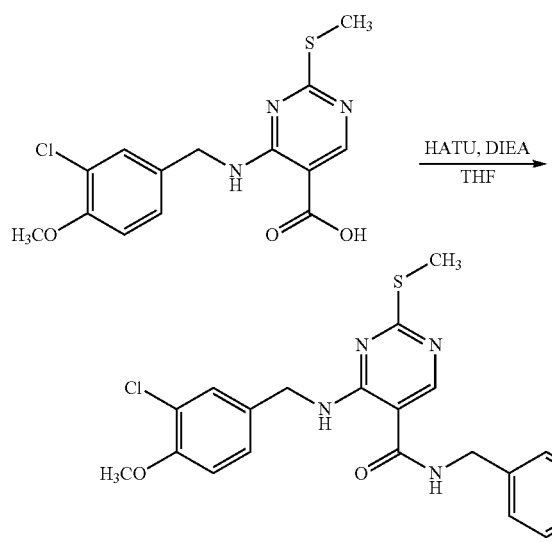

In THF (60 mL) were dissolved 4-((3-chloro-4-methoxybenzyl)amino)-2-(methylthio) pyrimidine-5-carboxylic acid (1.0 g, 2.95 mmol), benzylamine (379 mg, 3.54 mmol) and HATU (1.35 g, 3.54 mmol). DIEA (1 mL, 5.9 mmol) was added dropwisely. The reaction was conducted at ambient temperature for 8 h, followed by addition of water and extraction with DCM. The organic phase was dried over sodium sulfate. Then the solvent was removed by rotary evaporation. The obtained solid was purified by silica gel column chromatography (DCM/methanol=50/1). The product was N-benzyl-4-((3-chloro-4-methoxybenzyl)amino)-2-(methylthio) pyrimidine-5-formamide as a faint yellow solid (800 mg, yield 63%).

(2) Preparation: N-benzyl-4-((3-chloro-4-methoxybenzyl)amino)-2-(methylsulfinyl) pyrimidine-5-formamide

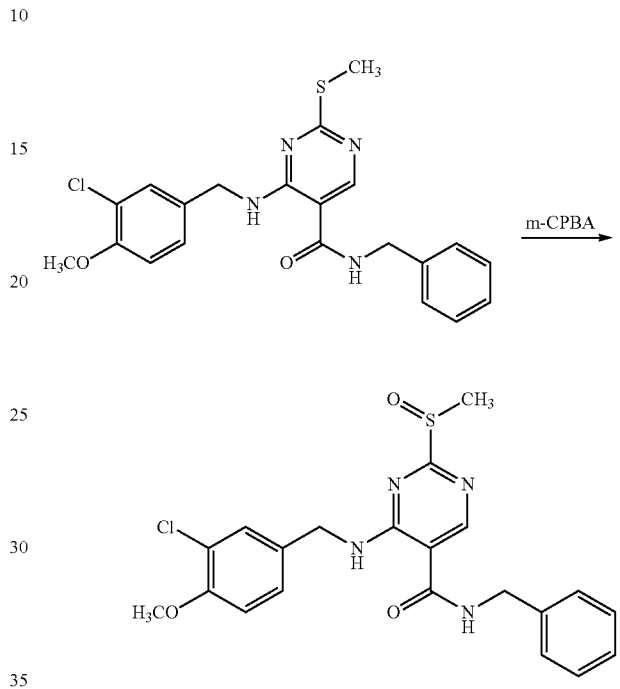

In DCM (20 mL) was dissolved N-benzyl-4-((3-chloro-4-methoxybenzyl)amino)-2-(methylthio)pyrimidine-5-formamide (201 mg, 0.47 mmol). Then was added m-CPBA (80 mg, 0.47 mmol). The reaction was conducted at ambient temperature for 5 h. After the reaction was completed, the reaction mixture was washed with water and extracted with DCM. The organic phase was dried, and the solvent was removed by rotary evaporation. The obtained solid was used in the subsequent procedure without further purification.

(3) Preparation: N-benzyl-2-(3-azabicyclo[3.1.0]hexan-3-yl)-4-((3-chloro-4-methoxybenzyl)amino)-pyrimidine-5-formamide

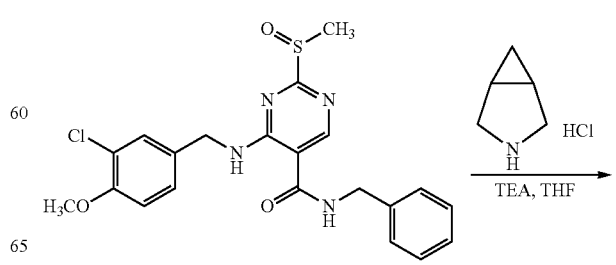

-continued

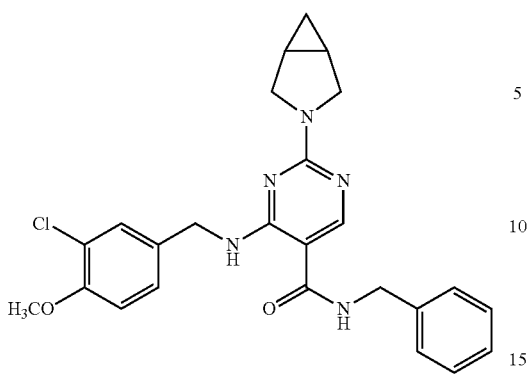

In absolute THF (15 mL) were dissolved N-benzyl-4-((3-chloro-4-methoxybenzyl)amino)-2-(methylsulfinyl)pyrimidine-5-formamide (200 mg, 0.45 mmol) and 3-azabicyclo[3.1.0]hexane hydrochloride salt (81 mg, 0.68 mmol). Triethylamine (137 mg, 1.35 mmol) was added dropwisely. The reaction was conducted at ambient temperature for 5 h. The solvent was removed by rotary evaporation, followed by addition of water and extraction with DCM. The organic phase was dried over sodium sulfate and concentrated. The obtained solid was purified by silica gel column chromatography (DCM/methanol=50/1) to give a yellow solid (50 mg, 24% yield).

Molecular formula: $C_{25}H_{26}ClN_5O_2$ Molecular weight: 463.9 MS (m/e): 464.0 (M+1)

$^1$H-NMR (400 MHz, DMSO-$d_6$, hydrochloride salt): δ 12.90 (br s, 1H), 10.01 (m, 1H), 9.40 (m, 1H), 8.44 (s, 1H), 7.46 (s, 1H), 7.22-7.34 (m, 5H), 7.23 (t, 1H), 7.09 (d, 1H), 4.56 (m, 2H), 4.40 (d, 2H), 3.89 (d, 1H), 3.86 (s, 3H), 3.72 (d, 1H), 3.60 (m, 2H), 1.74 (d, 2H), 0.78 (m, 1H), 0.21 (m, 1H).

Example 3-1

Preparation: N-benzyl-2-(3-azabicyclo[3.1.0]hexan-3-yl)-4-((3-chloro-4-methoxybenzyl)amino)-pyrimidine-5-formamide (Compound 3)

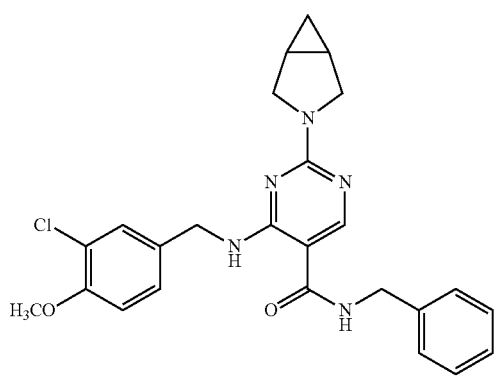

The procedures (1) to (2) were analogous to procedures (1) to (2) of Example 3.

(3) Preparation: N-benzyl-2-(3-azabicyclo[3.1.0]hexan-3-yl)-4-((3-chloro-4-methoxybenzyl)amino) pyrimidine-5-formamide

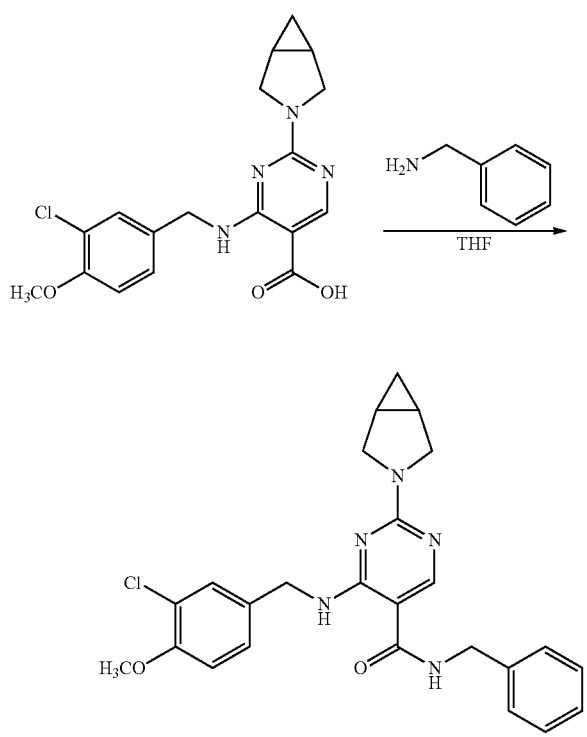 [SMILES: COc1ccc(CNc2nc(N3CC4CC4C3)ncc2C(=O)O)cc1Cl ; NCc1ccccc1 ; COc1ccc(CNc2nc(N3CC4CC4C3)ncc2C(=O)NCc2ccccc2)cc1Cl ; "THF"]

In THF (50 mL) were dissolved 2-(3-azabicyclo[3.1.0]hexan-3-yl)-4-((3-chloro-4-methoxybenzyl)amino)pyrimidine-5-carboxylic acid (16 g, 42.8 mmol), benzylamine (5.0 g, 47 mmol), HATU (17.9 g, 47 mmol) and DIEA (11 g, 85.6 mmol). The reaction mixture was stirred at ambient temperature overnight and concentrated, followed by addition of DCM (500 mL). After the completion of the reaction, water (500 mL×4) was added to the reaction mixture for extraction. The organic phase was concentrated. The crude product was purified by silica gel column chromatography to give N-benzyl-2-(3-azabicyclo[3.1.0]hexan-3-yl)-4-((3-chloro-4-methoxybenzyl)amino)pyrimidine-5-formamide as the product (50 mg, 24% yield).

Molecular formula: $C_{25}H_{26}ClN_5O_2$ Molecular weight: 463.9 MS (m/e): 464.0 (M+H$^+$)

$^1$H-NMR (400 MHz, CDCl$_3$): δ 8.99 (s, 1H), 8.14 (s, 1H), 7.40-7.28 (m, 5H), 7.20 (d, 1H), 6.86 (d, 1H), 6.20 (s, 1H), 4.59-4.53 (m, 4H), 3.88-3.79 (m, 5H), 3.50 (m, 2H), 1.59-1.57 (m, 2H), 0.76-0.71 (m, 1H), 0.20-0.19 (m, 1H).

Example 4

Preparation: 2-(3-azabicyclo[3.1.0]hexan-3-yl)-4-((3-chloro-4-methoxy benzyl)amino)-N-((5-methylpyrazin-2-yl)methyl)pyrimidine-5-formamide (Compound

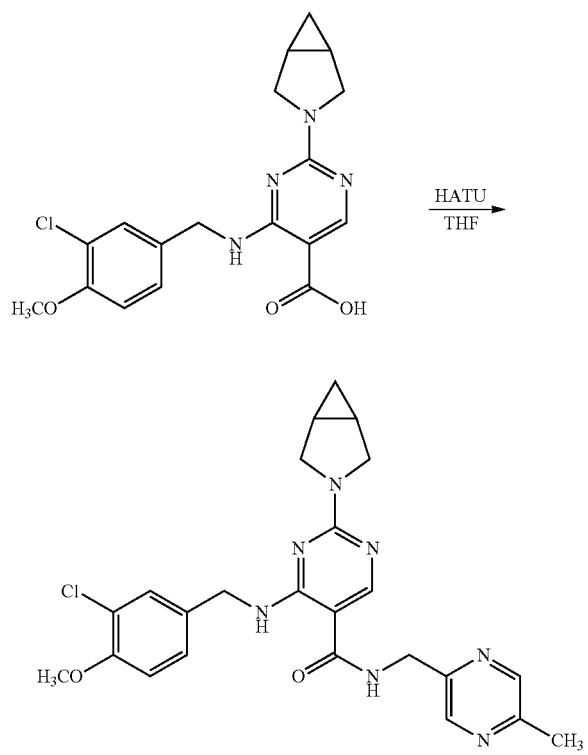

In THF (50 mL) were dissolved 2-(3-azabicyclo[3.1.0]hexan-3-yl)-4-((3-chloro-4-methoxybenzyl)amino)pyrimidine-5-carboxylic acid (202 mg, 0.54 mmol), (5-methylpyrazine-2-yl)methylamine (79 mg, 0.64 mmol) and triethylamine (0.2 mL). The solution was cooled in an ice bath and HATU (266 mg, 0.70 mmol) was then added. The reaction was conducted at ambient temperature for 18 h. The reaction mixture was concentrated, followed by addition of water and extraction with ethyl acetate. The organic phase was dried, concentrated, and purified by silica gel column chromatography (DCM/methanol=50/1) to give 2-(3-azabicyclo[3.1.0]hexan-3-yl)-4-((3-chloro-4-methoxybenzyl)amino)-N-((5-methylpyrazine-2-yl)methyl)pyrimidine-5-formamide (105 mg, 40% yield).

Molecular formula: $C_{24}H_{26}ClN_7O_2$ Molecular weight: 480.0 MS (m/e): 480.0 (M+H$^+$)

$^1$H-NMR (400 MHz, CDCl$_3$): δ 9.98 (t, 1H), 8.53 (s, 1H), 8.42 (s, 1H), 8.27 (s, 1H), 7.80 (t, 1H), 7.33 (s, 1H), 7.16 (d, 1H), 6.91 (d, 1H), 4.60 (m, 4H), 3.94 (d, 1H), 3.90 (s, 3H), 3.74 (m, 3H), 2.57 (s, 3H), 1.81 (m, 2H), 0.95 (m, 1H), 0.26 (m, 1H).

Example 4-1

Preparation: 2-(3-azabicyclo[3.1.0]hexan-3-yl)-4-((3-chloro-4-methoxy benzyl)amino)-N-((5-methylpyrazine-2-yl)methyl)pyrimidine-5-formamide (Compound 4)

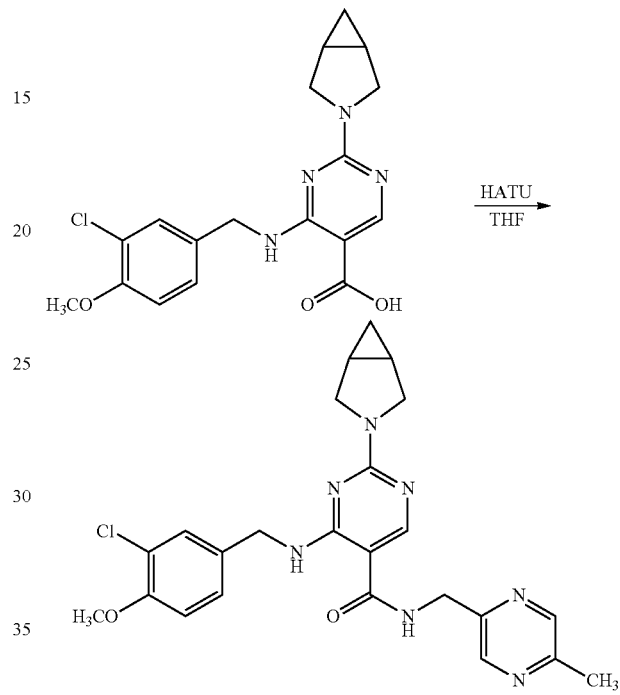

The procedures were analogous to Example 4.

Molecular formula: $C_{24}H_{26}ClN_7O_2$ Molecular weight: 480.0 MS (m/e): 480.0 (M+H$^+$)

$^1$H-NMR (400 MHz, CDCl$_3$): δ 9.98 (t, 1H), 8.53 (s, 1H), 8.42 (s, 1H), 8.27 (s, 1H), 7.80 (t, 1H), 7.33 (s, 1H), 7.16 (d, 1H), 6.91 (d, 1H), 4.64-4.57 (m, 4H), 3.94 (d, 1H), 3.90 (s, 3H), 3.75-3.72 (m, 3H), 2.57 (s, 3H), 1.81 (m, 2H), 0.95 (m, 1H), 0.26 (m, 1H).

Example 5

Preparation: 2-(3-azabicyclo[3.1.0]hexan-3-yl)-4-((3-chloro-4-methoxy benzyl)amino)-N-(4-fluorobenzyl)pyrimidine-5-formamide (Compound 5)

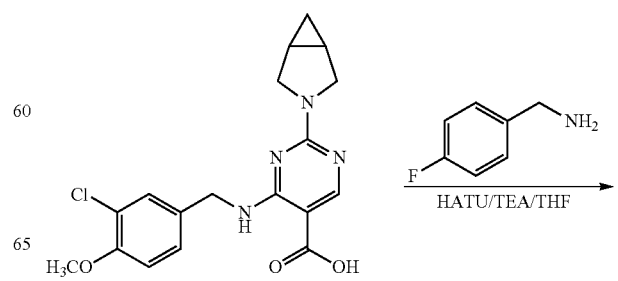

91
-continued

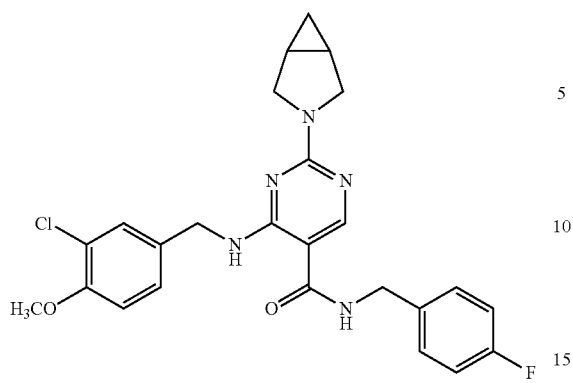

In THF (10 mL) were dissolved 2-(3-azabicyclo[3.1.0]hexan-3-yl)-4-((3-chloro-4-methoxybenzyl)amino)-pyrimidine-5-carboxylic acid (150 mg, 0.40 mmol), 4-fluorobenzylamine (56 mg, 0.45 mmol) and triethylamine (101 mg, 1 mmol). The reaction mixture was cooled in an ice bath and HATU (266 mg, 0.70 mmol) was added. The reaction was conducted at ambient temperature for 18 h. The reaction mixture was concentrated, followed by addition of water and extraction with ethyl acetate. The organic phase was dried, concentrated, and purified by silica gel column chromatography (DCM/methanol=20/1) to give 2-(3-azabicyclo[3.1.0]hexan-3-yl)-4-((3-chloro-4-methoxybenzyl)amino)-N-(4-fluorobenzyl)pyrimidine-5-formamide (30 mg, 16% yield).

Molecular formula: $C_{25}H_{25}ClFN_5O_2$ Molecular weight: 481.9 MS (m/e): 482.0 (M+1)

$^1$H-NMR (400 MHz, CDCl$_3$, hydrochloride salt): δ 13.20 (br s, 1H), 10.08 (t, 1H), 9.69 (t, 1H), 8.52 (s, 1H), 7.45 (s, 1H), 7.30-7.36 (m, 3H), 7.08-7.15 (m, 3H), 4.58 (m, 2H), 4.66 (d, 2H), 3.90 (d, 2H), 3.88 (s, 3H), 3.60 (m, 2H), 1.78 (d, 2H), 0.79 (m, 1H), 0.22 (m, 1H).

Example 5-1

Preparation: 2-(3-azabicyclo[3.1.0]hexan-3-yl)-4-((3-chloro-4-methoxy benzyl)amino)-N-(4-fluorobenzyl)pyrimidine-5-formamide (Compound 5)

92
-continued

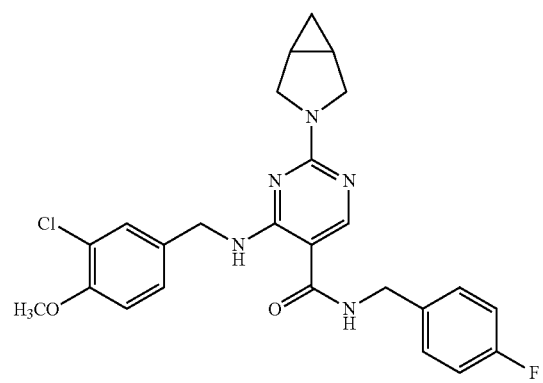

In THF (10 mL) were dissolved 2-(3-azabicyclo[3.1.0]hexan-3-yl)-4-((3-chloro-4-methoxybenzyl)amino)pyrimidine-5-carboxylic acid (150 mg, 0.40 mmol), 4-fluorobenzylamine (56 mg, 0.45 mmol) and triethylamine (101 mg, 1 mmol). The reaction mixture was cooled in an ice bath and HATU (266 mg, 0.70 mmol) was added. The reaction was conducted at ambient temperature for 4 h. The reaction mixture was diluted with water and extracted with DCM. The organic phase was dried, concentrated, and purified by silica gel column chromatography (DCM/methanol=20/1) to give 2-(3-azabicyclo[3.1.0]hexan-3-yl)-4-((3-chloro-4-methoxybenzyl)amino)-N-(4-fluorobenzyl) pyrimidine-5-formamide (30 mg, 16% yield).

Molecular formula: $C_{25}H_{25}ClFN_5O_2$ Molecular weight: 481.9 MS (m/e): 482.0 (M+H$^+$)

$^1$H-NMR (400 MHz, DMSO-d$_6$, hydrochloride salt): δ 13.20 (br s, 1H), 10.08 (t, 1H), 9.69 (t, 1H), 8.57 (s, 1H), 7.45 (s, 1H), 7.37-7.30 (m, 3H), 7.15-7.08 (m, 3H), 4.60-4.52 (m, 2H), 4.36 (d, 2H), 3.86 (d, 2H), 3.81 (s, 3H), 3.62-3.57 (m, 2H), 1.78 (d, 2H), 0.79 (m, 1H), 0.22 (m, 1H).

Example 6

Preparation: 2-(3-azabicyclo[3.1.0]hexan-3-yl)-4-((3-chloro-4-methoxy benzyl)amino)-N-(2-morpholinylethyl)pyrimidine-5-formamide (Compound 6)

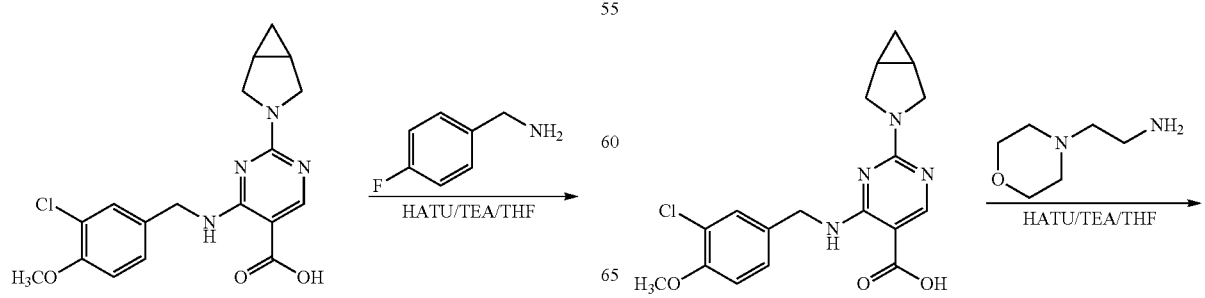

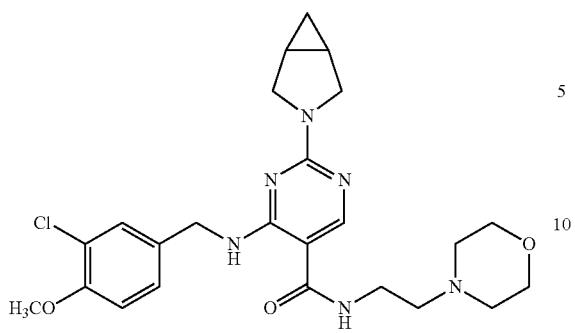

In THF (10 mL) were dissolved 2-(3-azabicyclo[3.1.0]hexan-3-yl)-4-((3-chloro-4-methoxybenzyl)amino)-pyrimidine-5-carboxylic acid (150 mg, 0.40 mmol), 2-morpholinylethylamine (59 mg, 0.45 mmol) and triethylamine (101 mg, 1 mmol). The reaction mixture was cooled in an ice bath and HATU (266 mg, 0.70 mmol) was added. The reaction was conducted at ambient temperature for 18 h. The reaction mixture was concentrated, followed by addition of water and extraction with ethyl acetate. The organic phase was dried, concentrated, and purified by silica gel column chromatography (DCM methanol=20/1) to give 2-(3-azabicyclo[3.1.0]hexan-3-yl)-4-((3-chloro-4-methoxybenzyl)amino)-N-(2-morpholinylethyl)pyrimidine-5-formamide (71 mg, 36.5% yield).

Molecular formula: $C_{24}H_{31}ClN_6O_3$ Molecular weight: 487.0 MS (m/e): 487.0 (M+1)

$^1$H-NMR (400 MHz, CDCl$_3$): δ 9.04 (t, 1H), 8.18 (s, 1H), 7.38 (d, 1H), 7.20 (d, 1H), 6.86 (d, 1H), 6.62 (t, 1H), 4.53 (m, 2H), 3.88 (s, 3H), 3.85 (d, 2H), 3.71 (t, 4H), 3.53 (m, 2H), 3.43 (m, 2H), 2.59 (t, 2H), 2.50 (m, 4H), 1.61 (m, 2H), 0.76 (m, 1H), 0.22 (m, 1H).

In THF (10 mL) were dissolved 2-(3-azabicyclo[3.1.0]hexan-3-yl)-4-((3-chloro-4-methoxybenzyl)amino)-pyrimidine-5-carboxylic acid (150 mg, 0.40 mmol) and 2-morpholinylethylamine (59 mg, 0.45 mmol). HATU (190 mg, 0.50 mmol) and triethylamine (101 mg, 1 mmol) were then added. The reaction was conducted at ambient temperature for 4 h. Then the reaction mixture was diluted with water and extracted with DCM. The organic phase was dried, concentrated, and purified by silica gel column chromatography (DCM/methanol=20/1) to give 2-(3-azabicyclo[3.1.0]hexan-3-yl)-4-((3-chloro-4-methoxybenzyl)amino)-N-(2-morpholinylethyl)pyrimidine-5-formamide as a white solid (71 mg, 36.5% yield).

Molecular formula: $C_{24}H_{31}ClN_6O_3$ Molecular weight: 487.0 MS (m/e): 487.0 (M+H$^+$)

$^1$H-NMR (400 MHz, CDCl$_3$): δ 9.04 (t, 1H), 8.18 (s, 1H), 7.38 (d, 1H), 7.20 (d, 1H), 6.86 (d, 1H), 6.62 (t, 1H), 4.59-4.53 (m, 2H), 3.88 (s, 3H), 3.85 (d, 2H), 3.71 (t, 4H), 3.56-3.49(m, 2H), 3.44-3.41 (m, 2H), 2.59 (t, 2H), 2.50 (m, 4H), 1.62-1.60 (m, 2H), 0.79-0.74 (m, 1H), 0.23-0.20 (m, 1H).

Example 7

Preparation: 2-(3-azabicyclo[3.1.0]hexan-3-yl)-4-((3-chloro-4-methoxy benzyl)amino)-N-(piperdin-4-ylmethyl)pyrimidine-5-formamide (Compound 7)

Example 6-1

Preparation: 2-(3-azabicyclo[3.1.0]hexan-3-yl)-4-((3-chloro-4-methoxy benzyl)amino)-N-(2-morpholinylethyl)pyrimidine-5-formamide (Compound 6)

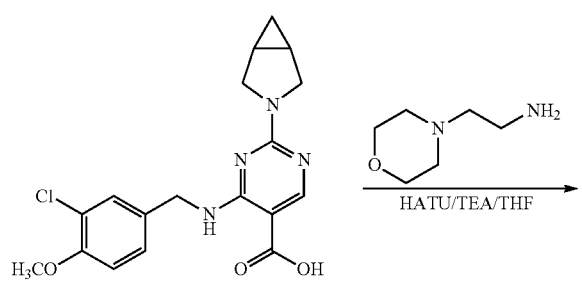

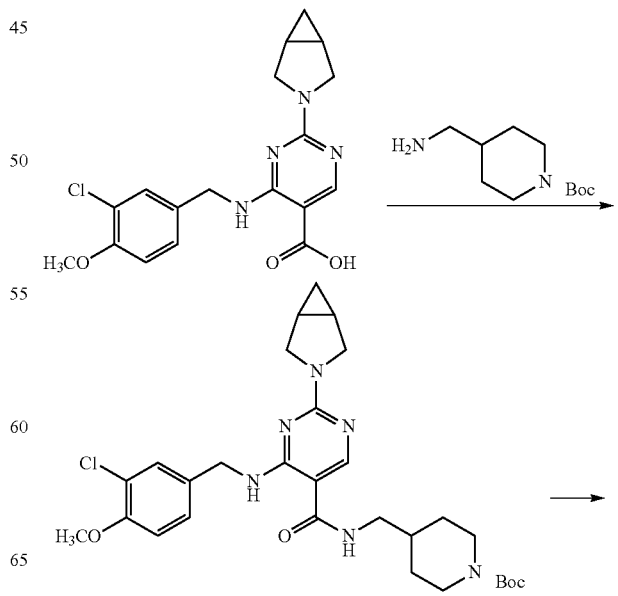

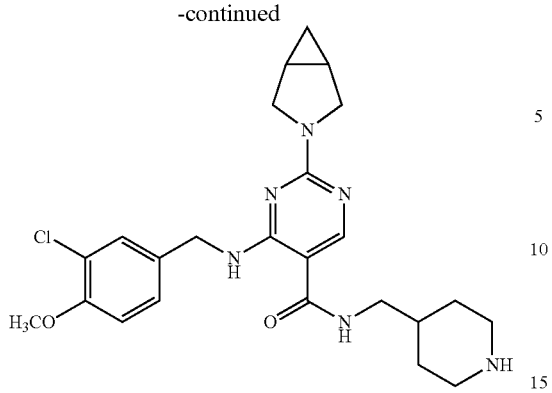

In THF (20 mL) were dissolved 2-(3-azabicyclo[3.1.0]hexan-3-yl)-4-((3-chloro-4-methoxybenzyl)amino)-pyrimidine-5-carboxylic acid (150 mg, 0.40 mmol), tert-butyl 4-(aminomethyl)piperidine-1-carboxylate (128 mg, 0.60 mmol) and HATU (182 mg, 0.48 mmol). DIEA (0.20 mL, 1.2 mmol) was added dropwisely. The reaction was conducted at ambient temperature for 8 h. The reaction mixture was concentrated, followed by addition of water and extraction with DCM. The organic phase was dried, concentrated, and purified by silica gel column chromatography (DCM/methanol=50/1) to give a white solid. The product was dissolved in DCM (10 mL), and trifluoroacetic acid (1 mL) was added. The reaction was conducted at ambient temperature for 4 h. Then the reaction mixture was adjusted to a pH of 9 with saturated aqueous sodium bicarbonate. The organic phase was dried and the solvent was removed by rotary evaporation to give 2-(3-azabicyclo[3.1.0]hexan-3-yl)-4-((3-chloro-4-methoxybenzyl)amino)-N-(piperdin-4-ylmethyl)pyrimidine-5-formamide (34 mg, 18% yield).

Molecular formula: $C_{24}H_{31}ClN_6O_2$ Molecular weight: 471.0 MS (m/e): 471.0 (M+H$^+$)

$^1$H-NMR (400 MHz, CDCl$_3$): δ 8.92 (t, 1H), 8.14 (s, 1H), 7.38 (d, 1H), 7.20 (d, 1H), 6.85 (d, 1H), 5.93 (t, 1H), 4.53 (m, 2H), 3.88 (s, 3H), 3.84 (d, 2H), 3.48 (m, 2H), 3.22 (t, 2H), 3.08 (d, 2H), 2.58 (t, 2H), 1.85 (m, 3H), 1.58 (m, 3H), 1.16 (m, 2H), 0.74 (m, 1H), 0.20 (m, 1H).

Example 8

Preparation: 2-(3-azabicyclo[3.1.0]hexan-3-yl)-4-((3-chloro-4-methoxy benzyl)amino)-N-((s)-caprolactam-3-yl)pyrimidine-5-formamide (Compound 8)

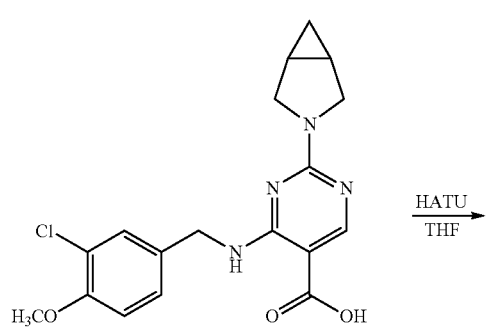

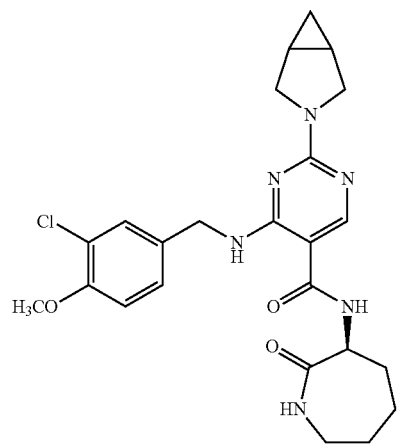

In THF (30 mL) were dissolved 2-(3-azabicyclo[3.1.0]hexan-3-yl)-4-((3-chloro-4-methoxybenzyl)amino)pyrimidine-5-carboxylic acid (202 mg, 0.54 mmol) and DIEA (0.3 mL, 1.78 mmol). The reaction mixture was cooled in an ice bath. HATU (250 mg, 0.65 mmol) and (s)-3-aminoazaheptane-2-one (76 mg, 0.60 mmol) were added. The reaction was conducted at ambient temperature overnight. The reaction mixture was concentrated, followed by addition of water and extraction with ethyl acetate. The organic phase was dried, concentrated, and purified by silica gel column chromatography (DCM/methanol=50/1) to give 2-(3-azabicyclo[3.1.0]hexan-3-yl)-4-((3-chloro-4-methoxybenzyl)amino)-N-((s)-caprolactam-3-yl)pyrimidine-5-formamide (60 mg, yield 23%).

Molecular formula: $C_{24}H_{29}ClN_6O_3$ Molecular weight: 485.0 MS (m/e): 485.0 (M+H$^+$)

$^1$H-NMR (400 MHz, CDCl$_3$): δ 8.92 (t, 1H), 8.31 (s, 1H), 7.38 (d, 1H), 7.36 (d, 1H), 7.19 (d, 1H), 6.86 (d, 1H), 5.98 (t, 1H), 4.56-4.60 (m, 3H), 3.88 (s, 3H), 3.86 (d, 2H), 3.51 (m, 2H), 3.28 (m, 2H), 2.12 (d, 1H), 2.02 (m, 1H), 1.86 (t, 2H), 1.25-1.57 (m, 4H), 0.74 (m, 1H), 0.21 (m, 1H).

Example 9

Preparation: 2-(3-azabicyclo[3.1.0]hexan-3-yl)-4-((3-chloro-4-methoxy benzyl)amino)-N-cycloheptanylpyrimidine-5-formamide (Compound 9)

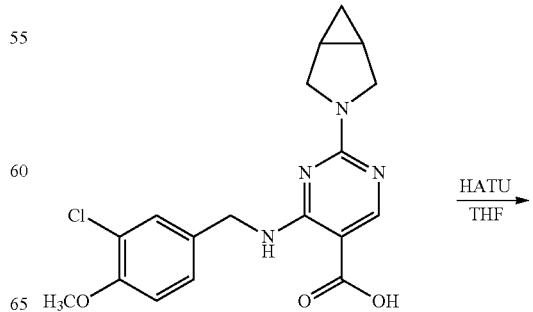

-continued

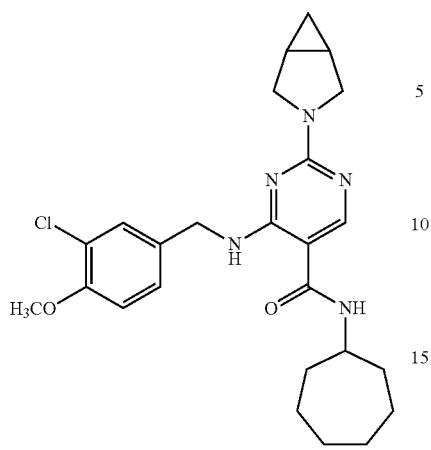

In THF (30 mL) were dissolved 2-(3-azabicyclo[3.1.0]hexan-3-yl)-4-(3-chloro-4-methoxybenzylamino)-pyrimidine-5-carboxylic acid (202 mg, 0.54 mmol) and DIEA (0.3 mL, 1.78 mmol). The reaction mixture was cooled in an ice bath, then HATU (250 mg, 0.65 mmol) and cycloheptanyl amine (67 mg, 0.60 mmol) were added. The reaction was conducted at ambient temperature overnight. The reaction mixture was concentrated, quenched with water and extracted with ethyl acetate. The organic phase was dried, concentrated, and purified by silica gel column chromatography (ethyl acetate/petroleum ether=3/1) to give 2-(3-azabicyclo[3.1.0]hexan-3-yl)-4-((3-chloro-4-meth oxybenzyl)amino)-N-cycloheptylpyrimidine-5-formamide (98 mg, 38.6% yield).

Molecular formula: $C_{25}H_{32}ClN_5O_2$ Molecular weight: 470.0 MS (m/e): 470.0 (M+H$^+$)

$^1$H-NMR (400 MHz, DMSO, hydrochloride salt): δ 12.8 (brs, 1H), 10.00 (brs, 1H), 8.71 (m, 1H), 8.34 (s, 1H), 7.46 (s, 1H), 7.32 (d, 1H), 7.10 (d, 1H), 4.56 (m, 2H), 3.88 (m, 2H), 3.87 (s, 3H), 3.84 (m, 1H), 3.60 (m, 2H), 1.33-1.82 (m, 13H), 0.74 (m, 1H), 0.22 (m, 1H).

Example 10

Preparation: 2-(3-azabicyclo[3.1.0]hexan-3-yl)-4-((3-chloro-4-methoxy benzyl)amino)-N-(1-methylpiperidin-4-yl)pyrimidine-5-formamide (Compound 10)

(1) Preparation: tert-butyl 4-(2-(3-azabicyclo[3.1.0]hexan-3-yl)-4-((3-chloro-4-methoxy benzylamino)pyrimidine-5-formamido)piperidine-1-carboxylate

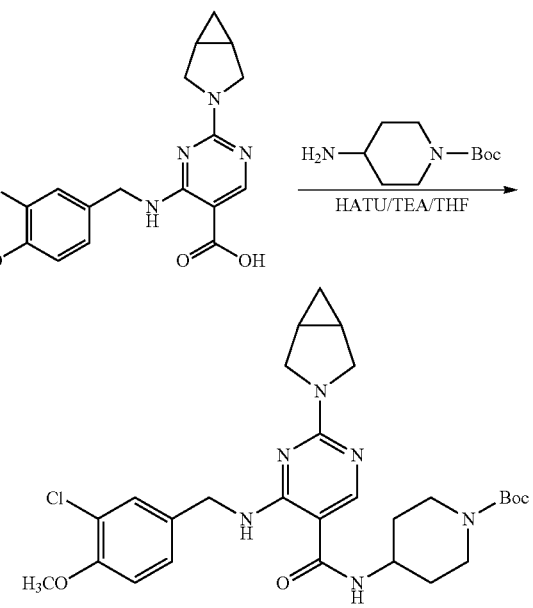

In THF (10 mL) were dissolved 2-(3-azabicyclo[3.1.0]hexan-3-yl)-4-((3-chloro-4-methoxybenzyl)amino)pyrimidine-5-carboxylic acid (187 mg, 0.50 mmol), tert-butyl 4-aminopiperidine-1-carboxylate (110 mg, 0.55 mmol) and triethylamine (101 mg, 1 mmol), and HATU (230 mg, 0.60 mmol) was then added. The reaction was conducted at ambient temperature for 4 h. The reaction mixture was concentrated, followed by addition of water (50 mL) and extraction with DCM. The organic phase was dried, concentrated, and purified by silica gel column chromatography (DCM methanol=20/1) to give tert-butyl 4-(2-(3-azabicyclo[3.1.0]hexan-3-yl)-4-((3-chloro-4-methoxybenzyl)amino)pyrimidine-5-formamido)piperidine-1-carboxylate (235 mg, 84.4% yield).

(2) Preparation: 2-(3-azabicyclo[3.1.0]hexan-3-yl)-4-((3-chloro-4-methoxybenzyl)amino)-N-(piperidin-4-yl)pyrimidine-5-formamido

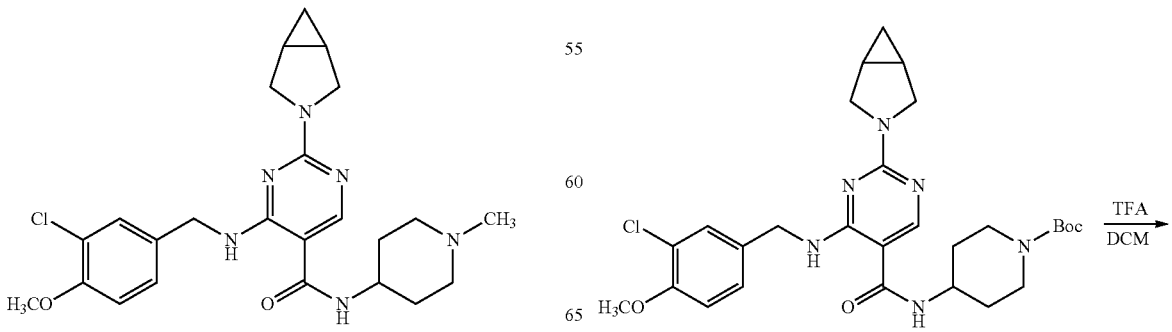

-continued

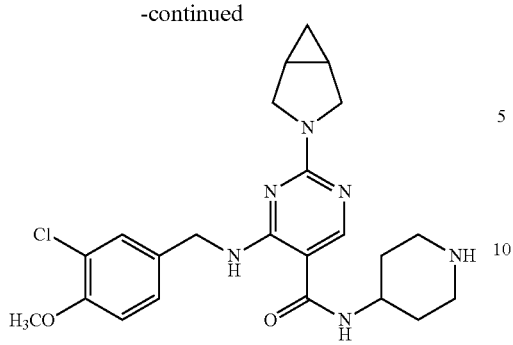

In DCM (15 mL) was dissolved tert-butyl 4-(2-(3-azabi-cyclo[3.1.0]hexan-3-yl)-4-(3-chloro-4-methoxybenzy-lamino)pyrimidine-5-formamido)piperidine-1-carboxylate (235 mg, 0.42 mmol), then trifluoroacetic acid (1 mL) was added. The reaction mixture was stirred at ambient temperature for 2 h and concentrated to give a solid. The product was used in the subsequent procedure without further purification.

(3) Preparation: 2-(3-azabicyclo[3.1.0]hexan-3-yl)-4-(3-chloro-4-methoxybenzyl amino)-N-(1-methylpip-eridin-4-yl)pyrimidine-5-formamide

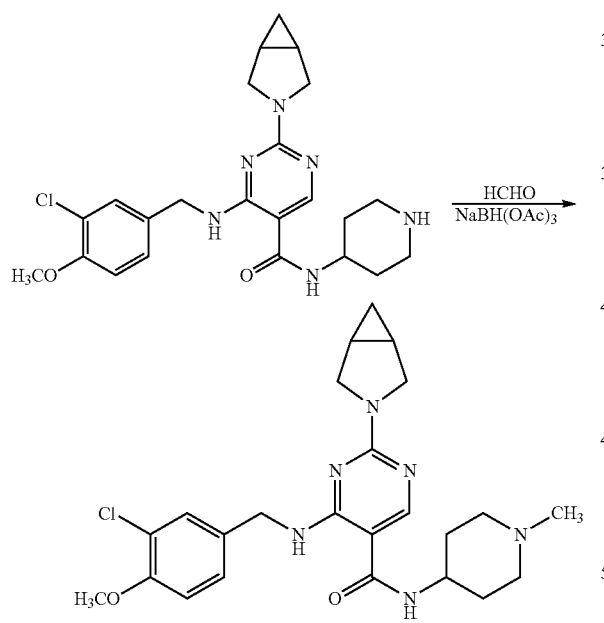

In THF (20 mL) was dissolved the above 2-(3-azabicyclo[3.1.0]hexan-3-yl)-4((3-chloro-4-methoxybenzyl)amino)-N-(1-piperidin-4-yl)pyrimidine-5-formamide, and formalin (1 mL) was added. The reaction was conducted at ambient temperature for 1 h, and sodium triacetoxyborohydride (134 mg, 0.633 mmol) was added. The reaction was continued for 4 h, then quenched with water, filtrated, dried and concentrated. The obtained solid was purified by silica gel column chromatography (DCM/methanol=20/1) to give 2-(3-azabi-cyclo[3.1.0]hexan-3-yl)-4-((3-chloro-4-methoxybenzyl)amino)-N-(1-methylpiperidin-4-yl)pyrimidine-5-formamide (55 mg, 28% yield).

Molecular formula: $C_{24}H_{31}ClN_6O_2$ Molecular weight: 471.0 MS (m/e): 471.0 (M+1)

$^1$H-NMR (400 MHz, CDCl$_3$): δ 8.95 (m, 1H), 8.33 (m, 1H), 7.36 (d, 1H), 7.20 (d, 1H), 6.86 (d, 1H), 6.65 (m, 1H), 4.53 (m, 2H), 4.10 (m, 1H), 3.88 (s, 3H), 3.86 (d, 2H), 3.48 (m, 2H), 2.80 (m, 2H), 2.74 (s, 3H), 2.18 (m, 4H), 1.60 (m, 2H), 1.23 (m, 2H), 0.76 (m, 1H), 0.20 (m, 1H).

Example 10-1

Preparation: 2-(3-azabicyclo[3.1.0]hexan-3-yl)-4-((3-chloro-4-methoxy benzyl)amino)-N-(1-methylpi-peridin-4-yl)pyrimidine-5-formamide (Compound 10)

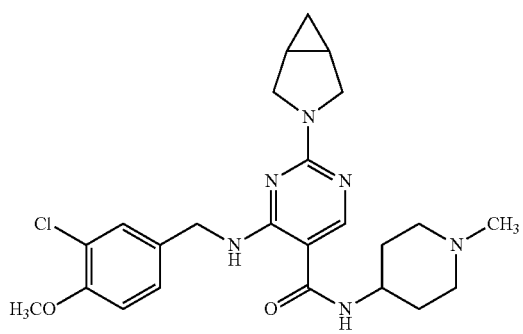 [SMILES: COc1ccc(CNc2nc(N3CC4CC4C3)ncc2C(=O)NC2CCN(C)CC2)cc1Cl]

The procedures (1) to (2) were analogous to procedures (1) to (2) of Example 10.

(3) Preparation: 2-(3-azabicyclo[3.1.0]hexan-3-yl)-4-((3-chloro-4-methoxybenzyl)amino)-N-(1-methylpi-peridin-4-yl)pyrimidine-5-formamide

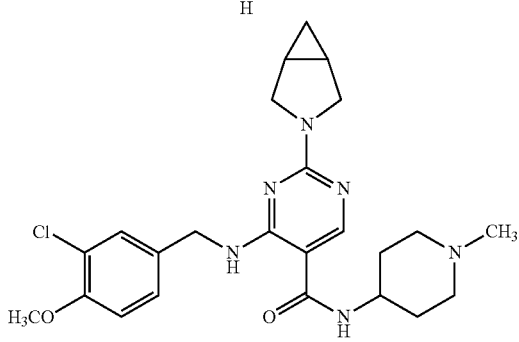

In THF (20 mL) was dissolved the above 2-(3-azabicyclo[3.1.0]hexan-3-yl)-4-((3-chloro-4-methoxybenzyl)amino)-

N-(1-piperidin-4-yl)pyrimidine-5-formamide, formalin (1 mL) was added at 0° C. The reaction was conducted at ambient temperature for 1 h, and sodium triacetoxyborohydride (134 mg, 0.633 mmol) was added at 0° C. The reaction was continued for 4 h, then quenched with water, filtrated, dried and concentrated. The obtained solid was purified by silica gel column chromatography (DCM/methanol=20/1) to give 2-(3-azabicyclo[3.1.0]hexan-3-yl)-4-((3-chloro-4-methoxybenzyl)amino)-N-(1-methylpiperidin-4-yl)pyrimidine-5-formamide (55 mg, 7.7% yield).

Molecular formula: $C_{24}H_{31}ClN_6O_2$ Molecular weight: 471.0 MS (m/e): 471.0 (M+H$^+$)

$^1$H-NMR (400 MHz, CDCl$_3$): δ 8.95 (m, 1H), 8.31 (m, 1H), 7.36 (d, 1H), 7.20 (d, 1H), 6.86 (d, 1H), 6.65 (m, 1H), 4.56-4.52 (m, 2H), 4.11-4.10 (m, 1H), 3.88 (s, 3H), 3.86 (d, 2H), 3.51-3.46 (m, 2H), 2.80-2.74 (m, 5H), 2.18-2.05 (m, 4H), 1.60 (m, 2H), 1.26-1.19 (m, 2H), 0.78-0.75 (m, 1H), 0.21-0.18 (m, 1H).

Example 11

Preparation: 2-(3-azabicyclo[3.1.0]hexan-3-yl)-4-((3-chloro-4-methoxy benzyl)amino)-N-(trans-4-hydroxycyclohexyl)pyrimidine-5-formamide (Compound 11)

(1) Preparation: ethyl 4-((3-chloro-4-methoxybenzyl)amino)-2-(methylthio) pyrimidine-5-carboxylate

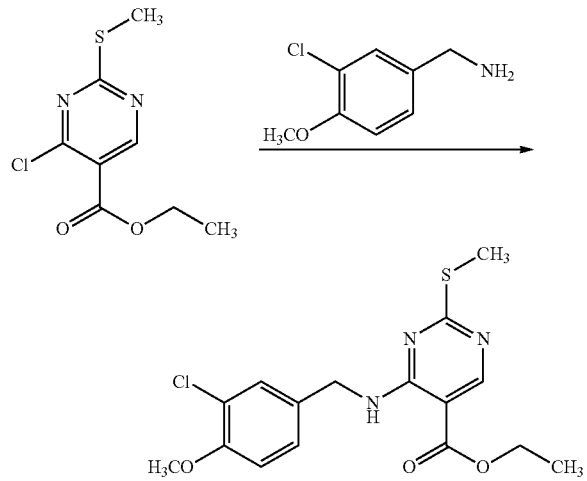

In DCM (100 mL) were dissolved ethyl 4-chloro-2-(methylthio)pyrimidine-5-carboxylate (5.0 g, 21.55 mmol), 3-chloro-4-methoxybenzylamine hydrochloride salt (4.0 g, 23.4 mmol) and triethylamine (4.35 g, 43.1 mmol). The reaction mixture was stirred at ambient temperature for 10 h and washed with water. The organic phase was dried over magnesium sulfate and concentrated to give ethyl 4-((3-chloro-4-methoxybenzyl)amino)-2-(methylthio)pyrimidine-5-carboxylate as a solid (6.0 g, 76% yield).

(2) Preparation: 4-((3-chloro-4-methoxybenzyl)amino)-2-(methylthio)pyrimidine-5-carboxylic acid

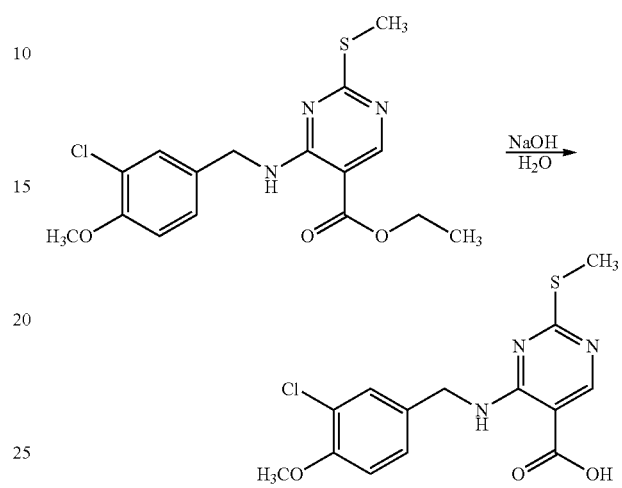

In the mixture of water (10 mL), methanol (30 mL) and THF (30 mL) were dissolved ethyl 4-((3-chloro-4-methoxybenzyl)amine)-2-(methylthio)pyrimidine-5-carboxylate (6.0 g, 16.3 mmol) and sodium hydrate (1.14 g, 28.57 mmol). The reaction was conducted at 60° C. for 10 h. The reaction mixture was cooled to ambient temperature and adjusted to a pH of 4 by adding dilute hydrochloric acid dropwise. The solid was precipitated, filtrated, washed with methanol and dried to give 4-((3-chloro-4-methoxybenzyl)amino)-2-(methylthio) pyrimidine-5-carboxylic acid (4.2 g, 76% yield).

(3) Preparation: 4-((3-chloro-4-methoxybenzyl)amino)-2-(methylsulfinyl)pyrimidine-5-carboxylic acid

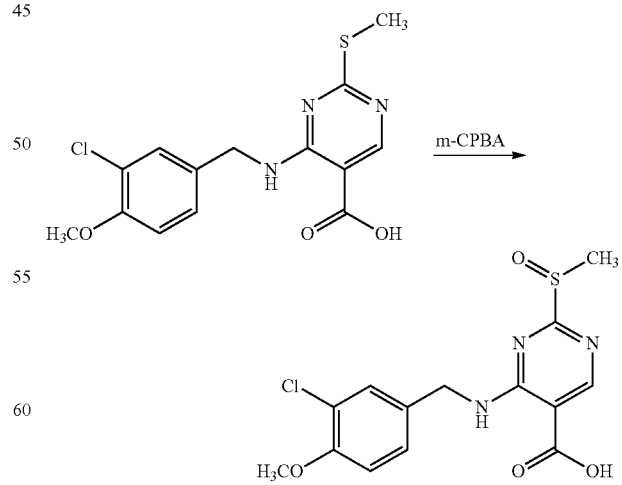

In DCM (20 mL) was dissolved 4-((3-chloro-4-methoxybenzyl)amino)-2-(methylthio) pyrimidine-5-carboxylic acid (200 mg, 0.59 mmol). The solution was cooled in an ice bath and m-CPBA (101 mg, 0.59 mmol) was added. The reaction was conducted at ambient temperature for 5 h, followed by addition of water and extraction with DCM. The organic phase was dried and concentrated to give a solid which was used in the subsequent procedure without further purification.

(4) Preparation: 2-(3-azabicyclo[3.1.0]hexan-3-yl)-4-((3-chloro-4-methoxybenzyl)amino) pyrimidine-5-carboxylic acid

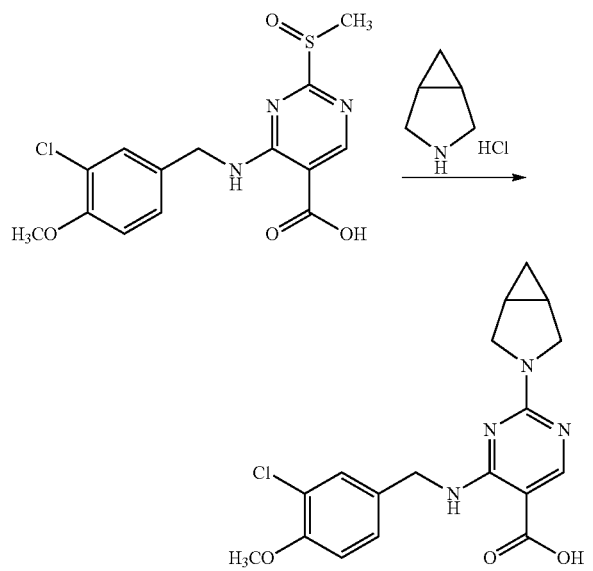

In THF (15 mL) were dissolved 4-((3-chloro-4-methoxybenzyl)amino)-2-(methylsulfinyl) pyrimidine-5-carboxylic acid (196 mg, 0.55 mmol) and 3-azabicyclo[3.1.0]hexane hydrochloride salt (79 mg, 0.66 mmol). The solution was cooled in an ice bath, and triethylamine (167 mg, 1.65 mmol) was added dropwisely. The reaction was allowed to warm to ambient temperature for 5 h, followed by addition of water and extracted with DCM. The organic phase was dried and concentrated to give a solid which was used in the subsequent procedure without further purification.

(5) Preparation: 2-(3-azabicyclo[3.1.0]hexan-3-yl)-4-((3-chloro-4-methoxybenzyl)amino)-N-(trans-4-hydroxycyclohexanyl)pyrimidine-5-formamide

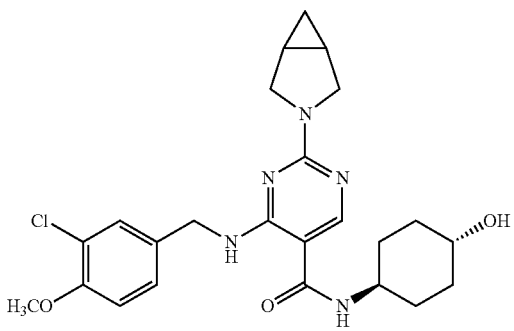

In THF (20 mL) were dissolved 2-(3-azabicyclo[3.1.0]hexan-3-yl)-4-((3-chloro-4-methoxybenzyl)amino)pyrimidine-5-carboxylic acid (180 mg, 0.48 mmol), trans-4-hydroxycyclohexanylamine (66 mg, 0.58 mmol) and HATU (220 mg, 0.58 mmol). The solution was cooled in an ice bath and DIEA (0.25 mL, 1.44 mmol) was added then. The reaction was conducted at ambient temperature for 8 h, followed by concentration, addition of water and extraction with ethyl acetate. The organic phase was dried, concentrated and purified by silica gel column chromatography (DCM/methanol=20/1) to give 2-(3-azabicyclo[3.1.0]hexan-3-yl)-4-((3-chloro-4-methoxybenzyl)amino)-N-(trans-4-hydroxycyclohexanyl)pyrimidine-5-formamide (141 mg, 62% yield).

Molecular formula: $C_{24}H_{30}ClN_5O_3$ Molecular weight: 472.0 MS (m/e): 472.0 (M+1)

$^1$H-NMR (400 MHz, DMSO-$d_6$, hydrochloride salt): δ 13.40 (brs, 1H), 10.08 (t, 1H), 9.73 (t, 1H), 8.77 (d, 2H), 8.60 (s, 1H), 7.51 (s, 1H), 7.42 (m, 3H), 4.55 (m, 4H), 3.89 (d, 2H), 3.65 (m, 2H), 2.85 (s, 6H), 1.75 (d, 2H), 0.74 (m, 1H), 0.22 (m, 1H).

Example 11-1

Preparation: 2-(3-azabicyclo[3.1.0]hexan-3-yl)-4-((3-chloro-4-methoxy benzyl)amino)-N-(trans-4-hydroxycyclohexanyl)pyrimidine-5-formamide (Compound 11)

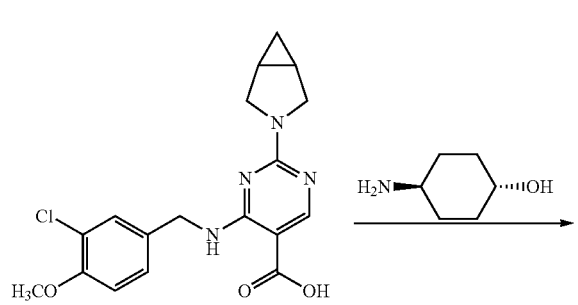

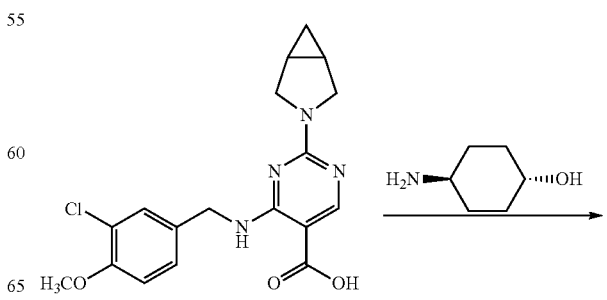

105
-continued

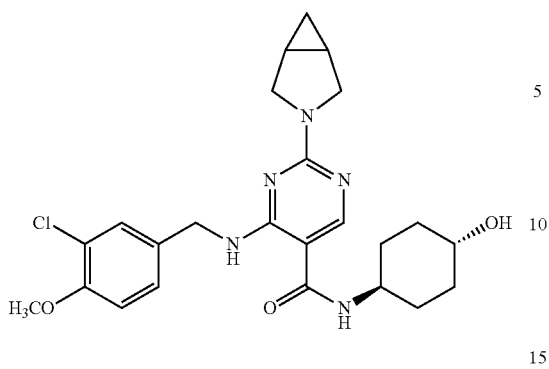

In THF (20 mL) were dissolved 2-(3-azabicyclo[3.1.0]hexan-3-yl)-4-((3-chloro-4-methoxybenzyl)amine)pyrimidin-5-carboxylic acid (180 mg, 0.48 mmol), trans-4-hydroxycyclohexylamine (66 mg, 0.57 mmol) and HATU (220 mg, 0.58 mmol). DIEA (0.25 mL, 1.44 mmol) was added at ambient temperature. The reaction was conducted for 8 h at ambient temperature, followed by concentration, addition of water and extraction with DCM. The organic phase was dried, concentrated and purified by silica gel column chromatography (DCM/methanol=20/1) to give 2-(3-azabicyclo[3.1.0]hexan-3-yl)-4-((3-chloro-4-methoxybenzyl)amino)-N-(trans-4-hydroxycyclohexanyl)pyrimidine-5-form amide (141 mg, 62% yield).

Molecular formula: $C_{24}H_{30}ClN_5O_3$ Molecular weight: 472.0 MS (m/e): 472.0 (M+H$^+$)

$^1$H-NMR (400 MHz, CDCl$_3$): δ 9.00 (t, 1H), 8.72 (d, 2H) 8.42 (s, 1H), 7.39 (s, 1H), 7.32 (t, 1H), 7.25 (t, 1H), 7.20 (d, 1H), 6.86 (d, 1H), 4.80 (d, 2H), 4.56 (d, 2H), 3.88 (s, 3H), 3.74 (m, 4H), 1.94 (m, 2H), 1.82 (m, 4H), 1.59 (m, 4H).

Example 12

Preparation: 2-(3-azabicyclo[3.1.0]hexan-3-yl)-4-((3-chloro-4-methoxybenzyl)amino)-pyrimidin-5-yl)(4-methylpiperazin-1-yl)ketone (Compound 12)

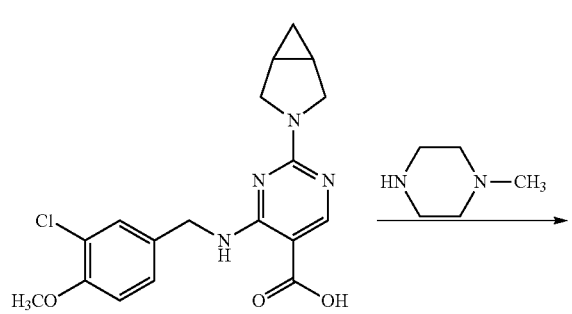

106
-continued

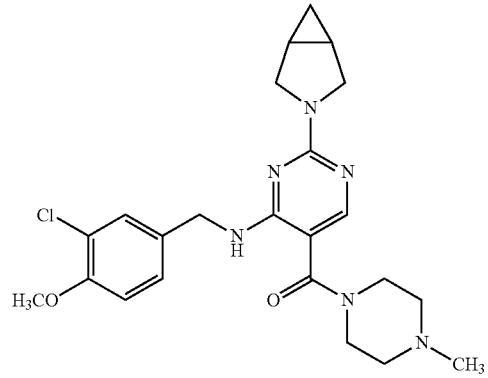

In THF (20 mL) were dissolved 2-(3-azabicyclo[3.1.0]hexan-3-yl)-4-((3-chloro-4-methoxybenzyl)amine)pyrimidine-5-carboxylic acid (153 mg, 0.41 mmol), 1-methylpiperazine (49 mg, 0.49 mmol) and HATU (188 mg, 0.49 mmol). The solution was cooled in an ice bath then DIEA was added dropwisely (0.14 mL, 0.82 mmol). The reaction was conducted at ambient temperature for 8 h, followed by addition of water (20 mL) and extraction with ethyl acetate or DCM. The organic phase was dried, concentrated and purified by silica gel column chromatography (DCM/methanol=25/1) to give 2-(3-azabicyclo[3.1.0]hexan-3-yl)-4-((3-chloro-4-methoxybenzyl)amino)pyrimidin-5-yl)(4-methylpiperazin-1-yl)ketone (35 mg, 19% yield).

Molecular formula: $C_{23}H_{29}ClN_6O_2$ Molecular weight: 457.0 MS (m/e): 457.0 (M+H$^+$)

$^1$H-NMR (400 MHz, CDCl$_3$): δ 9.02 (t, 1H), 8.74 (d, 2H), 8.42 (s, 1H), 7.39 (s, 1H), 7.34 (t, 1H), 7.25 (t 1H), 7.20 (d, 1H), 6.86 (d, 1H), 4.80 (d, 2H), 4.57 (d, 2H), 3.88 (s, 3H), 3.87 (t, 4H), 1.39 (t, 4H), 0.38 (s, 4H).

Example 13

Preparation: 2-(3-azabicyclo[3.1.0]hexan-3-yl)-4-((3-chloro-4-(dimethyl amino)benzyl)amino)-N-(pyrimidin-2-ylmethyl)pyrimidine-5-formamide (Compound

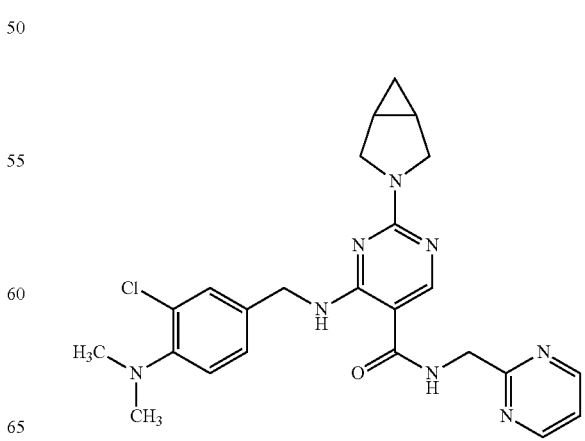

(1) Preparation: ethyl 4-((3-chloro-4-(dimethylamino)benzyl)amino)-2-(methylthio) pyrimidine-5-carboxylate

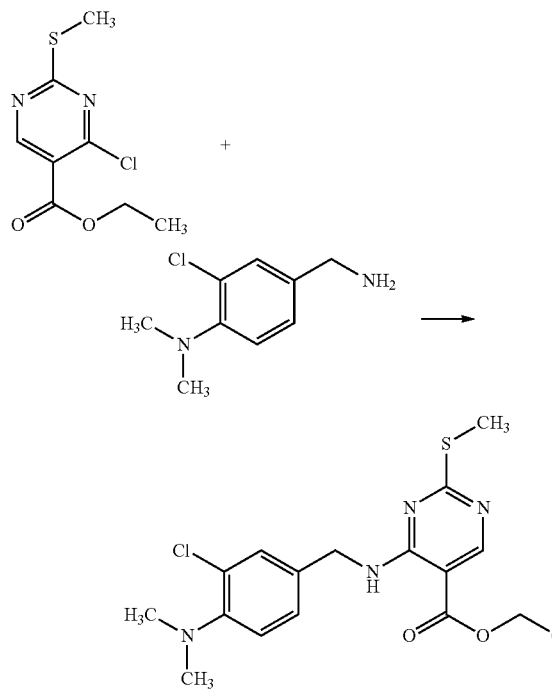

The procedures were analogous to Example 1(1), 77% yield.

(2) Preparation: 4-((3-chloro-4-(dimethylamino)benzyl)amino)-2-(methylthio)pyrimidine-5-carboxylic acid

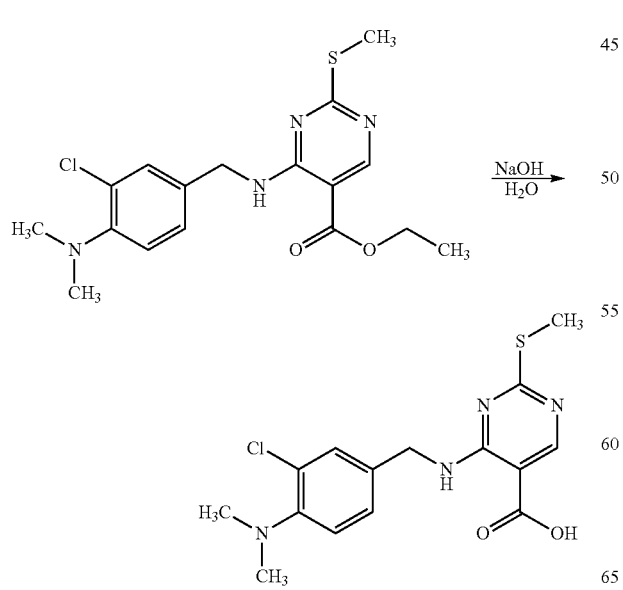

The procedures were analogous to Example 1(2), 95% yield.

(3) Preparation: 4-((3-chloro-4-(dimethylamino)benzyl)amino)-2-(methylthio)-N-(pyrimidin-2-ylmethyl)pyrimidine-5-formamide

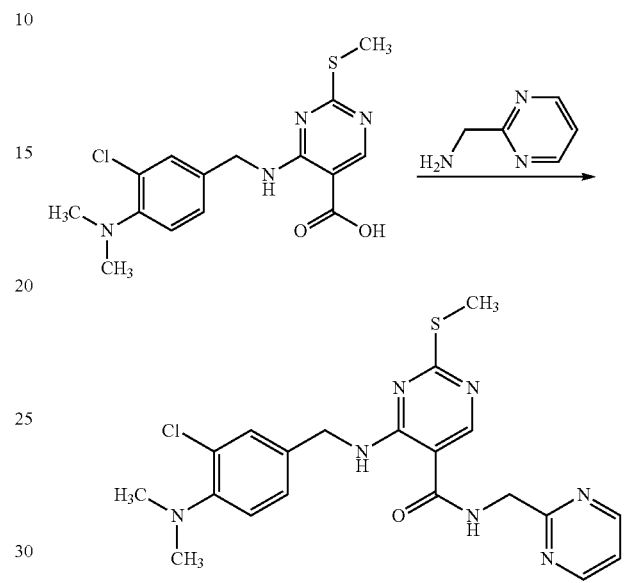

The procedures were analogous to Example 1(3), 79% yield.

(4) Preparation: 4-((3-chloro-4-(dimethylamino)benzyl)amino)-2-(methylsulfinyl)-N-(pyrimidin-2-ylmethyl)pyrimidine-5-formamide

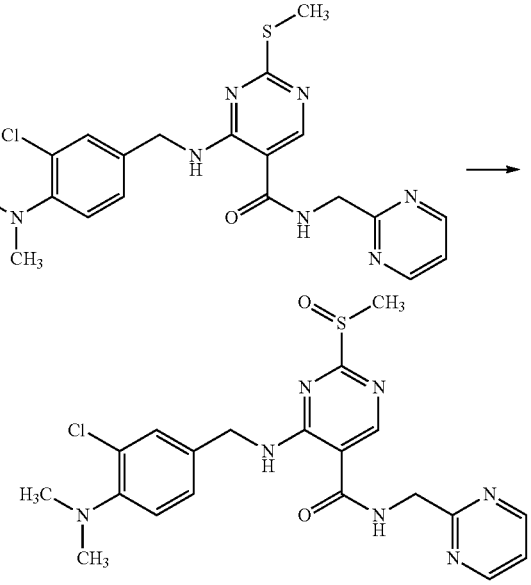

The procedures were analogous to Example 1(4). The product was used in the subsequent procedure without further purification.

(5) Preparation: 2-(3-azabicyclo[3.1.0]hexan-3-yl)-4-((3-chloro-4-(dimethylamino)benzyl)amino)-N-(pyrimidin-2-ylmethyl)pyrimidine-5-formamide

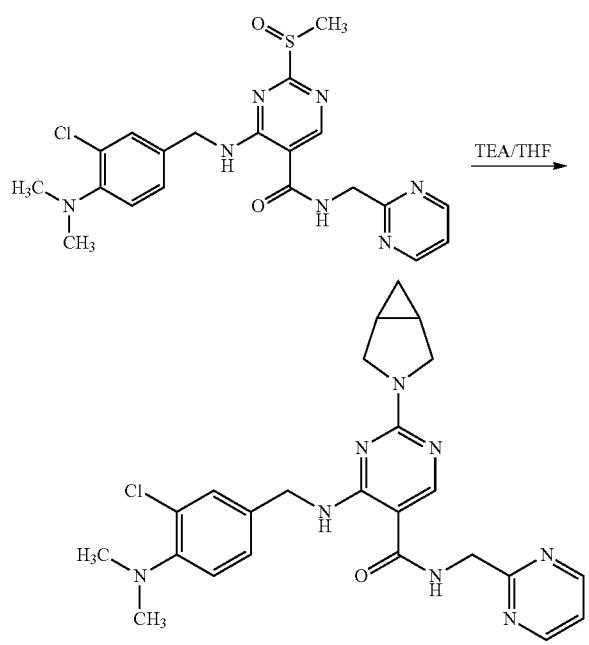

The procedures were analogous to Example 1(5), 4% yield.

Molecular formula: $C_{24}H_{27}ClN_8O$ Molecular weight: 479.0 MS (m/e): 479.0 (M+H$^+$)

$^1$H-NMR (400 MHz, DMSO-d$_6$, triflouroacetate salt): δ 9.90 (brs, 1H), 9.18 (m, 3H), 8.41 (s, 1H), 7.24-7.48 (m, 7H), 7.10 (m, 1H), 4.58 (m, 2H), 4.22 (d, 2H), 4.04 (m, 2H), 3.94 (m, 2H), 3.83 (d, 2H), 3.81 (s, 3H), 3.74 (m, 2H), 3.56 (m, 2H), 0.27 (m, 2H).

Example 14

Preparation: 4-((3-chloro-4-methoxybenzyl)amino)-N-(pyrimidin-2-ylmethyl)-2-(7-azaspiro[3.5]nonan-7-yl)pyrimidine-5-formamide (Compound 14)

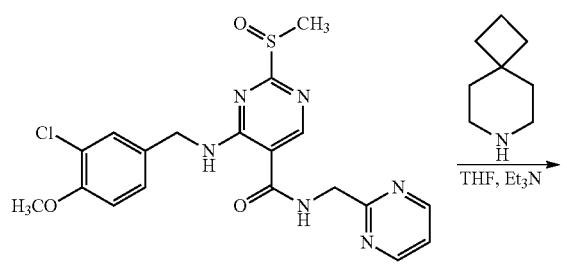

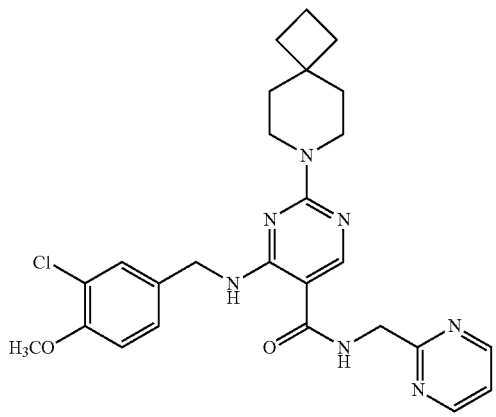

In THF (20 mL) were dissolved 4-((3-chloro-4-methoxybenzyl)amino)-2-(methylsulfinyl)-N-(pyrimidin-2-ylmethyl)pyrimidine-5-formamide (201 mg, 0.45 mmol) and 7-azaspiro[3.5]nonane (62 mg, 0.5 mmol). Triethylamine (137 mg, 1.35 mmol) was added dropwisely. The reaction was conducted at ambient temperature for 8 h, followed by addition of water and extraction with DCM. The organic phase was dried over sodium sulfate and purified by silica gel column chromatography (DCM/methanol=50/1) to give a white solid (83 mg, 36% yield).

Molecular formula: $C_{26}H_{30}ClN_7O_2$ Molecular weight: 508.0 MS (m/e): 508.0 (M+H$^+$)

$^1$H-NMR (400 MHz, CDCl$_3$): δ 9.02 (m, 1H), 8.74 (m, 2H), 8.43 (s, 1H), 7.42 (s, 1H), 7.22-7.32 (m, 3H), 6.87 (d, 1H), 4.80 (m, 2H), 4.59 (m, 2H), 3.89 (s, 3H), 3.42-3.89 (m, 4H), 2.54 (m, 2H), 2.52 (s, 3H), 2.00 (m, 2H), 1.78 (m, 4H), 0.52 (m, 2H).

Example 15

Preparation: 4-((3-chloro-4-methoxybenzyl)amino)-N-(pyrimidin-2-ylmethyl)-2-(6-azaspiro[2.5]octan-6-yl)pyrimidine-5-formamide (Compound 15)

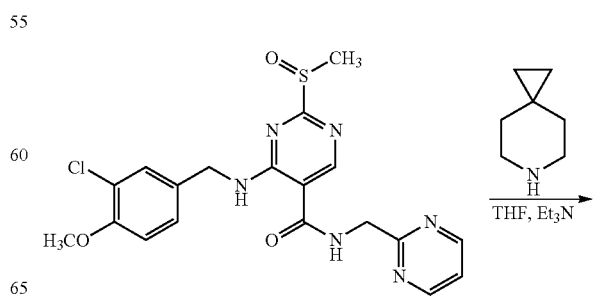

-continued

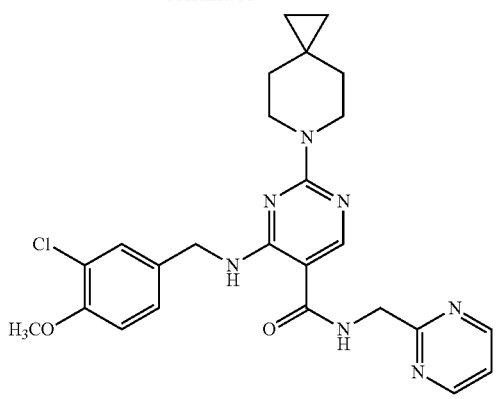

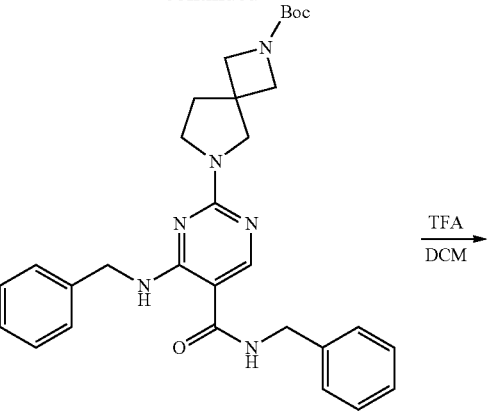

→ TFA/DCM

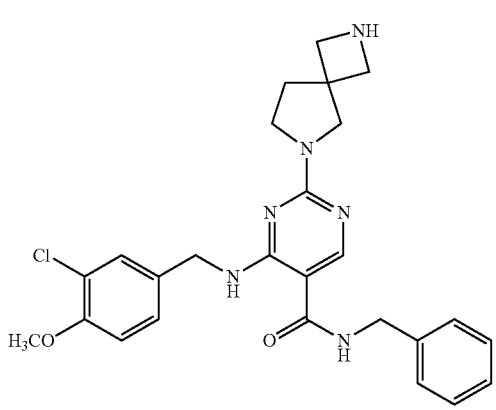

In THF (15 mL) were dissolved 4-((3-chloro-4-methoxybenzyl)amino)-2-(methylsulfinyl)-N-(pyrimidin-2-ylmethyl)pyrimidine-5-formamide (134 mg, 0.30 mmol) and 6-azaspiro[2.5]octane (50 mg, 0.45 mmol). Triethylamine (61 mg, 0.60 mmol) was added dropwisely. The reaction was conducted at ambient temperature for 8 h, followed by addition of water and extraction with DCM. The organic phase was dried over sodium sulfate and purified by silica gel column chromatography (DCM/methanol=80/1) to give a white solid (41 mg, 28% yield).

Molecular formula: $C_{25}H_{28}ClN_7O_2$ Molecular weight: 494.0 MS (m/e): 495.0 (M+H$^+$)

$^1$H-NMR (400 MHz, CDCl$_3$): δ 9.07 (m, 1H), 8.74 (m, 2H), 8.43 (s, 1H), 7.21-7.41 (m, 4H), 6.88 (d, 1H), 4.81 (m, 2H), 4.57 (m, 2H), 3.89 (s, 3H), 3.56-3.65 (m, 4H), 2.80 (m, 2H), 2.15 (m, 2H), 2.06 (s, 3H), 1.17 (m, 4H).

Example 16

Preparation: N-benzyl-4-((3-chloro-4-methoxybenzyl)amino)-2-(2,6-diazaspiro[3.4]octan-6-yl)pyrimidine-5-formamide (Compound 16)

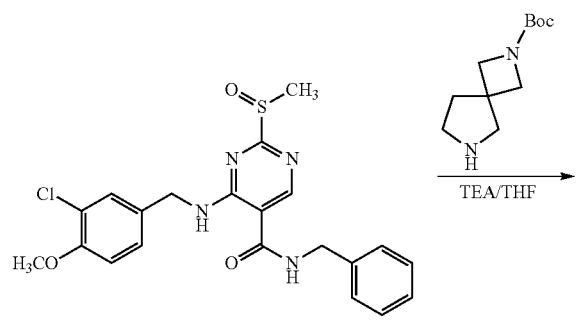

→ TEA/THF

In absolute anhydrous THF (10 mL) were dissolved N-benzyl-4-((3-chloro-4-methoxybenzyl)amino)-2-(methyl sulfinyl)pyrimidine-5-formamide (170 mg, 0.38 mmol) and tert-butyl 2,6-diazaspiro[3.4]octane-2-carboxylate (74 mg, 0.35 mmol). Triethylamine (101 mg, 1.0 mmol) was added dropwisely. The reaction was conducted at ambient temperature for 4 h, followed by addition of water and extraction with DCM. The organic phase was dried over sodium sulfate and concentrated. The obtained solid was purified by silica gel column chromatography (DCM/methanol=80/1) to give a white solid (100 mg). The product was dissolved in DCM (15 mL), and trifluoroacetic acid (1 mL) was added. The reaction mixture was stirred at ambient temperature for 2 h. The solvent was removed to give N-benzyl-4-((3-chloro-4-methoxybenzyl)amino)-2-(2,6-diazaspiro[3.4]octan-6-yl)pyrimidine-5-formamide (38 mg, 20% total yield).

Molecular formula: $C_{26}H_{29}ClN_6O_2$ Molecular weight: 493.0 MS (m/e): 493.0 (M+H$^+$)

$^1$H-NMR (400 MHz, DMSO-d$_6$, hydrochloride salt): δ 13.8 (brs, 1H), 10.89 (brs, 1H), 10.06 (t, 1H), 9.68 (t, 1H), 8.75 (d, 2H), 8.67 (s, 1H), 7.44 (s, 1H), 7.40 (d, 1H), 7.30 (d, 1H), 7.09 (d, 1H), 4.58 (m, 4H), 3.98 (m, 4H), 3.80 (s, 3H), 3.33 (d, 2H), 2.96 (m, 2H), 2.68 (s, 3H), 2.02 (m, 4H).

Example 17

Preparation: 4-((3-chloro-4-methoxybenzyl)amino)-2-(7-methyl-2,7-diazaspiro[4.5]decan-2-yl)-N-(pyrimidin-2-ylmethyl)pyrimidine-5-formamide (Compound 17)

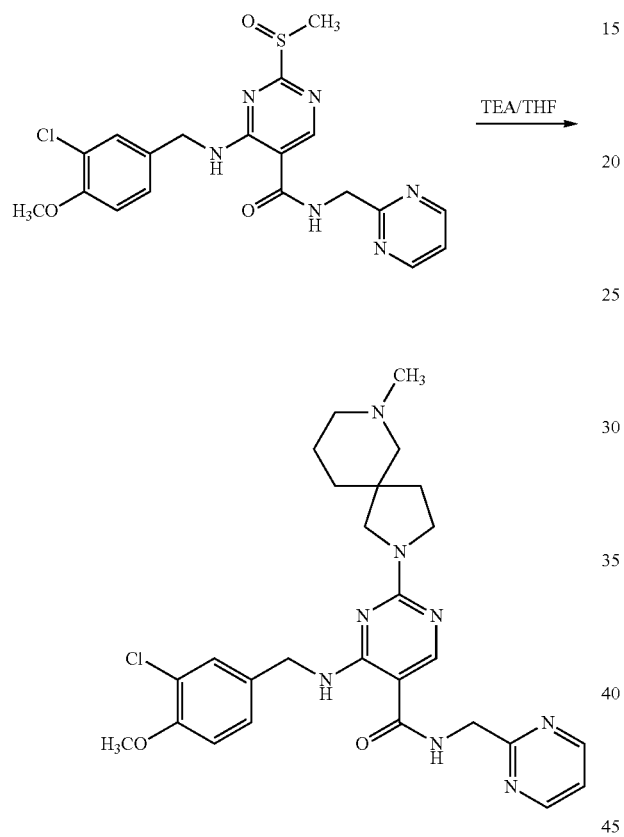

In THF (10 mL) were dissolved 4-((3-chloro-4-methoxybenzyl)amino)-2-(methylsulfinyl)-N-(pyrimidin-2-ylmethyl)pyrimidine-5-formamide (100 mg, 0.22 mmol) and 7-methyl-2,7-diazaspiro[4.5]decane (42 mg, 0.27 mmol). Triethylamine (68 mg, 0.67 mmol) was added dropwisely. The reaction was conducted at ambient temperature for 4 h, followed by addition of water and extraction with DCM. The organic phase was dried over sodium sulfate and purified by silica gel column chromatography (DCM/methanol=20/1) to give 4-((3-chloro-4-methoxybenzyl)amino)-2-(7-methyl-2,7-diazaspiro[4.5]decan-2-yl)-N-(pyrimidin-2-ylmethyl)pyrimidine-5-formamide as a white solid (20 mg, 17% yield).

Molecular formula: $C_{27}H_{33}ClN_8O_2$ Molecular weight: 537.0 MS (m/e): 537.0 (M+H$^+$)

$^1$H-NMR (400 MHz, CDCl$_3$): δ 9.07 (t, 1H), 8.72 (d, 2H), 8.38 (s, 1H), 7.39 (d, 1H), 7.36 (t, 1H), 7.24 (t, 1H), 7.20 (d, 1H), 6.86 (d, 1H), 4.78 (d, 2H), 4.53 (d, 2H), 4.20 (s, 4H), 3.88 (s, 3H), 3.43 (s, 4H), 2.35 (s, 3H).

Example 18

Preparation: 4-((3-chloro-4-methoxybenzyl)amino)-2-(7-methyl-2,7-diazaspiro[4.4]nonan-2-yl)-N-(pyrimidin-2-ylmethyl)pyrimidine-5-formamide (Compound 18)

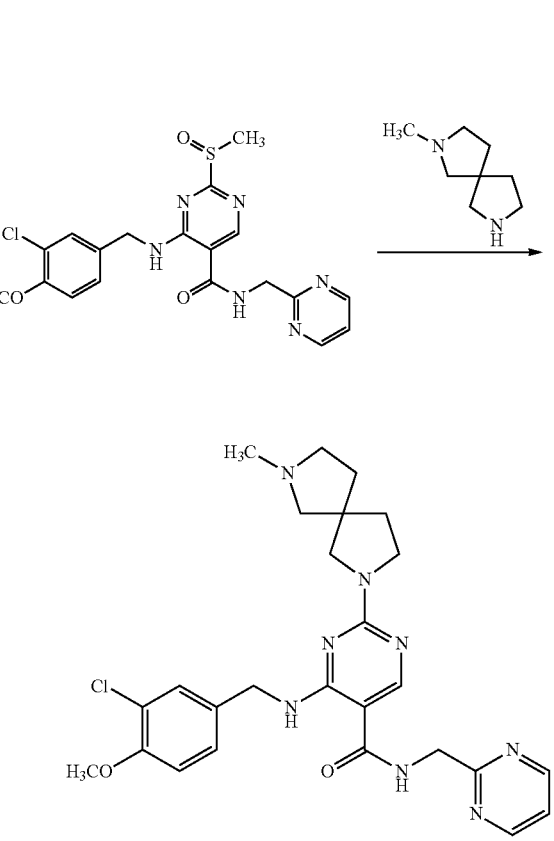

In DCM (30 mL) were dissolved 4-((3-chloro-4-methoxybenzyl)amino)-2-(methylsulfinyl)-N-(pyrimidin-2-ylmethyl)pyrimidine-5-formamide (429 mg, 0.96 mmol) and DIEA (0.22 mL, 1.12 mmol). 2-Methyl-2,7-diazaspiro[4.4]nonane (154 mg, 1.1 mmol) was then added. The reaction was conducted at ambient temperature overnight. The solvent was removed by rotary evaporation, followed by addition of water and extraction with ethyl acetate. The organic phase was dried over sodium sulfate and purified by silica gel column chromatography (DCM/methanol=20/1 to 10/1) to give a white solid (20 mg, 4% yield).

Molecular formula: $C_{26}H_{31}ClN_8O_2$ Molecular weight: 523.0 MS (m/e): 523.0 (M+H$^+$)

$^1$H-NMR (400 MHz, CDCl$_3$): □ δ 9.07 (m, 1H), 8.74 (m, 2H), 8.43 (s, 1H), 7.21-7.41 (m, 4H), 6.88 (d, 1H), 4.81 (m,

2H), 4.57 (m, 2H), 3.89 (s, 3H), 3.56-3.65 (m, 4H), 2.80 (m, 2H), 2.15 (m, 2H), 2.06 (s, 3H), 1.17 (m, 4H).

Example 19

Preparation: 4-((3-chloro-4-methoxybenzyl)amino)-2-(7-methyl-2,7-diazaspiro[3.5]nonan-2-yl)-N-(pyrimidin-2-ylmethyl)pyrimidine-5-formamide (Compound 19)

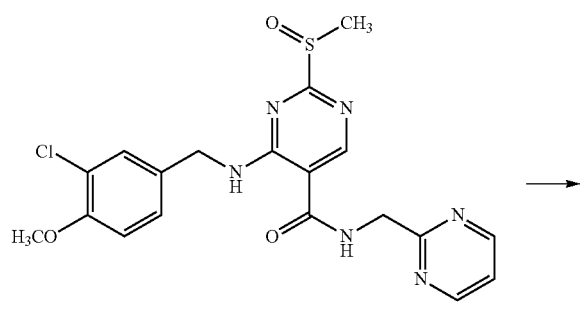

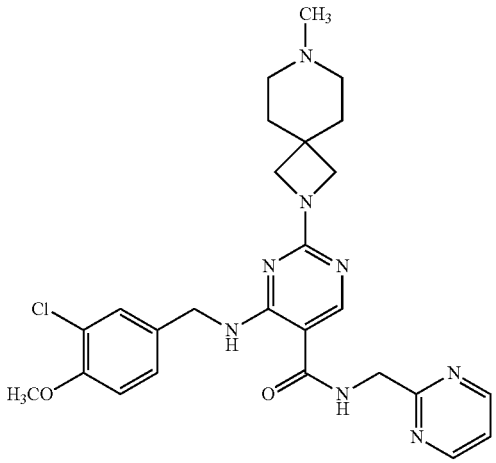

In THF (10 mL) were dissolved 4-((3-chloro-4-methoxybenzyl)amino)-2-(methyl sulfinyl)-N-(pyrimidin-2-ylmethyl)pyrimidine-5-formamide (152 mg, 0.34 mmol) and 2-methyl-2,7-diazaspiro[3.5]nonane (70 mg, 0.50 mmol). Then triethylamine (68 mg, 0.67 mmol) was added dropwisely. The reaction was conducted at ambient temperature for 4 h. The solvent was removed by rotary evaporation, followed by addition of water and extraction with DCM. The organic phase was dried over sodium sulfate and purified by silica gel column chromatography (DCM/methanol=20/1) to give 4-((3-chloro-4-methoxybenzyl)amino)-2-(7-methyl-2,7-diazaspiro[3.5]nonan-2-yl)-N-(pyrimidin-2-ylmethyl)pyrimidine-5-formamide as a white solid (16 mg, 9% yield).

Example 19-1

Preparation: 4-((3-chloro-4-methoxybenzyl)amino)-2-(7-methyl-2,7-diazaspiro[3.5]nonan-2-yl)-N-(pyrimidin-2-ylmethyl)pyrimidine-5-formamide (Compound 19)

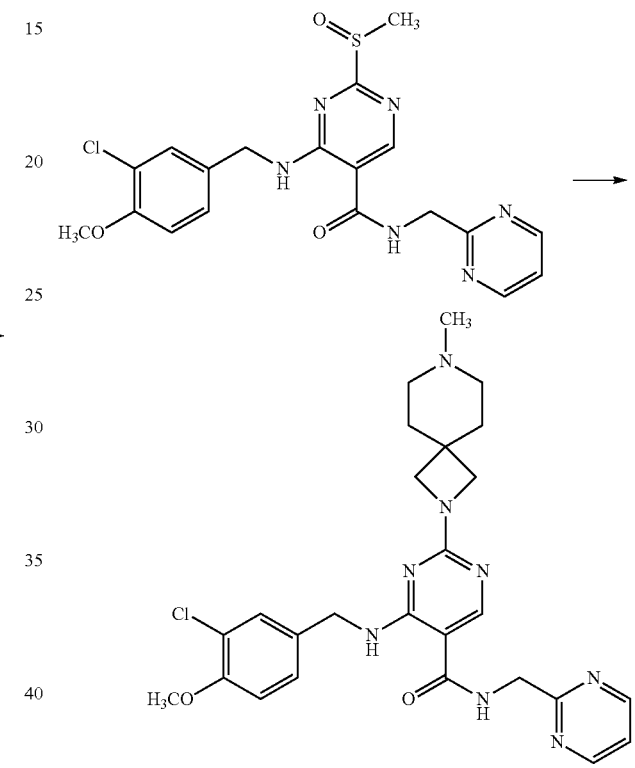

In THF (10 mL) were dissolved 4-((3-chloro-4-methoxybenzyl)amino)-2-(methyl sulfinyl)-N-(pyrimidin-2-ylmethyl)pyrimidine-5-formamide (152 mg, 0.34 mmol), 2-methyl-2,7-diazaspiro[3.5]nonane (70 mg, 0.50 mmol) and HATU (383 mg, 1 mmol). Triethylamine (68 mg, 0.67 mmol) was added dropwisely. The reaction was conducted at ambient temperature for 4 h, followed by addition of water (50 mL) and extraction with DCM. The organic phase was dried over sodium sulfate and purified by silica gel column chromatography (DCM/methanol=20/1) to give 4-((3-chloro-4-methoxybenzyl)amino)-2-(7-methyl-2,7-diazaspiro[3.5]nonan-2-yl)-N-(pyrimidin-2-ylmethyl)pyrimidine-5-formamide as a white solid (16 mg, 9% yield).

Molecular formula: $C_{26}H_{31}ClN_8O_2$ Molecular weight: 523.0 MS (m/e): 524.0 (M+H$^+$)

$^1$H-NMR (400 MHz, DMSO-d$_6$, hydrochloride salt): δ 13.8 (brs, 1H), 10.89 (brs, 1H), 10.06 (t, 1H), 9.68 (t, 1H), 8.75 (d, 2H), 8.67 (s, 1H), 7.44 (s, 1H), 7.40 (d, 1H), 7.30 (d, 1H), 7.09 (d, 1H), 4.58 (m, 4H), 3.98 (m, 4H), 3.80 (s, 3H), 3.33 (d, 2H), 2.96 (m, 2H), 2.68 (s, 3H), 2.02 (m, 4H).

Example 20

Preparation: 4-((3-chloro-4-methoxybenzyl)amino)-2-(6-methyl-2,6-diazaspiro[3.3]heptan-2-yl)-N-(pyrimidin-2-ylmethyl)pyrimidine-5-formamide (Compound 20)

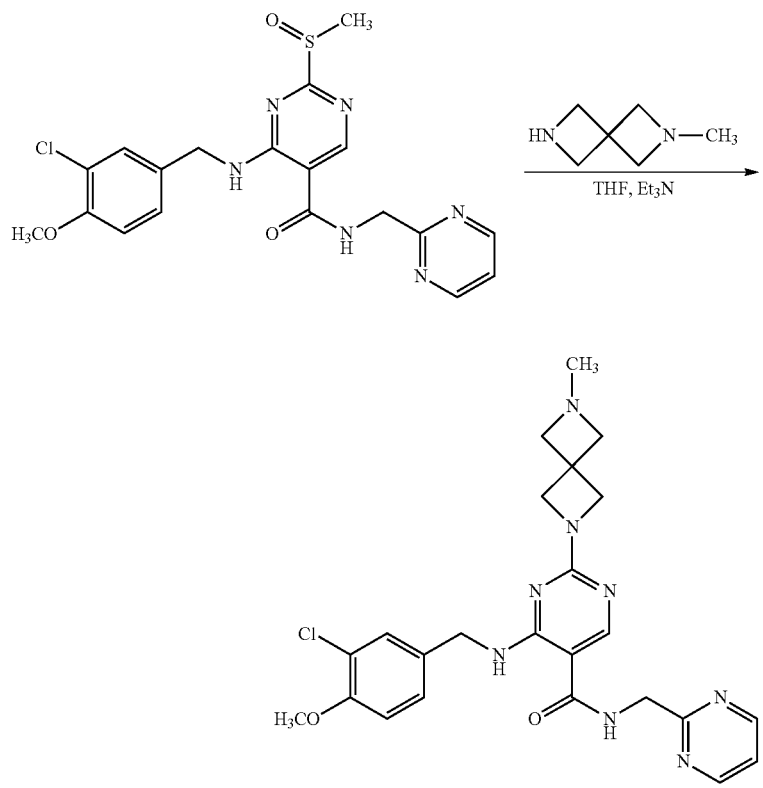

In THF (15 mL) were dissolved 4-((3-chloro-4-methoxybenzyl)amino)-2-(methyl sulfinyl)-N-(pyrimidin-2-ylmethyl)pyrimidine-5-formamide (120 mg, 0.27 mmol) and 2-methyl-2,6-diazaspiro[3.3]heptane (45 mg, 0.40 mmol). The solution was cooled in an ice bath, and triethylamine (82 mg, 0.81 mmol) was added dropwisely. The reaction was conducted at ambient temperature for 8 h. The solvent was removed by rotary evaporation, followed by addition of water and extraction with DCM. The organic phase was dried over sodium sulfate and purified by silica gel column chromatography (DCM/methanol/triethylamine=10/1/0.008) to give 4-((3-chloro-4-methoxybenzyl)amino)-2-(6-methyl-2,6-diazaspiro[3.3]heptan-2-yl)-N-(pyrimidin-2-ylmethyl)pyrimidine-5-formamide as a white solid (35 mg, 26% yield).

Molecular formula: $C_{24}H_{27}ClN_8O_2$ Molecular weight: 495.0 MS (m/e): 495.0 (M+H$^+$)

$^1$H-NMR (400 MHz, CDCl$_3$): δ □9.07 (t, 1H), 8.72 (d, 2H), 8.38 (s, 1H), 7.39 (d, 1H), 7.36 (t, 1H), 7.24 (t, 1H), 7.20 (d, 1H), 6.86 (d, 1H), 4.78 (d, 2H), 4.53 (d, 2H), 4.20 (s, 4H), 3.88 (s, 3H), 3.43 (s, 4H), 2.35 (s, 3H).

Example 21

Preparation: N-benzyl-4-((3-chloro-4-methoxybenzyl)amino)-2-(5-azaspiro[2.4]heptan-5-yl)pyrimidine-5-formamide (Compound 21)

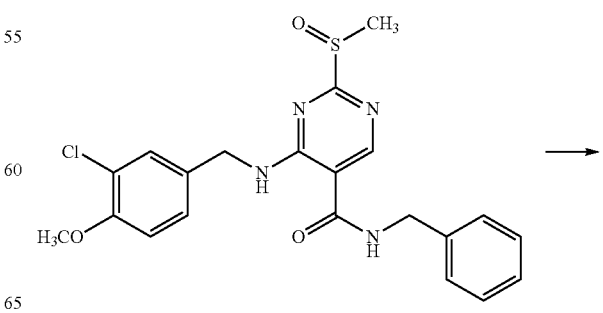

-continued

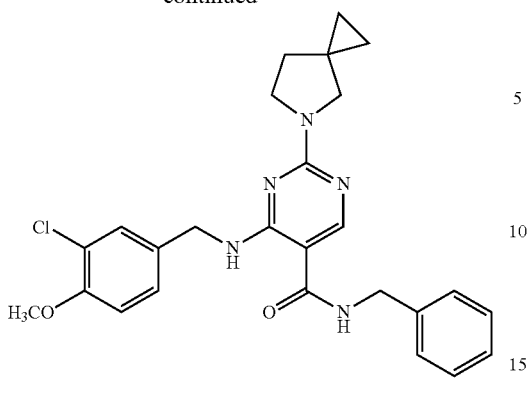

The procedures were analogous to Example 3 (3), 18% yield.

In absolute anhydrous THF (15 mL) were dissolved N-benzyl-4-((3-chloro-4-methoxybenzyl)amino)-2-(methylsulfinyl)pyrimidine-5-formamide (180 mg, 0.41 mmol) and 5-azaspiro[2.4]heptane (59 mg, 0.61 mmol). The solution was cooled in an ice bath, and triethylamine (82 mg, 0.82 mmol) was added dropwisely. The reaction was conducted at ambient temperature for 8 h then was quenched with water. The reaction mixture was extracted with DCM. The organic phase was dried over sodium sulfate and concentrated. The obtained solid was purified by silica gel column chromatography (DCM/methanol=50/1) to give the product as a solid (35 mg, 18% yield).

Molecular formula: $C_{26}H_{28}ClN_5O_2$ Molecular weight: 478.0 MS (m/e): 479.0 (M+H$^+$)

$^1$H-NMR (400 MHz, DMSO-d$_6$, hydrochloride salt): δ 10.0 (br s, 1H), 9.30 (m, 1H), 8.42 (s, 1H), 7.45 (m, 1H), 7.24-7.35 (m, 6H), 7.09 (m, 1H), 4.58 (m, 2H), 4.52 (d, 2H), 3.80 (s, 3H), 3.66 (m, 2H), 3.42 (m, 2H), 1.95 (m, 2H), 0.92 (s, 4H).

Example 22

Preparation: N-benzy-4-((3-chloro-4-methoxybenzyl)amino)-2-(2-methyl-2,7-diazaspiro[3.5]nonan-7-yl)pyrimidine-5-formamide (Compound 22)

(1) Preparation: N-benzyl-4-((3-chloro-4-methoxybenzyl)amino)-2-(2,7-diazaspiro[13.5]nonan-7-yl)pyrimidine-5-formamide

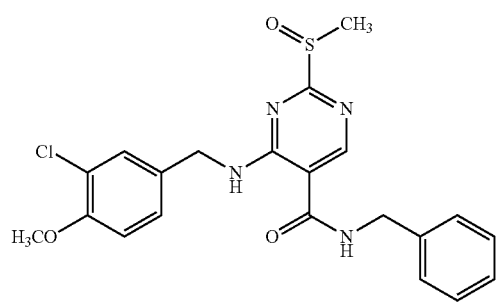

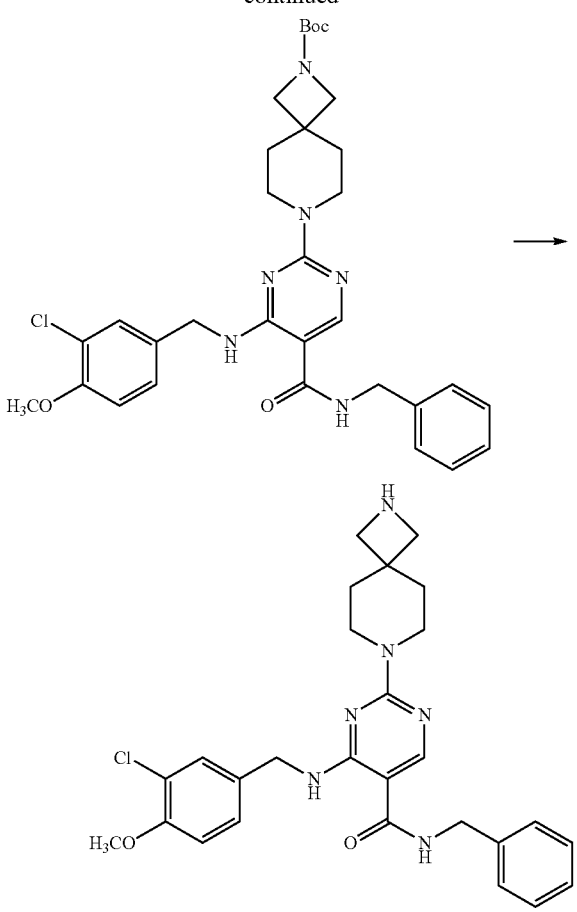

The procedures were analogous to Example 16. Tert-butyl 2,7-azaspiro[3.5]nonane-2-carboxylate (112 mg, 0.5 mmol) was used instead of tert-butyl 2,6-diazaspiro[3.4]octane-2-carboxylate. Yield: 42%.

(2) Preparation: N-benzyl-4-((3-chloro-4-methoxybenzyl)amino)-2-(2-methyl-2,7-diazaspiro[3.5]nonan-7-yl)pyrimidine-5-formamide

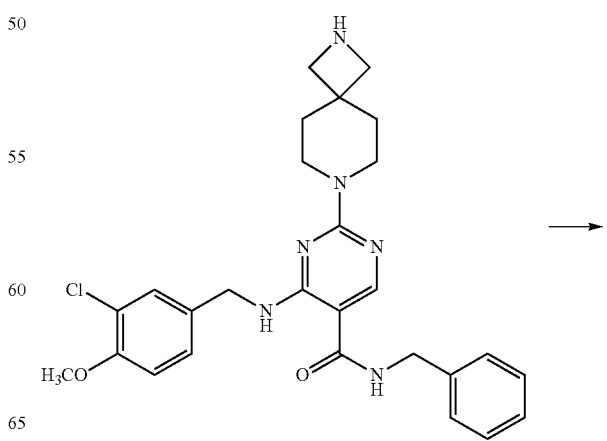

-continued

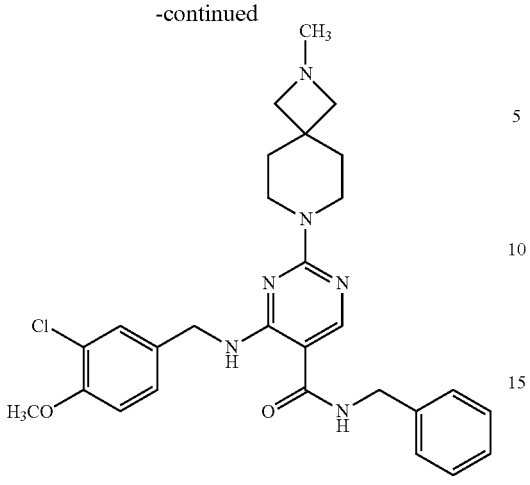

The procedures were analogous to Example 10 (3). NaBH$_4$ (57 mg, 1.5 mol) was used in step 3 instead of sodium triacetoxyborohydride. Yield: 76%.

Molecular formula: C$_{28}$H$_{33}$ClN$_6$O$_2$ Molecular weight: 521.0 MS (m/e): 521.0 (M+H$^+$)

$^1$H-NMR (400 MHz, CDCl$_3$): δ 9.05 (m, 1H), 8.17 (s, 1H), 7.30-7.37 (m, 6H), 7.18 (d, 1H), 6.87(d, 1H), 6.18(m, 1H), 4.54 (m, 4H), 3.88 (s, 3H), 3.72 (m, 4H), 3.50 (m, 4H), 2.64 (s, 3H), 1.83 (m, 4H).

Example 23

Preparation: N-benzyl-2-(3-oxo-8-azabicyclo[3.2.1]octan-8-yl)-4-((3-chloro-4-methoxybenzyl)amino)pyrimidine-5-formamide (Compound 23)

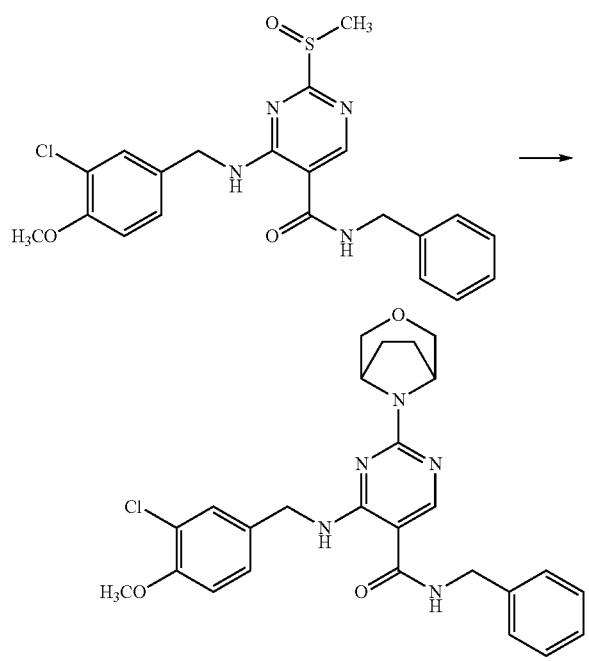

In absolute anhydrous THF (30 mL) were dissolved 4-((3-chloro-4-methoxybenzyl)amino)-2-(methylsulfinyl)-N-(pyrimidin-2-ylmethyl)pyrimidine-5-formamide (222 mg, 0.5 mmol) and triethylamine (0.25 mL, 1.35 mmol). 3-oxo-8-azabicyclo[3.2.1]octane hydrochloride salt (90 mg, 0.6 mmol) was then added. The reaction was conducted at ambient temperature overnight. The solvent was removed by rotary evaporation, followed by addition of water and extraction with DCM. The organic phase was dried over sodium sulfate and purified by silica gel column chromatography (petroleum ether/ethyl acetate=1/1) to give a white solid (60 mg, 24% yield).

Example 23-1

Preparation: N-benzyl-2-(3-oxo-8-azabicyclo[3.2.1]octan-8-yl)-4-((3-chloro-4-methoxybenzyl)amino)pyrimidine-5-formamide (Compound 23)

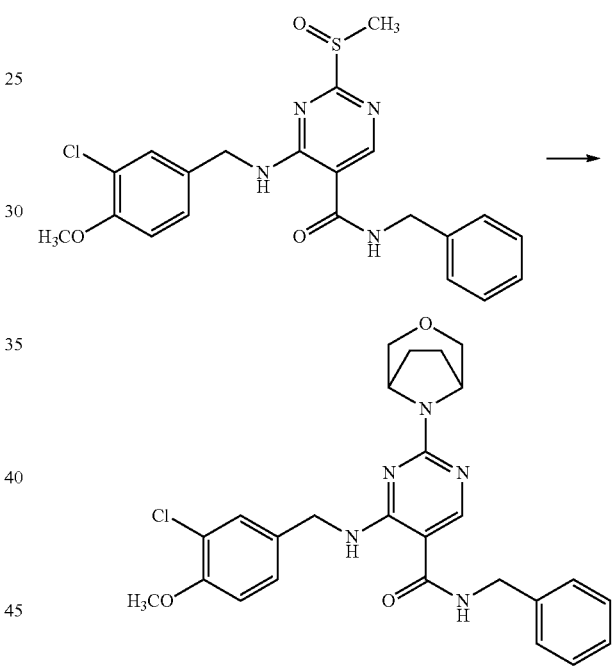

In DCM were dissolved N-benzyl-4-((3-chloro-4-methoxybenzyl)amino)-2-(methyl sulfinyl)pyrimidine-5-formamide (222 mg, 0.5 mmol) and DIEA (0.25 mL, 1.35 mmol). 3-oxo-8-azabicyclo[3.2.1] octane hydrochloride salt (90 mg, 0.6 mmol) was dissolved in THF and added to the reaction mixture at 0° C. The reaction was conducted at ambient temperature, followed by addition of water and extraction with ethyl acetate. The organic phase was washed sequentially with water and brine, and dried over sodium sulfate. The solvent was removed by rotary evaporation. Purification was performed by silica gel column chromatography (petroleum ether/ethyl acetate=1/1) to give a white solid (50 mg, 19% yield).

Molecular formula: C$_{26}$H$_{28}$ClN$_5$O$_3$ Molecular weight: 494.0 MS (m/e): 494 (M+H$^+$)

$^1$H-NMR (400 MHz, DMSO-d$_6$, hydrochloride salt): δ 10.00 (brs, 1H), 9.36 (brs, 1H), 8.51 (s, 1H), 7.44 (s, 1H),

123

7.23-7.34 (m, 6H), 7.08 (d, 1H), 4.77 (s, 2H), 4.56 (m, 2H), 4.42 (d, 2H), 3.80 (s, 3H), 3.60 (m, 4H), 1.99 (m, 4H).

Example 24

Preparation: N-benzyl-2-(3,8-diazabicyclo[3.2.1]octan-3-yl)-4-((3-chloro-4-methoxybenzyl)amino)pyrimidine-5-formamide (Compound 24)

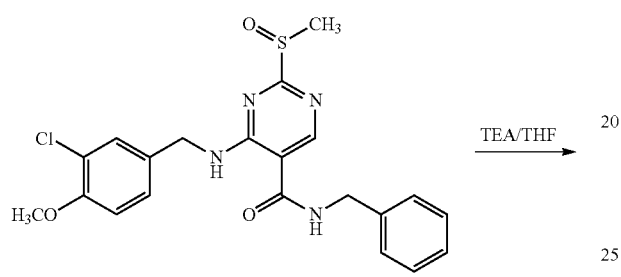

The procedures were analogous to Example 16. Tert-butyl (1R,5S)-3,8-diazabicyclo[3.2.1]octane-8-carboxylate (129 mg, 0.61 mmol) was used instead of tert-butyl 2,6-diazabicyclo[3.4]octane-2-carboxylate. The total yield of the two steps was 35%.

Molecular formula: $C_{26}H_{29}ClN_6O_2$ Molecular weight: 493.0 MS (m/e): 493 (M+H$^+$)

124

$^1$H-NMR (400 MHz, CDCl$_3$): δ 9.01 (m, 1H), 8.16 (s, 1H), 7.29-7.38 (m, 6H), 7.20 (d, 1H), 6.86 (d, 1H), 6.10 (m, 1H), 4.55 (m, 4H), 4.36 (d, 2H), 3.88 (s, 3H), 3.55 (s, 2H), 3.02 (d, 2H), 1.72 (m, 4H).

Example 25

Preparation: 2-(3-diazabicyclo[3.1.0]hexan-3-yl)-4-(((5-chloro-6-methoxy pyridin-3-yl)methyl)amino)-N-(pyrimidin-2-ylmethyl)pyrimidine-5-formamide (Compound 25)

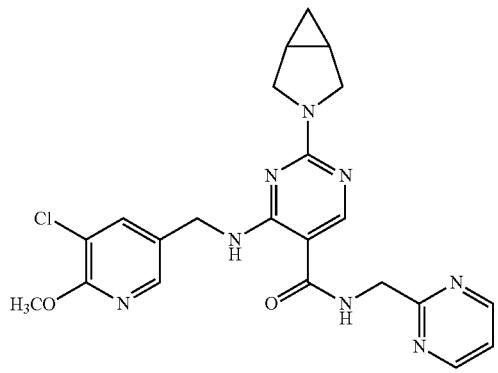

(1) Preparation: ethyl 4-(((5-chloro-6-methoxypyridin-3-yl)methyl)amino)-2-(methylthio) pyrimidine-5-carboxylate

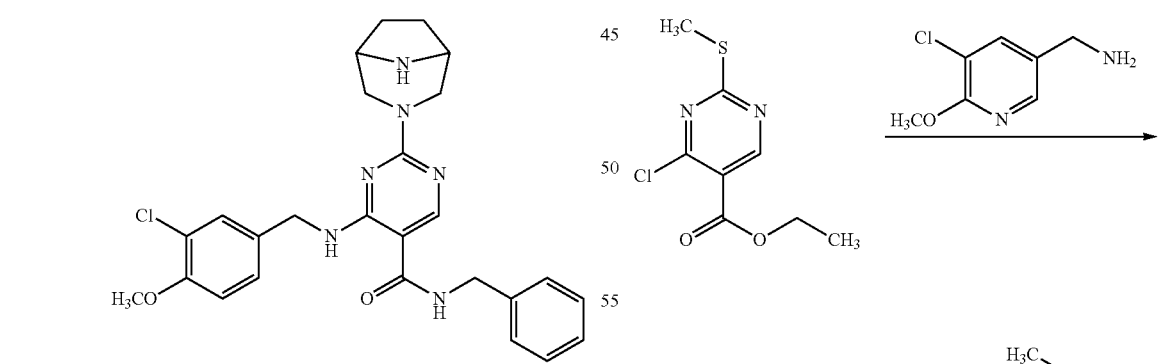

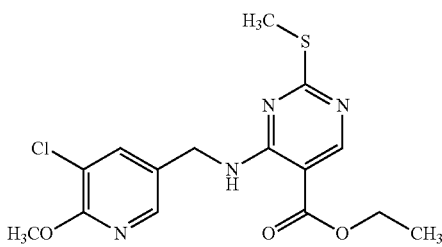

The procedures were analogous to Example 1(1). (5-chloro-6-methoxypyridin-3-yl)methylamine was used instead of 3-chloro-4-methoxybenzylamine in step 1. Yield: 23.3%.

(2) Preparation: 4-(((5-chloro-6-methoxypyridin-3-yl)methyl)amino)-2-(methylthio) pyrimidine-5-carboxylic acid

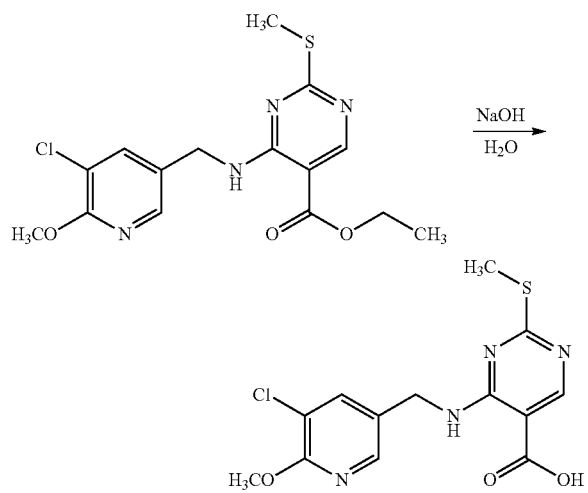

The procedures were analogous to Example 1(2). Yield: 63.2%.

(3) Preparation: 4-(((5-chloro-6-methoxypyridin-3-yl)methyl)amino)-2-(methylthio)-N-(pyrimidin-2-ylmethyl)pyrimidine-5-formamide

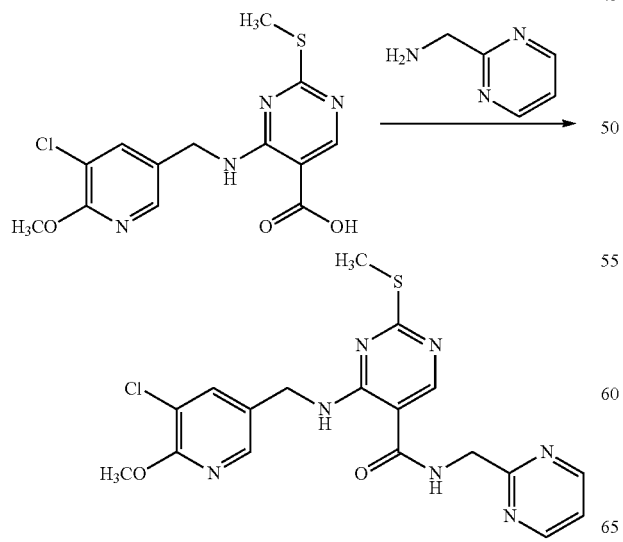

The procedures were analogous to Example 1(3). Yield: 61.2%.

(4) Preparation: 4-(((5-chloro-6-methoxypyridin-3-yl)methyl)amino)-2-(methylsulfinyl)-N-(pyrimidin-2-ylmethyl)pyrimidine-5-formamide

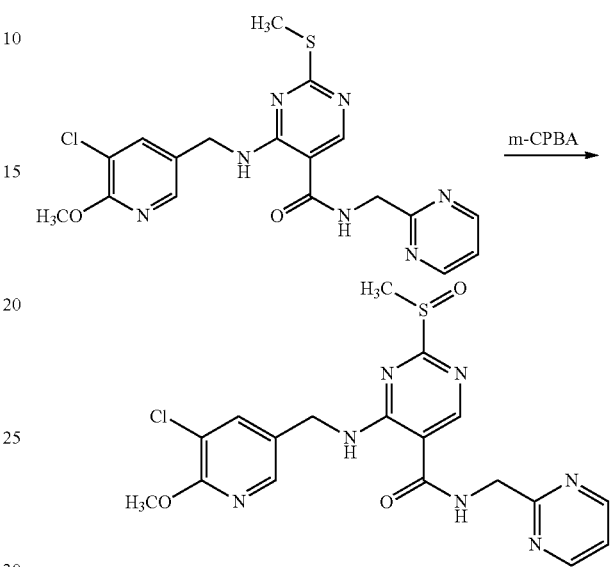

The procedures were analogous to Example 1(4). The crude product was used in the subsequent procedure without further purification.

(5) Preparation: 2-(3-azabicyclo[3.1.0]hexan-3-yl)-4-(((5-chloro-6-methoxypyridin-3-yl)methyl)amino)-N-(pyrimidin-2-ylmethyl)pyrimidine-5-formamide

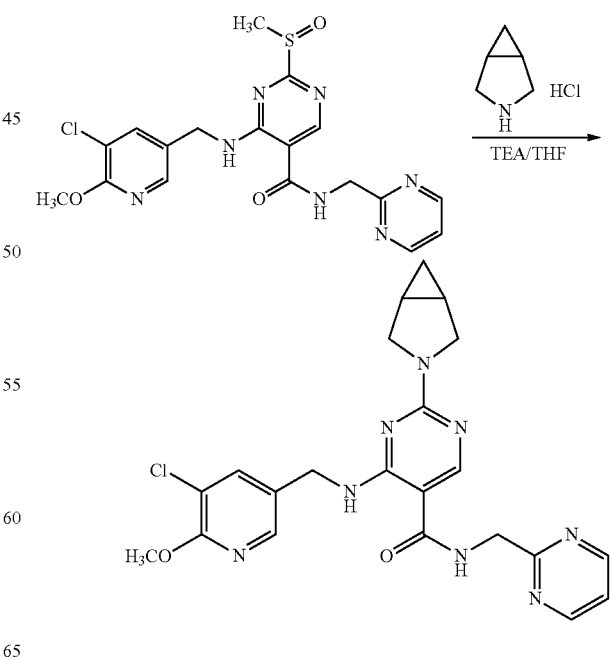

The procedures were analogous to Example 1(5). Yield: 25.7%.

Molecular formula: $C_{22}H_{23}ClN_8O_2$ Molecular weight: 466.9 MS (m/e): 466.9 (M+H⁺)

$^1$H NMR (400 MHz, CDCl$_3$): δ 9.07 (t, 1H), 8.73 (d, 2H), 8.41 (s, 1H), 8.06 (s, 1H), 7.70 (d, 1H), 7.33 (t, 1H), 7.24 (t, 1H), 4.80 (d, 2H), 4.58 (m, 2H), 4.01 (s, 3H), 3.89 (m, 2H), 3.52 (m, 2H), 1.62 (s, 2H), 0.75 (m, 1H), 0.23 (m, 1H).

Example 26

Preparation: 2-(3-azabicyclo[3.1.0]hexan-3-yl)-4-((3-chloro-4-methoxy benzyl)amino)-N-((7-methyl-7-azaspiro[3.5]nonan-2-yl)methyl)pyrimidine-5-formamide (Compound 26)

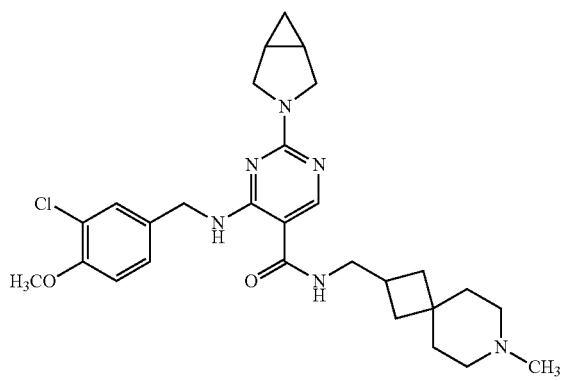

(1) Preparation: tert-butyl 2-((2-(3-azabicyclo[3.1.0]hexan-3-yl)-4-((3-chloro-4-methoxy benzyl)amino)pyrimidine-5-formamido)methyl)-7-azaspiro[3.5]nonae-7-carboxylate

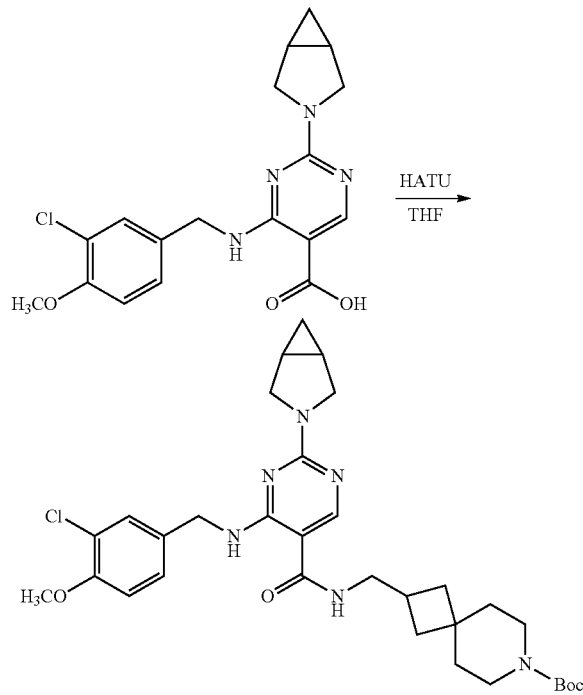

In THF (10 mL) were dissolved 2-(3-azabicyclo[3.1.0]hexan-3-yl)-4-((3-chloro-4-methoxybenzyl)amino)pyrimidine-5-carboxylic acid (187 mg, 0.50 mmol), tert-butyl 2-(aminomethyl)-7-azaspiro[3.5]nonane-7-carboxylate (140 mg, 0.55 mmol) and triethylamine (101 mg, 1 mmol). The solution was cooled in an ice bath and HATU (266 mg, 0.70 mmol) was added then. The reaction was conducted at ambient temperature for 4 h. The reaction mixture was concentrated, followed by addition of water and extraction with ethyl acetate. The organic phase was dried, concentrated and purified by silica gel column chromatography (DCM/methanol=20/1) to give tert-butyl 2-((2-(3-azabicyclo[3.1.0]hexan-3-yl)-4-((3-chloro-4-methoxybenzyl)amino)pyrimidine-5-formamido)methyl)-7-azaspiro[3.5]nonane-7-carboxylate (220 mg, 72% yield).

(2) Preparation: N-(7-azaspiro[3.5]nonan-2-ylmethyl)-2-(3-azabicyclo[3.1.0]hexan-3-yl)-4-((3-chloro-4-methoxybenzyl)amino)pyrimidine-5-formamide

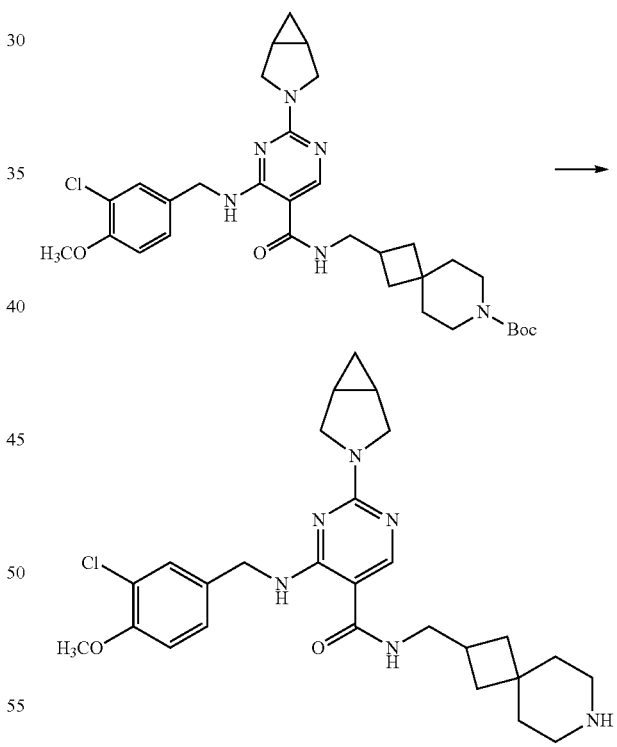

In DCM (15 mL) was dissolved tert-butyl 2-((2-(3-azabicyclo[3.1.0]hexan-3-yl)-4-((3-chloro-4-methoxybenzyl)amino)pyrimidine-5-formamido)methyl)-7-azaspiro[3.5]nonane-7-carboxylate (220 mg, 0.36 mmol). Trifluoroacetic acid (1 mL) was added. The reaction mixture was stirred at ambient temperature for 2 h then concentrated to give a solid. The yield was 100%. The product was used in the subsequent procedure without further purification.

(3) Preparation: 2-(3-azabicyclo[3.1.0]hexan-3-yl)-4-((3-chloro-4-methoxybenzyl)amino)-N-((7-methyl-7-azaspiro[3.5]nonan-2-yl)methyl)pyrimidine-5-formamide

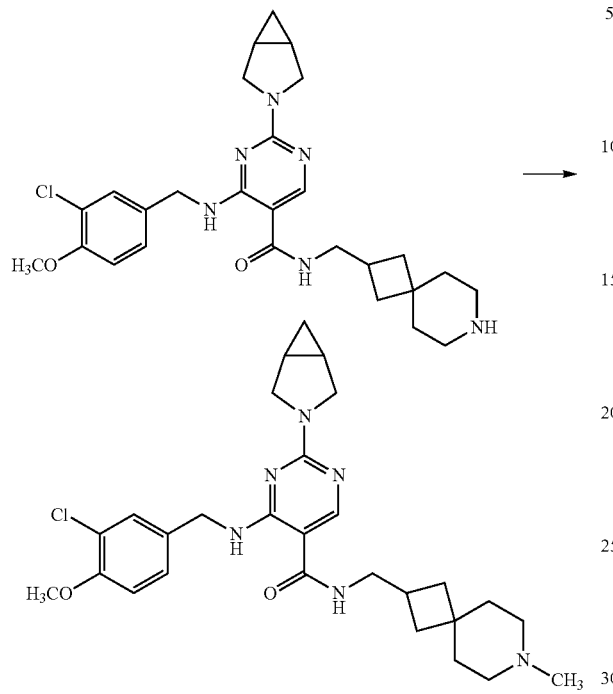

In THF (20 mL) was dissolved the above N-(7-azaspiro[3.5]nonan-2-ylmethyl)-2-(3-azabicyclo[3.1.0]hexan-3-yl)-4-((3-chloro-4-methoxybenzyl)amino)pyrimidine-5-formamide. Formalin (1 mL) was added. The reaction was conducted at ambient temperature for 1 h, sodium triacetoxyborohydride (134 mg, 0.63 mmol) was added and the reaction was continued for 4 h. The reaction was quenched with water. The reaction mixture was filtrated. The organic phase was dried and concentrated. The obtained solid was purified by silica gel column chromatography (DCM/methanol=20/1) to give 2-(3-azabicyclo[3.1.0]hexan-3-yl)-4-((3-chloro-4-methoxybenzyl)amino)-N-((7-methyl-7-azaspiro[3.5]nonan-2-yl)methyl) pyrimidine-5-formamide (39 mg, 21% yield).

Example 26-1

Preparation: 2-(3-azabicyclo[3.1.0]hexan-3-yl)-4-((3-chloro-4-methoxy benzyl)amino)-N-((7-methyl-7-azaspiro[3.5]nonan-2-yl)methyl)pyrimidine-5-formamide (Compound 26)

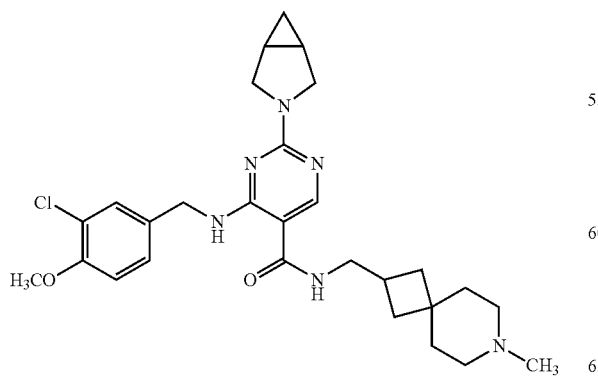

(1) Preparation: tert-butyl 2-((2-(3-azabicyclo[3.1.0]hexan-3-yl)-4-((3-chloro-4-methoxy benzyl)amino)pyrimidine-5-formamido)methyl)-7-azaspiro[3.5]nonane-7-carboxylate

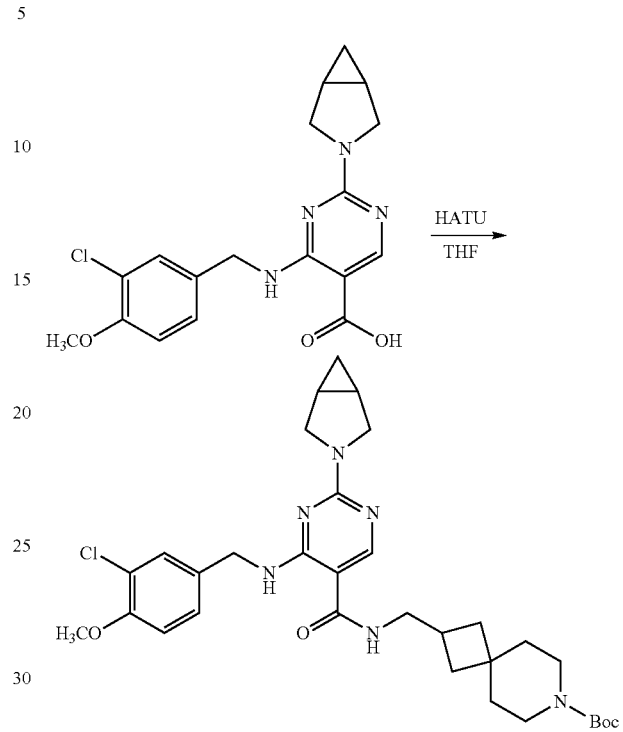

In THF (40 mL) were dissolved 2-(3-azabicyclo[3.1.0]hexan-3-yl)-4-((3-chloro-4-methoxybenzyl)amino)pyrimidine-5-carboxylic acid (375 mg, 1 mmol), tert-butyl 2-(aminomethyl)-7-azaspiro[3.5]nonane-7-carboxylate (275 mg, 1.1 mmol) and DIEA (0.5 mL, 2.8 mmol). The solution was cooled in an ice bath and HATU (439 mg, 1.2 mmol) was added then. The reaction was conducted at ambient temperature for 12 h. The reaction was quenched with water, followed by extraction with DCM. The organic phase was washed sequentially with water and brine, dried over sodium sulfate, concentrated and purified by silica gel column chromatography (DCM/methanol=20/1) to give tert-butyl 2-((2-(3-azabicyclo[3.1.0]hexan-3-yl)-4-((3-chloro-4-methoxybenzyl)amino)pyrimidine-5-formamido)methyl)-7-azaspiro[3.5]nonane-7-carboxylate (420 mg, 69% yield).

(2) Preparation: N-(7-azaspiro[3.5]nonan-2-ylmethyl)-2-(3-azabicyclo[3.1.0]hexan-3-yl)-4-((3-chloro-4-methoxybenzyl)amino)pyrimidine-5-formamide

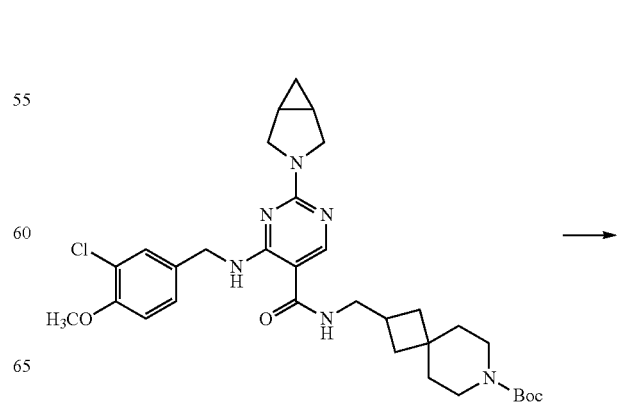

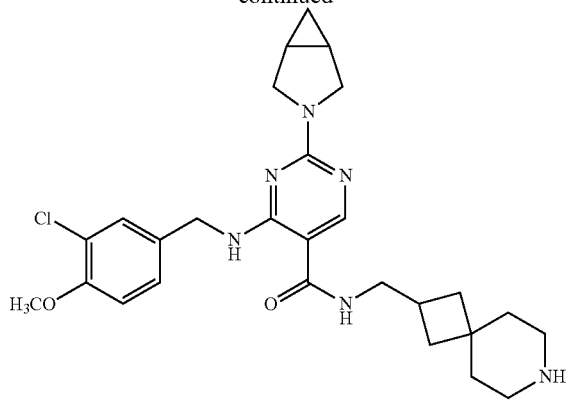

In DCM (50 mL) was dissolved tert-butyl 2-((2-(3-azabicyclo[3.1.0]hexan-3-yl)-4-((3-chloro-4-methoxybenzyl)amino)pyrimidine-5-formamido)methyl)-7-azaspiro[3.5]nonane-7-carboxylate (420 mg, 0.69 mmol). Trifluoroacetic acid (0.6 mL, 7.2 mol) was added. The reaction mixture was stirred at ambient temperature for 5 h then concentrated to give a solid. The product was used in the subsequent procedure without further purification.

(3) Preparation: 2-(3-azabicyclo[3.1.0]hexan-3-yl)-4-((3-chloro-4-methoxybenzyl)amino)-N-((7-methyl-7-azaspiro[3.5]nonan-2-yl)methyl) pyrimidine-5-formamide

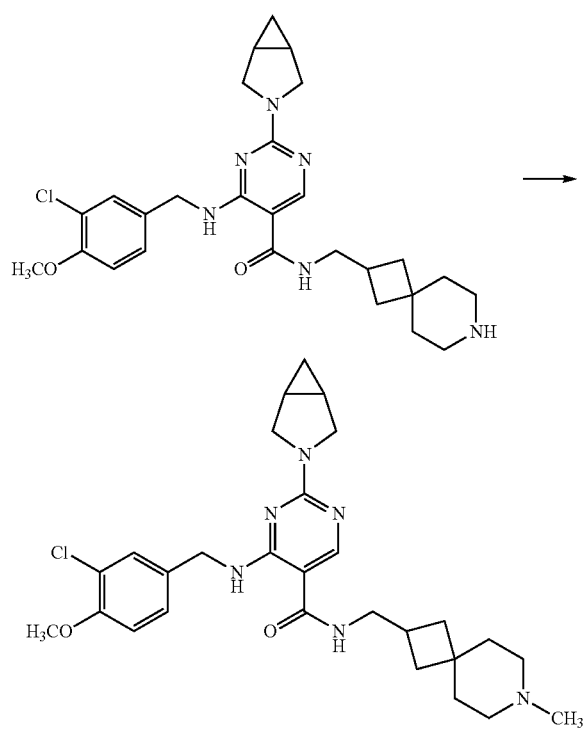

In methanol (50 mL) was dissolved the above N-(7-azaspiro[3.5]nonan-2-ylmethyl)-2-(3-azabicyclo[3.1.0]hexan-3-yl)-4-((3-chloro-4-methoxybenzyl)amino)pyrimidine-5-formamide (357 mg, 0.7 mmol). Formalin (284 mg, 3.5 mmol) was added. Sodium borohydride (133 mg, 3.5 mmol) was added slowly. The reaction was continued for 10 h then quenched with water. The reaction mixture was extracted with ethyl acetate. The organic phase was dried and concentrated. The obtained solid was purified by silica gel column chromatography (DCM/methanol=20/1) to give 2-(3-azabicyclo[3.1.0]hexan-3-yl)-4-((3-chloro-4-methoxybenzyl)amino)-N-((7-methyl-7-azaspiro[3.5]nonan-2-yl)methyl) pyrimidine-5-form amide (100 mg, 27.4% yield).

Molecular formula: $C_{28}H_{37}ClN_6O_2$ Molecular weight: 525.1 MS (m/e): 526 (M+H$^+$)

$^1$H-NMR (400 MHz, CDCl$_3$): δ 8.92 (s, 1H), 8.14 (s, 1H), 7.39 (s, 1H), 7.20 (d, 1H), 6.87 (d, 1H), 5.88 (s, 1H), 4.53 (m, 2H), 3.89 (s, 3H), 3.85 (d, 2H), 3.51 (m, 2H), 3.37 (m, 2H), 2.81 (s, 1H), 2.22 (m, 4H), 2.20 (s, 3H), 1.94 (m, 2H), 1.43-1.78 (m, 8H), 0.75 (m, 1H), 0.21 (m, 1H).

Example 27

Preparation: 4-((3-chloro-4-methoxybenzyl)amino)-2-(2-(hydroxylmethyl)-3-azabicyclo[3.1.0]hexan-3-yl)-N-(pyrimidin-2-ylmethyl)pyrimidine-5-formamide (Compound 27)

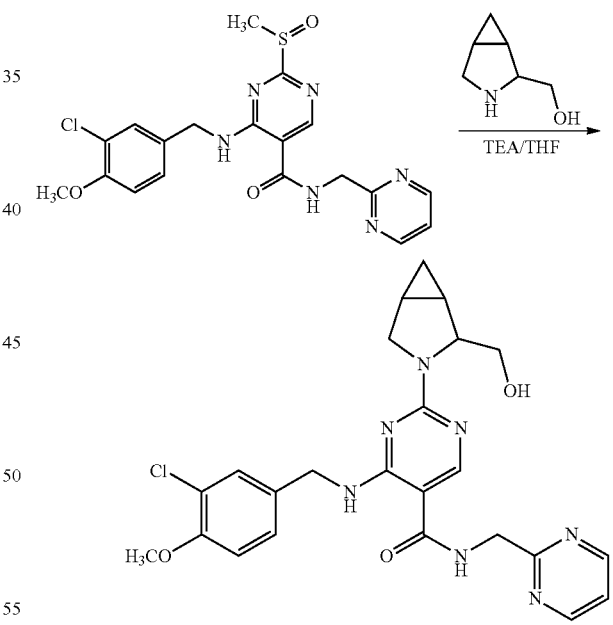

The procedures were analogous to Example 1(5). (3-azabicyclo[3.1.0]hexan-2-yl) methanol hydrochloride salt (65 mg, 0.54 mmol) was used in step 5 instead of 3-azabicyclo[3.1.0] hexan hydrochloride salt to give Compound 27.

Molecular formula: $C_{24}H_{26}ClN_7O_3$ Molecular weight: 496.0 MS (m/e): 496.2 (M+H$^+$)

$^1$H-NMR (400 MHz, CDCl$_3$): δ 9.10 (brs, 1H), 8.73 (d, 2H), 8.27 (s, 1H), 7.38 (m, 2H), 7.26 (m, 1H), 7.19 (d, 1H), 6.87 (d, 1H), 4.77 (d, 2H), 4.58 (m, 2H), 4.47 (m, 1H), 4.08

(m, 1H), 3.88 (s, 3H), 3.85 (m, 1H), 3.74 (m, 1H), 3.55 (m, 1H), 1.55 (m, 1H), 1.33 (m, 2H), 0.76 (m, 1H), 0.17 (s, 1H).

Example 28

Preparation: N-benzyl-4-((3-chloro-4-methoxybenzyl)amino)-2-(6-azaspiro[3.4]octan-6-yl)pyrimidine-5-formamide (Compound 28)

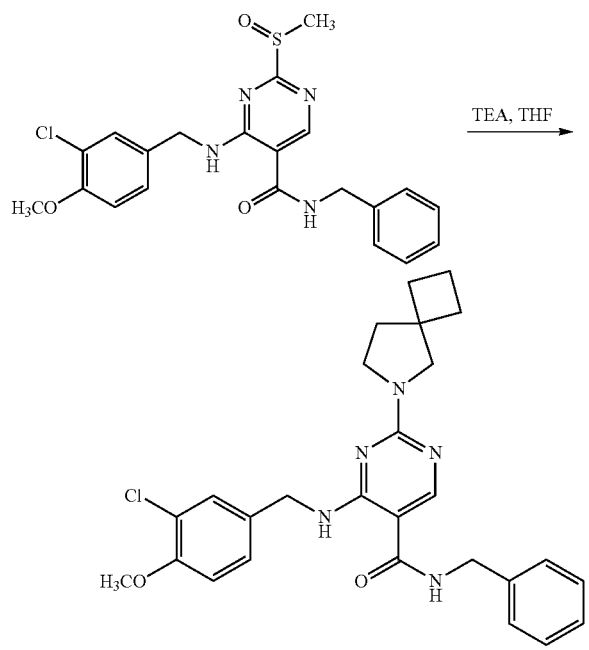

The procedures were analogous to Example 1 (5). Yield: 80%.

Molecular formula: $C_{27}H_{30}ClN_5O_2$ Molecular weight: 492.0 MS (m/e): 492.3 (M+H$^+$)

$^1$H-NMR (400 MHz, DMSO-d$_6$): δ 9.19 (m, 1H), 8.71 (m, 1H), 8.46 (s, 1H), 7.43 (d, 1H), 7.22-7.32 (m, 5H), 7.19 (t, 1H), 7.06 (d, 1H), 4.48(d, 2H), 4.38 (d, 2H), 3.80 (s, 3H), 3.43(m, 4H), 1.87-1.95 (m, 8H).

Example 28-1

Preparation: N-benzyl-4-((3-chloro-4-methoxybenzyl)amino)-2-(6-azaspiro[3.4]octan-6-yl)pyrimidine-5-formamide (Compound 28)

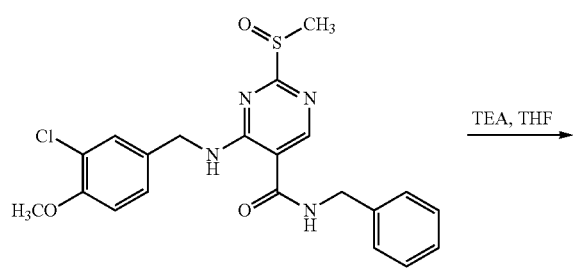

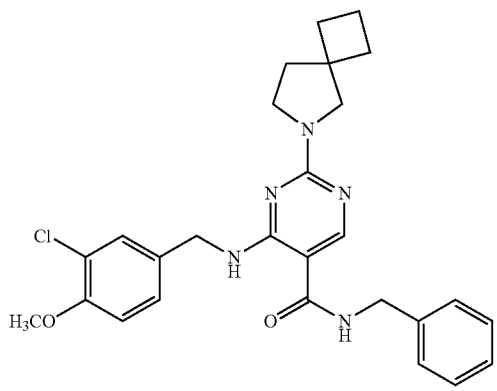

The procedures were analogous to Example 21. 6-azaspiro[3.4]octane (50 mg, 0.45 mmol) was used instead of 5-azaspiro[2.4]heptane to give Compound 28. Yield: 80%.

Molecular formula: $C_{27}H_{30}ClN_5O_2$ Molecular weight: 492.0 MS (m/e): 492.3 (M+H$^+$)

$^1$H-NMR (400 MHz, DMSO-d$_6$): δ 9.19 (m, 1H), 8.71 (m, 1H), 8.46 (s, 1H), 7.43 (d, 1H), 7.22-7.32 (m, 5H), 7.19 (t, 1H), 7.06 (d, 1H), 4.48(d, 2H), 4.38 (d, 2H), 3.80 (s, 3H), 3.43(m, 4H), 1.87-1.95 (m, 8H).

Example 29

Preparation: N-benzyl-4-((3-chloro-4-methoxybenzyl)amino)-2-(4-azaspiro[2.4]heptan-4-yl)pyrimidine-5-formamide (Compound 29)

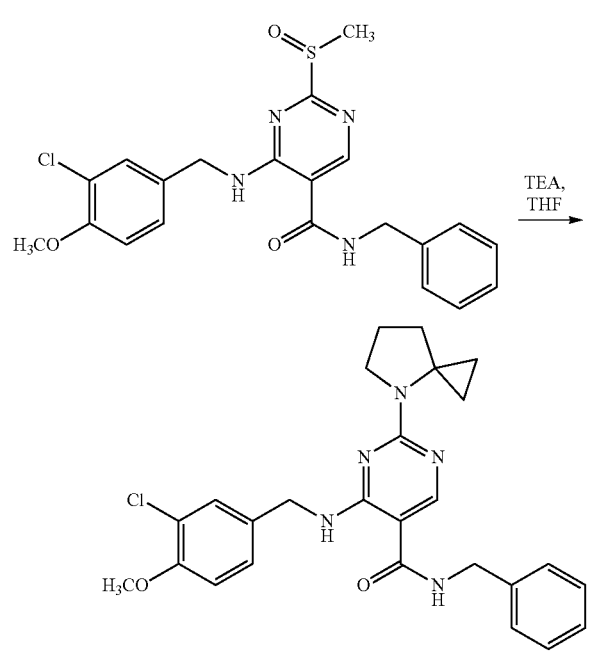

The procedures were analogous to Example 1 (5). Yield: 15%.

Molecular formula: $C_{26}H_{28}ClN_5O_2$ Molecular weight: 478.0 MS (m/e): 478.2 (M+H$^+$)

$^1$H-NMR (400 MHz, DMSO-d$_6$, hydrochloride salt): δ 9.90 (brs, 1H), 9.32 (brs, 1H), 8.40 (s, 1H), 7.33 (m, 6H), 7.32 (s, 1H), 7.19 (d, 1H), 7.11 (d, 1H), 4.54(d, 2H), 4.42 (d, 2H), 3.83 (s, 3H), 3.69(m, 2H), 1.97(s, 4H), 1.85(s, 2H), 0.52 (s, 2H).

Example 29-1

Preparation: N-benzyl-4-((3-chloro-4-methoxybenzyl)amino)-2-(4-azaspiro[2.4]heptan-4-yl)pyrimidine-5-formamide (Compound 29)

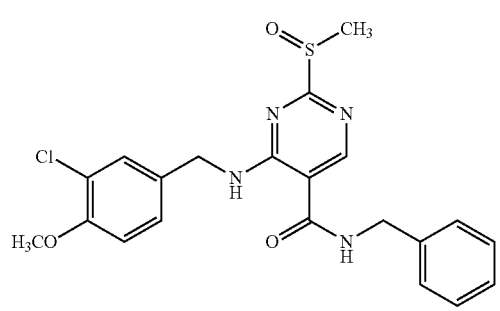

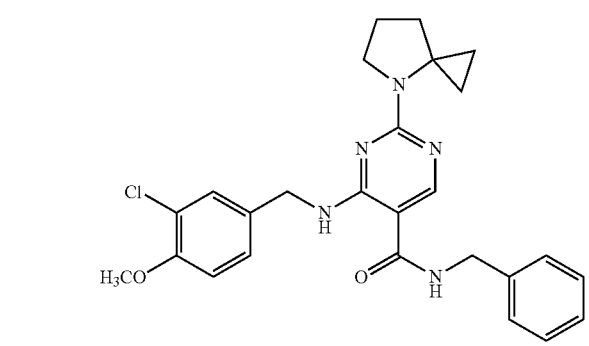

The procedures were analogous to Example 21. 4-azaspiro[2.4]heptane (190 mg, 2.0 mmol) was used instead of 5-azaspiro[2.4]heptane to give Compound 29. Yield: 15%.

Molecular formula: $C_{26}H_{28}ClN_5O_2$ Molecular weight: 478.0 MS (m/e): 478.2 (M+H$^+$)

$^1$H-NMR (400 MHz, DMSO-d$_6$, hydrochloride salt): δ 9.90 (brs, 1H), 9.32 (brs, 1H), 8.40 (s, 1H), 7.33 (m, 6H), 7.32 (s, 1H), 7.19 (d, 1H), 7.11 (d, 1H), 4.54(d, 2H), 4.42 (d, 2H), 3.83 (s, 3H), 3.69(m, 2H), 1.97(s, 4H), 1.85(s, 2H), 0.52 (s, 2H).

Example 30

Preparation: N-benzyl-4-((3-chloro-4-methoxybenzyl)amino)-2-(6,6-dimethyl-3-azabicyclo[3.1.0]hexan-3-yl)pyrimidine-5-formamide (Compound 30)

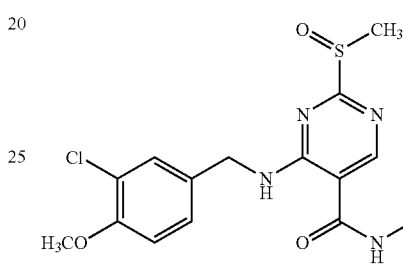
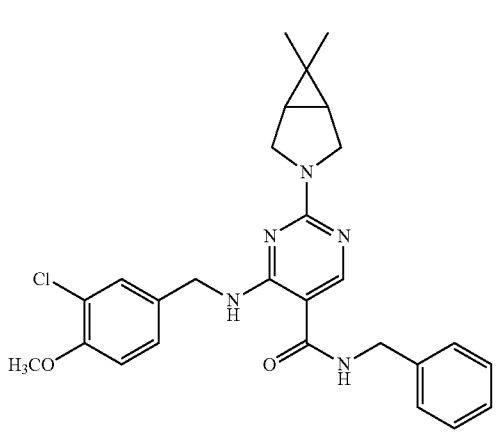

The procedures were analogous to Example 1 (5). Yield: 42%.

Molecular formula: $C_{27}H_{30}ClN_5O_2$ Molecular weight: 492.0 MS (m/e): 492.0 (M+H$^+$)

$^1$H-NMR (400 MHz, CDCl$_3$): δ 8.99 (m, 1H), 8.16 (s, 1H), 7.41 (d, 1H), 7.27-7.36 (m, 5H), 7.20 (d, 1H), 6.86 (d, 1H), 6.08(m, 1H), 4.55 (m, 4H), 3.88 (s, 3H), 3.62 (m, 4H), 1.43 (s, 2H), 1.06 (s, 3H), 0.89 (s, 3H).

Example 30-1

Preparation: N-benzyl-4-((3-chloro-4-methoxyben-zyl)amino)-2-(6,6-dimethyl-3-azabicyclo[3.1.0]hexan-3-yl)pyrimidine-5-formamide (Compound 30)

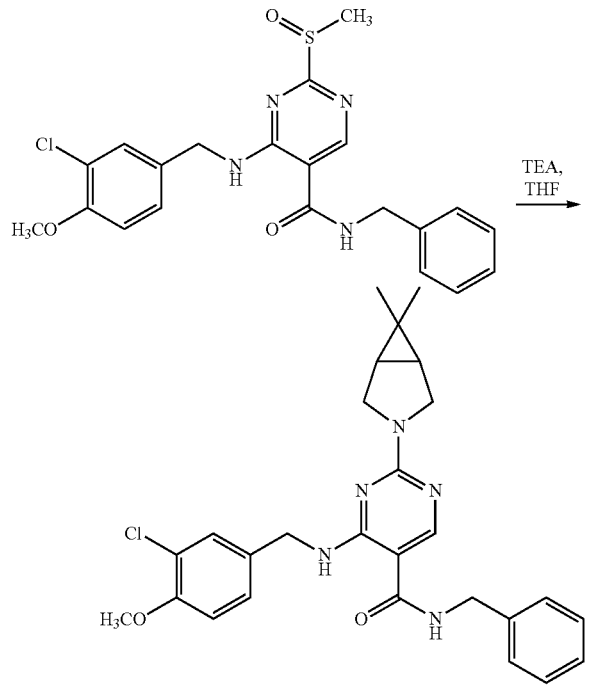 [SMILES: COc1ccc(CNc2nc(S(C)=O)ncc2C(=O)NCc2ccccc2)cc1Cl ; COc1ccc(CNc2nc(N3CCCC34CC4)ncc2C(=O)NCc2ccccc2)cc1Cl]

The procedures were analogous to Example 21. 6,6-dimethyl-3-azabicyclo[3.1.0]hexan (68 mg, 0.61 mmol) was used instead of 5-azaspiro[2.4]heptane to give Compound 30. Yield: 42%.

Molecular formula: $C_{27}H_{30}ClN_5O_2$ Molecular weight: 492.0 MS (m/e): 492.0 (M+H$^+$)

$^1$H-NMR (400 MHz, CDCl$_3$): δ 8.99 (m, 1H), 8.16 (s, 1H), 7.41 (d, 1H), 7.27-7.36 (m, 5H), 7.20 (d, 1H), 6.86 (d, 1H), 6.08(m, 1H), 4.55 (m, 4H), 3.88 (s, 3H), 3.62 (m, 4H), 1.43 (s, 2H), 1.06 (s, 3H), 0.89 (s, 3H).

Example 31

Preparation: 2-(3-azabicyclo[3.1.0]hexan-3-yl)-4-((5-chloro-6-methoxy-2,3-dihydro-1H-indene-2-yl)amino)-N-(pyrimidin-2-ylmethyl)pyrimidine-5-formamide (Compound 31)

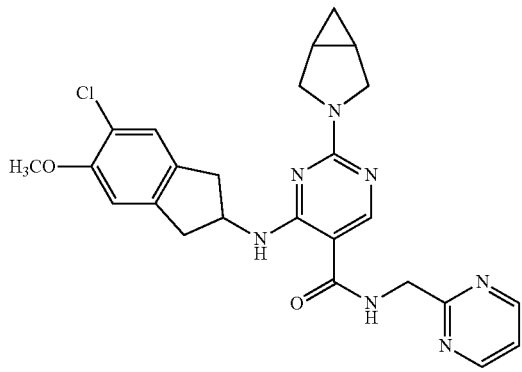 [SMILES: COc1cc2c(cc1Cl)CC(Nc1nc(N3CC4CC4C3)ncc1C(=O)NCc1ncccn1)C2]

(1) Preparation: ethyl 4-((5-chloro-6-methoxy-2,3-dihydro-1H-indene-2-yl)amino)-2-(methylthio)pyrimidine-5-carboxylate

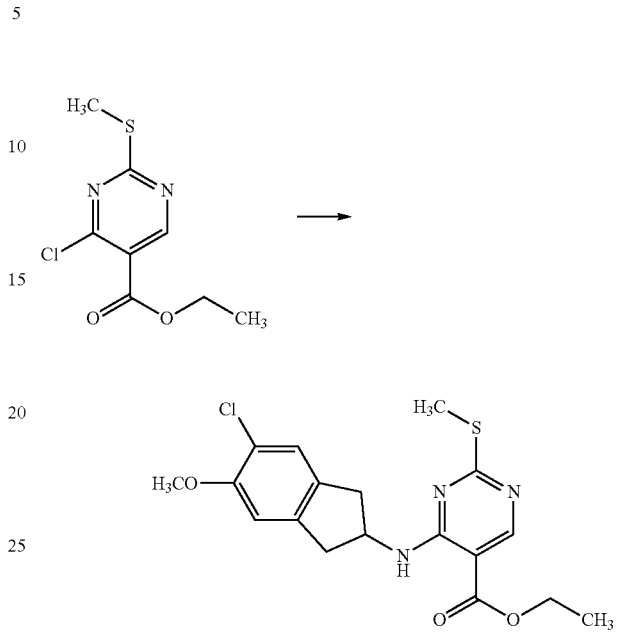

The procedures were analogous to Example 1(1). 5-chloro-6-methoxy-2,3-dihydro-1H-indene-2-amine (1 g, 4.3 mmol) was used in step 1 instead of 3-chloro-4-methoxybenzylamine to give the product, which was used in the subsequent procedure without further purification.

(2) Preparation: 4-((5-chloro-6-methoxy-2,3-dihydro-1H-indene-2-yl)amino)-2-(methylthio) pyrimidine-5-carboxylic acid

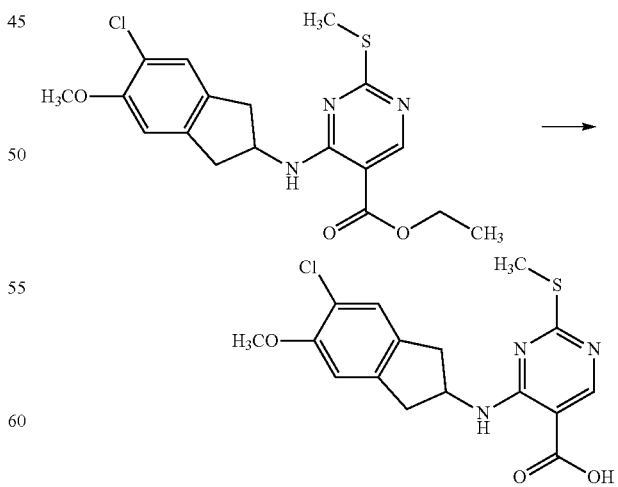

The procedures were analogous to Example 1(2). The product was used in the subsequent procedure without further purification.

(3) Preparation: 4-((5-chloro-6-methoxy-2,3-dihydro-1H-indene-2-yl)amino)-2-(methylthio)-N-(pyrimidin-2-ylmethyl)pyrimidine-5-formamide

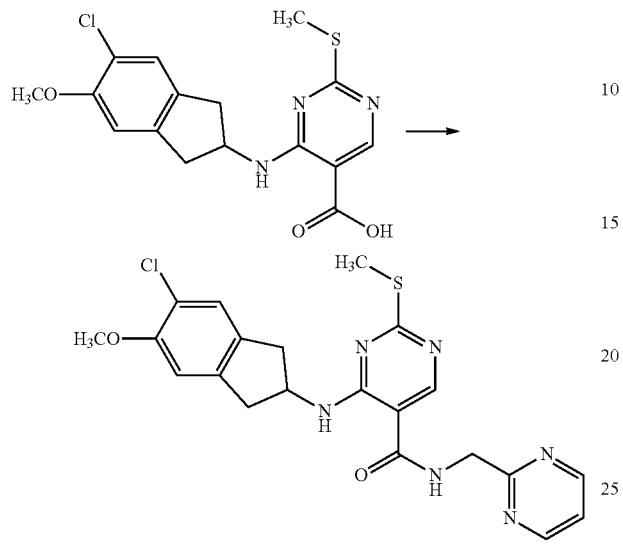

The procedures were analogous to Example 1(3). The product was used in the subsequent procedure without further purification.

(4) Preparation: 4-((5-chloro-6-methoxy-2,3-dihydro-1H-indene-2-yl)amino)-2-(methyl sulfinyl)-N-(pyrimidin-2-ylmethyl)pyrimidine-5-formamide

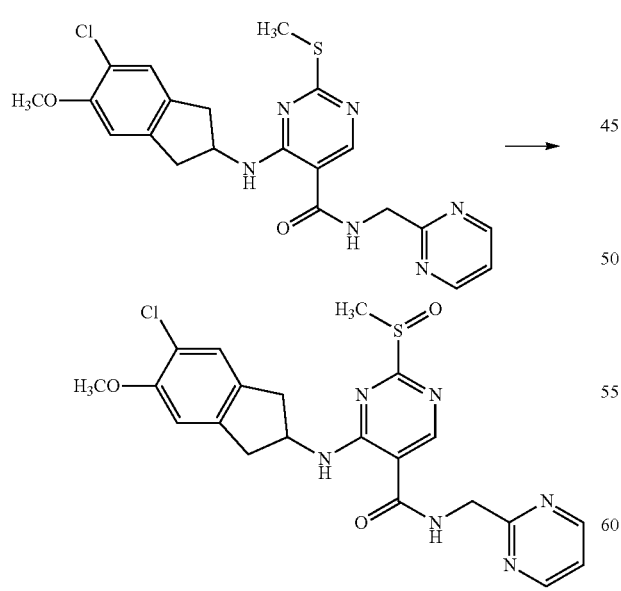

The procedures were analogous to Example 1(4). The product was used in the subsequent procedure without further purification.

(5) Preparation: 2-(3-azabicyclo[3.1.0]hexan-3-yl)-4-((5-chloro-6-methoxy-2,3-dihydro-1H-indene-2-yl)amino)-N-(pyrimidin-2-ylmethyl)pyrimidine-5-formamide

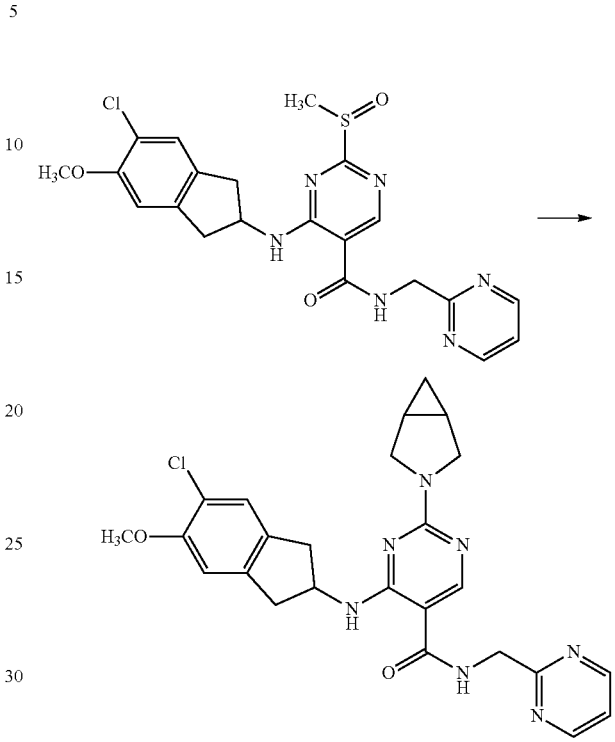

The procedures were analogous to Example 1(5). Yield: 24%.

Molecular formula: $C_{25}H_{26}ClN_7O_2$ Molecular weight: 492.0 MS (m/e): 492.2 (M+H$^+$)

$^1$H-NMR (400 MHz, CDCl$_3$): δ 8.84 (d, 1H), 8.73 (d, 2H), 8.41 (s, 1H), 7.33 (m, 1H), 7.22 (m, 2H), 6.83(s, 1H), 4.93 (m, 1H), 4.78 (d, 2H), 3.92 (d, 2H), 3.81 (s, 3H), 3.57 (m, 2H), 3.35 (m, 2H), 2.92 (m, 2H), 1.58 (m, 2H), 0.78 (m, 1H), 0.26 (s, 1H).

Example 32

Preparation: N-benzyl-4-((3-chloro-4-methoxybenzyl)amino)-2-(2-(hydroxymethyl)-3-azabicyclo[3.1.0]hexan-3-yl)pyrimidine-5-formamide (Compound

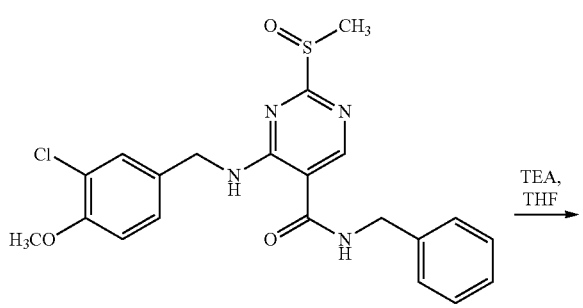

-continued

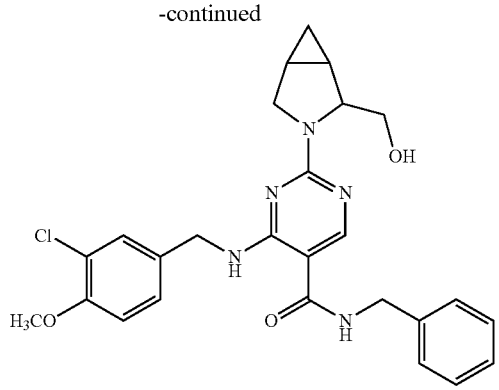

The procedures were analogous to Example 1(5). Yield: 28%.

Molecular formula: C$_{26}$H$_{28}$ClN$_5$O$_3$ Molecular weight: 494.0 MS (m/e): 494.2 (M+H$^+$)

$^1$H-NMR (400 MHz, CDCl$_3$): δ 9.1 (m, 1H), 8.05 (s, 1H), 7.29-7.38 (m, 6H), 7.21 (m, 1H), 6.88 (d, 1H), 6.15 (m, 1H), 4.58 (m, 4H), 4.41 (m, 1H), 4.07 (d, 1H), 3.89 (s, 3H), 3.81 (m, 1H), 3.68 (m, 1H), 3.55 (m, 1H), 1.61 (m, 3H), 0.87 (m, 1H), 0.20 (m, 1H).

Example 32-1

Preparation: N-benzyl-4-((3-chloro-4-methoxybenzyl)amino)-2-(2-(hydroxymethyl)-3-azabicyclo[3.1.0]hexan-3-yl)pyrimidine-5-formamide (Compound 32)

The procedures were analogous to Example 21. (3-azabicyclo[3.1.0]hexan-2-yl)methanol (65 mg, 0.54 mmol) was used instead of 5-azaspiro[2.4]heptane to give Compound 32. Yield: 28%.

Molecular formula: C$_{26}$H$_{28}$ClN$_5$O$_3$ Molecular weight: 494.0 MS (m/e): 494.2 (M+H$^+$)

$^1$H-NMR (400 MHz, CDCl$_3$): δ 9.1 (m, 1H), 8.05 (s, 1H), 7.29-7.38 (m, 6H), 7.21 (m, 1H), 6.88 (d, 1H), 6.15 (m, 1H), 4.58 (m, 4H), 4.41 (m, 1H), 4.07 (d, 1H), 3.89 (s, 3H), 3.81 (m, 1H), 3.68 (m, 1H), 3.55 (m, 1H), 1.61 (m, 3H), 0.87 (m, 1H), 0.20 (m, 1H).

Example 33

Preparation: 4-((3-chloro-4-methoxybenzyl)amino)-N-(4-fluorobenzyl)-2-(2-(hydroxymethyl)-3-azabicyclo[3.1.0]hexan-3-yl)pyrimidine-5-formamide (Compound 33)

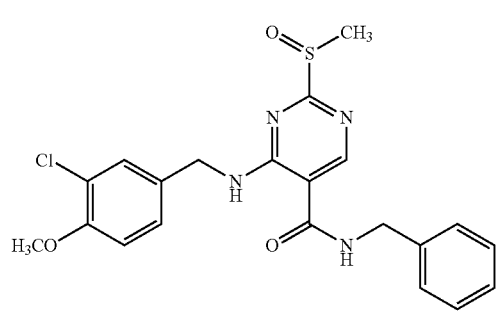

The procedures were analogous to Example 2(3). (4-fluorophenyl)methylamine (41 mg, 0.33 mmol) was used in step 3 instead of pyridine-2-ylmethylamine to give Compound 33. Yield: 32%.

Molecular formula: $C_{26}H_{27}ClFN_5O_3$ Molecular weight: 512.0 MS (m/e): 512.2 (M+H$^+$)

$^1$H-NMR (400 MHz, CDCl$_3$): δ 9.08 (m, 1H), 8.05 (s, 1H), 7.37 (m, 1H), 7.29 (m, 1H), 7.20 (d, 1H), 7.02 (m, 2H), 6.88 (d, 1H), 6.20 (m, 1H), 4.52 (m, 4H), 4.41 (m, 1H), 4.07 (d, 1H), 3.89 (s, 3H), 3.82 (m, 1H), 3.68 (m, 1H), 3.52 (m, 1H), 1.56 (m, 1H), 1.32 (m, 2H), 0.88 (m, 1H), 0.15 (m, 1H).

Example 34

Preparation: 4-((3-chloro-4-methoxybenzyl)amino)-2-(2-(hydroxymethyl)-3-azabicyclo[3.1.0]hexan-3-yl)-N-(2-morpholinoethyl)pyrimidine-5-formamide (Compound 34)

Molecular formula: $C_{25}H_{33}ClN_6O_4$ Molecular weight: 517.0 MS (m/e): 517.3 (M+H$^+$)

$^1$H-NMR (400 MHz, CDCl$_3$): δ 9.10 (m, 1H), 8.05 (s, 1H), 7.36 (s, 1H), 7.21 (d, 1H), 6.88 (d, 1H), 6.51 (m, 1H), 4.55 (m, 2H), 4.45 (m, 2H), 4.09 (m, 1H), 3.89 (s, 3H), 3.85 (m, 1H), 3.53-3.72 (m, 5H), 3.41 (m, 2H), 2.48-2.57 (m, 6H), 1.56 (m, 1H), 1.32 (m, 2H), 0.75 (m, 1H), 0.15 (m, 1H).

Example 35

Preparation: 4-((3-chloro-4-methoxybenzyl)amino)-N-(trans-4-hydroxycyclohexyl)-2-(2-(hydroxymethyl)-3-azabicyclo[3.1.0]hexan-3-yl)pyrimidine-5-formamide (Compound 35)

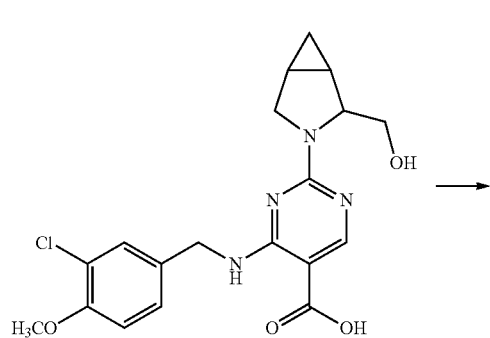

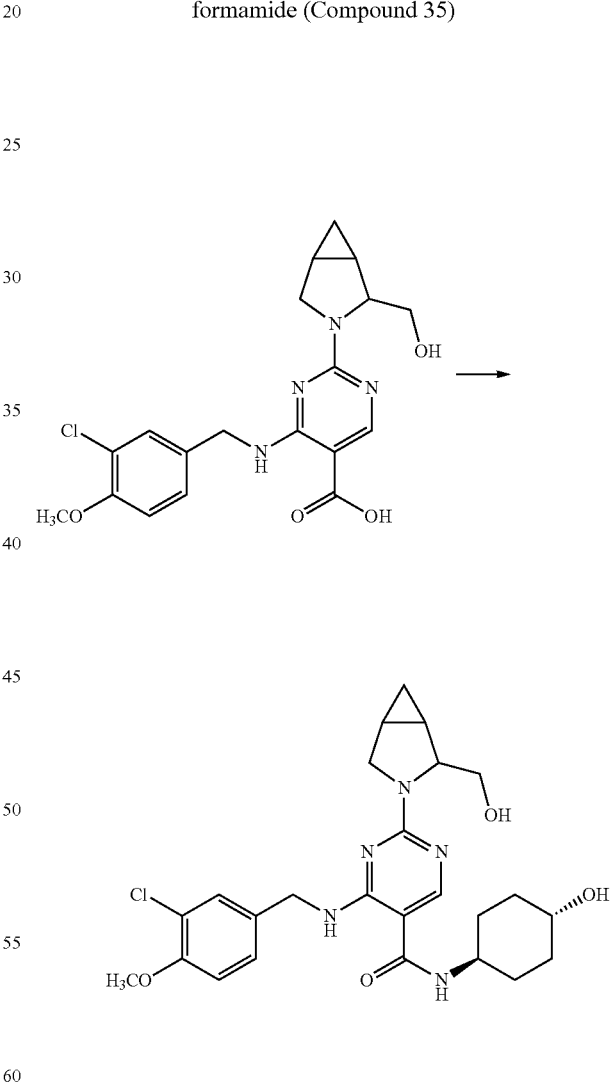

The procedures were analogous to Example 2(3). 2-morpholinoethane-1-amine (41 mg, 0.32 mmol) was used in step 3 instead of pyridine-2-ylmethylamine to give Compound 34. Yield: 24%.

The procedures were procedures were analogous to Example 2(3). Trans-4-hydroxycyclohexylamine (64 mg, 0.55 mmol) was used in step 3 instead of pyridine-2-ylmethylamine to give Compound 35. Yield: 28%.

145

Molecular formula: $C_{25}H_{32}ClN_5O_4$ Molecular weight: 502.0 MS (m/e): 502.3 (M+H$^+$)

$^1$H-NMR (400 MHz, CDCl$_3$): δ 9.08 (m, 1H), 8.00 (s, 1H), 7.37 (s, 1H), 7.20 (d, 1H), 6.87 (d, 1H), 5.64 (m, 1H), 4.55 (m, 2H), 4.43 (m, 1H), 4.08 (d, 1H), 3.89 (s, 3H), 3.87 (m, 2H), 3.64 (m, 2H), 3.51 (m, 1H), 2.03 (m, 6H), 1.57 (m, 1H), 1.41 (m, 2H), 1.28 (m, 3H), 0.76 (m, 1H), 0.15 (m, 1H).

Example 36

Preparation: 4-((3-chloro-4-methoxybenzyl)amino)-N-(trams-4-hydroxy cyclohexyl)-2-(6-azaspiro[2.5]octan-6-yl)pyrimidine-5-formamide (Compound 36)

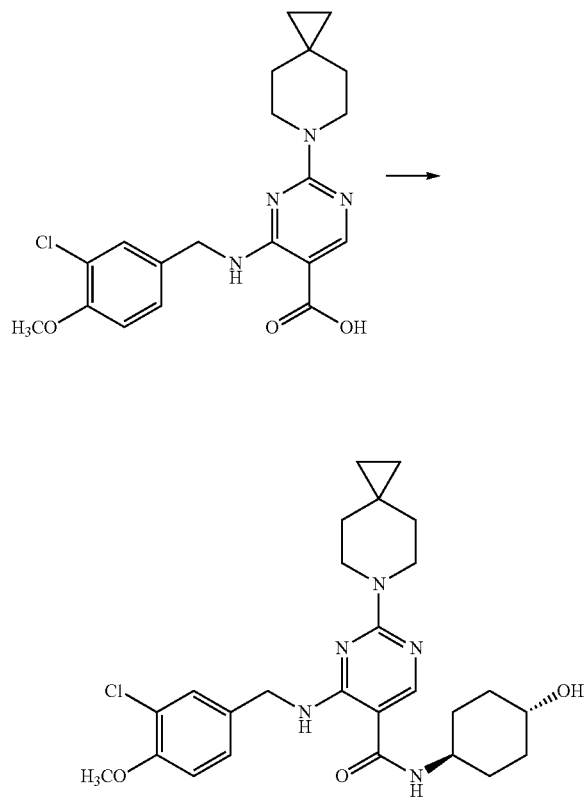 [SMILES: COc1ccc(CNc2nc(N3CCC4(CC3)CC4)ncc2C(=O)O)cc1Cl ; COc1ccc(CNc2nc(N3CCC4(CC3)CC4)ncc2C(=O)N[C@H]2CC[C@H](O)CC2)cc1Cl]

The procedures were procedures were analogous to Example 2(3). Trans-4-hydroxycyclohexylamine (104 mg, 0.90 mmol) was used in step 3 instead of pyridine-2-ylmethylamine to give Compound 36.

Molecular formula: $C_{26}H_{34}ClN_5O_3$ Molecular weight: 500.0 MS (m/e): 500.3 (M+H$^+$)

146

$^1$H-NMR (400 MHz, CDCl$_3$): δ 8.92 (m, 1H), 8.11 (s, 1H), 7.37 (s, 1H), 7.18 (d, 1H), 6.85 (d, 1H), 5.56 (d, 1H), 4.54 (d, 2H), 3.85-3.87 (m, 8H), 3.65 (m, 1H), 2.04 (m, 4H), 1.22-1.61 (m, 9H), 0.36 (s, 4H).

Example 37

Preparation: 4-((3-chloro-4-methoxybenzyl)amino)-2-(2-(hydroxymethyl)-3-azabicyclo[3.1.0]hexan-3-yl)-N-(pyridin-2-ylmethyl)pyrimidine-5-formamide (Compound 37)

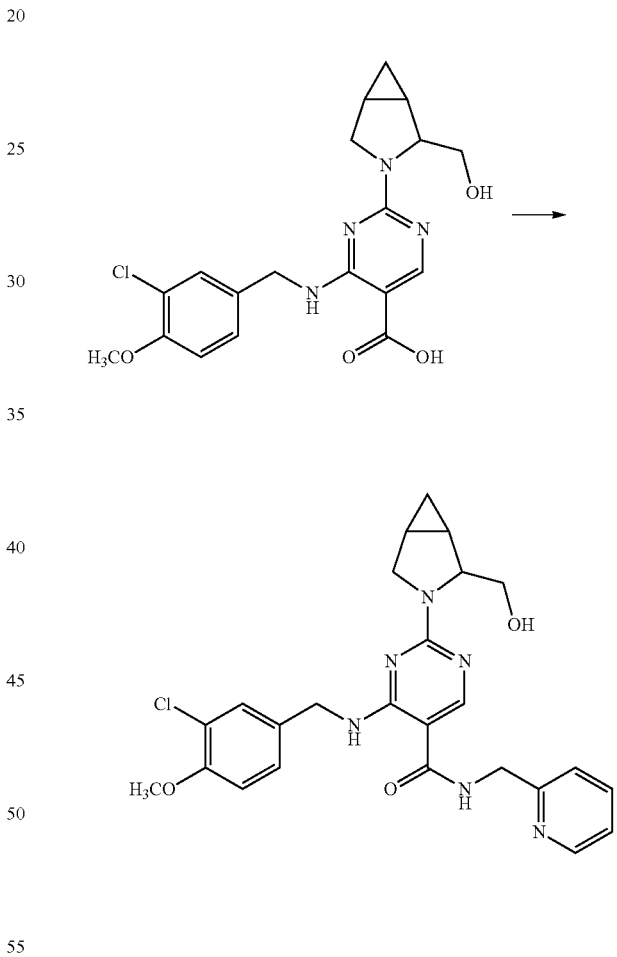

The procedures were procedures were analogous to Example 2(3). Pyridine-2-ylmethylamine (59 mg, 0.55 mmol) was used in step 3 to give Compound 37. Yield: 44%.

Molecular formula: $C_{25}H_{27}ClN_6O_3$ Molecular weight: 495 MS (m/e): 495.2 (M+H$^+$)

$^1$H-NMR (400 MHz, CDCl$_3$): δ 9.10 (m, 1H), 8.56 (m, 1H), 8.24 (s, 1H), 7.66 (t, 1H), 7.37 (m, 2H), 7.28 (d, 1H), 7.19 (m, 2H), 6.87 (d, 1H), 4.64 (m, 2H), 4.57 (m, 2H), 4.53 (m,

1H), 4.08 (m, 1H), 3.89 (s, 3H), 3.87 (m, 1H), 3.72 (m, 1H), 3.48 (m, 1H), 1.55 (m, 1H), 1.34 (m, 2H), 0.75 (m, 1H), 0.16 (m, 1H).

Example 38

Preparation: 4-((3-chloro-4-methoxybenzyl)amino)-N-(trans-4-hydroxycyclohexyl)-2-(5-azaspiro[2.4]heptan-5-yl)pyrimidine-5-formamide (Compound 38)

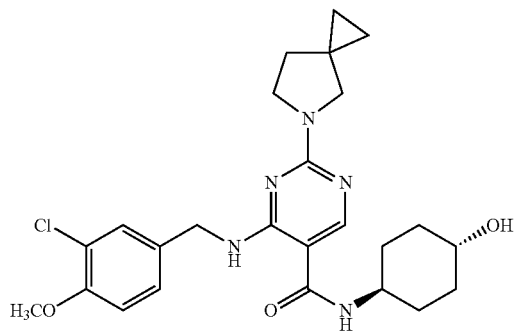 [SMILES: COc1ccc(CNc2nc(N3CCC4(CC4)C3)ncc2C(=O)N[C@H]2CC[C@H](O)CC2)cc1Cl]

(1) Preparation: ethyl 4-((3-chloro-4-methoxybenzyl)amino)-2-(methylsulfinyl)pyrimidine-5-carboxylate

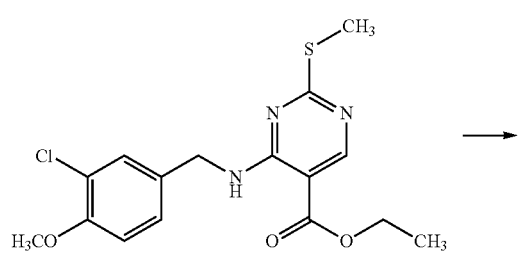

The procedures were analogous to Example 2(1). The product was used in the subsequent procedure without further purification.

(2) Preparation: ethyl 4-((3-chloro-4-methoxybenzyl)amino)-2-(5-azaspiro[2.4]heptan-5-yl) pyrimidine-5-carboxylate

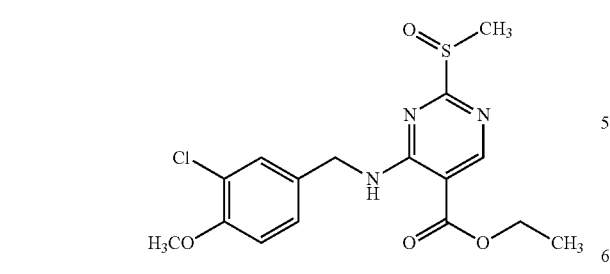

The material was 5-azaspiro[2.4]heptane hydrochloride salt (14.6 mg, 109 mmol). The procedures were analogous to Example 2(2). Yield: 81%.

(3) Preparation: 4-((3-chloro-4-methoxybenzyl)amino)-2-(5-azaspiro[2.4]heptan-5-yl) pyrimidine-5-carboxylic acid

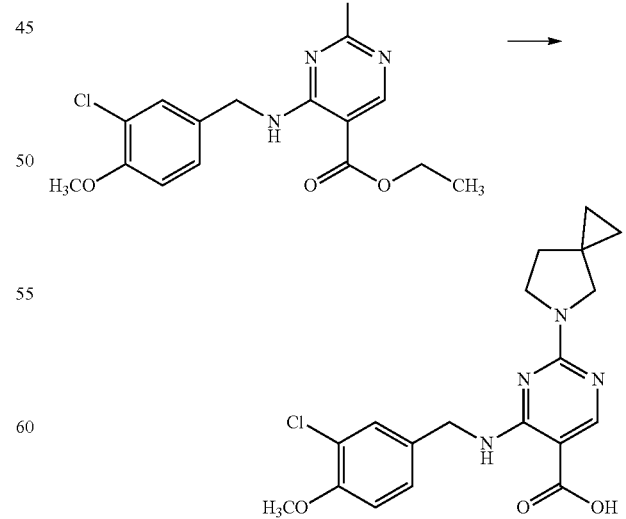

The procedures were analogous to Example 1(2). Ethyl 4-((3-chloro-4-methoxybenzyl)amino)-2-(5-azaspiro[2.4]

heptan-5-yl)pyrimidine-5-carboxylate (3.4 g, 8.17 mmol) was used in step 2 instead of ethyl 4-((3-chloro-4-methoxybenzyl)amino)-2-(methylthio)pyrimidine-5-carboxylate. Yield: 54%.

(4) Preparation: 4-((3-chloro-4-methoxybenzyl)amino)-N-(trans-4-hydroxycyclohexyl)-2-(5-azaspiro[2.4]heptan-5-yl)pyrimidine-5-formamide

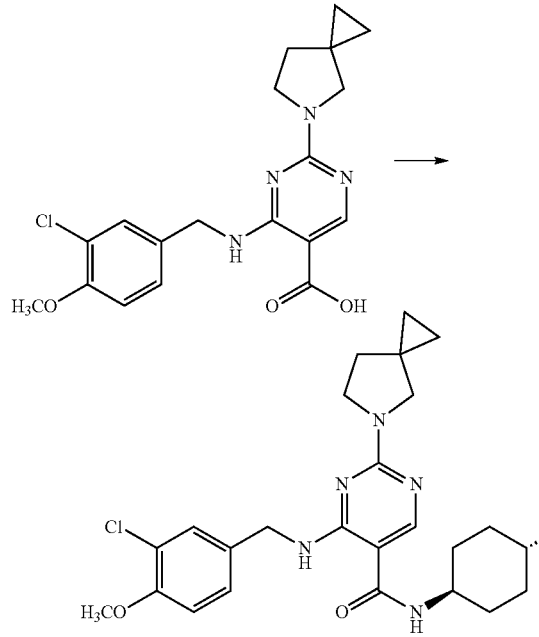

The procedures were analogous to Example 2 (3). Yield: 44%.

Molecular formula: $C_{25}H_{32}ClN_5O_3$ Molecular weight: 486.0 MS (m/e): 486.3 (M+1)

$^1$H-NMR (400 MHz, CDCl$_3$): δ 8.96 (m, 1H), 8.11 (m, 1H), 7.37 (m, 1H), 7.18 (m, 1H), 6.85 (m, 1H), 5.64 (m, 1H), 4.53 (m, 2H), 3.88 (s, 3H), 3.87 (m, 1H), 3.72 (m, 2H), 3.66 (m, 1H), 3.45 (m, 2H), 2.05 (m, 4H), 1.86 (m, 2H), 1.45 (m, 2H), 1.28 (m, 2H), 0.59 (m, 4H).

Example 38-1

Preparation: 4-((3-chloro-4-methoxybenzyl)amino)-N-(trans-4-hydroxycyclohexyl)-2-(5-azaspiro[2.4]heptan-5-yl)pyrimidine-5-formamide (Compound 38)

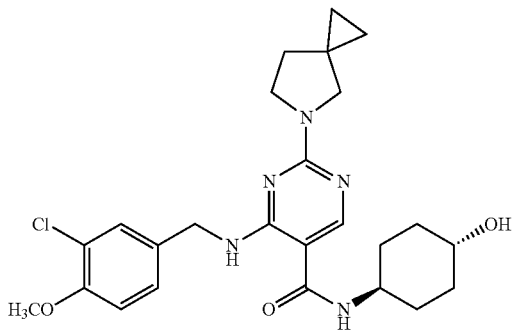 [SMILES: COc1ccc(CNc2nc(N3CCC4(CC4)C3)ncc2C(=O)N[C@H]2CC[C@H](O)CC2)cc1Cl]

The procedures were analogous to Example 38 (1)-(3).

(4) Preparation: 4-((3-chloro-4-methoxybenzyl)amino)-N-(trans-4-hydroxycyclohexyl)-2-(5-azaspiro[2.4]heptan-5-yl)pyrimidine-5-formamide

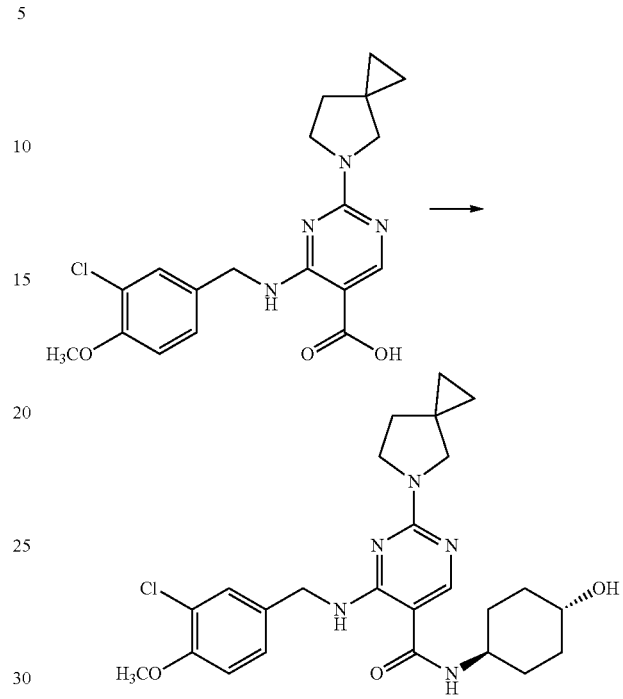

The procedures were analogous to Example 2(3). Trans-4-hydroxycyclohexylamine hydrochloride salt (1.12 g, 7.37 mmol) was used in step 3 instead of pyridin-2-ylmethylamine to give Compound 38. Yield: 69%.

Molecular formula: $C_{25}H_{32}ClN_5O_3$ Molecular weight: 486.0 MS (m/e): 486.3 (M+H$^+$)

$^1$H-NMR (400 MHz, CDCl$_3$): δ 8.95 (s, 1H), 8.10 (d, 1H), 7.39-7.38 (m, 1H), 7.20 (m, 1H), 6.86-6.85 (m, 1H), 5.58 (d, 1H), 4.57-4.51 (m, 2H), 3.88 (s, 3H), 3.85-3.81 (m, 1H), 3.74-3.71 (m, 2H), 3.69-3.63 (m, 1H), 3.45-3.42 (m, 2H), 2.08-2.00 (m, 4H), 1.88-1.85 (m, 2H), 1.43-1.39 (m, 2H), 1.29-1.23 (m, 2H), 0.63-0.59 (m, 4H).

Example 39

Preparation: 4-((3-chloro-4-methoxybenzyl)amino)-N-(2-morpholinoethyl)-2-(5-azaspiro[2.4]heptan-5-yl)pyrimidine-5-formamide (Compound 39)

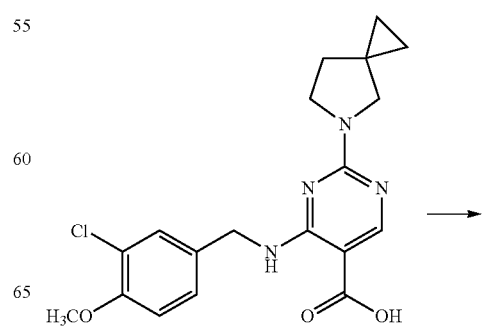

-continued

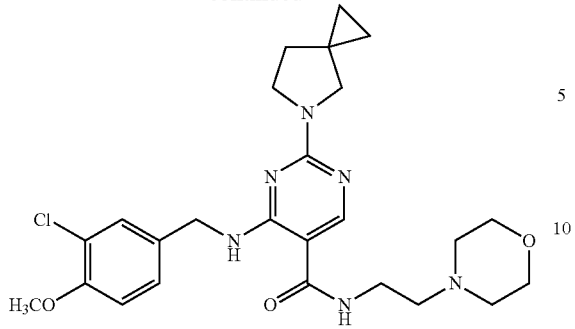

The procedures were analogous to Example 2(3). 2-morpholino ethan-1-amine (100 mg, 0.77 mmol) was used in step 3 instead of pyridin-2-ylmethylamine to give Compound 39. Yield: 59%.

Molecular formula: $C_{25}H_{33}ClN_6O_3$ Molecular weight: 501.0 MS (m/e): 501.3 (M+H$^+$)

$^1$H-NMR (400 MHz, CDCl$_3$): δ 9.02 (s, 1H), 8.19 (d, 1H), 7.38 (m, 1H), 7.19 (m, 1H), 6.85 (m, 1H), 6.61 (m, 1H), 4.55 (m, 2H), 3.87 (s, 3H), 3.71 (m, 6H), 3.44 (m, 4H), 2.56 (t, 2H), 2.47 (m, 4H), 1.86 (m, 2H), 0.61 (m, 4H).

Example 40

Preparation: 4-((3-chloro-4-methoxybenzyl)amino)-N-(pyridin-2-ylmethyl)-2-(5-azaspiro[2.4]heptan-5-yl)pyrimidine-5-formamide (Compound 40)

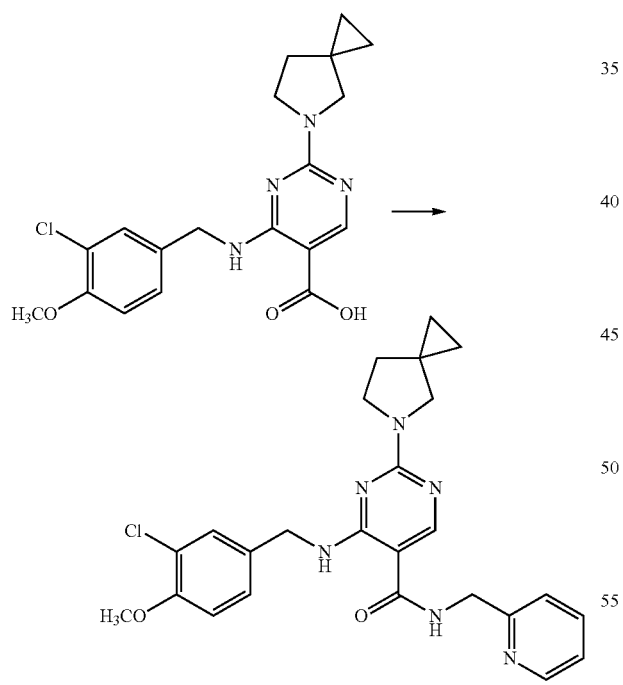

The procedures were analogous to Example 2(3). pyridin-2-ylmethylamine (117 mg, 1.08 mmol) was used in step 3 instead of pyridin-2-ylmethylamine to give Compound 40. Yield: 60%.

Molecular formula: $C_{25}H_{27}ClN_6O_2$ Molecular weight: 479.0 MS (m/e): 479.2 (M+1)

$^1$H-NMR (400 MHz, CDCl$_3$): δ 9.03 (s, 1H), 8.51 (d, 1H), 8.37 (d, 1H), 7.68 (t, 1H), 7.39 (m, 2H), 7.31 (d, 1H), 7.18 (m, 2H), 6.85 (s, 1H), 4.67 (d, 2H), 4.55 (d, 2H), 3.87 (s, 3H), 3.73 (m, 2H), 3.45 (m, 2H), 1.86 (m, 2H), 0.61 (m, 4H).

Example 41

Preparation: 4-((3-chloro-4-methoxybenzyl)amino)-N-(pyrimidin-2-ylmethyl)-2-(5-azaspiro[2.4]heptan-5-yl)pyrimidine-5-formamide (Compound 41)

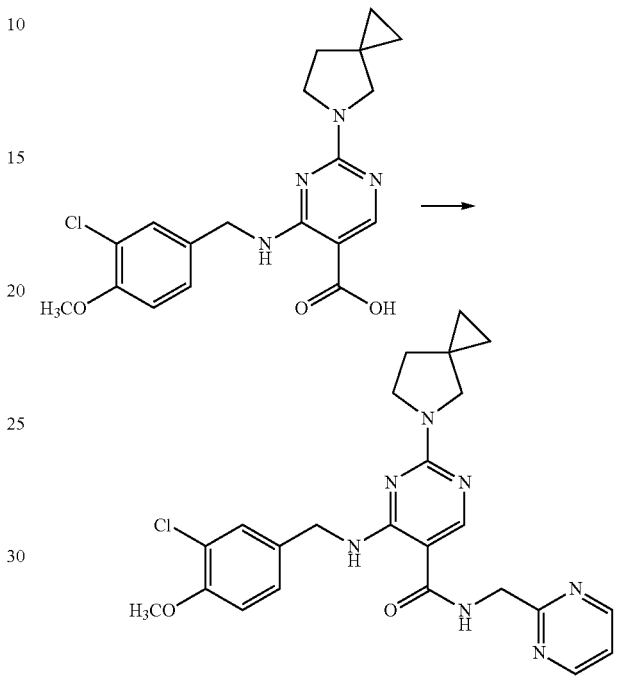

The procedures were analogous to Example 2(3). pyrimidin-2-ylmethylamine (117 mg, 1.08 mmol) was used in step 3 to give Compound 40. Yield: 60%.

Molecular formula: $C_{24}H_{26}ClN_7O_2$ Molecular weight: 480.0 MS (m/e): 480.2 (M+H$^+$)

$^1$H-NMR (400 MHz, CDCl$_3$): δ 9.03 (s, 1H), 8.72 (d, 2H), 8.42 (d, 1H), 7.38 (m, 2H), 7.24 (m, 2H), 6.86 (m, 1H), 4.81 (d, 2H), 4.57 (m, 2H), 3.87 (s, 3H), 3.75 (m, 2H), 3.45 (m, 2H), 1.87 (m, 2H), 0.61 (m, 4H).

Example 42

Preparation: 4-((3-chloro-4-methoxybenzyl)amino)-N-(2-(piperazin-1-yl)ethyl)-2-(5-azaspiro[2.4]heptan-5-yl)pyrimidine-5-formamide (Compound 42)

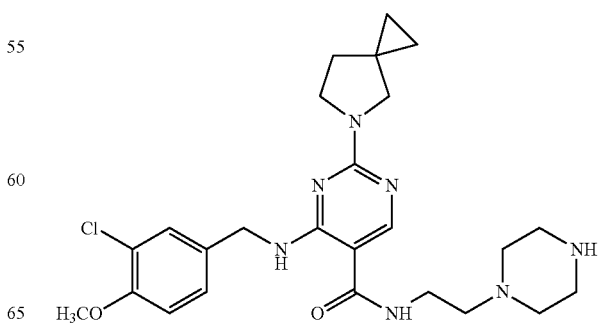

(1) Preparation: tert-butyl 4-(2-(4-((3-chloro-4-methoxybenzyl)amino)-2-(5-azaspiro[2.4]heptan-5-yl)pyrimidine-5-formamido)ethyl)piperazine-1-carboxylate

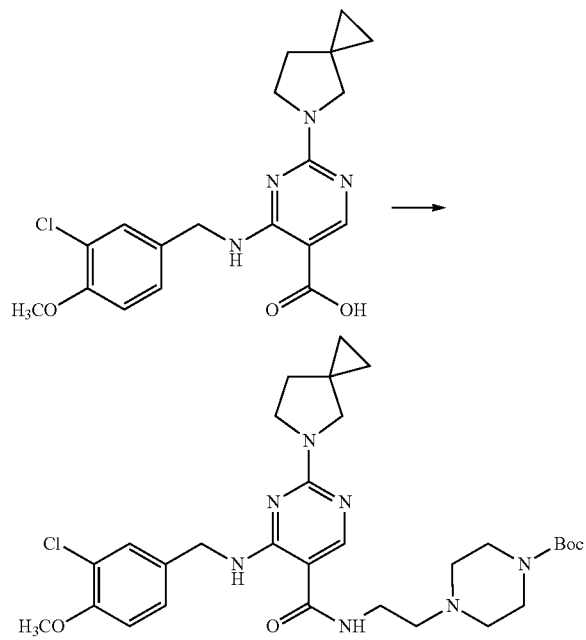

In THF (50 mL) were dissolved 4-((3-chloro-4-methoxybenzyl)amino)-2-(5-azaspiro[2.4]heptan-5-yl)pyrimidine-5-carboxylic acid (1.0 g, 2.58 mmol), tert-butyl 4-(2-aminoethyl)piperazine-1-carboxylate (708 mg, 3.09 mmol) and HATU (1.17 g, 3.09 mmol). DIEA (1 mL, 5.16 mmol) was added. The reaction was conducted at ambient temperature for 8 h, followed by addition of water and extraction with DCM. The organic phase was dried, concentrated and purified by silica gel column chromatography (DCM/methanol=150/1) to give tert-butyl 4-(2-(4-((3-chloro-4-methoxybenzyl)amino)-2-(5-azaspiro[2.4]heptane-5-yl)pyrimidine-5-formamido)ethyl)piperazine-1-carboxylate (871 mg, 56% yield).

(2) Preparation: 4-((3-chloro-4-methoxybenzyl)amino)-N-(2-(piperazin-1-yl)ethyl)-2-(5-azaspiro[2.4]heptan-5-yl)pyrimidine-5-formamide

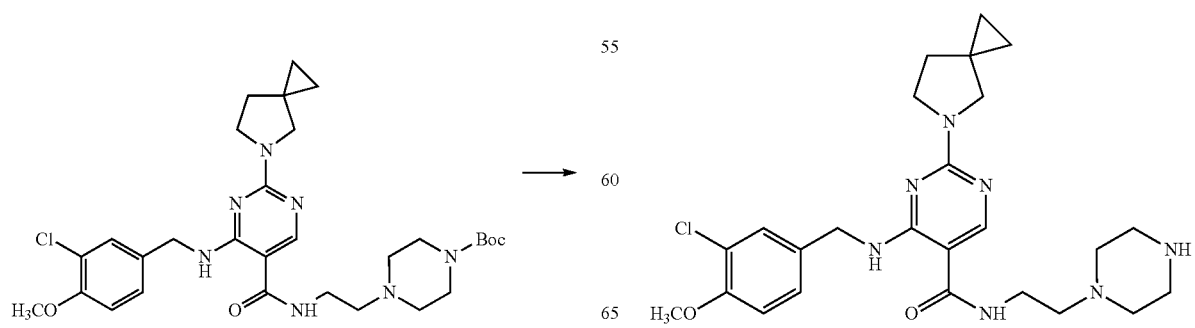

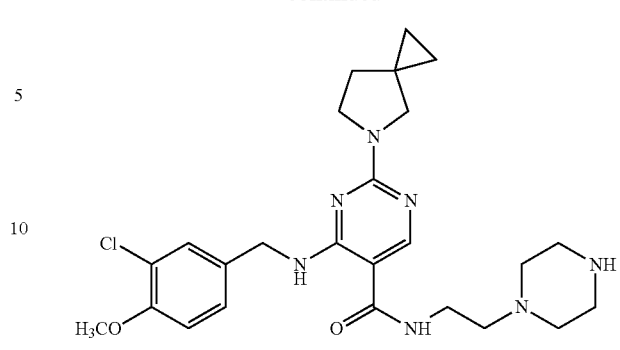

In DCM (10 mL) was dissolved tert-butyl 4-(2-(4-((3-chloro-4-methoxybenzyl)amino)-2-(5-azaspiro[2.4]heptan-5-yl)pyrimidine-5-formamido)ethyl)piperazine-1-carboxylate (871 mg, 1.45 mmol). TFA (1 mL) was added. The reaction mixture was stirred at ambient temperature for 6 h then concentrated to give 4-((3-chloro-4-methoxybenzyl)amino)-N-[2-(piperazin-1-yl)ethyl]-2-(5-azaspiro[2.4]heptan-5-yl)pyrimidine-5-formamide as a white solid (660 mg, 91% yield).

Molecular formula: $C_{25}H_{34}ClN_7O_2$ Molecular weight: 500.0 MS (m/e): 500.3 (M+H$^+$)

$^1$H-NMR (400 MHz, CDCl$_3$): δ 9.06 (m, 1H), 8.24 (d, 1H), 7.37 (m, 1H), 7.20 (t, 1H), 6.86 (d, 1H), 6.60 (m, 1H), 4.56 (d, 2H), 3.88 (s, 3H), 3.74 (m, 2H), 3.45 (m, 4H), 3.16 (m, 4H), 2.76 (m, 4H), 2.66 (t, 2H), 1.88 (m, 2H), 0.62 (m, 4H).

Example 42

Preparation: 4-((3-chloro-4-methoxybenzyl)amino)-N-(2-(piperazin-1-yl)ethyl)-2-(5-azaspiro[2.4]heptan-5-yl) pyrimidine-5-formamide (Compound 42)

(1) Preparation: tert-butyl 4-(2-(4-((3-chloro-4-methoxybenzyl)amino)-2-(5-azaspiro[2.4]heptan-5-yl)pyrimidine-5-formamido)ethyl)piperazine-1-carboxylate

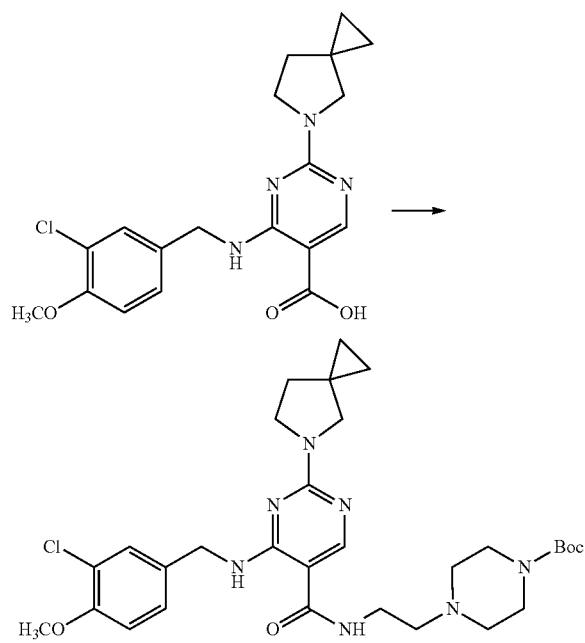

In THF (50 mL) were dissolved 4-((3-chloro-4-methoxybenzyl)amino)-2-(5-azaspiro[2.4]heptan-5-yl)pyrimidine-5-carboxylic acid (1.0 g, 2.58 mmol), tert-butyl 4-(2-aminoethyl)piperazine-1-carboxylate (709 mg, 3.1 mmol) and HATU (1.18 g, 3.09 mmol). DIEA (1 mL, 5.16 mmol) was added. The reaction was conducted at ambient temperature for 8 h. The solvent was removed, and DCM (50 mL) was added for resolution. The DCM phase was washed with water (50 mL×3). The organic phase was dried, concentrated and purified by silica gel column chromatography (DCM/methanol=150/1) to give tert-butyl 4-(2-(4-((3-chloro-4-methoxybenzyl)amino)-2-(5-azaspiro[2.4]heptan-5-yl) pyrimidine-5-formamido)ethyl)piperazine-1-carboxylate as a white solid (910 mg, 59% yield).

(2) Preparation: 4-((3-chloro-4-methoxybenzyl)amino)-N-(2-(piperazin-1-yl)ethyl)-2-(5-azaspiro[2.4]heptan-5-yl)pyrimidine-5-formamide

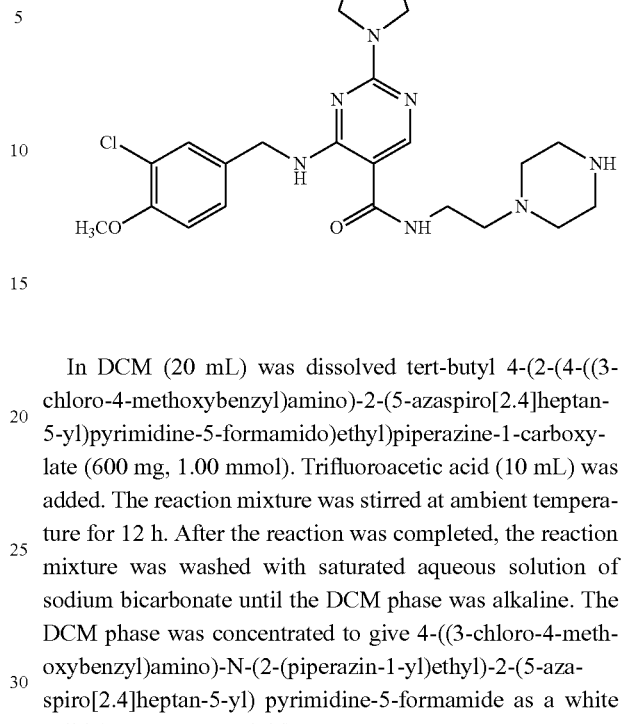

In DCM (20 mL) was dissolved tert-butyl 4-(2-(4-((3-chloro-4-methoxybenzyl)amino)-2-(5-azaspiro[2.4]heptan-5-yl)pyrimidine-5-formamido)ethyl)piperazine-1-carboxylate (600 mg, 1.00 mmol). Trifluoroacetic acid (10 mL) was added. The reaction mixture was stirred at ambient temperature for 12 h. After the reaction was completed, the reaction mixture was washed with saturated aqueous solution of sodium bicarbonate until the DCM phase was alkaline. The DCM phase was concentrated to give 4-((3-chloro-4-methoxybenzyl)amino)-N-(2-(piperazin-1-yl)ethyl)-2-(5-azaspiro[2.4]heptan-5-yl) pyrimidine-5-formamide as a white solid (454 mg, 91% yield).

Molecular formula: $C_{25}H_{34}ClN_7O_2$ Molecular weight: 500.0 MS (m/e): 500.3 (M+H$^+$)

$^1$H-NMR (400 MHz, CDCl$_3$): δ 9.06 (m, 1H), 8.24 (d, 1H), 7.37 (m, 1H), 7.20 (t, 1H), 6.86 (d, 1H), 6.60 (m, 1H), 4.56 (d, 2H), 3.88 (s, 3H), 3.74 (m, 2H), 3.45 (m, 4H), 3.16 (m, 4H), 2.76 (m, 4H), 2.66 (t, 2H), 1.88 (m, 2H), 0.62 (m, 4H).

Example 43

Preparation: 4-((3-chloro-4-methoxybenzyl)amino)-N-(trans-4-hydroxycyclohexyl)-2-(5-azaspiro[2.4]heptan-5-yl)pyrimidine-5-formamide (Compound 43)

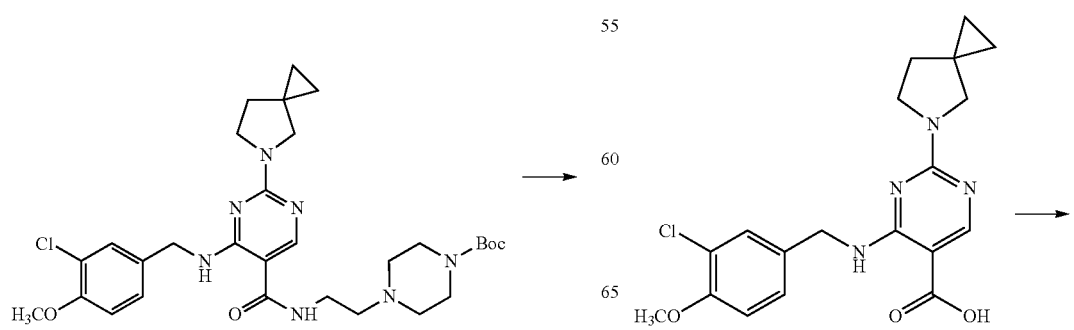

-continued

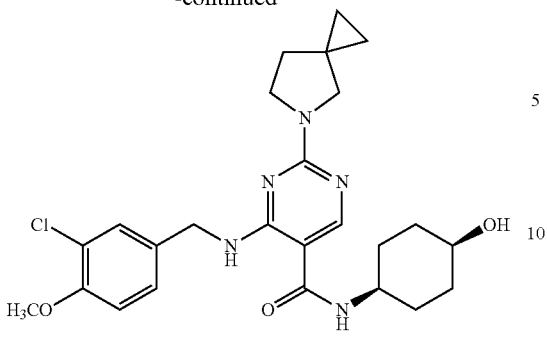

The procedures were analogous to Example 42(1). Trans-4-hydroxycyclohexylamine hydrochloride salt (234 mg, 1.55 mmol) was used in step 1 instead of tert-butyl 4-(2-amino ethyl)piperazine-1-carboxylate to give Compound 43. Yield: 32%.

Molecular formula: $C_{25}H_{32}ClN_5O_3$ Molecular weight: 486.0 MS (m/e): 86.3 (M+H$^+$)

$^1$H-NMR (400 MHz, CDCl$_3$): δ 8.95 (s, 1H), 8.14 (d, 1H), 7.38 (d, 1H), 7.20 (t, 1H), 6.86 (s, 1H), 5.73 (d, 1H), 4.54 (m, 2H), 3.94 (m, 2H), 3.88 (s, 3H), 3.72 (m, 2H), 3.44 (d, 2H), 1.87 (t, 2H), 1.72 (m, 9H), 0.62 (m, 4H).

Example 44

Preparation: N-(trans-4-aminocyclohexyl)-4-(3-chloro-4-methoxybenzyl amino)-2-(5-azaspiro[2.4]heptan-5-yl)pyrimidine-5-formamide (Compound 44)

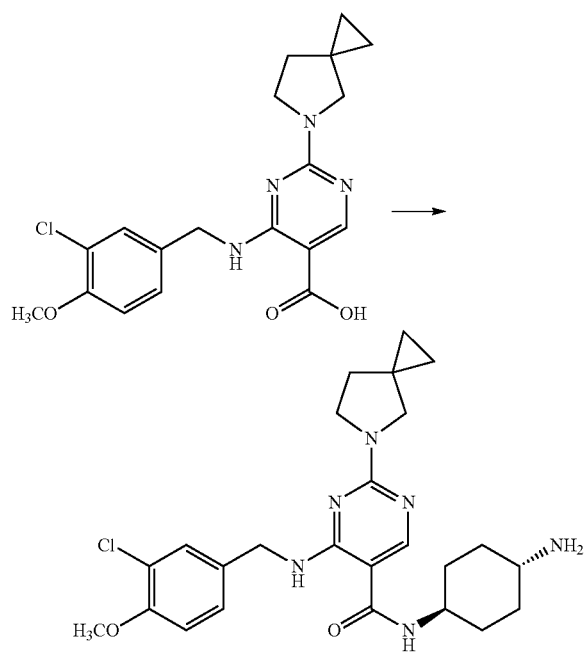

The procedures were analogous to Example 42(1). Trans-4-aminocyclohexylamine hydrochloride salt (147 mg, 1.29 mmol) was used in step 1 instead of tert-butyl 4-(2-aminoethyl)piperazine-1-carboxylate to give Compound 44. Yield: 32%.

Molecular formula: $C_{25}H_{33}ClN_6O_2$ Molecular weight: 485.0 MS (m/e): 485.3 (M+H$^+$)

$^1$H-NMR (400 MHz, CDCl$_3$): δ 9.03 (m, 1H), 8.43 (m, 1H), 7.33 (s, 1H), 7.16 (m, 1H), 6.82 (m, 1H), 6.60 (m, 1H), 4.49 (d, 2H), 3.84 (m, 4H), 3.65 (m, 2H), 3.51 (m, 1H), 3.48 (m, 2H), 3.04 (m, 2H), 2.17 (m, 2H), 2.03 (m, 2H), 1.84 (m, 2H), 1.42 (m, 2H), 1.32 (m, 2H), 0.60 (m, 4H).

Example 45

Preparation: 4-((3-chloro-4-methoxybenzyl)amino))-N-(piperidin-4-yl)-2-(5-azaspiro[2.4]heptan-5-yl)pyrimidine-5-formamide (Compound 45)

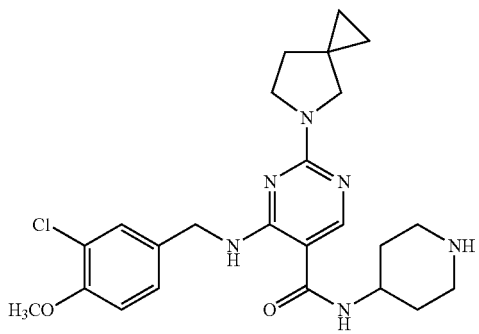 [SMILES: COc1ccc(CNc2nc(N3CCC4(CC4)C3)ncc2C(=O)NC2CCNCC2)cc1Cl]

(1) Preparation: tert-butyl 4-(4-((3-chloro-4-methoxybenzyl)amino)-2-(5-azaspiro[2.4]heptan-5-yl)pyrimidine-5-formamido)piperidine-1-carboxylate

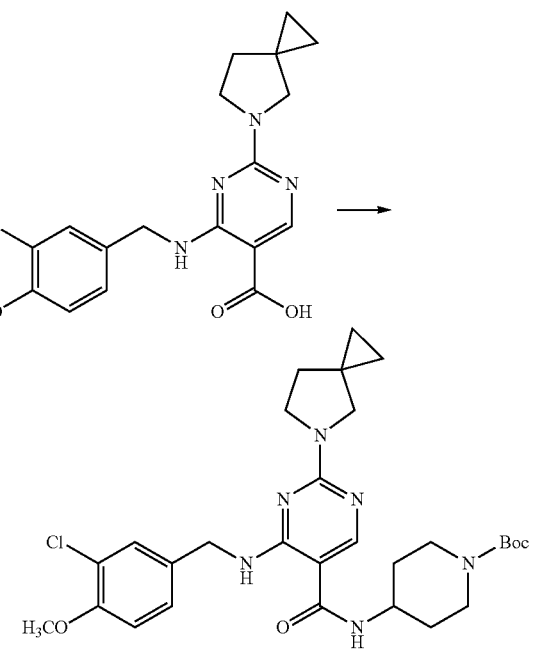

The procedures were analogous to Example 42(1). Tert-butyl 4-aminopiperidine-1-carboxylate (308 mg, 1.55 mmol)

was used in step 1 instead of tert-butyl 4-(2-aminoethyl) piperazine-1-carboxylate to give Compound 45. Yield: 37%.

(2) Preparation: 4-((3-chloro-4-methoxybenzyl) amino)-N-(piperidin-4-yl)-2-(5-azaspiro[2.4]heptan-5-yl)pyrimidine-5-formamide

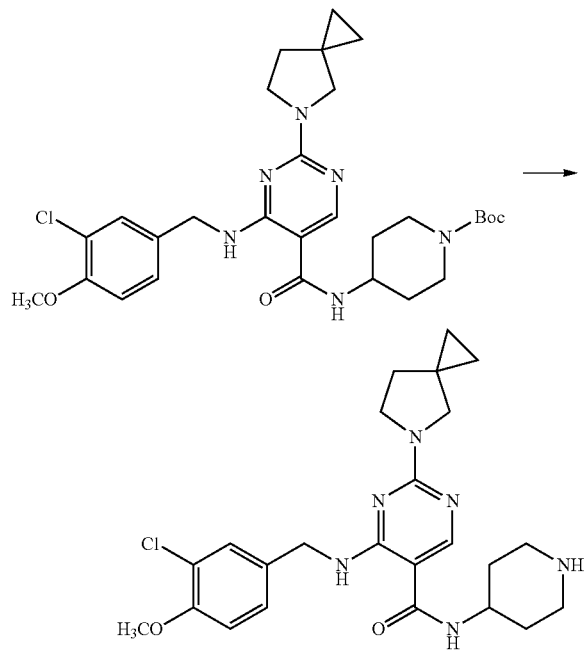

The procedures were analogous to Example 42(2). Yield: 80%.

Molecular formula: $C_{24}H_{31}ClN_6O_2$ Molecular weight: 471.0 MS (m/e): 471.2 (M+H$^+$)

$^1$H-NMR (400 MHz, CDCl$_3$, hydrochloride salt): δ 12.83 (m, 1H), 9.96 (m, 1H), 9.61 (m, 1H), 9.22 (s, 1H), 9.15 (m, 1H), 8.88 (m, 1H), 7.31 (d, 1H), 7.14 (d, 1H), 6.88 (d, 1H), 4.55 (d, 2H), 4.07 (m, 1H), 3.96 (m, 1H), 3.89 (s, 3H), 3.79 (s, 2H), 3.55 (s, 1H), 3.05 (m, 4H), 2.24 (m, 4H), 1.99 (m, 1H), 1.89 (m, 1H), 0.87 (m, 4H).

Example 46

Preparation: 4-((3-chloro-4-methoxybenzyl)amino)-N-(2-(4-methyl piperazin-1-yl)ethyl)-2-(5-azaspiro[2.4]heptan-5-yl)pyrimidine-5-formamide (Compound 46)

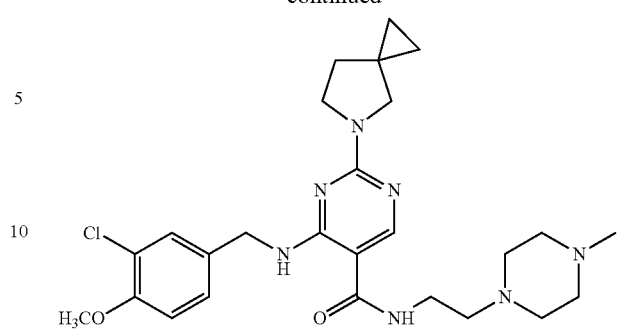

In methanol (20 mL) was dissolved 4-((3-chloro-4-methoxybenzyl)amino)-N-(2-(piperazin-1-yl)ethyl)-2-(5-azaspiro[2.4]heptan-5-yl)pyrimidine-5-formamide (250 mg, 0.5 mmol). Formalin (37%, 61 mg, 0.75 mmol) was added. The reaction was conducted at 0° C. for 1 h. Sodium borohydride (38 mg, 1.0 mmol) was added at 0° C. The reaction was continued for 2 h, then quenched with water. The reaction mixture was filtrated, dried and concentrated to give 4-((3-chloro-4-methoxybenzyl)amino)-N-(2-(4-methylpiperazin-1-yl)ethyl)-2-(5-azaspiro[2.4]heptan-5-yl)pyrimidine-5-formamide (168 mg, 65% yield). The product was dissolved in methanol (5 mL), and hydrochloric acid (0.1 mL) was added. The reaction mixture was stirred at ambient temperature for 30 min. The solvent was removed by evaporation to give the hydrochloride salt of the compound as a white solid.

Molecular formula: $C_{26}H_{36}ClN_7O_2$ Molecular weight: 514.1 MS (m/e): 514.2 (M+H$^+$)

$^1$H-NMR (400 MHz, CDCl$_3$): δ 12.79 (m, 1H), 12.27 (m, 1H), 9.94 (m, 1H), 9.49 (m, 1H), 8.90 (m, 1H), 7.32 (d, 1H), 7.19 (s, 1H), 6.89 (s, 1H), 4.56 (d, 2H), 4.24 (m, 2H), 3.78 (m, 10H), 3.77 (s, 3H), 3.65 (m, 3H), 3.44 (m, 2H), 3.06 (s, 2H), 1.91 (d, 2H), 0.86 (m, 4H).

Example 46-1

Preparation: 4-((3-chloro-4-methoxybenzyl)amino)-N-(2-(4-methyl piperazin-1-yl)ethyl)-2-(5-azaspiro[2.4]heptan-5-yl)pyrimidine-5-formamide (Compound 46)

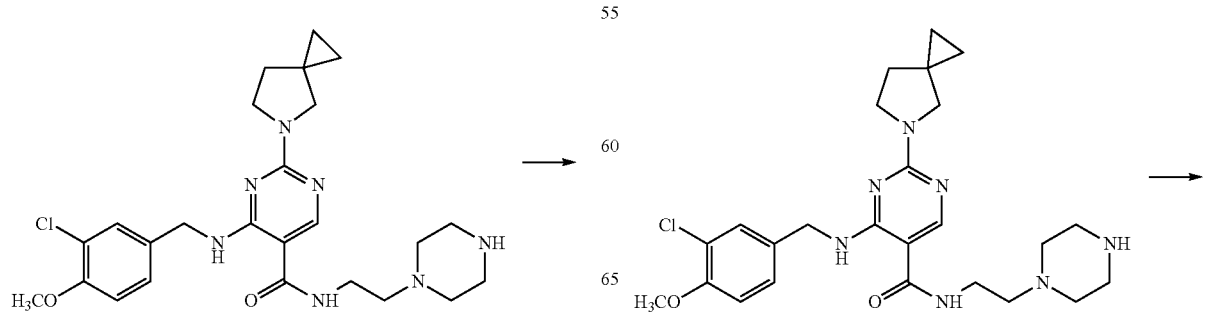

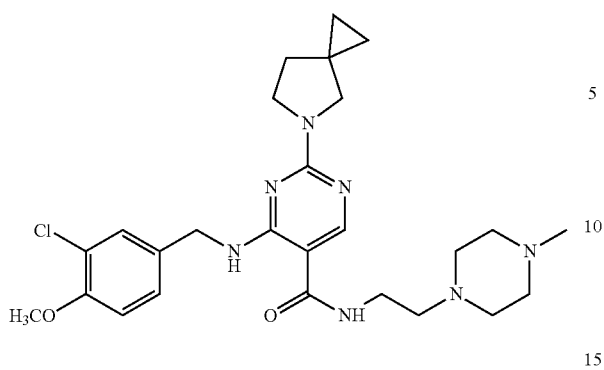

In methanol (10 mL) was dissolved 4-((3-chloro-4-methoxybenzyl)amino)-N-(2-(piperazin-1-yl)ethyl)-2-(5-azaspiro[2.4]heptan-5-yl)pyrimidine-5-formamide (250 mg, 0.5 mmol). Formalin (37%, 61 mg, 0.75 mmol) was added. The reaction was conducted at ambient temperature for 1 h. Sodium borohydride (28 mg, 0.75 mmol) was added. The reaction was continued for 8 h, followed by addition of DCM (50 mL). The reaction mixture was washed with water for three times (50 mL at a time). The organic phase was dried and concentrated to give 4-((3-chloro-4-methoxybenzyl)amino)-N-[2-(4-methylpiperazin-1-yl)ethyl]-2-(5-azaspiro[2.4]heptan-5-yl)pyrimidine-5-formamide (168 mg, 65% yield). The product was dissolved in methanol (5 mL). Hydrochloric acid (0.1 mL) was added. The reaction mixture was stirred at ambient temperature for 30 min. The solvent was removed by evaporation to give the hydrochloride salt of the compound as a white solid.

Molecular formula: $C_{26}H_{36}ClN_7O_2$ Molecular weight: 514.1 MS (m/e): 514.2 (M+H$^+$)

$^1$H-NMR (400 MHz, CDCl$_3$): δ 12.79 (m, 1H), 12.27 (m, 1H), 9.94 (m, 1H), 9.49 (m, 1H), 8.90 (m, 1H), 7.32 (d, 1H), 7.19 (s, 1H), 6.89 (s, 1H), 4.56 (d, 2H), 4.24 (m, 2H), 3.78 (m, 10H), 3.77 (s, 3H), 3.65 (m, 3H), 3.44 (m, 2H), 3.06 (s, 2H), 1.91 (d, 2H), 0.86 (m, 4H).

Example 47

Preparation: 4-((3-chloro-4-methoxybenzyl)amino)-N-(4-hydroxycyclohexyl)methyl-2-(5-azaspiro[2.4]heptan-5-yl)pyrimidine-5-formamide (Compound 47)

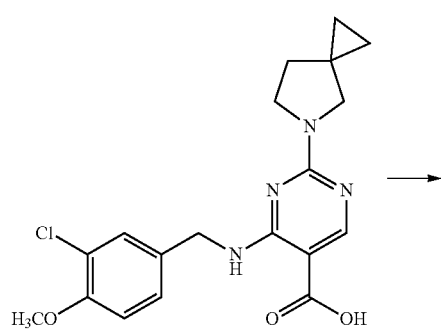

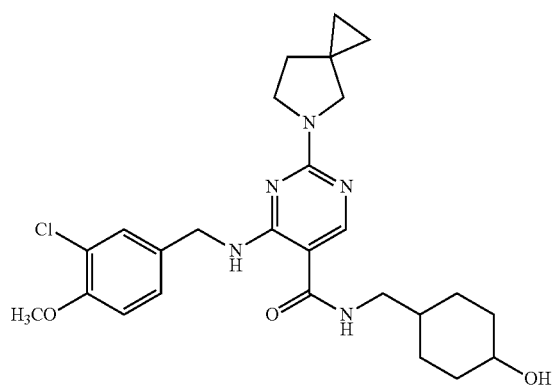

The procedures were analogous to Example 42(1). 4-Aminomethylcyclohexanol (40 mg, 0.31 mmol) was used in step 1 instead of tert-butyl 4-(2-aminoethyl)piperazine-1-carboxylate to give Compound 47.

Molecular formula: $C_{26}H_{34}ClN_5O_3$ Molecular weight: 500.0 MS (m/e): 500.2 (M+H$^+$)

$^1$H-NMR (400 MHz, CDCl$_3$): δ 8.96 (m, 1H), 8.17 (s, 1H), 7.38 (s, 1H), 7.19 (m, 1H), 6.85 (m, 1H), 5.95 (m, 1H), 4.56 (d, 2H), 3.99 (s, 1H), 3.87 (s, 3H), 3.72 (m, 2H), 3.55 (m, 1H), 3.44 (m, 2H), 3.21 (m, 2H), 2.01 (m, 2H), 1.86 (m, 2H), 1.55 (m, 2H), 1.25 (m, 2H), 1.04 (m, 1H), 0.89 (m, 2H), 0.61 (m, 4H).

Example 48

Preparation: 2-(3-azabicyclo[3.1.0]hexan-3-yl)-4-((3-fluoro-4-methoxy benzyl)amino)-N-(trans-4-hydroxycyclohexyl)pyrimidine-5-formamide (Compound 48)

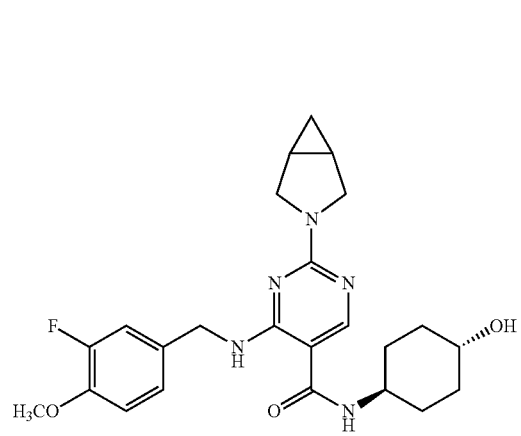

(1) Preparation: ethyl 4-((3-fluoro-4-methoxybenzyl)amino)-2-(methylthio) pyrimidine-5-carboxylate

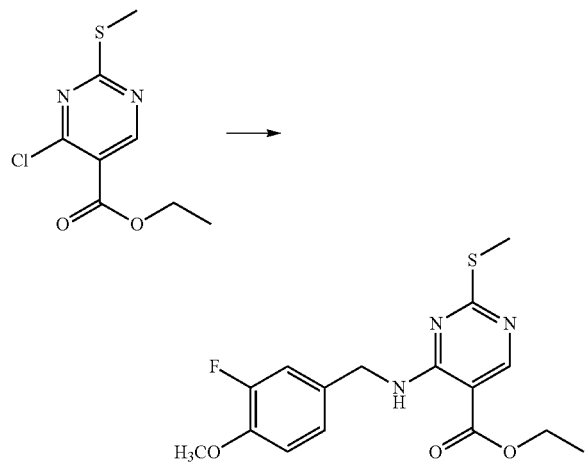

In DCM (50 mL) were dissolved ethyl 4-chloro-2-(methylthio)pyrimidine-5-carboxylate (1.5 g, 6.46 mmol), 3-fluoro-4-methoxybenzylamine (1.0 g, 6.45 mmol) and triethylamine (1.3 g, 12.9 mmol). The reaction mixture was stirred at ambient temperature for 30 min, and washed with water. The organic phase was dried over sodium sulfate and concentrated to give ethyl 4-((3-fluoro-4-methoxybenzyl)amino)-2-(methylthio)pyrimidine-5-carboxylate as a yellow oil (2.2 g, yield: 97%).

(2) Preparation: ethyl 4-((3-fluoro-4-methoxybenzyl)amino)-2-(methylsulfinyl)pyrimidine-5-carboxylate

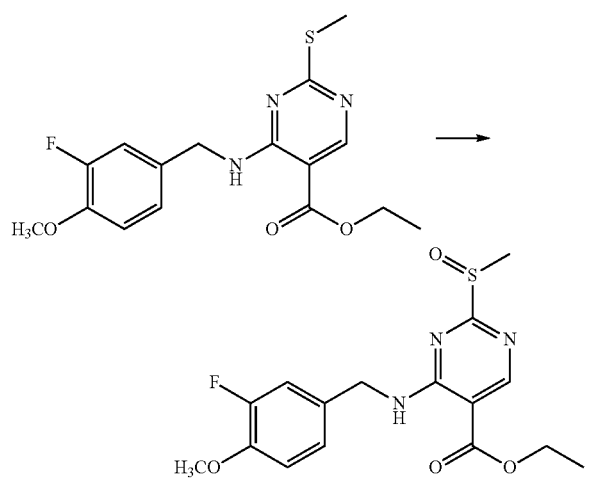

In DCM (50 mL) was dissolved ethyl 4-((3-fluoro-4-methoxybenzyl)amino)-2-(methylthio)pyrimidine-5-carboxylate (2.2 g, 6.3 mmol). m-CPBA (3-chloroperbenzoic acid, 1.1 g, 6.4 mmol) was added. The reaction was conducted at ambient temperature for 30 min. The reaction mixture was washed with water. The organic phase was dried over sodium sulfate and concentrated to give ethyl 4-((3-fluoro-4-methoxybenzyl)amino)-2-(methylsulfinyl)pyrimidine-5-carboxylate. The product was used in the subsequent procedure without further purification.

(3) Preparation: ethyl 2-(3-azabicyclo[3.1.0]hexan-3-yl)-4-((3-fluoro-4-methoxybenzyl)amino)pyrimidine-5-carboxylate

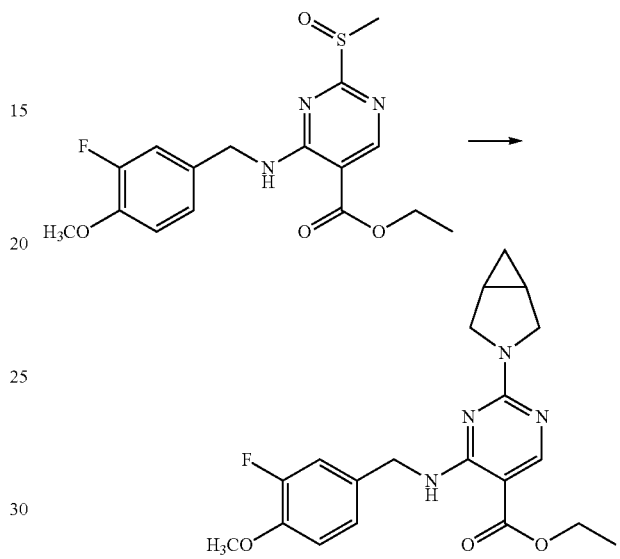

In DCM (50 mL) was dissolved the above product ethyl 4-((3-fluoro-4-methoxybenzyl)amino)-2-(methylsulfinyl)pyrimidine-5-carboxylate. To the solution were added 3-azabicyclo[3.1.0]hexan hydrochloride salt (0.8 g, 6.67 mmol) and triethylamine (4 mL, 28.8 mmol). The reaction was conducted at ambient temperature for 18 h, followed by addition of water and extraction with DCM. The organic phase was dried over sodium sulfate, and the solvent was removed by rotary evaporation to give ethyl 2-(3-azabicyclo[3.1.0]hexan-3-yl)-4-((3-fluoro-4-methoxybenzyl)amino)pyrimidine-5-carboxylate as a faint yellow oil (3.1 g). The product was used in the subsequent procedure without further purification.

(4) Preparation: 2-(3-azabicyclo[3.1.0]hexan-3-yl)-4-((3-fluoro-4-methoxybenzyl)amino) pyrimidine-5-carboxylic acid

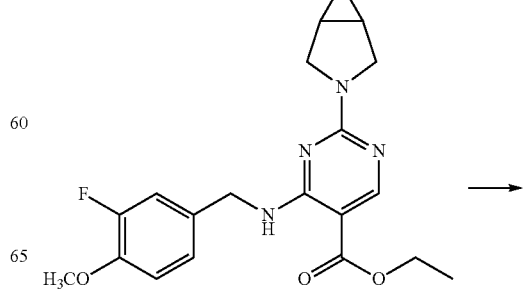

-continued

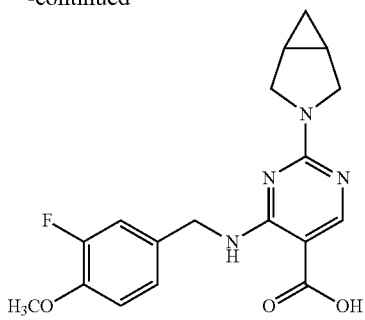

In the mixture of water (5 mL), ethanol (5 mL) and THF (15 mL) were dissolved ethyl 2-(3-azabicyclo[3.1.0]hexan-3-yl)-4-((3-fluoro-4-methoxybenzyl)amino)pyrimidine-5-carboxylate (1.5 g, 3.9 mmol) and sodium hydroxide (260 mg, 6.5 mmol). The reaction was conducted at ambient temperature for 5 h. The solvent was removed by evaporation, followed by addition of water and washing with DCM. The aqueous phase was adjusted to a pH of 2 with dilute hydrochloric acid, and extracted with DCM. The organic phase was dried over sodium sulfate and concentrated to give 2-(3-azabicyclo[3.1.0]hexan-3-yl)-4-((3-fluoro-4-methoxybenzyl)amino)pyrimidine-5-carboxylic acid as a faint yellow solid (580 mg, 41.5% yield).

(5) Preparation: 2-(3-azabicyclo[3.1.0]hexan-3-yl)-4-((3-fluoro-4-methoxybenzyl)amino)-N-(trans-4-hydroxycyclohexyl)pyrimidine-5-formamide

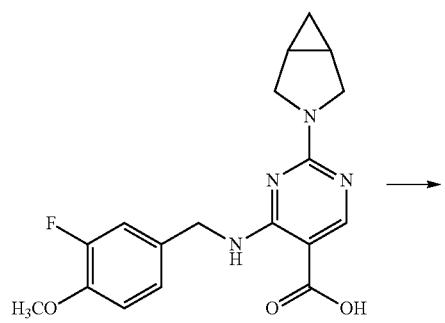

In the mixture of DCM (20 mL) and THF (20 mL) were dissolved 2-(3-azabicyclo[3.1.0]hexan-3-yl)-4-((3-fluoro-4-methoxybenzyl)amino)pyrimidine-5-carboxylic acid (580 mg, 1.62 mmol), trans-4-hydroxycyclohexylamine (187 mg, 1.62 mmol), TEA (485 mg, 4.79 mmol) and HATU (2-(7-azobenzotriazole)-N,N,N',N'-tetramethyluroniumhexafluorophosphate (743 mg, 1.95 mmol). The reaction was conducted at ambient temperature for 17 h. The solvent was removed by evaporation, followed by addition of water and extraction with DCM. The organic phase was dried over sodium sulfate and concentrated to give a solid, which was purified by silica gel column chromatography (DCM/methanol=50/1) to give 2-(3-azabicyclo[3.1.0]hexan-3-yl)-4-((3-fluoro-4-methoxybenzyl)amino)-N-(trans-4-hydroxycyclohexyl)pyrimidine-5-formamide as a faint yellow solid (200 mg, 27.1% yield).

Molecular formula: $C_{24}H_{30}FN_5O_3$ Molecular weight: 455.5 MS (m/e): 455.9 (M+H$^+$)

$^1$H-NMR (400 MHz, CDCl$_3$): δ 8.92 (t, 1H), 8.10 (s, 1H), 7.10 (d, 1H), 7.06 (d, 1H), 6.90 (t, 1H), 5.55 (d, 1H), 4.55 (d, 2H), 3.86 (m, 6H), 3.65 (m, 1H), 3.50 (t, 2H), 2.05 (t, 4H), 1.60 (s, 2H), 1.45 (m, 2H), 1.27 (m, 3H), 0.83 (m, 1H), 0.20 (m, 1H).

Example 49

Preparation: 2-(3-azabicyclo[3.1.0]hexan-3-yl)-4-((3-fluoro-4-ethoxybenzyl)amino)-N-((trans)-4-hydroxycyclohexyl)pyrimidine-5-formamide (Compound 49)

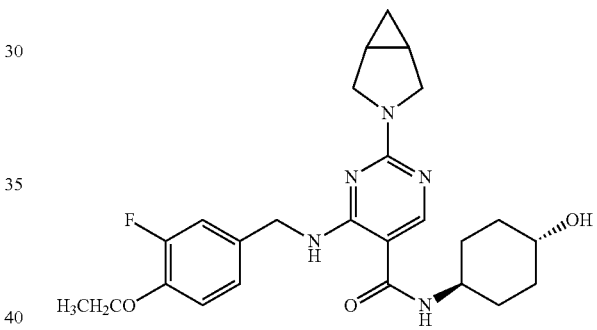

(1) Preparation: ethyl 4-((3-fluoro-4-ethoxybenzyl)amino)-2-(methylthio)pyrimidine-5-carboxylate

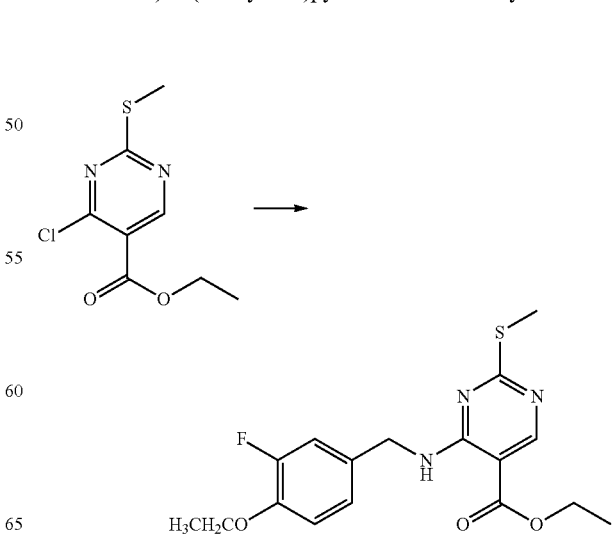

The procedures were analogous to Example 48(1). 3-fluoro-4-ethoxybenzylamine was used in step 1 instead of 3-fluoro-4-methoxybenzylamine. Yield: 100%.

(2) Preparation: ethyl 4-((3-fluoro-4-ethoxybenzyl)amino)-2-(methylsulfinyl)pyrimidine-5-carboxylate

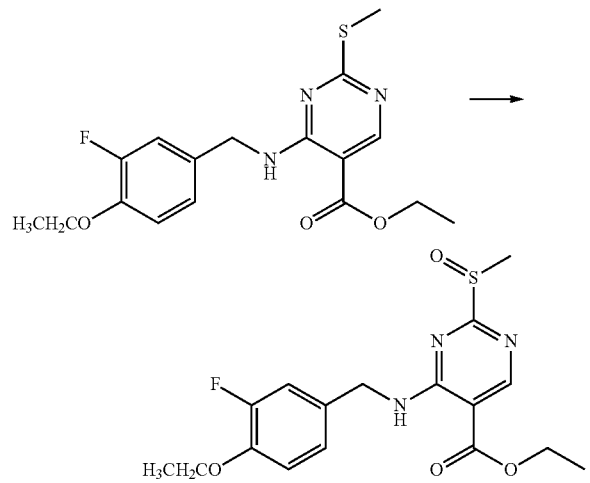

The procedures were analogous to Example 48(2). The product was used in the subsequent procedure without further purification.

(3) Preparation: ethyl 2-(3-azabicyclo[3.1.0]hexan-3-yl)-4-((3-fluoro-4-ethoxybenzyl)amino) pyrimidine-5-carboxylate

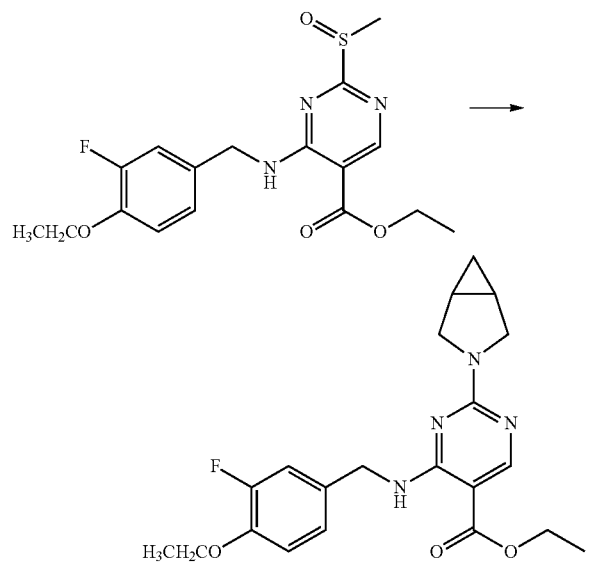

The procedures were analogous to Example 48(3). Yield: 48%.

(4) Preparation: 2-(3-azabicyclo[3.1.0]hexan-3-yl)-4-((3-fluoro-4-ethoxybenzyl)amino) pyrimidine-5-carboxylic acid

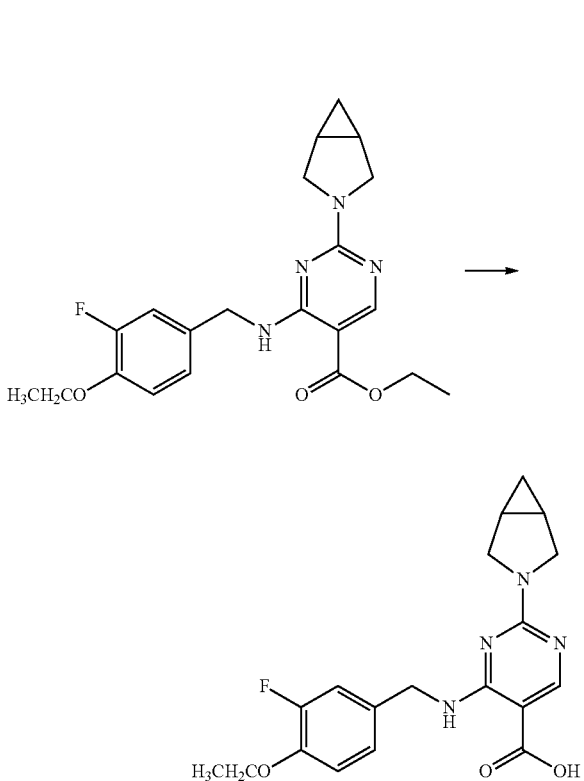

The procedures were analogous to Example 48(4). Yield: 48%.

(5) Preparation: 2-(3-azabicyclo[3.1.0]hexan-3-yl)-4-((3-fluoro-4-ethoxybenzyl)amino)-N-((trans)-4-hydroxycyclohexyl)pyrimidine-5-formamide

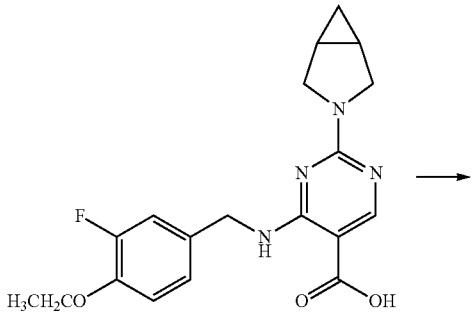

169
-continued

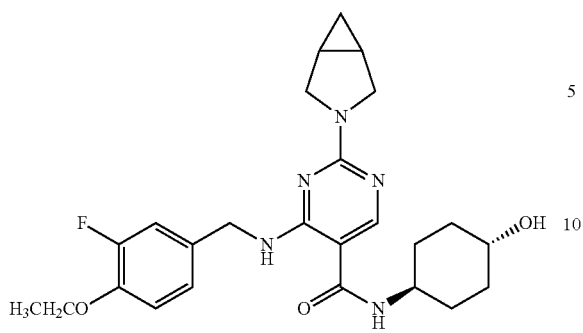

The procedures were analogous to Example 48(5). Yield: 61%.

Molecular formula: $C_{25}H_{32}FN_5O_3$ Molecular weight: 469.6 MS (m/e): 469.9 (M+H$^+$)

$^1$H-NMR (400 MHz, CDCl$_3$): δ 8.90 (t, 1H), 8.08 (s, 1H), 7.08 (d, 1H), 7.02 (d, 1H), 6.90 (t, 1H), 5.42 (d, 1H), 4.58 (d, 2H), 4.09 (m, 2H), 3.82 (m, 3H), 3.65(m, 1H), 3.49 (t, 2H), 1.99-2.07 (t, 4H), 1.39-1.59 (m, 5H), 1.22-1.38 (m, 5H), 0.78 (m, 1H), 0.21 (m, 1H).

Example 50

Preparation: 2-(3-azabicyclo[3.1.0]hexan-3-yl)-N-((trans)-4-hydroxycyclohexyl)-4-((4-methoxy-3-methylbenzyl)amino)pyrimidine-5-formamide (Compound 50)

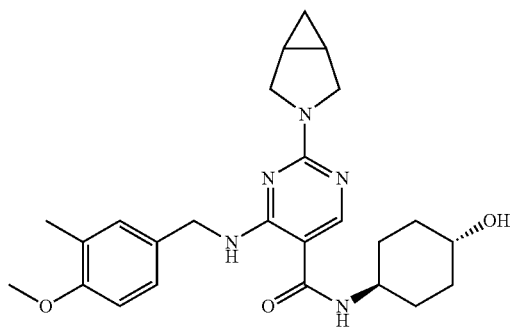

(1) Preparation: ethyl 4-((4-methoxy-3-methylbenzyl)amino)-2-(methylthio)pyrimidine-5-carboxylate

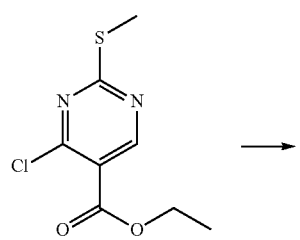

170
-continued

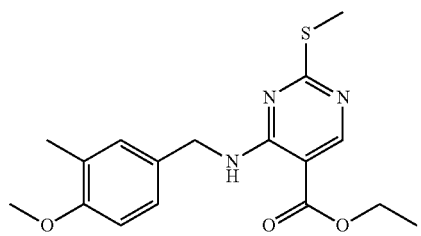

The procedures were analogous to Example 48(1). 3-methyl-4-methoxybenzylamine (0.72 g, 4.7 mmol) was used in step 1 instead of 3-fluoro-4-methoxybenzylamine. Yield: 92%.

(2) Preparation: ethyl 4-((4-methoxy-3-methylbenzyl)amino)-2-(methylsulfinyl)pyrimidine-5-carboxylate

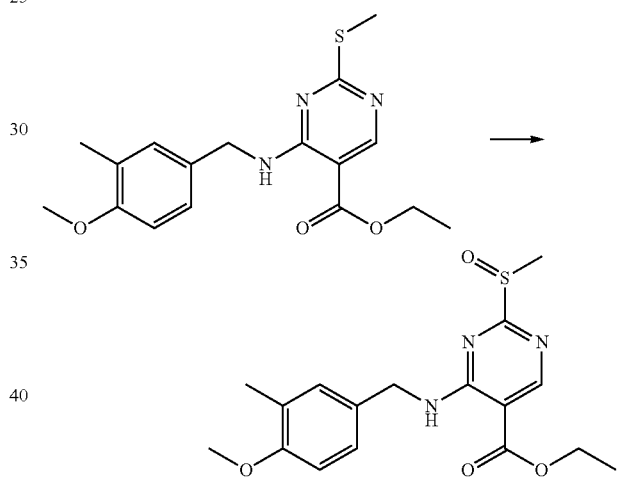

The procedures were analogous to Example 48(2). The product was used in the subsequent procedure without further purification.

(3) Preparation: ethyl 2-(3-azabicyclo[13.1.0]hexan-3-yl)-4-((4-methoxy-3-methylbenzyl)amino)pyrimidine-5-carboxylate

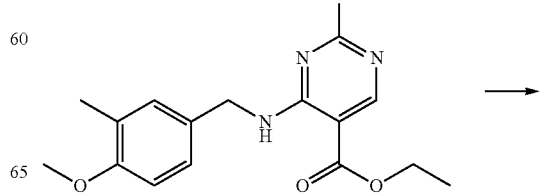

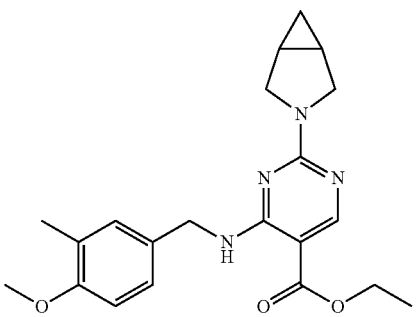

The procedures were analogous to Example 48(3). Yield: 92%.

(4) Preparation: 2-(3-azabicyclo[3.1.0]hexan-3-yl)-4-((4-methoxy-3-methylbenzyl)amino) pyrimidine-5-carboxylic acid

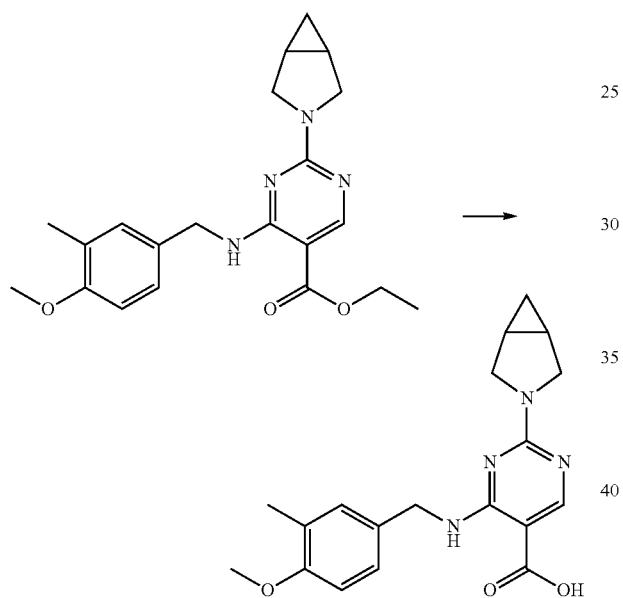

The procedures were analogous to Example 48(4). Yield: 86%.

(5) Preparation: 2-(3-azabicyclo[3.1.0]hexan-3-yl)-N-((trans)-4-hydroxycyclohexyl)-4-((4-methoxy-3-methylbenzyl)amino)pyrimidine-5-formamide

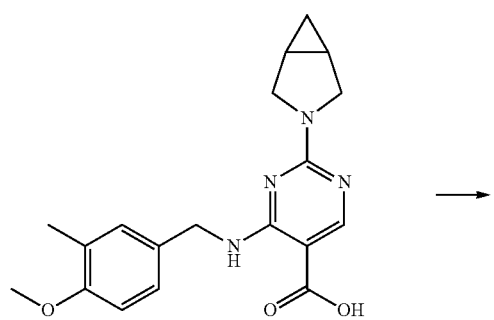

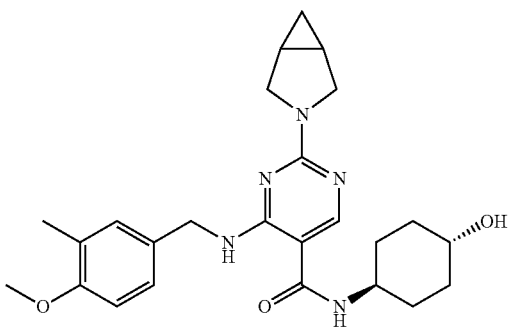 [SMILES: COc1ccc(CNc2nc(N3CC4CC4C3)ncc2C(=O)N[C@H]2CC[C@H](O)CC2)cc1C]

The procedures were analogous to Example 48(5). Yield: 52%.

Molecular formula: $C_{25}H_{33}N_5O_3$ Molecular weight: 451.6
MS (m/e): 451.9 (M+H$^+$)

$^1$H-NMR (400 MHz, CDCl$_3$): δ 8.82 (s, 1H), 8.21 (t, 1H), 8.07 (s, 1H), 7.14 (d, 2H), 6.75 (d, 1H), 5.55 (d, 1H), 4.54 (t, 2H), 3.77-3.92 (m, 6H), 3.60-3.67 (m, 1H), 3.51 (d, 2H), 2.19 (s, 3H), 2.02 (m, 4H), 1.59 (m, 2H), 1.37-1.46 (m, 2H), 1.20-1.30 (m, 2H), 0.75 (m, 1H), 0.22 (m, 1H).

Example 51

Preparation: 2-(3-azabicyclo[3.1.0]hexan-3-yl)-N-((trans)-4-hydroxycyclohexyl)-4-((4-ethoxy-3-methylbenzyl)amino)pyrimidine-5-formamide (Compound 51)

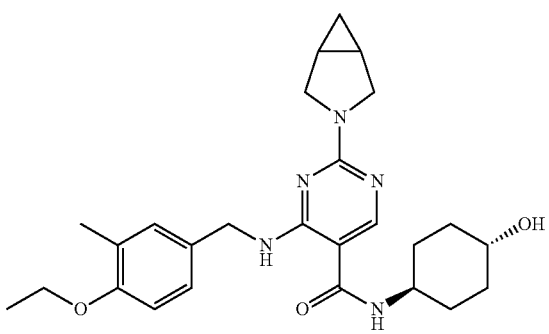 [SMILES: CCOc1ccc(CNc2nc(N3CC4CC4C3)ncc2C(=O)N[C@H]2CC[C@H](O)CC2)cc1C]

(1) Preparation: ethyl 4-((4-ethoxy-3-methylbenzyl)amino)-2-(methylthio)pyrimidine-5-carboxylate

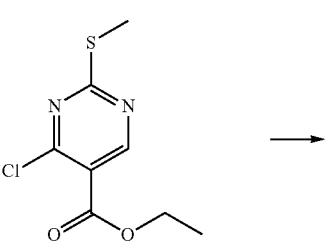

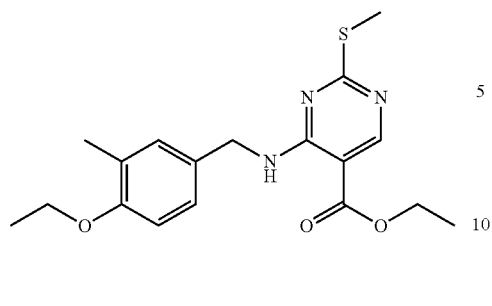

The procedures were analogous to Example 48(1). 3-Methyl-4-ethoxybenzylamine was used in step 1 instead of 3-fluoro-4-methoxybenzylamine. Yield: 99%.

(2) Preparation: ethyl 4-((4-ethoxy-3-methylbenzyl)amino)-2-(methylsulfinyl)pyrimidine-5-carboxylate

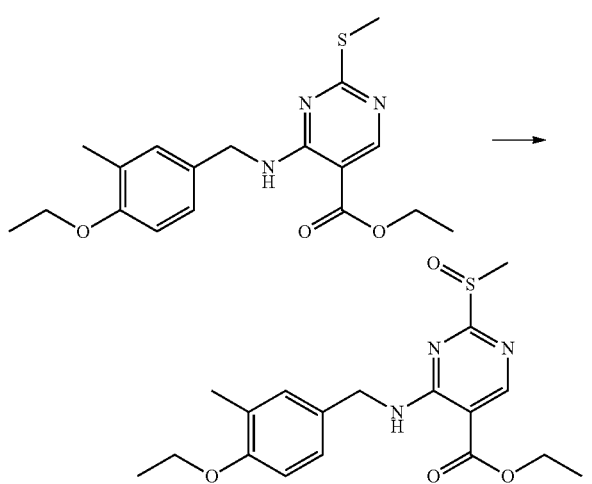

The procedures were analogous to Example 48(2). The product was used in the subsequent procedure without further purification.

(3) Preparation: ethyl 2-(3-azabicyclo[3.1.0]hexan-3-yl)-4-((4-ethoxy-3-methylbenzyl)amino) pyrimidine-5-carboxylate

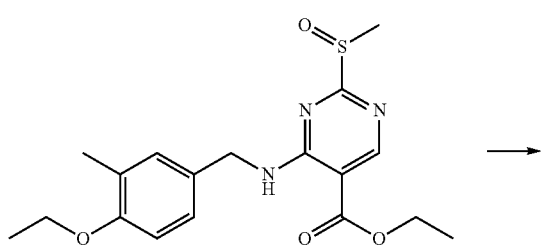

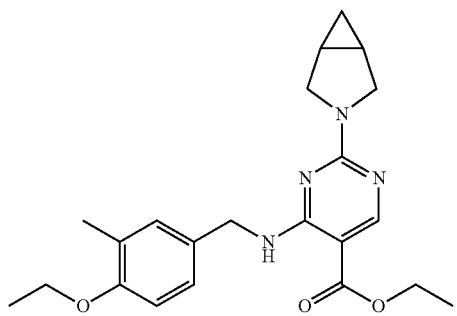

The procedures were analogous to Example 48(3). Yield: 71%.

(4) Preparation: 2-(3-azabicyclo[3.1.0]hexan-3-yl)-4-((4-ethoxy-3-methylbenzyl)amino) pyrimidine-5-carboxylic acid

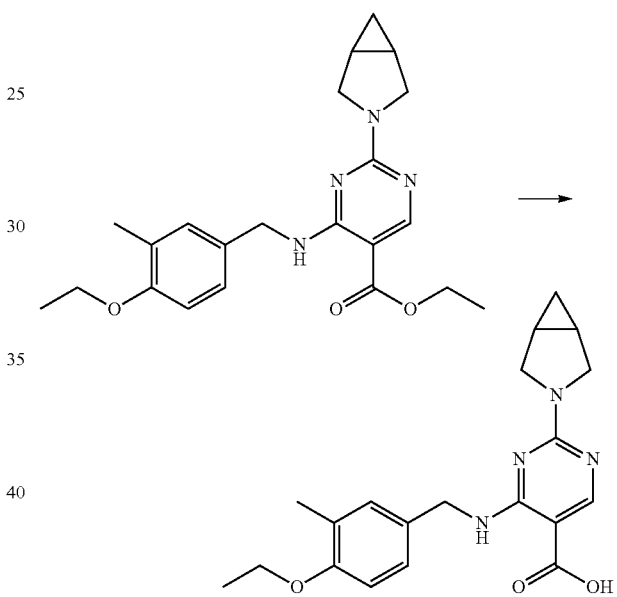

The procedures were analogous to Example 48(4). Yield: 100%.

(5) Preparation: 2-(3-azabicyclo[3.1.0]hexan-3-yl)-N-((trans)-4-hydroxycyclohexyl)-4-(4-ethoxy-3-methylbenzyl)amino)pyrimidine-5-formamide

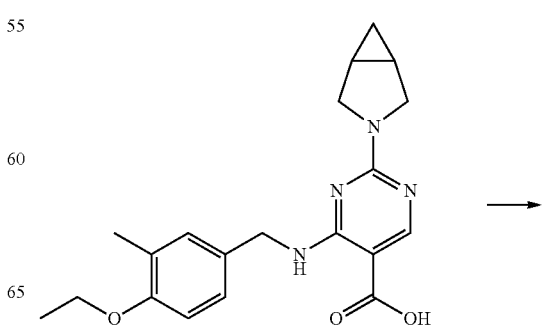

-continued

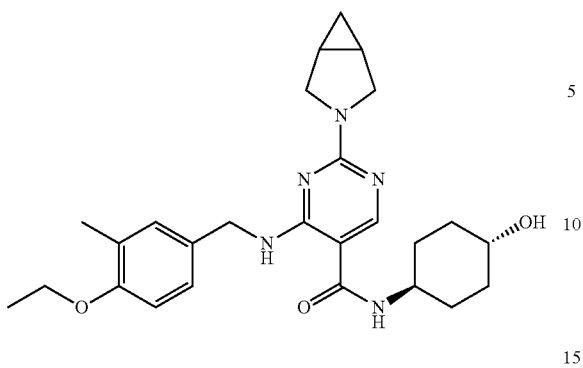

The procedures were analogous to Example 48(5). Yield: 65%.

Molecular formula: $C_{26}H_{35}N_5O_3$ Molecular weight: 465.6
MS (m/e): 465.8 (M+H$^+$)

$^1$H-NMR (400 MHz, CDCl$_3$): δ 8.97 (t, 1H), 8.10 (s, 1H), 7.58 (s, 1H), 7.45 (d, 1H), 6.92 (d, 1H), 5.60 (d, 1H), 4.58 (d, 2H), 4.12 (m, 2H), 3.86 (m, 3H), 3.65(m, 1H), 3.50 (t, 2H), 2.20(s,3H), 2.05 (t, 4H), 1.60 (m, 3H), 1.45 (m, 5H), 1.30 (m, 2H), 0.83 (m, 1H), 0.20 (m, 1H).

Example 51-1

Preparation: 2-(3-azabicyclo[3.1.0]hexan-3-yl)-N-(trans-4-hydroxycyclohexyl)-4-((4-ethoxy-3-methylbenzyl)amino)pyrimidine-5-formamide (Compound 51)

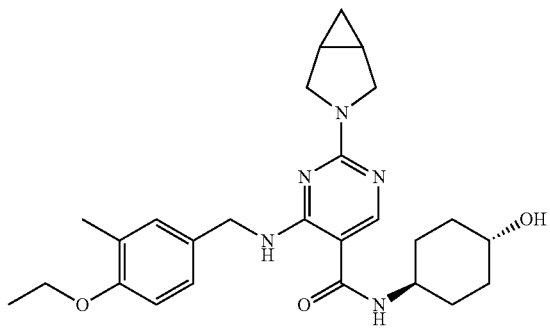 [SMILES: CCOc1ccc(CNc2nc(N3CC4CC4C3)ncc2C(=O)N[C@H]2CC[C@H](O)CC2)cc1C]

The procedures were analogous to Example 51 (1) to (5).

Molecular formula: $C_{26}H_{35}N_5O_3$ Molecular weight: 465.6
MS (m/e): 465.8 (M+H$^+$)

$^1$H-NMR (400 MHz, CDCl$_3$): δ 8.81 (t, 1H), 8.07 (s, 1H), 7.13 (s, 1H), 7.11 (s, 1H), 6.74 (d, 1H), 5.52 (d, 1H), 4.53 (m, 2H), 4.02 (d, 2H), 3.86 (m, 3H), 3.64 (m, 1H), 3.51 (d, 2H), 2.12 (s, 3H), 2.02 (t, 4H), 1.41 (m, 4H), 1.26 (m, 5H), 0.74 (m, 1H), 0.20 (m, 1H).

Example 52

Preparation: 2-(3-azabicyclo[3.1.0]hexan-3-yl)-4-((3-chloro-4-ethoxybenzyl)amino)-N-((trans)-4-hydroxycyclohexyl)pyrimidine-5-formamide (Compound 52)

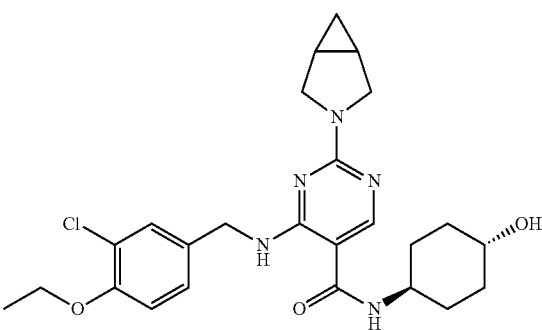

(1) Preparation: ethyl 4-((3-chloro-4-ethoxybenzyl)amino)-2-(methylthio)pyrimidine-5-carboxylate

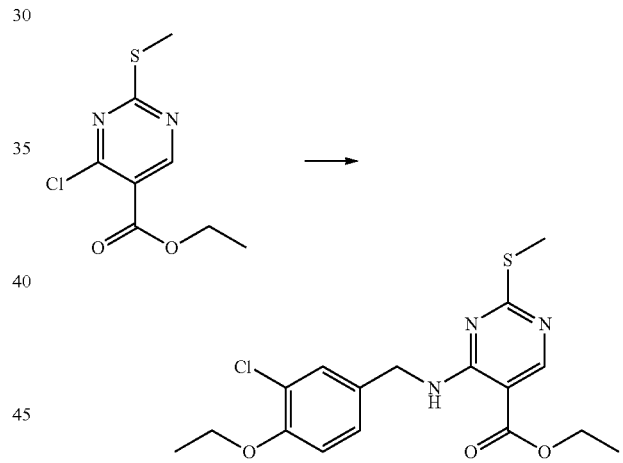

The procedures were analogous to Example 48(1). 3-chloro-4-ethoxybenzylamine was used in step 1 instead of 3-fluoro-4-methoxybenzylamine.

(2) Preparation: ethyl 4-((3-chloro-4-ethoxybenzyl)amino)-2-(methylsulfinyl)pyrimidine-5-carboxylate

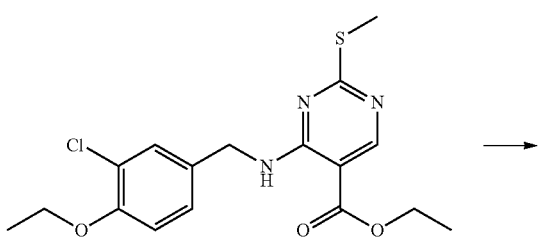

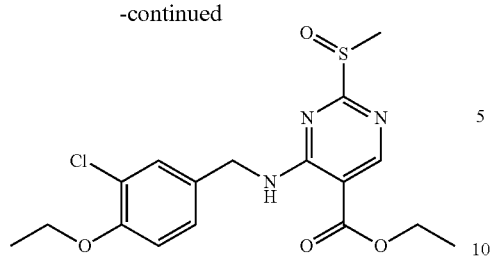

The procedures were analogous to Example 48(2). The product was used in the subsequent procedure without further purification.

(3) Preparation: ethyl 2-(3-azabicyclo[3.1.0]hexan-3-yl)-4-((3-chloro-4-ethoxylbenzyl)amino) pyrimidine-5-carboxylate

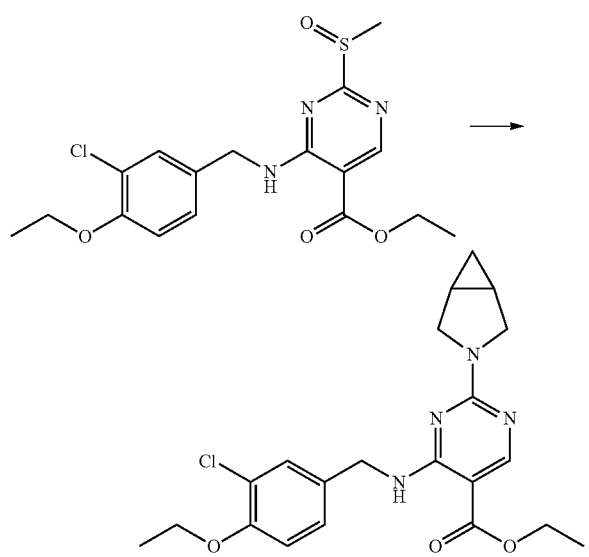

The procedures were analogous to Example 48(3). The product was used in the subsequent procedure without further purification.

(4) Preparation: 2-(3-azabicyclo[3.1.0]hexan-3-yl)-4-((3-chloro-4-ethoxybenzyl)amino) pyrimidine-5-carboxylic acid

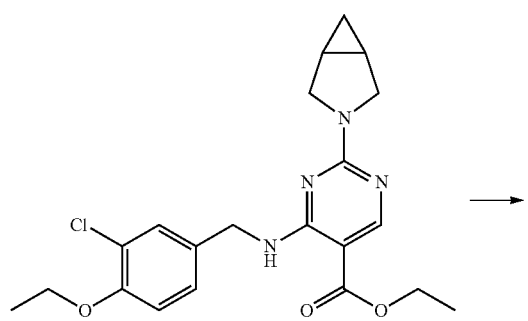

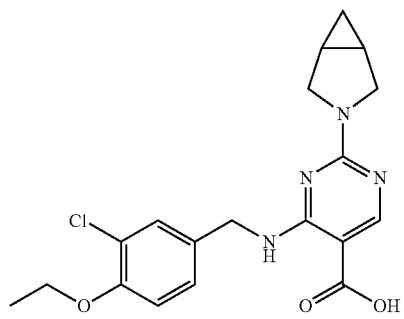

The procedures were analogous to Example 48(4). Yield: 96%.

(5) Preparation: 2-(3-azabicyclo[3.1.0]hexan-3-yl)-4-((3-chloro-4-ethoxybenzyl)amino)-N-((trans)-4-hydroxycyclohexyl)pyrimidine-5-formamide

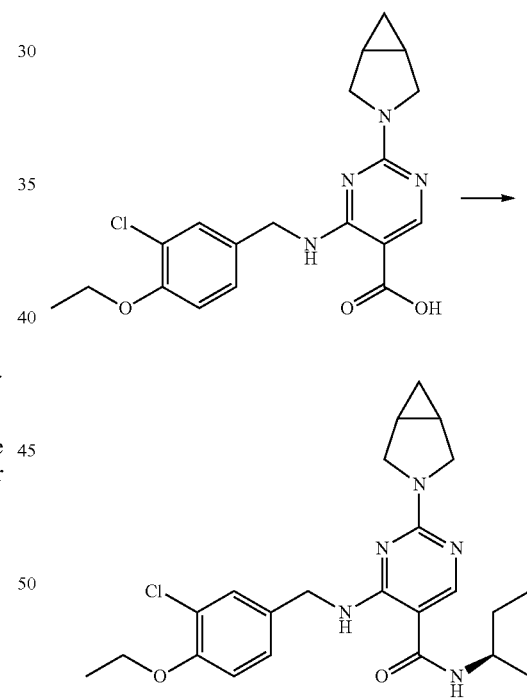

The procedures were analogous to Example 48(5). Yield: 10%.

Molecular formula: $C_{25}H_{32}ClN_5O_3$ Molecular weight: 486.0 MS (m/e): 485.9 (M+H$^+$)

$^1$H-NMR (400 MHz, CDCl$_3$): δ 8.90 (t, 1H), 8.12 (d, 1H), 7.36 (d, 1H), 7.17 (d, 1H), 6.85 (d, 1H), 5.56 (d, 1H), 4.55 (m, 2H), 4.06 (m, 2H), 3.81 (m, 3H), 3.64(m, 1H), 3.49 (m, 2H), 2.03 (m, 4H), 1.50 (m, 8H), 1.25 (m, 2H), 0.73 (m, 1H), 0.20 (m, 1H).

Example 53

Preparation 2-(3-azabicyclo[3.1.0]hexan-3-yl)-N-((trans)-4-hydroxy cyclohexyl)-4-((4-methoxy-3-(trifluoromethyl)benzyl)amino)pyrimidine-5-formamide (Compound 53)

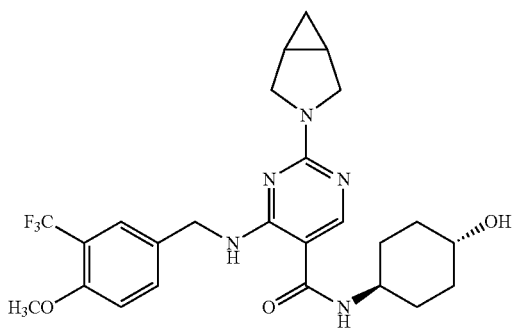

(1) Preparation: ethyl 4-((4-methoxy-3-(trifluoromethyl)benzyl)amino)-2-(methylthio) pyrimidine-5-carboxylate

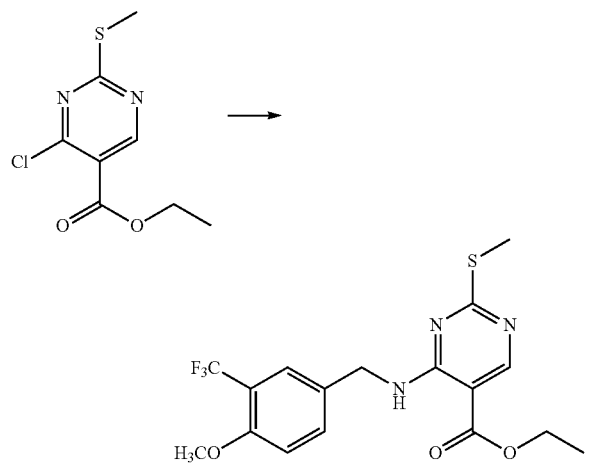

The procedures were analogous to Example 48(1). 4-methoxy-3-(trifluoromethyl)benzylamine was used in step 1 instead of 3-fluoro-4-methoxybenzylamine. Yield: 41%.

(2) Preparation: ethyl 4-((4-methoxy-3-(trifluoromethyl)benzyl)amino)-2-(methylsulfinyl) pyrimidine-5-carboxylate

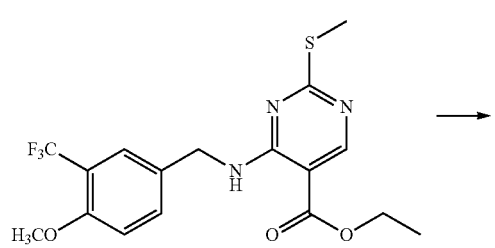

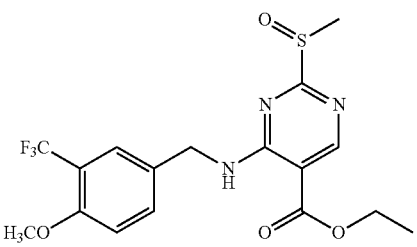

The procedures were analogous to Example 48(2). Yield: 99%.

(3) Preparation: ethyl 2-(3-azabicyclo[3.1.0]hexan-3-yl)-4-((4-methoxy-3-(trifluoromethyl)benzyl)amino)pyrimidine-5-carboxylate

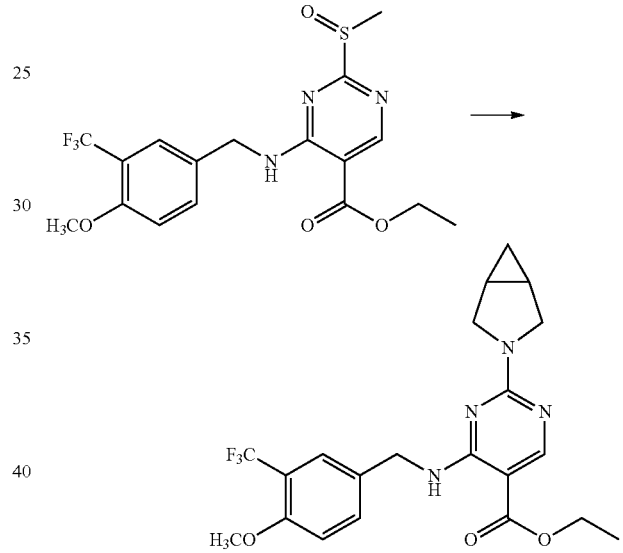

The procedures were analogous to Example 48(3). Yield: 89%.

(4) Preparation: 2-(3-azabicyclo[3.1.0]hexan-3-yl)-4-((4-methoxy-3-(trifluoromethyl)benzyl)amino)pyrimidine-5-carboxylic acid

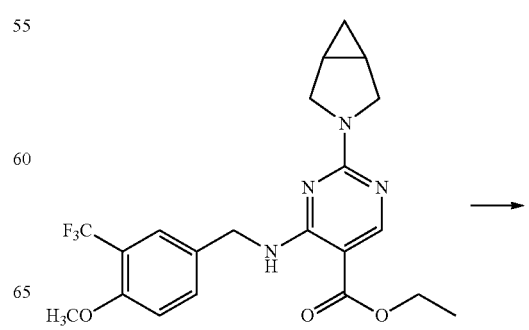

181
-continued

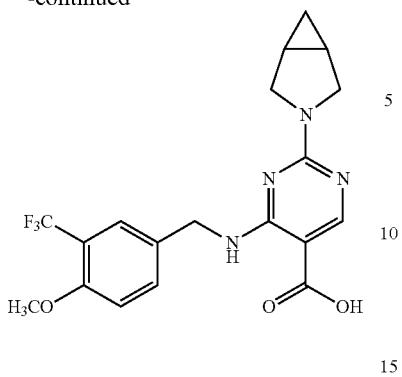

The procedures were analogous to Example 48(4). Yield: 43%.

(5) Preparation: 2-(3-azabicyclo[3.1.0]hexan-3-yl)-N-((trans)-4-hydroxycyclohexyl)-4-((4-methoxy-3-(trifluoromethyl)benzyl)amino)pyrimidine-5-formamide

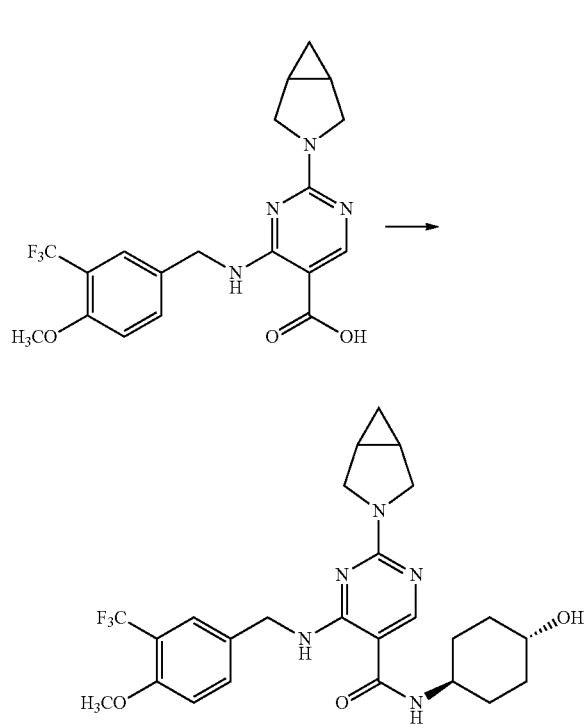

The procedures were analogous to Example 48(5). Yield: 56%.

Molecular formula: $C_{25}H_{30}F_3N_5O_3$ Molecular weight: 505.5 MS (m/e): 505.8 (M+H$^+$)

$^1$H-NMR (400 MHz, CDCl$_3$): δ 8.96 (t, 1H), 8.08 (s, 1H), 7.59 (s, 1H), 7.48 (d, 1H), 6.94 (d, 1H), 5.56 (b, 1H), 4.56 (m, 2H), 3.79-3.88 (m, 6H), 3.63 (m, 1H), 3.50(m, 2H), 2.06 (m, 4H), 1.58-1.64 (m, 5H), 1.45 (q, 2H), 0.75 (m, 1H), 0.21 (m, 1H).

182

Example 54

Preparation: 2-(3-azabicyclo[3.1.0]hexan-3-yl)-N-((trans)-4-hydroxy cyclohexyl)-4-((4-ethoxy-3-(trifluoromethyl)benzyl)amino)pyrimidine-5-formamide
(Compound 54)

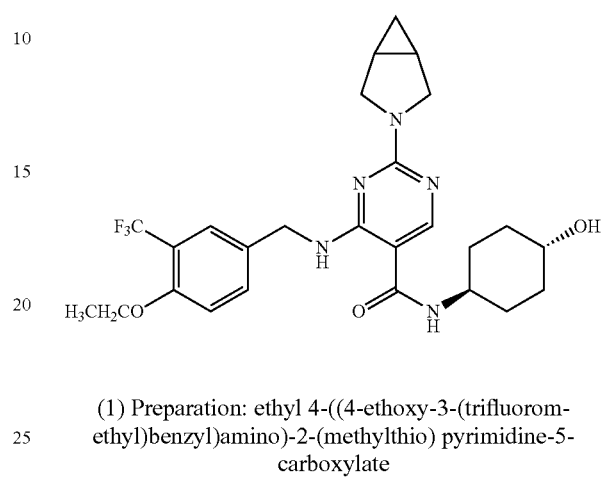

(1) Preparation: ethyl 4-((4-ethoxy-3-(trifluoromethyl)benzyl)amino)-2-(methylthio) pyrimidine-5-carboxylate

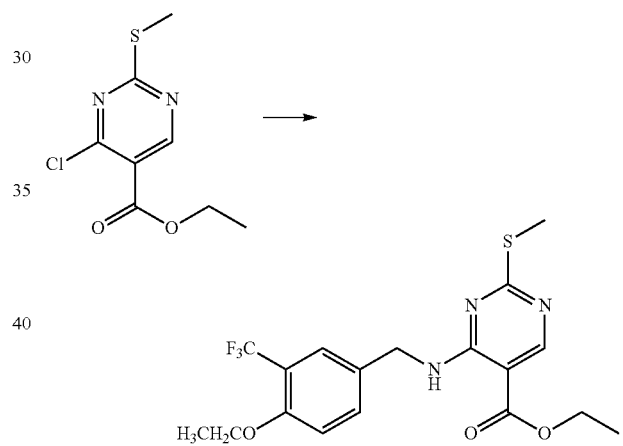

The procedures were analogous to Example 48(1). 4-ethoxyl-3-(trifluoromethyl)benzylamine was used in step 1 instead of 3-fluoro-4-methoxybenzylamine. Yield: 45.5%.

(2) Preparation: ethyl 4-((4-ethoxy-3-(trifluoromethyl)benzyl)amino)-2-(methylsulfinyl) pyrimidine-5-carboxylate

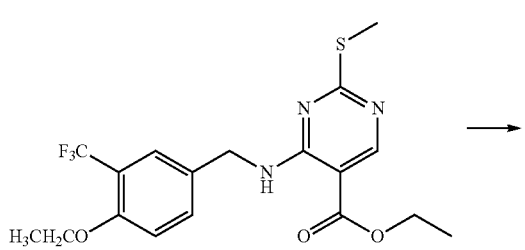

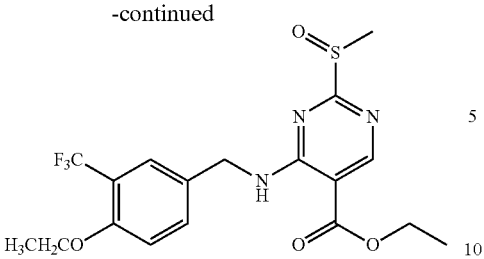

The procedures were analogous to Example 48(2). The product was used in the subsequent procedure without further purification.

(3) Preparation: ethyl 2-(3-azabicyclo[3.1.0]hexan-3-yl)-4-((4-ethoxy-3-(trifluoromethyl)benzyl)amino) pyrimidine-5-carboxylate

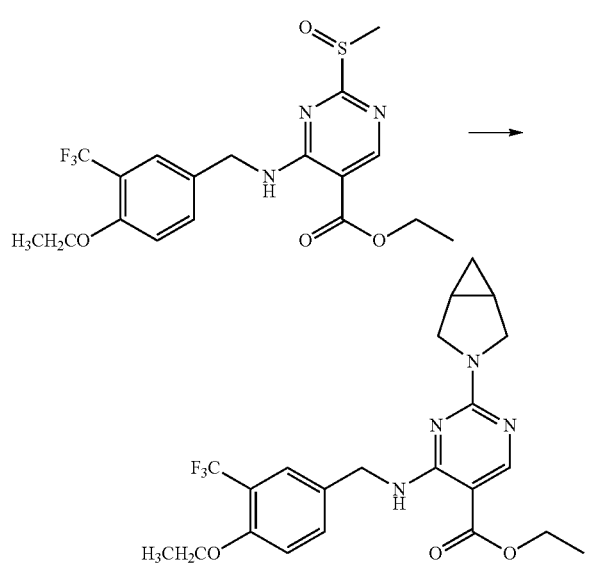

The procedures were analogous to Example 48(3). Yield: 90%.

(4) Preparation: 2-(3-azabicyclo[3.1.0]hexan-3-yl)-4-((4-ethoxy-3-(trifluoromethyl)benzyl)amino)pyrimidine-5-carboxylic acid

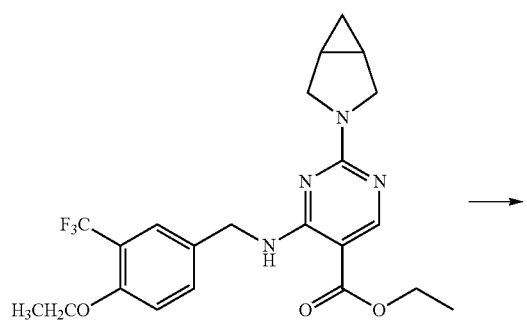

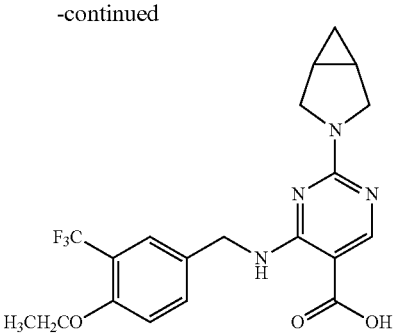

The procedures were analogous to Example 48(4). Yield: 77.7%.

(5) Preparation: 2-(3-azabicyclo[3.1.0]hexan-3-yl)-N-((trans)-4-hydroxycyclohexyl)-4-((4-ethoxy-3-(trifluoromethyl)benzyl)amino)pyrimidine-5-formamide

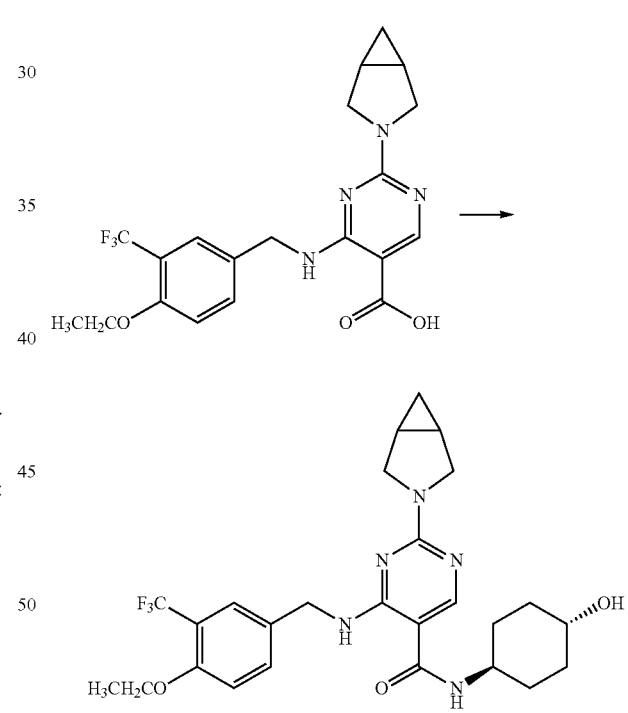

The procedures were analogous to Example 48(5). Yield: 28%.

Molecular formula: $C_{26}H_{32}F_3N_5O_3$ Molecular weight: 519.6 MS (m/e): 519.8 (M+1)

$^1$H-NMR (400 MHz, CDCl$_3$): δ 8.97 (t, 1H), 8.10 (s, 1H), 7.58 (s, 1H), 7.45 (d, 1H), 6.92 (d, 1H), 5.60 (d, 1H), 4.58 (d, 2H), 4.12 (m, 2H), 3.86 (m, 3H), 3.65(m, 1H), 3.50 (t, 2H), 2.05 (t, 4H), 1.60 (m, 3H), 1.45 (m, 5H), 1.30 (m, 2H), 0.83 (m, 1H), 0.20 (m, 1H).

Example 55

Preparation: N-((trans)-4-hydroxylcyclohexan-1-yl)-4-((3-chloro-4-methoxybenzyl)amino)-2-((s)-2-(hydroxymethyl)tetrahydropyrrole-1-yl)-5-pyrimidine formamide (Compound WO-88)

(1) Preparation: ethyl 4-((3-chloro-4-methoxybenzyl)amino)-2-thiomethyl-5-pyrimidine carboxylate

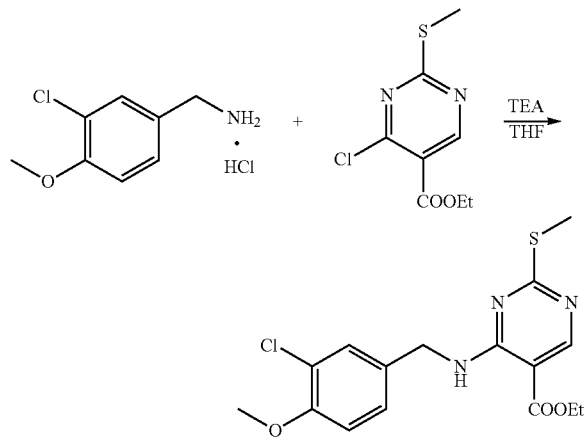

In THF (150 mL) was suspended 3-chloro-4-methoxybenzylamine hydrochloride salt (16.0 g, 76.9 mmol). The suspension was cooled in an ice bath, and triethylamine (19.4 g, 192.3 mmol) was added dropwisely. The reaction mixture was stirred at ambient temperature for 15 min, then was added ethyl 4-chloro-2-thiomethyl-5-pyrimidine carboxylate (14.9 g, 64.1 mmol). The reaction mixture was stirred at ambient temperature overnight. TLC was used to monitor the reaction. After the completion of the reaction, the solvent was removed by rotary evaporation. Acetic ether (500 mL) and water (200 mL) were added. The organic phase was separated, washed with hydrochloric acid (1N), saturated aqueous solution of sodium bicarbonate and brine, dried over sodium sulfate and filtrated. The filtrate was concentrated under reduced pressure. The solvent was removed by rotary evaporation to give oil. Methanol (100 mL) was added to precipitate a large amount of white solid. The mixture was filtrated and the solid was dried in vacuum to give ethyl 4-((3-chloro-4-methoxybenzyl)amine)-2-thiomethyl-5-pyrimidine carboxylate (21 g, 74.2% yield).

(2) Preparation: ethyl 4-((3-chloro-4-methoxybenzyl)amino)-2-methanesulfinyl-5-pyrimidine carboxylate

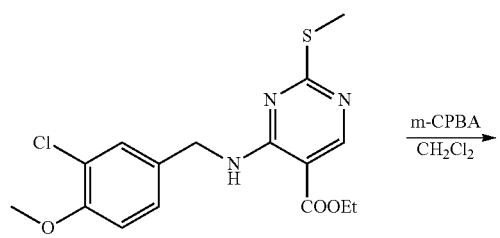

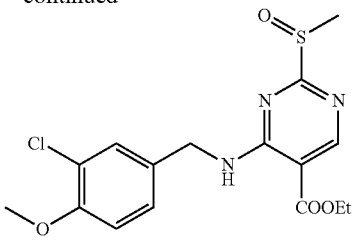

In DCM (80 mL) was dissolved ethyl 4-((3-chloro-4-methoxybenzyl)amine)-2-thiomethyl-5-pyrimidine carboxylate (8.0 g, 21.75 mmol). The solution was cooled in an ice bath, and 3-chloroperbenzoic acid (4.88 g, 28.27 mmol) was added. The reaction mixture was stirred at ambient temperature for 2 h. The reaction was monitored by TLC. After the completion of the reaction, the reaction mixture was washed with saturated aqueous solution of sodium bicarbonate (800 mL). The organic phase was separated. The aqueous phase was extracted with EA twice. The organic phase was combined, washed with saturated aqueous solution of sodium bicarbonate three times, and dried. The obtained solution of ethyl 4-((3-chloro-4-methoxybenzyl)amino)-2-methanesulfinyl-5-pyrimidine carboxylate in DCM was used in subsequent reaction.

(3) Preparation: ethyl (s)-4-((3-chloro-4-methoxybenzyl)amino)-2-(2-(hydroxymethyl)tetrahydropyrrole-1-yl)-5-pyrimidine carboxylate

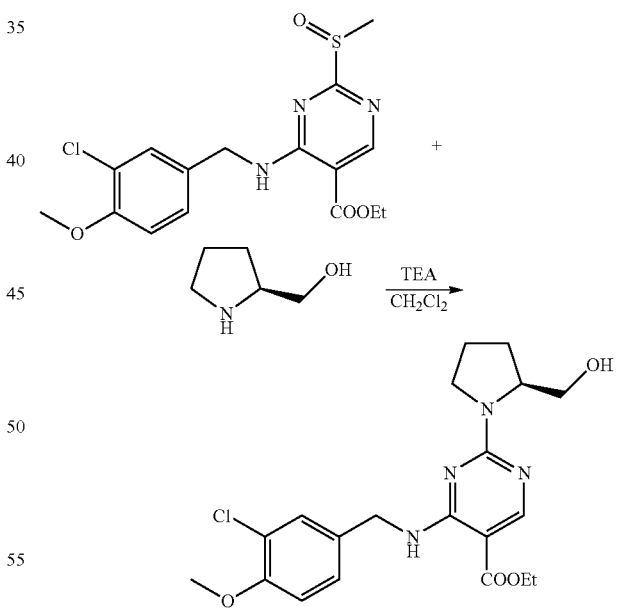

In the solution of ethyl 4-((3-chloro-4-methoxybenzyl)amino)-2-methanesulfinyl-5-pyrimidine carboxylate in DCM was added triethylamine (4.24 g, 42 mmol). The mixture was cooled in an ice bath, then was added L-prolinol (2.2 g, 19.8 mmol) dropwise. The reaction mixture was stirred at ambient temperature for 3 h. The reaction was monitored by LC-MS. After the completion of the reaction, the reaction mixture was washed with water, dilute hydrochloric acid, sodium bicarbonate aqueous solution and brine, each once.

The organic phase was dried over sodium sulfate and concentrated until the solvent was removed. The product was used in subsequent procedures without further purification.

(4) Preparation: (s)-4-((3-chloro-4-methoxybenzyl)amino)-2-(2-(hydroxymethyl)tetrahydropyrrole-1-yl)-5-pyrimidine carboxylic acid

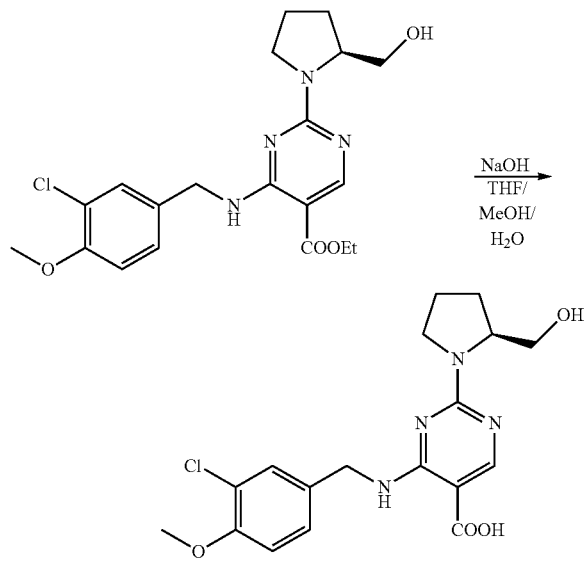 [SMILES: CCOC(=O)c1cnc(N2CCC[C@H]2CO)nc1NCc1ccc(OC)c(Cl)c1 ; "NaOH" ; "THF/MeOH/H2O" ; COc1ccc(CNc2nc(N3CCC[C@H]3CO)ncc2C(=O)O)cc1Cl]

Methanol (50 mL) was added in ethyl (s)-4-((3-chloro-4-methoxybenzyl)amino)-2-(2-(hydroxymethyl)tetrahydropyrrole-1-yl)-5-pyrimidine carboxylate (8.75 g, 20.8 mmol). In water (20 mL) was dissolved sodium hydrate (1.66 g, 41.6 mmol), then the aqueous solution was added to the reaction solution. The reaction was conducted in an oil bath of 50 to 60° C. overnight. The reaction was monitored by LC-MS. The organic solvent was removed by rotary evaporation. The residual aqueous phase was adjusted to a pH of 3 to 4. Then solid was precipitated. The precipitation was filtrated and dried to give a solid (3.9 g, 48.1% yield).

(5) Preparation: N-(trans-4-hydroxycyclohexan-1-yl)-4-((3-chloro-4-methoxybenzyl)amino)-2-((s)-2-(hydroxymethyl)tetrahydropyrrole-1-yl)-5-pyrimidine formamide

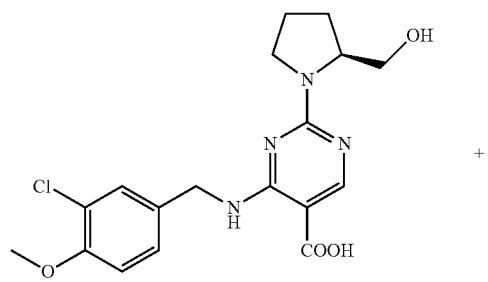

+

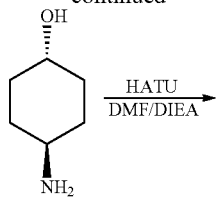

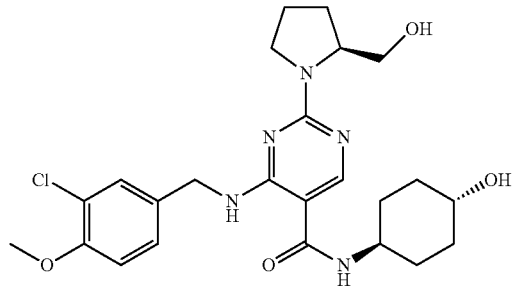

In DMF (20 mL) was dissolved (s)-4-((3-chloro-4-methoxybenzyl)amino)-2-(2-(hydroxymethyl)tetrahydropyrrole-1-yl)-5-pyrimidine carboxylic acid (3.9 g, 10 mmol). The solution was cooled in an ice bath. HATU (5.67 g, 15 mmol) and DIPEA (1.93 g, 15 mmol) were added. After 20 min, trans-4-aminocyclohexanol (1.39 g, 12 mmol) was added in batches. The reaction was conducted overnight. LC-MS was used to monitor the reaction. Ethyl acetate (50 mL) and water (50 mL) were added. The separate aqueous phase was washed with ethyl acetate twice. The organic phase was combined, dried, concentrated and purified by silica gel column chromatography ($V_{DCM}:V_{MeOH}$=15:1) to give the product (1.5 g, 31% yield).

Molecular formula: $C_{24}H_{32}ClN_5O_4$ Molecular weight: 489.21 LC-MS (M/e): 490.11 (M+H$^+$)

$^1$H-NMR (400 MHz, CDCl$_3$): δ 9.63 (1H, s), 8.15 (1H, s), 7.35(1H, s), 7.19 (1H, d), 7.1 (1H, d), 6.26 (1H, s), 4.58 (2H, d), 4.05-4.13 (1H, m), 3.79-3.90 (6H, m), 3.56-3.69 (3H, m), 2.22-2.27 (2 H, m), 1.72-2.17 (8H, m), 1.26-1.45 (4H, m).

Example 56

Preparation: N-(trans-4-hydroxycyclohexan-1-yl)-4-((3-chloro-4-methoxybenzyl)amino)-2-(5H-pyrrolo[3,4-b]pyridin-6(7H)yl)-5-pyrimidine formamide (Compound WO-93)

(1) Preparation: ethyl 4-((3-chloro-4-methoxybenzyl)amino)-2-methanesulfinyl-5-pyrimidine carboxylate

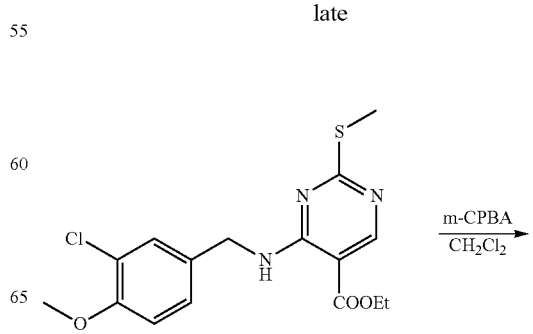

-continued

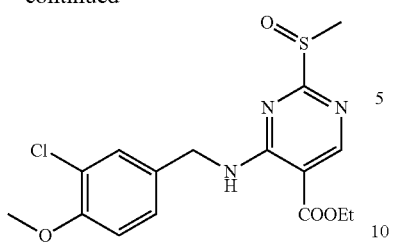

In DCM (40 mL) was dissolved ethyl 4-((3-chloro-4-methoxybenzyl)amino)-2-thiomethyl-5-pyrimidine carboxylate (4.0 g, 10.87 mmol). The solution was cooled in an ice bath. 3-Chloroperbenzoic acid (2.44 g, 14.14 mmol) was added. The reaction mixture was stirred at ambient temperature for 2 h. TLC was used to monitor the reaction. After the reaction was completed, the reaction mixture was washed with saturated aqueous solution of sodium bicarbonate (800 mL). The organic phase was separated. The aqueous phase was extracted with ethyl acetate twice. The organic phase was combined, washed with saturated aqueous solution of sodium bicarbonate three times and dried. The obtained solution of ethyl 4-((3-chloro-4-methoxybenzyl)amino)-2-methanesulfinyl-5-pyrimidine carboxylate in DCM was used in the subsequent procedure.

(2) Preparation: ethyl 4-((3-chloro-4-methoxybenzyl)amino)-2-(5H-pyrrolo[3,4-b]pyridin-6(7H)yl)-5-pyrimidine carboxylate

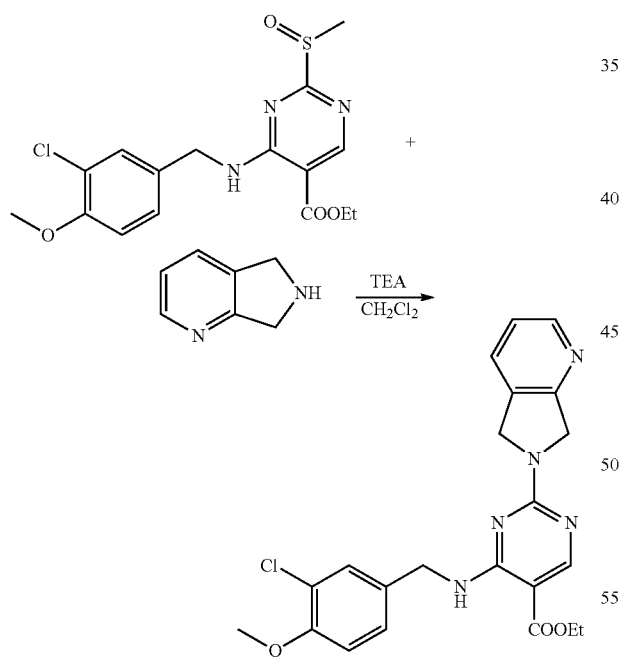

6,7-dihydro-5H-pyrrolo[3,4-b]pyridine hydrochloride salt (1.86 g, 12 mmol) was added into the solution of ethyl 4-((3-chloro-4-methoxybenzyl)amino)-2-methanesulfinyl-5-pyrimidine carboxylate in DCM. The mixture was cooled in an ice bath, and triethylamine was added dropwisely (2.5 mL, 17.9 mmol). The reaction mixture was stirred at ambient temperature overnight. LC-MS was used to monitor the reaction. After the completion of the reaction, water (30 mL) was added for precipitation. The solid was filtered and dried to give ethyl 4-((3-chloro-4-methoxybenzyl)amino)-2-(5H-pyrrolo[3,4-b]pyridine-6(7H)yl)-5-pyrimidine carboxylate (3.0 g, 65.6% yield).

(3) Preparation: 4-((3-chloro-4-methoxybenzyl)amino)-2-(5H-pyrrolo[3,4-b]pyridin-6(7H)yl)-5-pyrimidine carboxylic acid

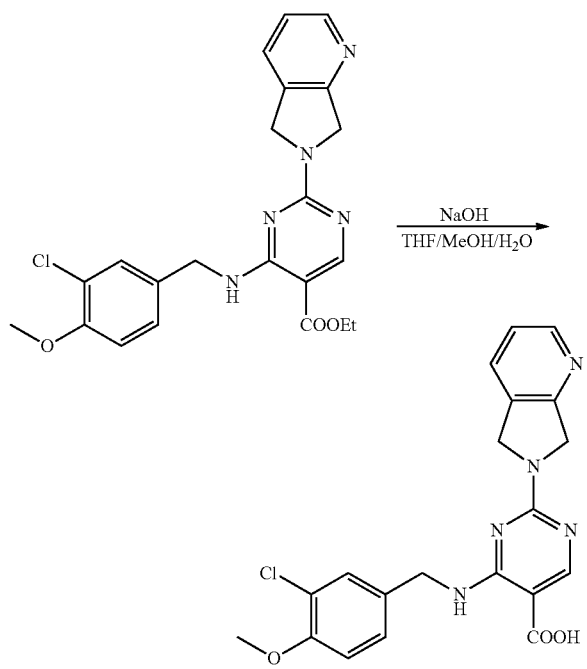

Methanol (30 mL) was added in ethyl 4-((3-chloro-4-methoxybenzyl)amino)-2-(5H-pyrrolo[3,4-b]pyridin-6 (7H) yl)-5-pyrimidine carboxylate (3.0 g, 6.82 mmol). Sodium hydrate (0.55 g, 13.6 mmol) was dissolved in water (10 mL) and added into the solution. The reaction was conducted in an oil bath of 50 to 60° C. overnight. LC-MS was used to monitor the reaction. The organic solvent was removed by rotary evaporation. The residual aqueous phase was adjusted to a pH of 3 to 4. Solid was precipitated, filtrated, and dried (1.0 g, 36.0% yield).

(4) Preparation: N-(trans-4-hydroxylcyclohexan-1-yl)-4-((3-chloro-4-methoxybenzyl)amino)-2-(5H-pyrrolo[3,4-b]pyridin-6(7H)yl)-5-pyrimidine formamide

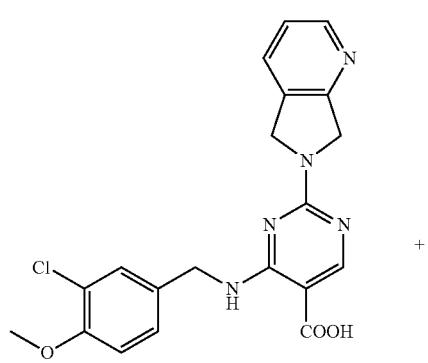

-continued

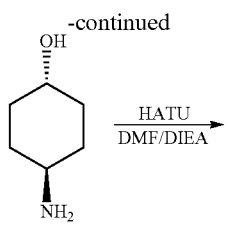

In DMF (10 mL) was dissolved 4-((3-chloro-4-methoxybenzyl)amino)-2-(5H-pyrrolo[3,4-b]pyridin-6(7H)yl)-5-pyrimidine formic acid (0.8 g, 1.94 mmol). The solution was cooled in an ice bath. HATU (1.11 g, 2.91 mmol) and DIPEA (0.37 g, 2.87 mmol) were added. After 20 min, trans-4-aminocyclohexanol (0.27 g, 2.3 mmol) was added in batches. The reaction was conducted overnight. LC-MS was used to monitor the reaction. The reaction mixture was poured into water (50 mL) and filtrated. The solid was recrystallized with acetone (20 mL) to give N-((trans)-4-hydroxycyclohexan-1-yl)-4-((3-chloro-4-methoxybenzyl)amino)-2-(5H-pyrrolo[3,4-b]pyridin-6(7H)yl)-5-pyrimidine formamide (300 mg, 30.3% yield).

Molecular formula: $C_{26}H_{29}ClN_6O_3$ Molecular weight: 508.20 LC-MS (M/e): 509.20 (M+H$^+$)

$^1$H-NMR (400 MHz, DMSO-d$_6$): δ 9.24 (1H, s), 8.47 (2H, s), 7.90(1H, d), 7.82 (1H, t), 7.46 (1H, s), 7.30-7.35 (2H, m), 7.10 (1H, d), 4.83 (2H, s), 4.76 (2H, s), 4.52-4.57 (2H, s), 3.80 (3H, s), 3.62-3.65 (1H, m), 1.76-1.84 (4H, m), 1.18-1.35 (6H, m).

The compounds below can be prepared following the above synthetic methods.

| Compound | Structure |
|---|---|
| 56 | 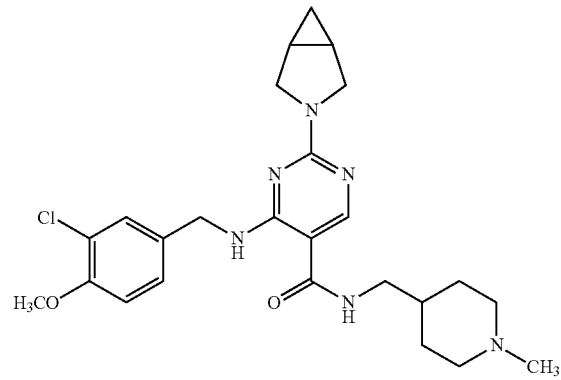 [SMILES: COc1ccc(CNc2nc(N3CC4CC4C3)ncc2C(=O)NCC2CCN(C)CC2)cc1Cl] |
| 57 | 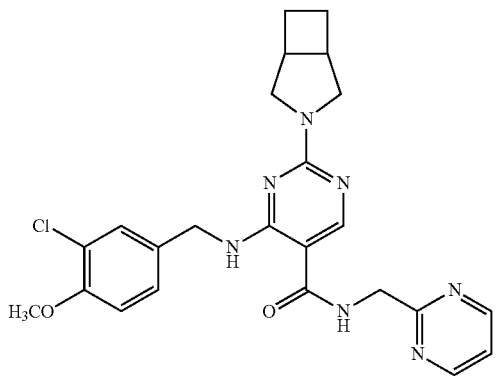 [SMILES: COc1ccc(CNc2nc(N3CC4CCC4C3)ncc2C(=O)NCc2ncccn2)cc1Cl] |

-continued
| Compound | Structure |
|---|---|
| 58 | 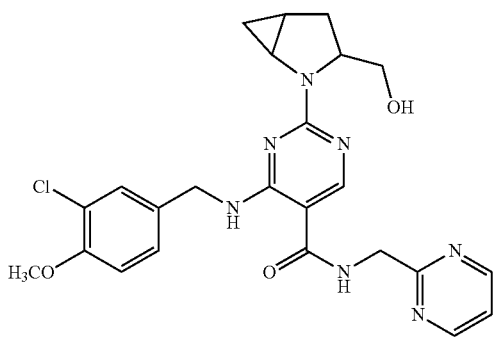 [SMILES: COc1ccc(CNc2nc(N3C(CO)CC4CC43)ncc2C(=O)NCc2ncccn2)cc1Cl] |
| 59 | 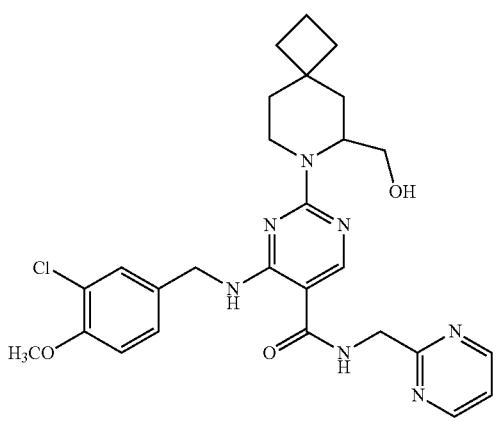 [SMILES: COc1ccc(CNc2nc(N3CCC4(CCC4)CC3CO)ncc2C(=O)NCc2ncccn2)cc1Cl] |
| 60 | 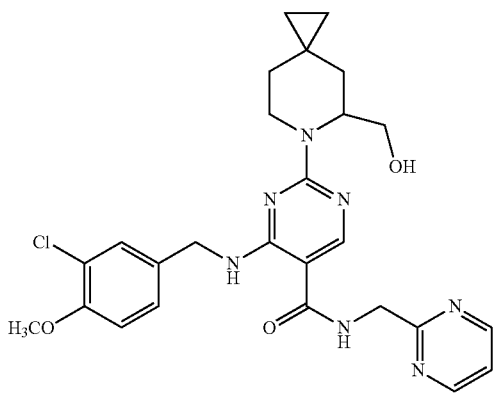 [SMILES: COc1ccc(CNc2nc(N3CCC4(CC4)CC3CO)ncc2C(=O)NCc2ncccn2)cc1Cl] |
| 61 | 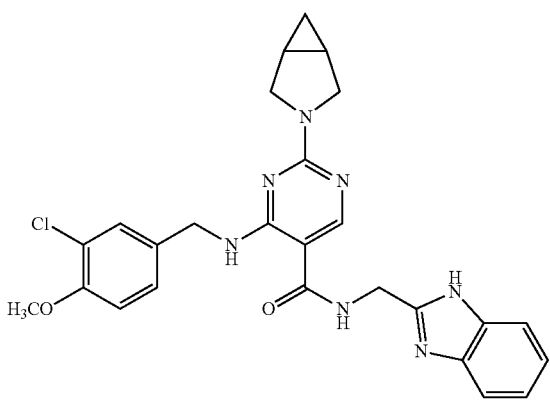 [SMILES: COc1ccc(CNc2nc(N3CC4CC4C3)ncc2C(=O)NCc2nc3ccccc3[nH]2)cc1Cl] |

-continued
| Compound | Structure |
|---|---|
| 62 | 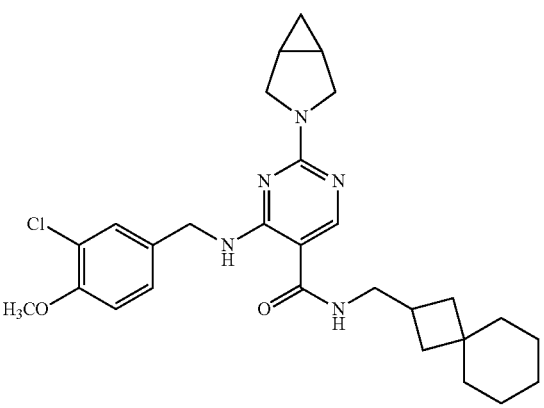 [SMILES: COc1ccc(CNc2nc(N3CC4CC4C3)ncc2C(=O)NCC2CC3(CCCCC3)C2)cc1Cl] |
| 63 | 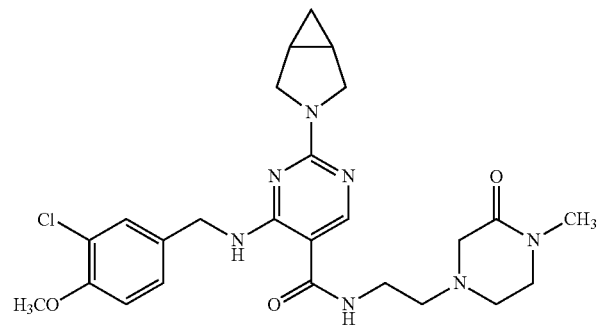 [SMILES: COc1ccc(CNc2nc(N3CC4CC4C3)ncc2C(=O)NCCN2CCN(C)C(=O)C2)cc1Cl] |
| 64 | 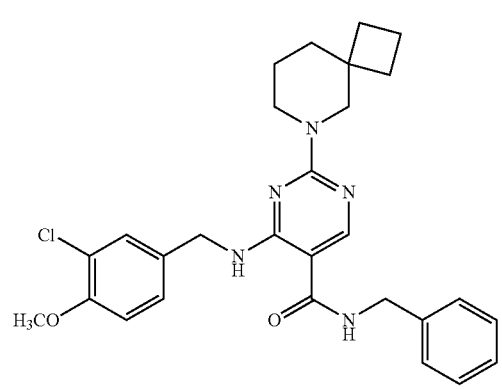 [SMILES: COc1ccc(CNc2nc(N3CCCC4(CCC4)C3)ncc2C(=O)NCc2ccccc2)cc1Cl] |
| 65 | 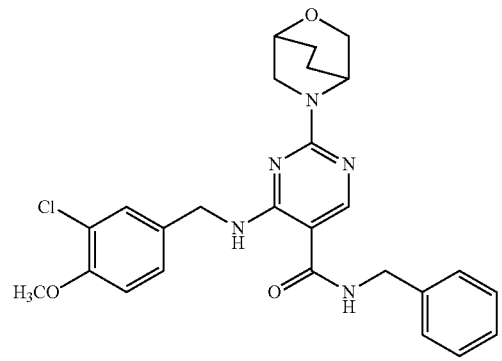 [SMILES: COc1ccc(CNc2nc(N3CC4CCC3CO4)ncc2C(=O)NCc2ccccc2)cc1Cl] |

| Compound | Structure |
|---|---|
| 66 | 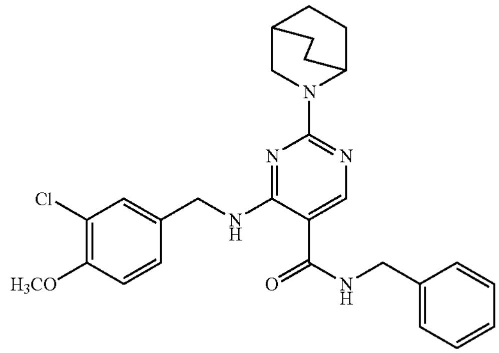 [SMILES: COc1ccc(CNc2nc(N3CC4CCC3CC4)ncc2C(=O)NCc2ccccc2)cc1Cl] |
| 67 | 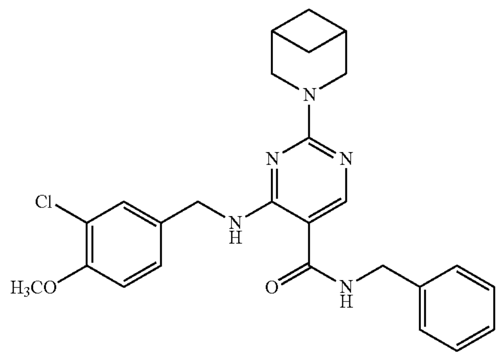 [SMILES: COc1ccc(CNc2nc(N3CC4CC(C4)C3)ncc2C(=O)NCc2ccccc2)cc1Cl] |

We claim:

1. A compound of Formula (I) or a pharmaceutically acceptable salt or a stereoisomer thereof:

(I)

wherein
- $R^1$ is selected from the group consisting of saturated 6 to 7 membered N-containing fused heterocyclyl, 7 to 12 membered N-containing spiro heterocyclyl and 7 to 12 membered N-containing bridged heterocyclyl; each attached to pyrimidyl via nitrogen and optionally substituted with a substituent selected from the group consisting of halogen, cyano, amino, hydroxyl, $C_{1-6}$ alkyl, halo $C_{1-6}$ alkyl, hydroxyl $C_{1-6}$ alkyl, $C_{1-6}$ alkoxyl, $C_{1-6}$ alkylcarbonyl and $C_{1-6}$ alkoxylcarbonyl, wherein the number of the substituent is 1 to 4;
- $R^2$ is selected from the group consisting of hydrogen, hydroxyl, amino, cyano, $C_{1-6}$ alkylamino, di($C_{1-6}$ alkyl) amino, $C_{1-6}$ alkyl, halo $C_{1-6}$ alkyl, hydroxyl $C_{1-6}$ alkyl and $C_{1-6}$ alkoxyl;
- $R^3$ and $R^4$ are each independently selected from hydrogen and -M-$R^7$,
- M is selected from a single bond and $C_{1-6}$ alkylene optionally substituted with substituent $L_1$,
- $R^7$ is selected from 3 to 14 membered cyclic group optionally substituted with substituent $L_2$,
- or $R^3$ and $R^4$ together with nitrogen attached to $R^3$ and $R^4$ form a 5 to 6 membered N-containing heterocyclyl optionally substituted with substituent $L_3$,
- said substituents $L_1$, $L_2$ and $L_3$ are selected from the group consisting of halogen, hydroxyl, cyano, amino, $C_{1-6}$ alkylamino, di($C_{1-6}$ alkyl)amino, oxo, $C_{1-6}$ alkyl, hydroxyl $C_{1-6}$ alkyl, halo $C_{1-6}$ alkyl, $C_{1-6}$ alkoxyl, $C_{1-6}$ alkylcarbonyl, $C_{1-6}$ alkylsulfonyl and di($C_{1-6}$ alkyl) phosphino, wherein the number of the substituent is 1 to 4;
- $R^5$ and $R^6$ are each independently selected from hydrogen and -Q-$R^8$,
- Q is selected from a single bond and $C_{1-6}$ alkylene optionally substituted with substituent $L_4$,
- $R^8$ is selected from the group consisting of 6 to 14 membered aryls, 5 to 7 membered monocyclic heterocyclyl, 8 to 9 membered fused cyclyl and 8 to 9 membered fused heterocyclyl; each optionally substituted with substituent $L_5$,
- said substituents $L_4$ and $L_5$ are selected from the group consisting of halogen, hydroxyl, $C_{1-6}$ alkyl, halo $C_{1-6}$ alkyl, carboxyl $C_{1-6}$ alkyl, $C_{2-6}$ alkenyl, $C_{2-6}$ alkynyl, $C_{1-6}$ alkoxyl, halo $C_{1-6}$ alkoxyl, amino, $C_{1-6}$ alkylamino, di($C_{1-6}$ alkyl)amino, cyano, nitro, $C_{1-6}$ alkylcarbonyl, sulfonyl amino and $C_{1-6}$ alkyl sulfonyl amino, wherein the number of the substituent is 1 to 4.

2. The compound of claim 1 or a pharmaceutically acceptable salt or a stereoisomer thereof, wherein $R^2$ is selected from the group consisting of hydrogen, hydroxyl and methyl;
$R^4$ is hydrogen;
$R^6$ is hydrogen.

3. The compound of claim 2 or a pharmaceutically acceptable salt or a stereoisomer thereof, wherein
$R^5$ is -Q-$R^8$,
Q is selected from $C_{1-6}$ alkylene,
$R^8$ is selected from the group consisting of 6 to 10 membered aryls, 5 to 7 membered monocyclic heterocyclyl, 8 to 9 membered fused cyclyl and 8 to 9 membered fused heterocyclyl; each optionally substituted with substituent $L_5$,
said substituent $L_5$ is selected from the group consisting of halogen, hydroxyl, $C_{1-6}$ alkyl, halo $C_{1-6}$ alkyl, carboxyl $C_{1-6}$ alkyl, $C_{1-6}$ alkoxyl, halo $C_{1-6}$ alkoxyl, amino, $C_{1-6}$ alkylamino, di($C_{1-6}$alkyl)amino, cyano, nitro, $C_{1-6}$ alkylcarbonyl, sulfonyl amino and $C_{1-6}$ alkyl sulfonyl amino, wherein the number of the substituent is 1 to 4.

4. The compound of claim 3 or a pharmaceutically acceptable salt or a stereoisomer thereof, wherein $R^1$ is selected from the group consisting of saturated 6 to 7 membered N-containing fused heterocyclyl, 7 to 12 membered N-containing spiro heterocyclyl and 7 to 12 membered N-containing bridged heterocyclyl; each attached to pyrimidyl via nitrogen and optionally substituted with a substituent selected from the group consisting of halogen, cyano, amino, hydroxyl, $C_{1-6}$ alkyl, halo $C_{1-6}$ alkyl, hydroxyl $C_{1-6}$ alkyl, $C_{1-6}$ alkoxyl, $C_{1-6}$ alkylcarbonyl and $C_{1-6}$ alkoxylcarbonyl, wherein the number of the substituent is 1 to 4.

5. The compound of claim 4 or a pharmaceutically acceptable salt or a stereoisomer thereof, wherein $R^1$ is selected from the group consisting of saturated 6 to 7 membered N-containing fused heterocyclyl, 7 to 10 membered N-containing spiro heterocyclyl and 7 to 8 membered N-containing bridged heterocyclyl; each attached to pyrimidyl via nitrogen and optionally substituted with a substituent selected from the group consisting of halogen, cyano, amino, hydroxyl, $C_{1-6}$ alkyl, halo $C_{1-6}$ alkyl, hydroxyl $C_{1-6}$ alkyl and $C_{1-6}$ alkoxyl, wherein the number of the substituent is 1 to 4;
$R^3$ is -M-$R^7$,
M is selected from a single bond and $C_{1-6}$ alkylene,
$R^7$ is selected from the group consisting of phenyl, 5 to 7 membered monocyclic heterocyclyl, 4 to 7 membered cycloalkyl, 8 to 9 fused cyclyl, 7 to 10 membered spiro cyclyl, 7 to 10 membered bridged cyclyl, 7 to 10 membered spiro heterocyclyl and 7 to 10 membered bridged heterocyclyl; each optionally substituted with substituent $L_2$,
or $R^3$ and $R^4$ together with nitrogen attached to $R^3$ and $R^4$ form a 5 to 6 membered N-containing heterocyclyl optionally substituted with substituent $L_3$,
said substituents $L_2$ and $L_3$ are selected from the group consisting of halogen, hydroxyl, cyano, amino, $C_{1-6}$ alkylamino, di($C_{1-6}$ alkyl)amino, oxo, $C_{1-6}$ alkyl, hydroxyl $C_{1-6}$ alkyl, halo $C_{1-6}$ alkyl and $C_{1-6}$ alkoxyl, wherein the number of the substituent is 1 to 4;
$R^5$ is -Q-$R^8$,
Q is selected from methylene and ethylene,
$R^8$ is selected from the group consisting of phenyl, 5 to 7 membered monocyclic heterocyclyl, 8 to 9 membered fused cyclyl and 8 to 9 fused heterocyclyl; each optionally substituted with substituent $L_5$,
said substituent $L_5$ is selected from the group consisting of fluoro, chloro, methyl, trifluoromethyl, methoxyl, ethoxyl, trifluoromethoxyl, dimethylamino and carboxylmethyl, wherein the number of the substituent is 1 to 4;
$R^2$ is hydrogen; $R^4$ is hydrogen; $R^6$ is hydrogen.

6. The compound of claim 5 or a pharmaceutically acceptable salt or a stereoisomer thereof, wherein $R^7$ is selected from the group consisting of phenyl, tetrahydrofuranyl, tetrahydrothienyl, tetrahydropyrrolyl, imidazolidinyl, pyrazolidinyl, piperidinyl, morpholinyl, piperazinyl, 2-oxo-azacycloheptanyl, 2-oxo-piperazinylfuranyl, dihydrothienyl, dihydropyrrolyl, dihydrooxazolyl, dihydropyrazolyl, thienyl, pyrrolyl, imidazolyl, thiazolyl, pyrazolyl, pyrimidyl, pyridyl, pyrazinyl, oxazolyl, cyclobutyl, cyclopentyl, cyclohexyl, cycloheptyl, naphthyl, indolyl, benzimidazolyl, 2,3-dihydrobenzfuranyl, quinolinyl, benzo[d][1,3]-meta-dioxa-cyclopentenyl, 7 to 10 membered spiro cyclyl, 7 to 10 membered bridged cyclyl, 7 to 10 membered spiro heterocyclyl and 7 to 10 membered bridged heterocyclyl; each optionally substituted with substituent $L_2$,
or $R^3$ and $R^4$ together with nitrogen attached to $R^3$ and $R^4$ form a 5 to 6 membered N-containing heterocyclyl optionally substituted with substituent $L_3$,
said substituents $L_2$ and $L_3$ are selected from the group consisting of halogen, hydroxyl, cyano, amino, $C_{1-6}$ alkylamino, di($C_{1-6}$ alkyl)amino, oxo, $C_{1-6}$ alkyl, hydroxyl $C_{1-6}$ alkyl, halo $C_{1-6}$ alkyl and $C_{1-6}$ alkoxyl, wherein the number of the substituent is 1 to 4;
$R^8$ is selected from the group consisting of phenyl, 8 to 9 membered fused cyclyl and 8 to 9 fused heterocyclyl; each optionally substituted with substituent $L_5$,
said substituent $L_5$ is selected from the group consisting of fluoro, chloro, methyl, trifluoromethyl, methoxyl, ethoxyl, trifluoromethoxyl, dimethylamino and carboxylmethyl, wherein the number of the substituent is 1 to 4.

7. The compound of claim 6 or a pharmaceutically acceptable salt or a stereoisomer thereof, wherein $R^1$ is selected from the group consisting of saturated 6 to 7 membered N-containing fused heterocyclyl, 7 to 10 membered N-containing spiro heterocyclyl and 7 to 8 membered N-containing bridged heterocyclyl; each attached to pyrimidyl via nitrogen and optionally substituted with a substituent selected from the group consisting of fluoro, chloro, amino, hydroxyl, $C_{1-6}$ alkyl and hydroxyl $C_{1-6}$ alkyl, wherein the number of the substituent is 1 to 2;
$R^3$ is -M-$R^7$,
M is selected from the group consisting of a single bond, methylene and ethylene,
$R^7$ is selected from the group consisting of cyclopentyl, cyclohexyl and cycloheptyl; each optionally substituted with substituent $L_2$,
said substituent $L_2$ is selected from the group consisting of fluoro, chloro, hydroxyl, amino, methylamino, dimethylamino, methyl, ethyl and methoxyl, wherein the number of the substituent is 1 to 2;
$R^5$ is -Q-$R^8$,
Q is selected from methylene and ethylene,
$R^8$ is phenyl optionally substituted with substituent $L_5$,
said substituent $L_5$ is selected from the group consisting of fluoro, chloro, methyl, trifluoromethyl, methoxyl, ethoxyl and trifluoromethoxyl, wherein the number of the substituent is 1 to 4.

8. The compound of claim 6 or a pharmaceutically acceptable salt or a stereoisomer thereof, wherein $R^1$ is selected from the group consisting of saturated 6 to 7 membered N-containing fused heterocyclyl and 7 to 10 membered N-containing spiro heterocyclyl; each attached to pyrimidyl via nitrogen and optionally substituted with a substituent selected from the group consisting of fluoro, chloro, amino, hydroxyl, $C_{1-6}$ alkyl and hydroxyl $C_{1-6}$ alkyl, wherein the number of the substituent is 1 to 2;

R³ is -M-R⁷,

M is selected from the group consisting of a single bond, methylene and ethylene, R⁷ is selected from the group consisting of piperidinyl, morpholinyl, piperazinyl, 2-oxo-azacycloheptanyl, 2-oxo-piperazinylfuranyl and 7 to 10 membered spiro cyclyl; each optionally substituted with substituent L₂, or R³ and R⁴ together with nitrogen attached to R³ and R⁴ form piperidinyl, piperazinyl or morpholinyl; each optionally substituted with substituent L₃, said substituents L₂ and L₃ are selected from the group consisting of fluoro, chloro, hydroxyl, amino, methylamino, dimethylamino, oxo, trifluoromethyl, methyl, ethyl and methoxyl, wherein the number of the substituent is 1 to 2;

R⁵ is -Q-R⁸,

Q is selected from methylene and ethylene,

R⁸ is phenyl optionally substituted with substituent L₅, said substituent L₅ is selected from the group consisting of fluoro, chloro, methyl, trifluoromethyl, methoxyl, ethoxyl and trifluoromethoxyl, wherein the number of the substituent is 1 to 4.

9. The compound of claim 6 or a pharmaceutically acceptable salt or a stereoisomer thereof, wherein R¹ is selected from the group consisting of saturated 6 to 7 membered N-containing fused heterocyclyl, 7 to 10 membered N-containing spiro heterocyclyl and 7 to 8 membered N-containing bridged heterocyclyl; each attached to pyrimidyl via nitrogen and optionally substituted with a substituent selected from the group consisting of fluoro, chloro, amino, hydroxyl, C₁₋₆ alkyl and hydroxyl C₁₋₆ alkyl, wherein the number of the substituent is 1 to 2;

R³ is -M-R⁷,

M is selected from the group consisting of a single bond, methylene and ethylene, R⁷ is selected from the group consisting of phenyl, thienyl, pyrrolyl, imidazolyl, thiazolyl, pyrazolyl, pyrimidyl, pyridyl, pyrazinyl, oxazolyl, naphthyl, indolyl, quinolinyl and 7 to 10 membered bridged cyclyl; each optionally substituted with substituent L₂, or R³ and R⁴ together with nitrogen attached to R³ and R⁴ form piperidinyl, piperazinyl or morpholinyl; each optionally substituted with substituent L₃, said substituents L₂ and L₃ are selected from the group consisting of fluoro, chloro, hydroxyl, amino, methylamino, dimethylamino, oxo, trifluoromethyl, methyl, ethyl and methoxyl, wherein the number of the substituent is 1 to 2;

R⁵ is -Q-R⁸,

Q is selected from methylene and ethylene,

R⁸ is selected from the group consisting of phenyl and 8 to 9 membered fused cyclyl; each optionally substituted with L₅, said substituent L₅ is selected from the group consisting of fluoro, chloro, methyl, trifluoromethyl, methoxyl, ethoxyl and trifluoromethoxyl, wherein the number of the substituent is 1 to 4.

10. The compound of claim 6 or a pharmaceutically acceptable salt or a stereoisomer thereof, wherein R¹ is selected from the group consisting of

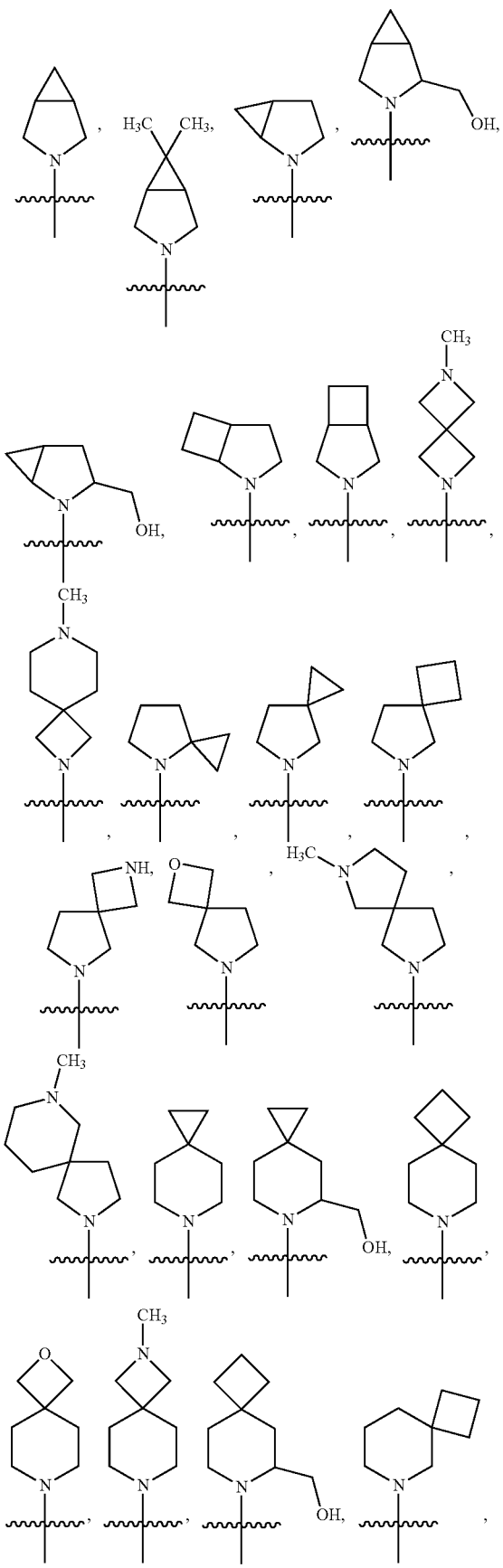

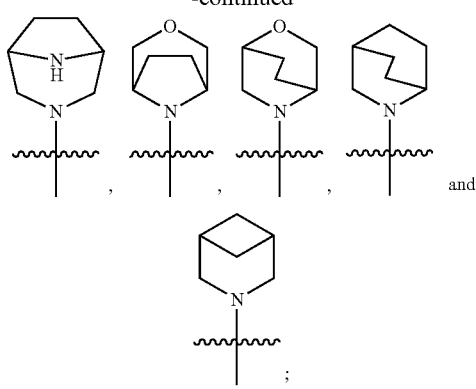
R³ is selected from the group consisting of
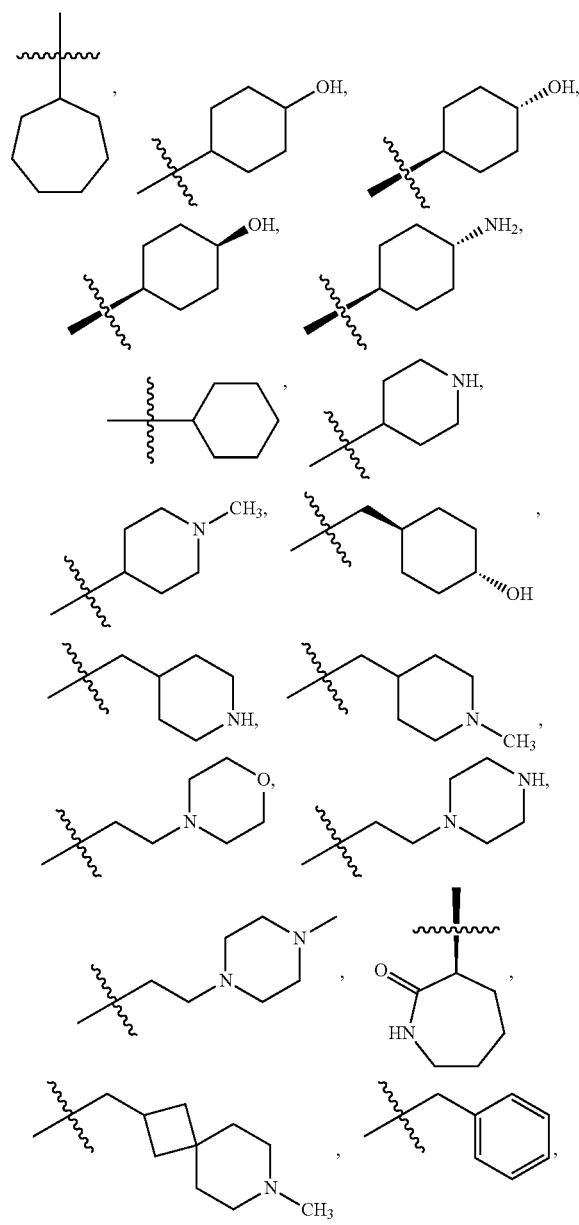
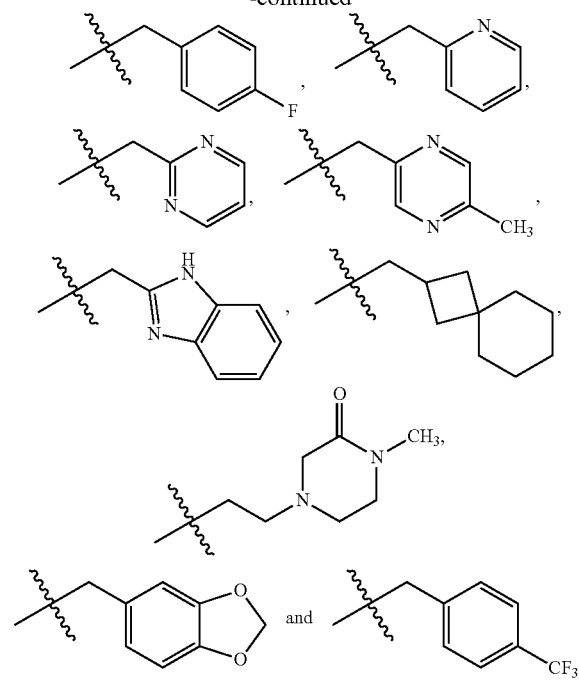
or R³ and R⁴ together with nitrogen attached to R³ and R⁴ form
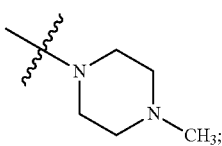 [SMILES: *N1CCN(C)CC1]
R⁵ is selected from the group consisting of
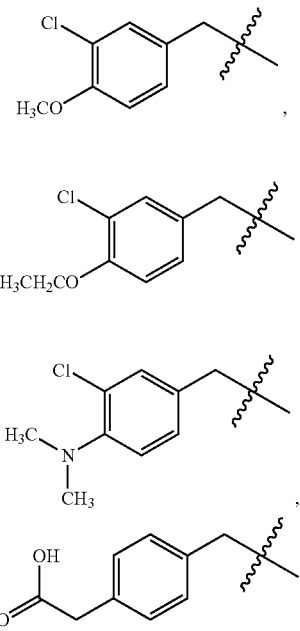

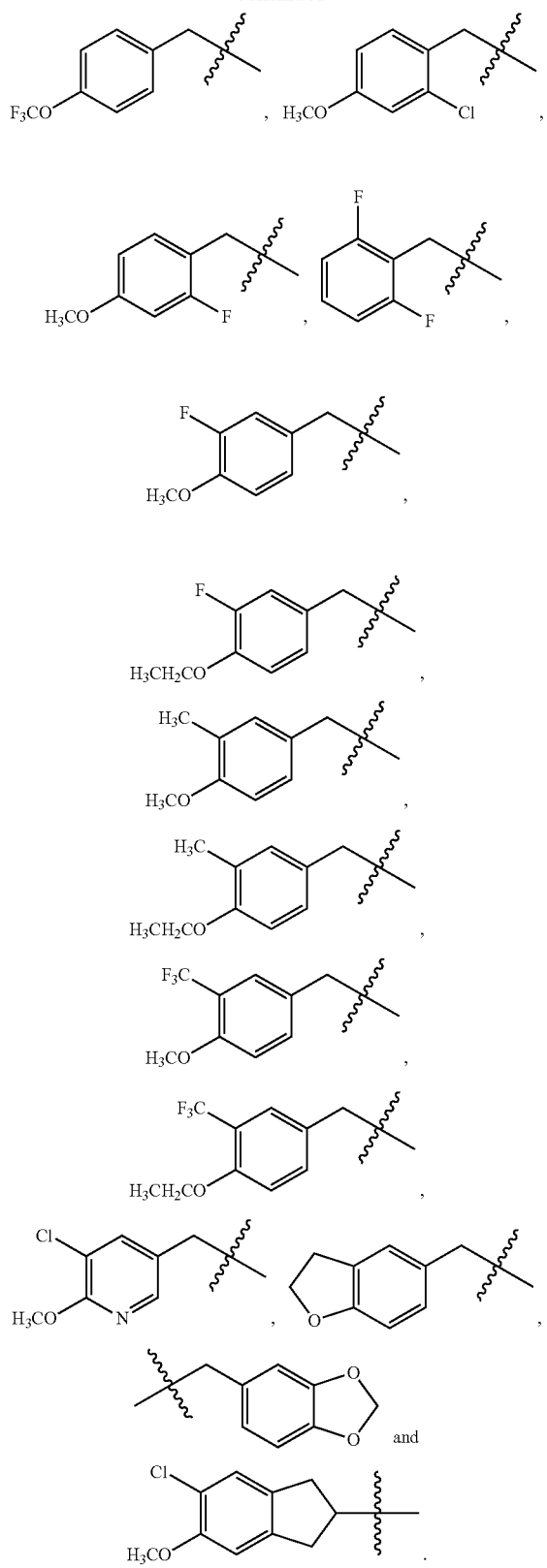
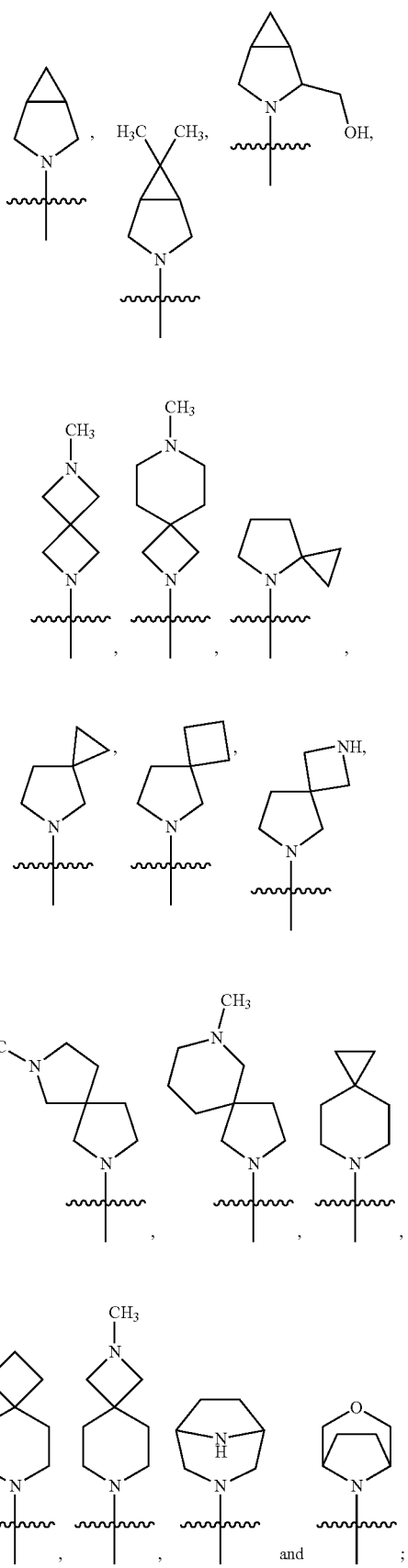
11. The compound of claim 10 or a pharmaceutically acceptable salt or a stereoisomer thereof, wherein $R^1$ is selected from the group consisting of

207
$R^3$ is selected from the group consisting of
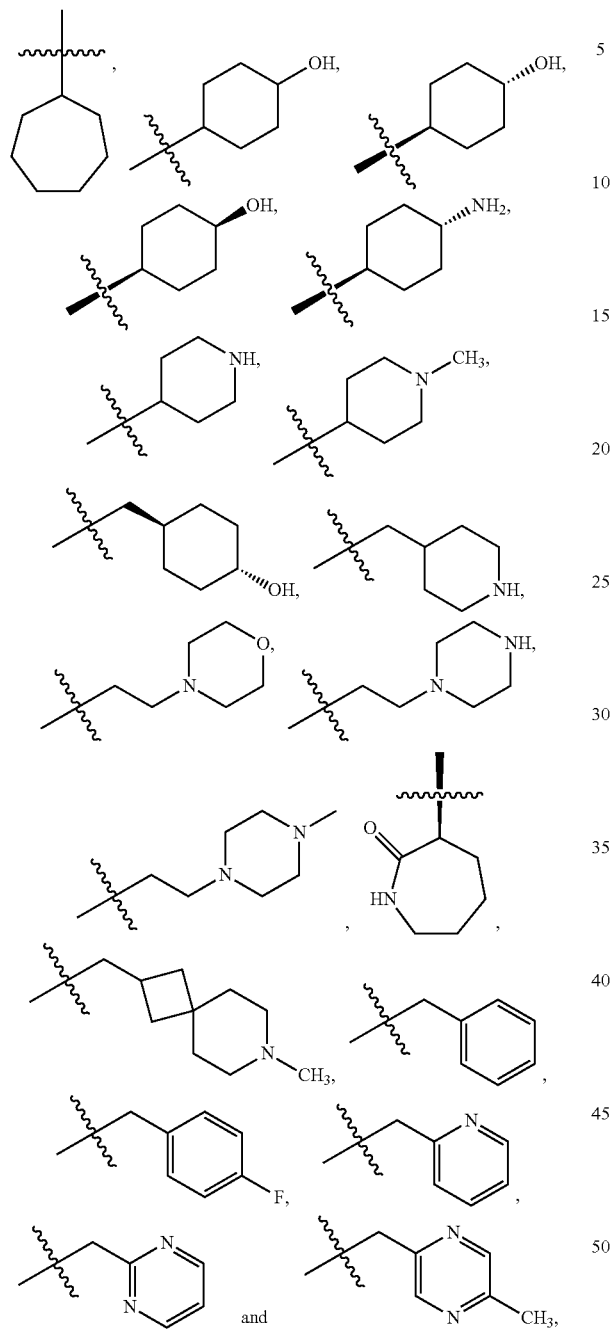
or $R^3$ and $R^4$ together with nitrogen attached to $R^3$ and $R^4$ form
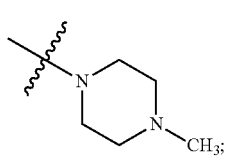
208
$R^5$ is selected from the group consisting of
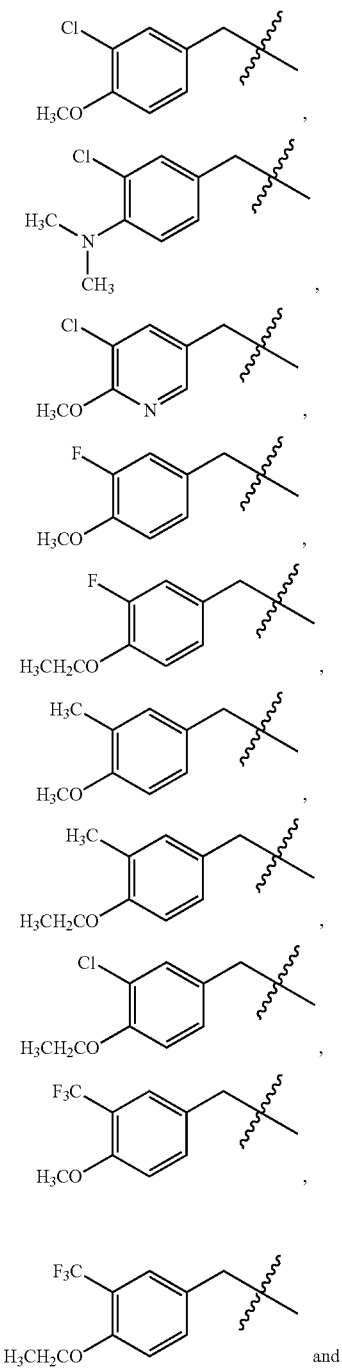
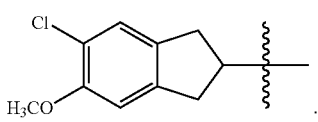
12. The compound of claim 1 or a pharmaceutically acceptable salt or a stereoisomer thereof, wherein said compound is selected from 209
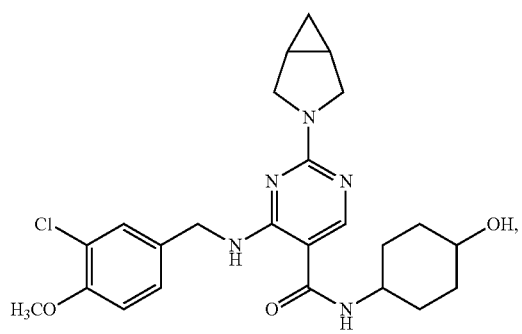
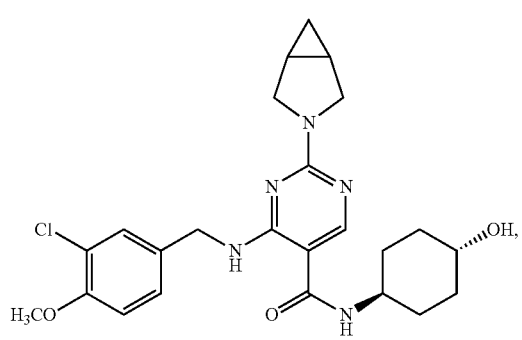
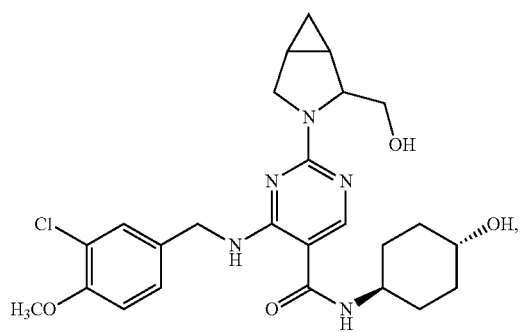
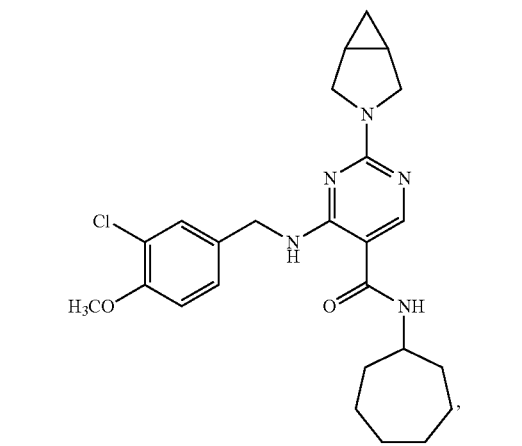
210
-continued
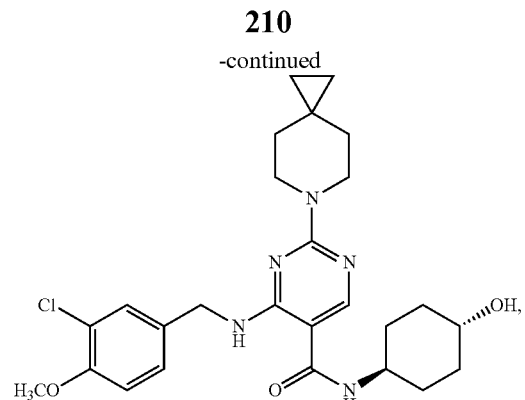
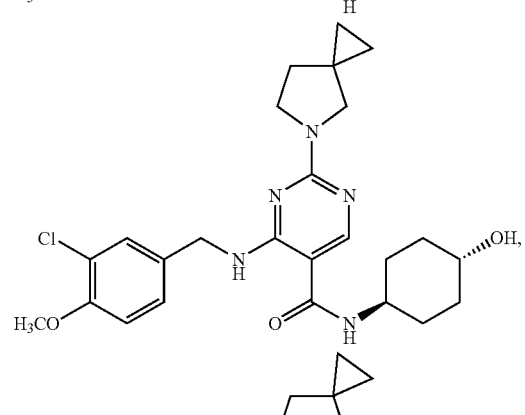
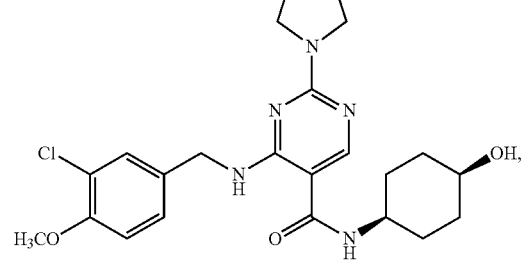
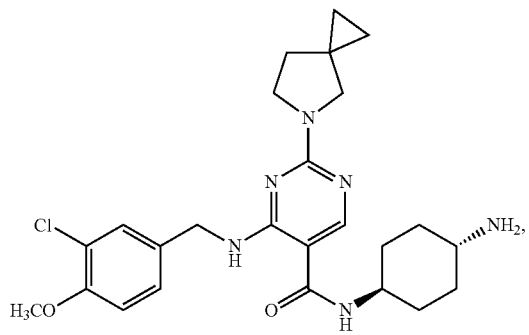
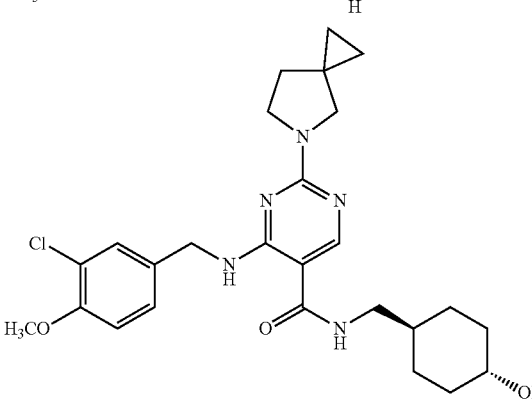

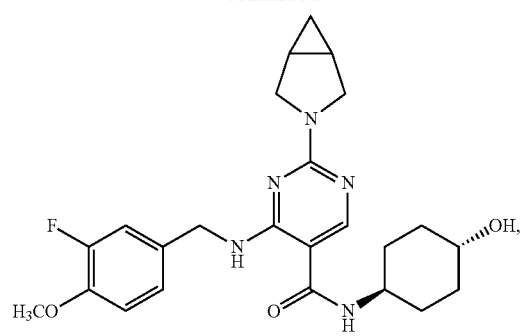
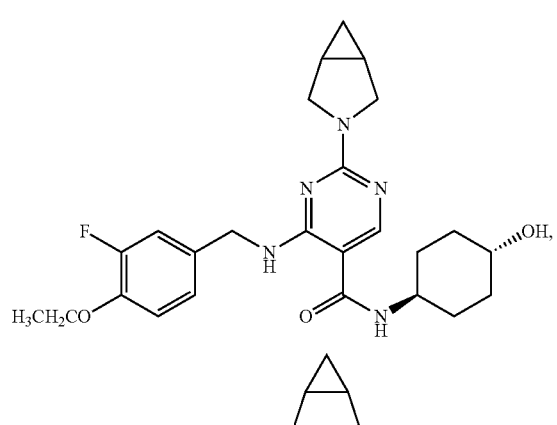
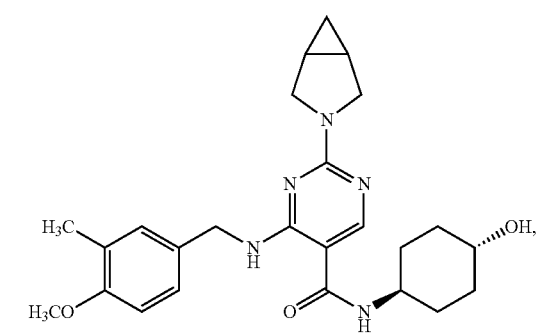
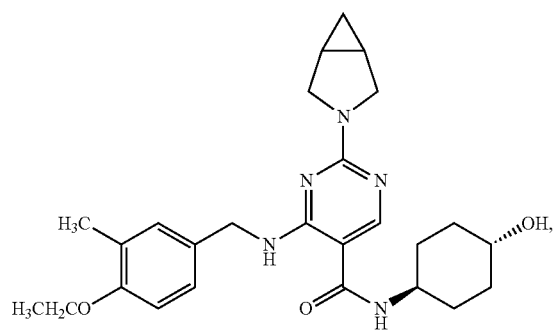
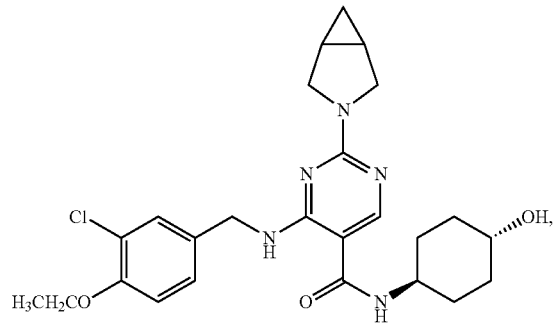
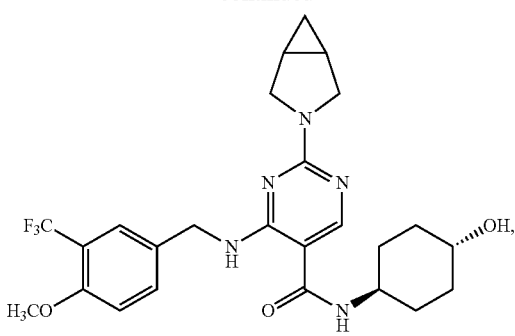
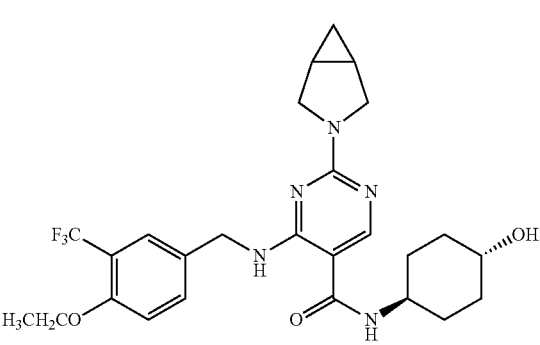
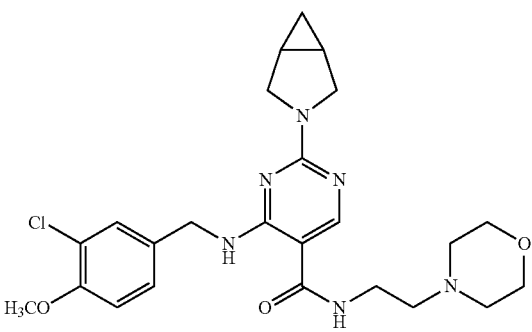
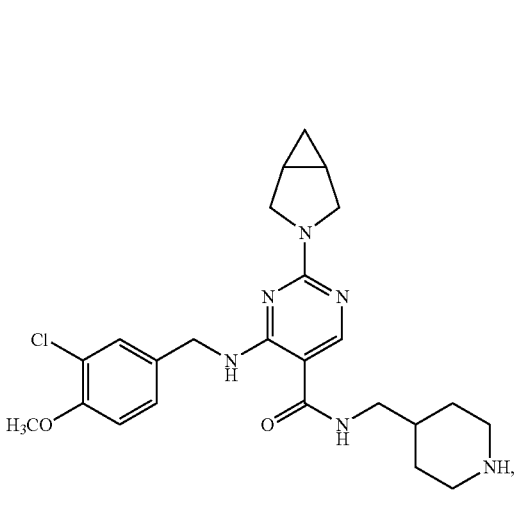
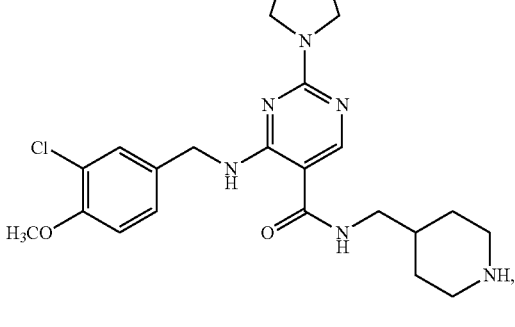

213
-continued
214
-continued
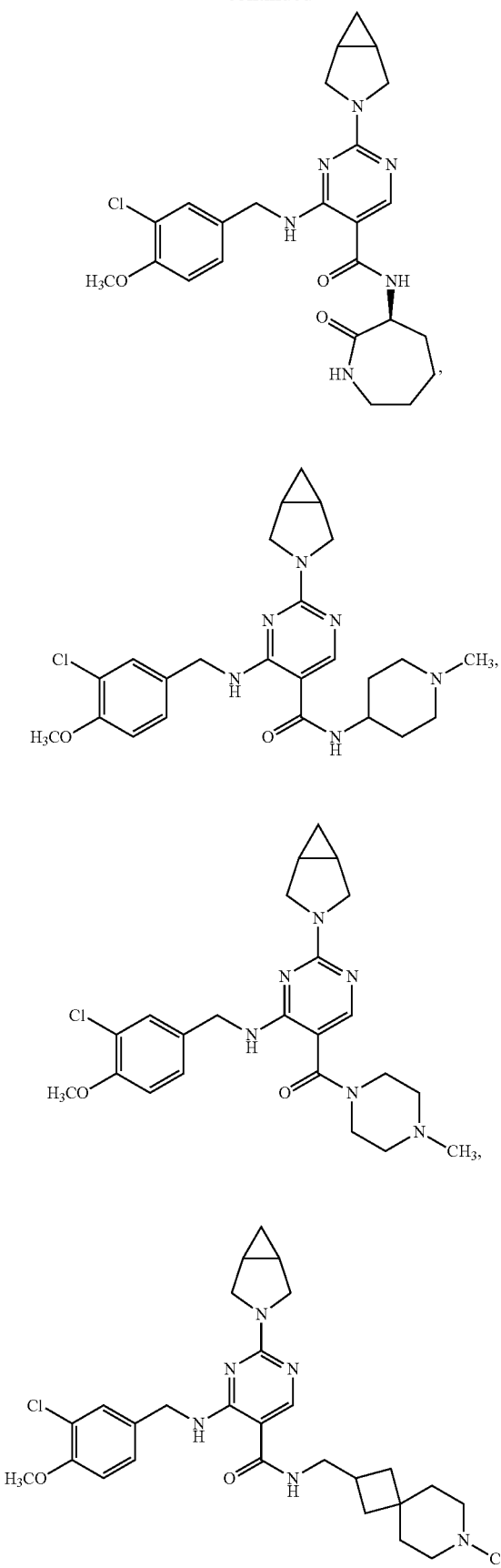
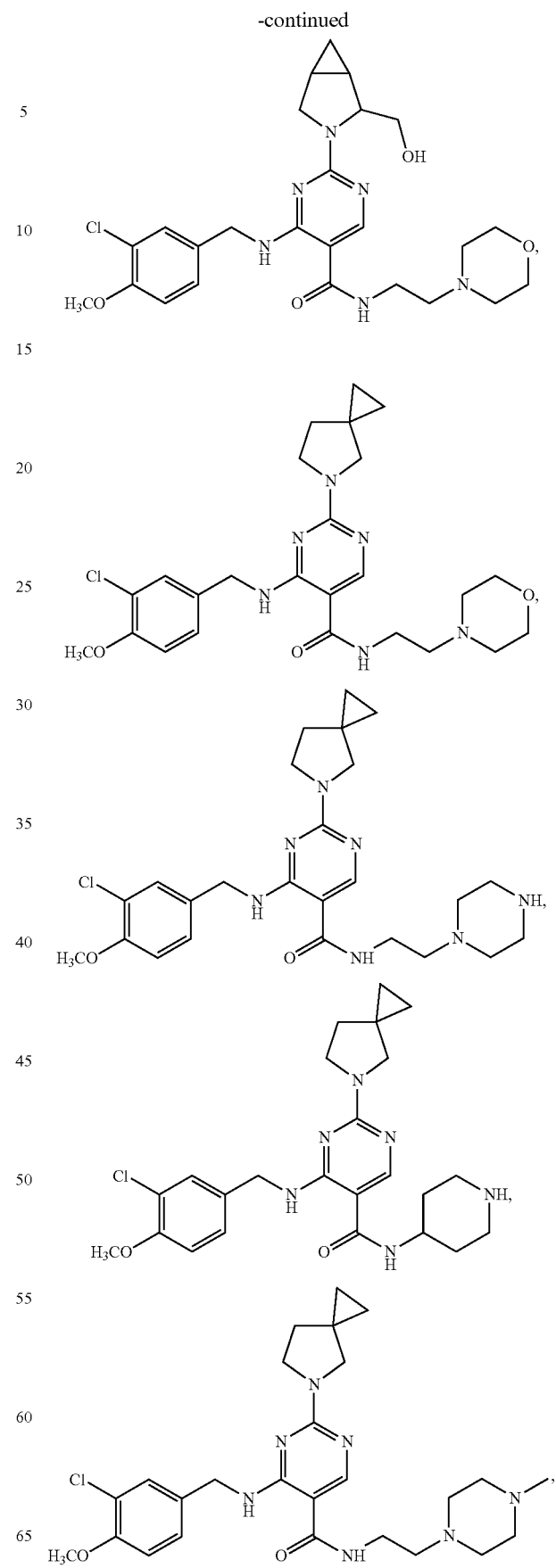

215
-continued
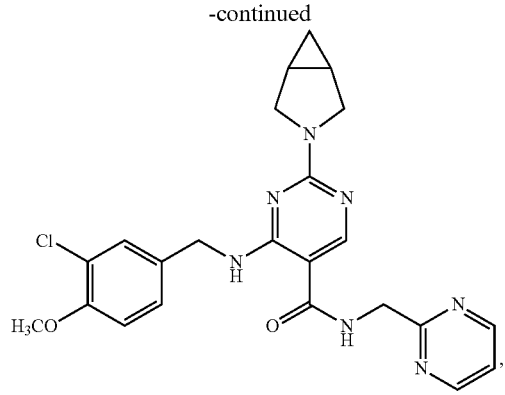
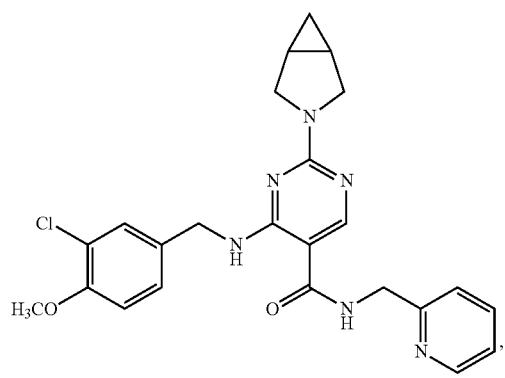
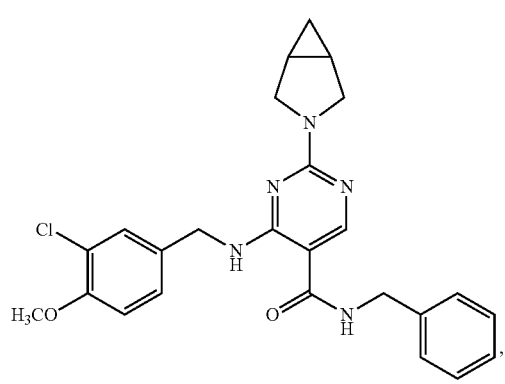
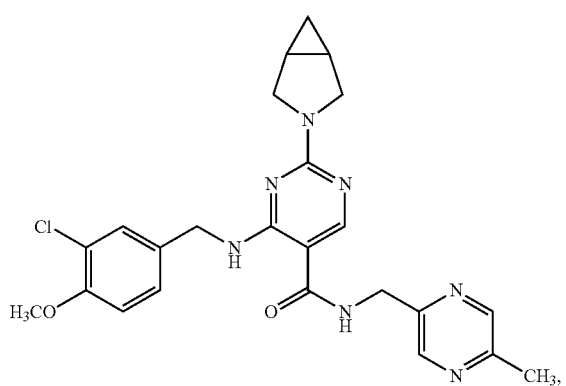
216
-continued
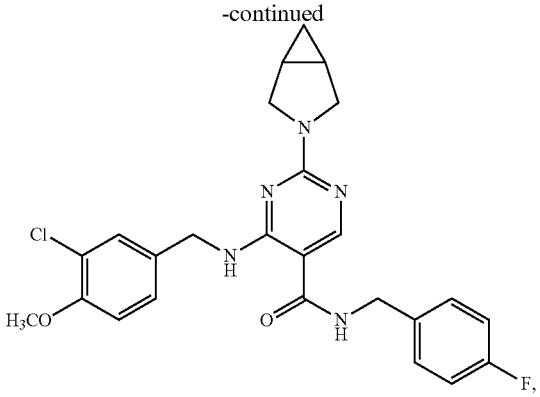
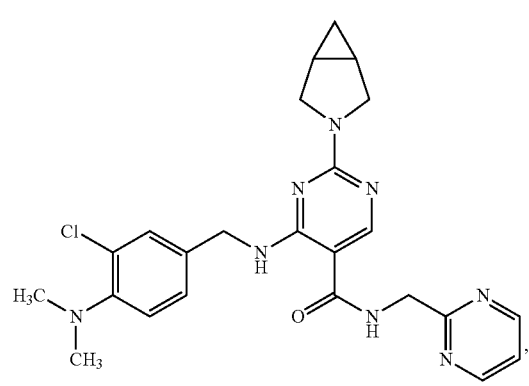
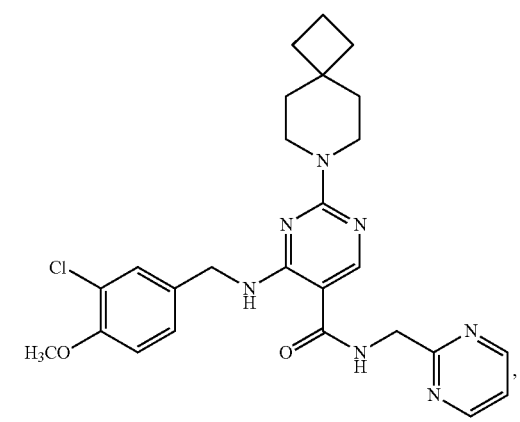
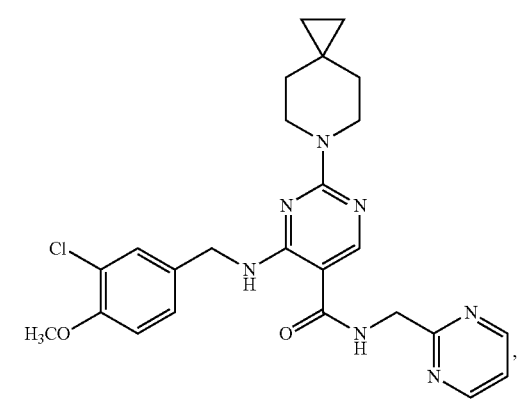

217
-continued
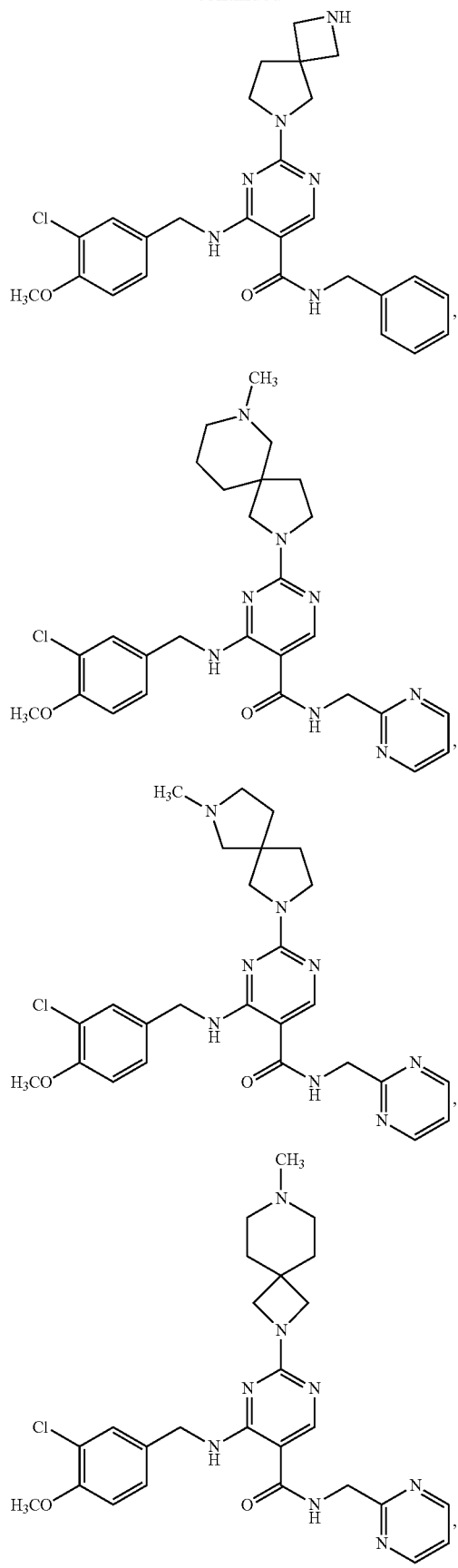
218
-continued
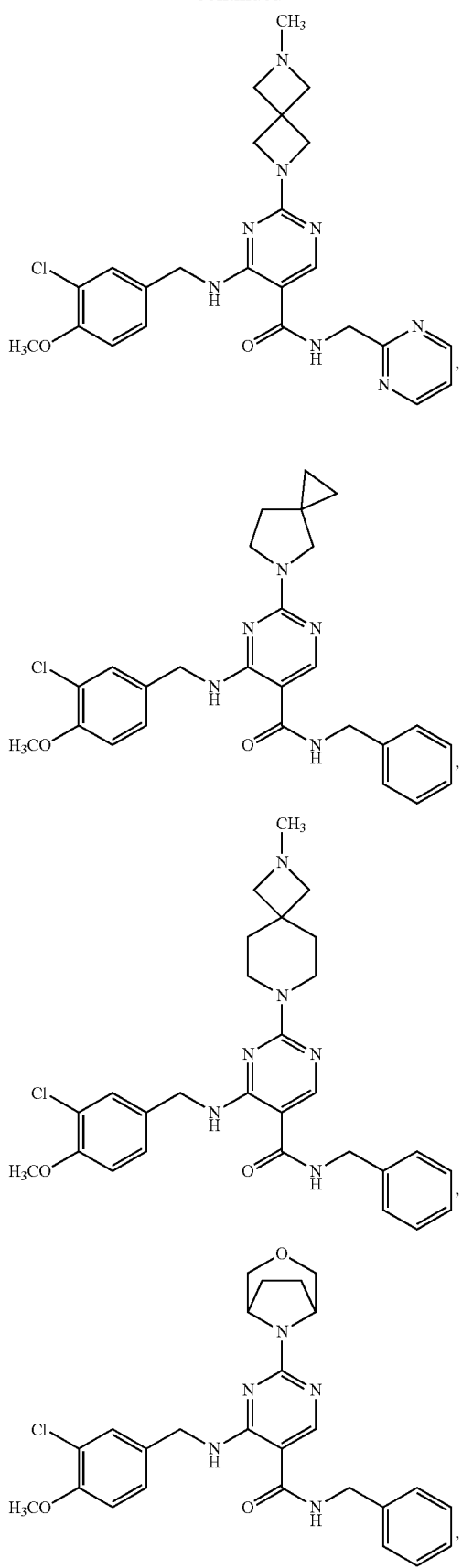

219
-continued
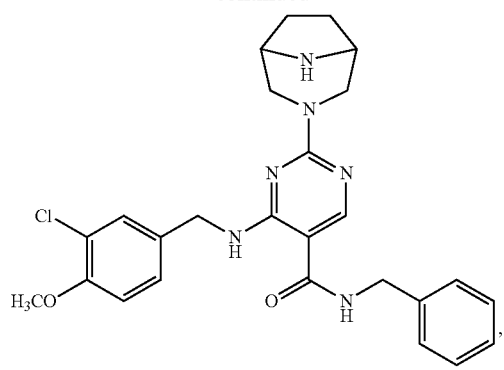
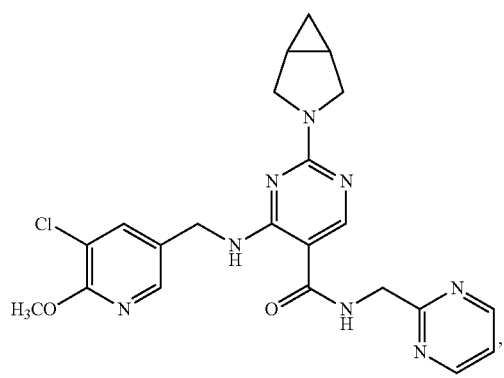
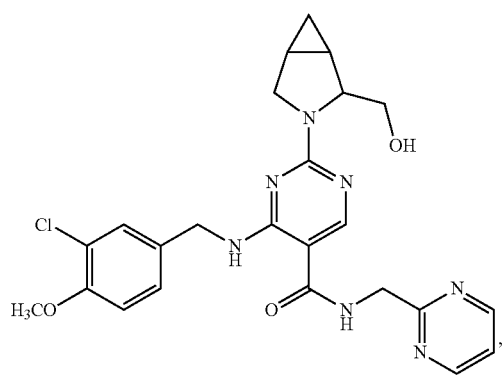
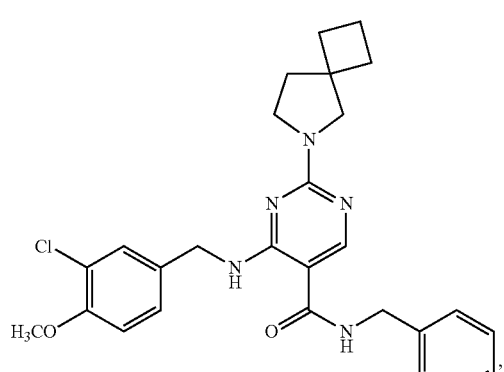
220
-continued
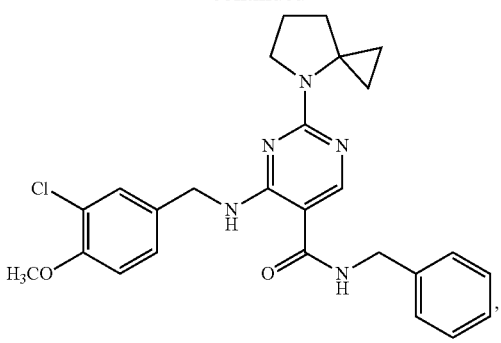
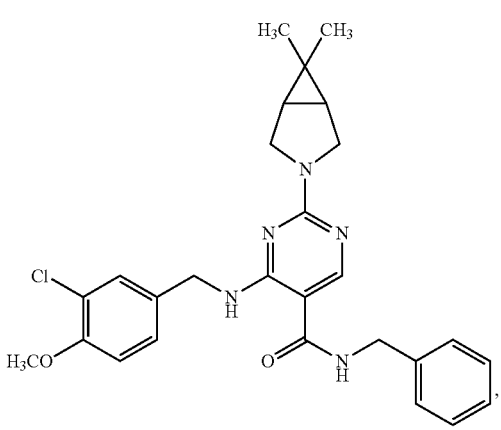
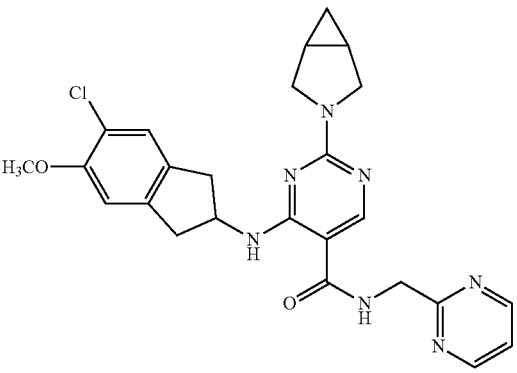
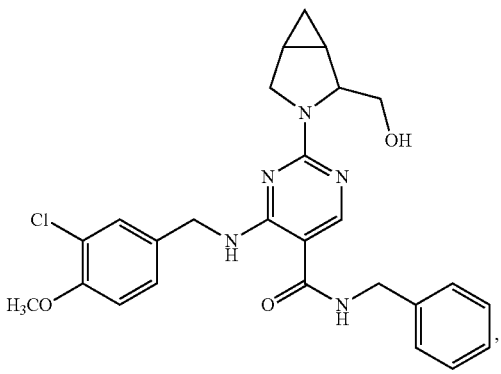

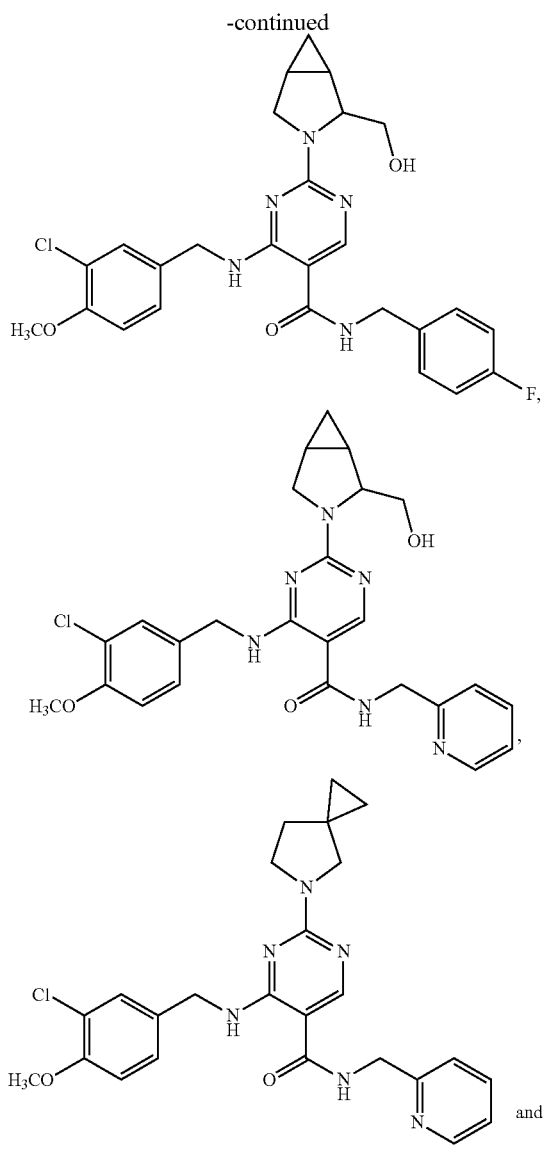

13. A pharmaceutical composition comprising the compound or a pharmaceutically acceptable salt or a stereoisomer thereof according to claim 1 and one or more pharmaceutical carrier and/or diluent.

14. The pharmaceutical composition according to claim 13, further comprising one or more second therapeutically active agents selected from the group consisting of vasodilator, prostaglandin E1, prostacyclin, α-adrenoreceptor blocker, mixed α, β-blocker, α-blocker, 5α-reductase inhibitor, α2-adrenoreceptor blocker, ACE inhibitor, NEP inhibitor, central dopaminergic agent, vasoactive intestinal peptide, calcium channel blocker, thiazines and the mixture thereof.

15. A method for treating in a subject a disease selected from the group consisting of diseases with lower urinary tract symptoms, hypertension, pulmonary hypertension, erectile dysfunction, and prostatic hyperplasia, comprising the step of administrating the compound or a pharmaceutically acceptable salt or a stereoisomer thereof according to claim 1, or a pharmaceutical composition comprising said compound or pharmaceutically acceptable salt or a stereoisomer thereof to the subject.

16. The method of claim 15, wherein said disease is selected from the group consisting of erectile dysfunction and benign prostatic hyperplasia.

* * * * *